US008871220B2

(12) United States Patent
Bublot et al.

(10) Patent No.: US 8,871,220 B2

(45) Date of Patent: Oct. 28, 2014

(54) NEWCASTLE DISEASE VIRUS VECTORED AVIAN VACCINES

(75) Inventors: Michel Bublot, Chaponost (FR); Frederic Reynard, Saint-Bonnet-de-Mure (FR); François-Xavier Le Gros, Saint Genis Laval (FR)

(73) Assignee: Merial Limited, Duluth, GA (US)

(*) Notice: Subject to any disclaimer, the term of this patent is extended or adjusted under 35 U.S.C. 154(b) by 696 days.

(21) Appl. No.: 12/753,597

(22) Filed: Apr. 2, 2010

(65) Prior Publication Data

US 2010/0255029 A1 Oct. 7, 2010

Related U.S. Application Data

(60) Provisional application No. 61/166,481, filed on Apr. 3, 2009.

(51) Int. Cl.

| | |
|---|---|
| ***A61K 39/295*** | (2006.01) |
| ***A61K 39/145*** | (2006.01) |
| ***A61K 39/17*** | (2006.01) |
| ***C12N 15/44*** | (2006.01) |
| ***C12N 15/86*** | (2006.01) |

(52) U.S. Cl.

USPC .................. 424/199.1; 435/235.1; 435/320.1; 424/209.1; 424/214.1

(58) Field of Classification Search

None

See application file for complete search history.

(56) References Cited

FOREIGN PATENT DOCUMENTS

| | | | | |
|---|---|---|---|---|
| WO | WO2007/104782 | | 9/2007 | |
| WO | WO 2007/104782 | * | 9/2007 | ............. C07K 14/11 |

OTHER PUBLICATIONS

Kattenbelt et al (Veterinary Microbiology 114:134-141, 2006.*

Mahmud et al (Bangladesh Journal of Veterinary Medicine 5:19-23, 2007, abstract only cited).*

Avinew package insert. Downloaded from <<http://ph.merial.com/poultry/pdf/poultry_avinew_product_insert.pdf>> on Aug. 30, 2012; available on web site since at least 2006.*

Mahmud et al (Bangladesh Journal of Veterinary Medicine 5:19-23, 2007).*

Li et al (Bing du xue bao 24:101-5, 2008, abstract only cited).*

Feldberg et al, J. Physiol. 143:68-75, 1958.*

Ge et al (Journal of Virology 85:8241, 2011, not prior art).*

Cho et al, Clinical and Vaccine Immunology. 2008, 15(10):1572-1579. "Characterization of a Recombinant Newcastle Disease Virus Vaccine Strain".*

Reimann et al. Virology 322 (2004) 143-157. "An avirulent chimeric Pestivirus with altered cell tropism protects pigs against lethal infection with classical swine fever virus."*

Rimmelzwaan et al. Expert Reviews Vaccines 8(4), 447-454 (2009). "Candidate influenza vaccines based on recombinant modified vaccinia virus Ankara."*

Saxena et al. Vaccine 26 (2008) 6592-6601. "A sindbis virus replicon-based DNA vaccine encoding the rabies virus glycoprotein elicits immune responses and complete protection in mice from lethal challenge."*

Marconi et al. Adv Exp Med Biol. 2009;655:118-44. "HSV as a vector in vaccine development and gene therapy."*

Nakaya et al (Journal of Virology 75:11868-11873, 2001).*

Swayne et al (Avian Diseases 47:1047-1050, 2003).*

Jiang et al (Antiviral Research 75:234-241, 2007).*

Genbank accession AF375823, Nov. 6, 2001.*

Genbank acession DQ420166, Oct. 17, 2007.*

Ge et al (Journal of Virology 81:150-158, 2007).*

Krishnamurthy et al., Virology 278, 168-182,2000, "Recovery of a Virulent Strain of Newcastle Disease Virus from Cloned cDNA: Expression of a Foreign Gene Results in Growth Retardation and Attenuation".

Huang et al., J. Gen. Virol. 82, 1729-1736, 2001, "High-level expression of a foreign gene from the most 3'-proximal locus of a recombinant Newcastle disease virus".

Nakaya et al., J. Virol. 75, 11868-11873, 2001, "Recombinant Newcastle Disease Virus as a Vaccine Vector".

Park et al. PNAS 103, 8203-8208, 2006, "Engineered viral vaccine constructs with dual specificity: avian influenza and newcastle disease".

Veits et al PNAS 103, 8197-8202, 2006, "Newcastle disease virus expressing H5 hemagglutinin gene protects chickens against Newcastle disease and avian influenza".

Ge et al. J. Virol. 81, 150-158, 2007, "Newcastle disease virus-based live attenuated vaccine completely protects chickens and mice from lethal challenge of homologous and heterologous H5N1 avian influenza viruses".

Romer-Oberdörfer et al. Vaccine 26, 2307-2313, 2008, "Level of protection of chickens against highly pathogeonic H5 avian influenza virus with Newcastle disease virus based live attenuated vector vaccine depends on homology of H5 sequence between vaccine and challenge virus".

Alexander, D. J., Diseases of Poultry, Iowa State Uni. Press, Ames IA, 541-569, 1997, "Newcastle disease and other avian paramyxoviridae infections".

Steward et al., 1993, Journal of General Virology 74:2539-2547, "RNA editing in Newcastle disease virus".

Conzelmann, K.K., Ann. Rev. Genet. 32, 123-162, 1998, "Nonsegmented negative-strand RNA viruses: Genetics and manimupation of Viral Genomics".

Roberts and Rose, Virology 247, 1-6, 1998, "Recovery of negative-strand RNA viruses from plasmid DNAs: a positive approach revitalizes a negative field".

Palese et al., PNAS 93, 11354-11358, 1996, "Negative-strand RNA viruses: Genetic engineering and appliations".

(Continued)

*Primary Examiner* — Mary E Mosher

(74) *Attorney, Agent, or Firm* — Judy Jarecki-Black; Ruoying Chen; Merial Limited

(57) ABSTRACT

The present invention encompasses engineered Newcastle Disease Virus (NDV) vaccines or compositions. The vaccine or composition may be a recombinant vaccine. The invention also encompasses recombinant vectors encoding and expressing avian pathogen antigens, more specifically avian influenza proteins, epitopes or immunogens. Such vaccines or compositions can be used to protect animals, in particular avian, against disease.

20 Claims, 61 Drawing Sheets

(56) References Cited

OTHER PUBLICATIONS

Nagai, Y., Rev. Med. Virol. 9, 83-99, 1999, "Paramyxovirus replication and pathogenesis. Reverse Genetics transforms understanding".

Bukreyev et al., J. Virol. 70, 6634-6641, 1996, "Recovery of infectious respiratory syncytial virus expressing an additional, foreign gene".

Mebatsion et al., PNAS 93, 7310-7314,1996, "Highly stable expression of a foreign gene from rabies virus vectors".

Schnell et al., PNAS 93, 11359-11365,1996, "Foreign glycoproteins expressed from recombinant vesicular stomatitis viruses are incorporated efficiently into virus particles".

Hasan et al., J. Gen. Virol. 78, 2813-2820,1997, "Creation of an infectious recombinant Sendai virus expressing the firefly luciferase gene from the 3' proximal first locus".

He et al., Virology 237, 249-260,1997, "Recovery of infectious SV5 from cloned DNA and expression of a foreign gene".

Sakai et al., FEBS Lett. 45, 221-226,1999, "Accomodation of foreign genes into the sendai virus genome: sizes of inserted genes and viral replication".

Peeters et al., J. Virol. 73, 5001-5009,1999, "Rescue of Newcastle disease virus from cloned cDNA: evidence that cleavability of the fusion protein is a major determinant for virulence".

Romer-Oberdorfer et al., Journal of General Virology, 80, 2987-2995,1999, "Generation of recombinant lentogenic Newcastle disease virus from cDNA".

de Jong et al., J Clin Virol. 35(1):2-13,2006, "Avian influenza A (H5N1)".

Olsen et al., Science 21;312(5772):384-8,2006, "Global patterns of influenza A virus in wild birds".

Database UniProt, Nov. 14, 2006, database accession No. Q00G25.

Database UniProt, Jul. 11, 2006, Database accession No. Q195D5.

Database UniProt, Feb. 7, 2008, Database accession No. AOD41076.

Database Geneseq, Jul. 10, 2008, Database accession No. ARW17912.

Database Geneseq, Nov. 15, 2007, Database accession No. AJF80522.

Database Geneseq, Nov. 15, 2007, Database accesion No. AJF80554.

Database Geneseq, Jul. 23, 2007, Database accession No. AGD56967.

Database UniProt, Apr. 17, 2007, Database accession No. A4GXN3.

Database UniProt, Oct. 23, 2007, Database accession No. A7Y8C7.

Database UniProt, Apr. 29, 2008, Database accession No. B1PM82.

* cited by examiner

Figure 4a

Avinew NDV genomic sequence with cloning sites (SEQ ID NO:24)

```
                                  T7 promoter
1     TTCGCCCTTA ACAGCGGCCG CTAATACGAC TCACTATAGG ACCAAACAGA GAATCCGTGA
                                        (GS)
61    GGTACGATAG AAGGCGAAGG AGCAATCGAA GTCGTACGGG TAGAAGGTGT GAATCTCGAG

                       NP protein(SEQ ID NO:3):  M  S  S   V  F  D  E
121   TGCGAGCCCG AAGCTCAAAC TCGAGAGAGC CTTCTGCCAA AATGTCTTCT GTATTCGATG

       Y  E  Q   L  L  A   A  Q  T  R   P  N  G   A  H  G   G  G  E  K
181   AGTACGAGCA GCTCCTCGCG GCTCAGACTC GCCCCAATGG AGCTCATGGC GGAGGAGAGA

       G  S  T   L  K  V   E  V  P  V   F  T  L   N  S  D   D  P  E  D
241   AGGGGAGCAC CTTAAAGGTA GAAGTCCCGG TATTCACTCT CAACAGTGAT GACCCAGAAG

       R  W  N   F  A  V   F  C  L  R   I  A  V   S  E  D   A  N  K  P
301   ATAGATGGAA CTTTGCAGTG TTTTGTCTTC GGATTGCTGT TAGCGAGGAT GCCAACAAAC

       L  R  Q   G  A  L   I  S  L  L   C  S  H   S  Q  V   M  R  N  H
361   CACTTAGGCA AGGTGCTCTC ATATCTCTCT TATGTTCCCA CTCTCAAGTG ATGAGGAACC

       V  A  L   A  G  K   Q  N  E  A   T  L  A   V  L  E   I  D  G  F
421   ATGTTGCCCT TGCGGGGAAA CAGAATGAGG CCACACTGGC TGTTCTTGAG ATCGATGGTT

       T  N  G   V  P  Q   F  N  N  R   S  G  V   S  E  E   R  A  Q  R
481   TTACCAACGG CGTGCCCCAG TTCAACAACA GGAGTGGAGT GTCTGAAGAG AGAGCACAGA

       F  M  M   I  A  G   S  L  P  R   A  C  S   N  G  T   P  F  V  T
541   GATTTATGAT GATAGCAGGG TCTCTCCCTC GGGCATGCAG CAACGGTACC CCGTTCGTCA

       A  G  V   E  D  D   A  P  E  D   I  T  D   T  L  E   R  I  L  S
601   CAGCTGGGGT TGAAGATGAT GCACCAGAAG ACATTACTGA TACCCTGGAG AGGATCCTCT

       I  Q  A   Q  V  W   V  T  V  A   K  A  M   T  A  Y   E  T  A  D
661   CTATCCAGGC TCAAGTATGG GTCACGGTGG CAAAGGCCAT GACTGCATAT GAGACAGCAG

       E  S  E   T  R  R   I  N  K  Y   M  Q  Q   G  R  V   Q  K  K  Y
721   ATGAGTCAGA AACAAGAAGA ATCAATAAGT ACATGCAGCA AGGCAGGGTC CAGAAGAAGT

       I  L  H   P  V  C   R  S  A  I   Q  L  T   I  R  Q   S  L  A  V
781   ACATCCTCCA CCCCGTATGC AGGAGCGCAA TCCAACTCAC AATCAGACAG TCTCTGGCGG

       R  I  F   L  V  S   E  L  K  R   G  R  N   T  A  G   G  T  S  T
841   TCCGCATCTT TTTGGTTAGC GAGCTTAAGA GAGGCCGCAA CACGGCAGGT GGGACCTCCA

       Y  Y  N   L  V  G   D  V  D  S   Y  I  R   N  T  G   L  T  A  F
901   CCTATTACAA CTTGGTGGGG GATGTAGACT CATACATCAG GAACACTGGG CTAACTGCAT

       F  L  T   L  K  Y   G  I  N  T   K  T  S   A  L  A   L  S  S  L
961   TCTTCCTGAC ACTTAAATAT GGAATTAACA CCAAGACATC AGCCCTTGCA CTTAGCAGCC

       S  G  D   I  Q  K   M  K  Q  L   M  R  L   Y  R  M   K  G  D  N
1021  TCTCAGGCGA TATCCAGAAA ATGAAGCAGC TCATGCGCTT GTATCGGATG AAAGGAGATA
```

Figure 4b

A P Y M T L L G D S D Q M S F A P A E Y
1081 ATGCGCCGTA CATGACATTG CTCGGTGACA GTGACCAGAT GAGCTTTGCA CCTGCCGAGT

A Q L Y S F A M G M A S V L D K G T S K
1141 ATGCACAACT TTACTCCTTT GCCATGGGTA TGGCATCAGT CCTAGATAAA GGAACTAGCA

Y Q F A R D F M S T S F W R L G V E Y A
1201 AATACCAATT TGCCAGGGAC TTTATGAGCA CATCATTCTG GAGACTTGGA GTAGAGTACG

Q A Q G S S I N E D M A A E L K L T P A
1261 CTCAGGCTCA AGGAAGTAGC ATCAATGAGG ATATGGCCGC CGAGCTAAAG CTAACCCCAG

A R R G L A A A A Q R V S E E T S S M D
1321 CAGCAAGGAG AGGCCTGGCA GCTGCTGCCC AAAGAGTGTC TGAGGAGACC AGCAGCATGG

M P T Q Q A G V L T G L S D G G S Q A P
1381 ACATGCCCAC CCAACAAGCC GGGGTCCTCA CTGGACTCAG CGACGGAGGC TCCCAAGCCC

Q G A L N R S Q G Q P D T G D G E T Q F
1441 CCCAAGGTGC ACTGAACAGA TCACAAGGGC AACCGGACAC CGGGGATGGG GAGACCCAAT

L D L M R A V A N S M R E A P N S A Q G
1501 TTCTGGATCT GATGAGAGCG GTGGCAAATA GCATGAGAGA AGCGCCAAAC TCTGCGCAGG

T P Q P G P P P T P G P S Q D N D T D W
1561 GCACCCCTCA ACCGGGGCCT CCCCCAACCC CTGGGCCCTC TCAAGACAAT GACACCGACT

G Y *
1621 GGGGGTACTG ACCGACAGCA CCCAGTTTGC TTCTATGAGG TCATCCCAAT TCCTCTGCCC

1681 ACACCCCACC CCTCAATCCG CAATCCCGCA TGGCCAAACC CACAAACGAA CCCCCCTGTC

1741 TCCCTCCTCT CCCCCAGCCC CACAACCCCA CCTGCCCAGG GCAACATAGG TACAATGCGA (GE) (GS)
1801 CCCACTAATA ATCAATACAG GGCCAAAGAA ATTAGAAAAA AGTACGGGTA GAAGGGAGAC

1861 ATTCAGAGAT CAGGGCGAGT CACCCGGGTC TCTGCTCTCC CTTCTACCTA GTGGATTAGG

P protein (SEQ ID NO:5)
M A T F T D A E I D E L F E T S G T
1921 ATGGAGATGG CCACCTTTAC AGATGCGGAG ATCGACGAGC TATTTGAGAC CAGTGGAACT V I D S I I T A Q G K P V E T V G R S A
1981 GTCATTGACA GCATAATTAC GGCCCAGGGA AAACCAGTAG AGACTGTTGG AAGGAGTGCA I P Q G K T K A L S A A W E K H G S I Q
2041 ATCCCACAAG GCAAAACTAA GGCTTTGAGC GCAGCATGGG AGAAGCATGG GAGCATCCAG S P A S Q D T P D R Q D R S D K Q L S T
2101 TCACCAGCCA GCCAAGACAC CCCTGATCGA CAGGACAGAT CAGATAAACA ACTGTCCACA P E Q A S P N D S P P A T S T D Q P P T
2161 CCCGAGCAAG CGAGTCCAAA CGACAGCCCC CCAGCCACAT CCACTGACCA GCCTCCCACT

Figure 4c

```
      Q  A  A  D  E  A  G  D  T  Q  L  K  T  G  A  S  N  S  L  L
2221  CAGGCTGCAG ATGAGGCCGG CGATACACAG CTCAAGACCG GAGCAAGCAA CTCTCTGCTG

      S  M  L  D  K  L  S  N  K  S  S  N  A  K  K  G  P  G  S  S
2281  TCGATGCTTG ATAAACTCAG CAATAAGTCA TCTAATGCTA AAAAGGGCCC AGGGTCGAGC

      P  Q  E  R  H  H  Q  R  L  T  Q  Q  Q  G  S  Q  Q  S  R  G
2341  CCTCAAGAAA GGCATCATCA ACGTCTGACT CAACAACAGG GGAGTCAACA AAGCCGCGGA

      N  S  Q  E  R  P  Q  N  Q  A  K  A  I  P  G  N  Q  V  T  D
2401  AACAGCCAAG AGAGACCGCA GAACCAGGCC AAGGCCATCC CTGGAAACCA GGTCACAGAC

      A  N  T  A  Y  H  G  Q  W  E  E  S  Q  L  S  A  G  A  T  H
2461  GCGAACACAG CATATCATGG ACAATGGGAG GAGTCACAAC TATCAGCTGG TGCAACCCAT

      H  A  L  R  S  E  Q  S  Q  D  N  T  P  A  P  V  D  H  V  Q
2521  CATGCTCTCC GATCAGAGCA GAGCCAAGAC AATACTCCTG CACCTGTGGA TCATGTCCAG

      L  P  V  D  F  V  Q  A  M  M  S  M  M  E  A  I  S  Q  R  V
2581  CTACCTGTCG ACTTTGTGCA GGCGATGATG TCTATGATGG AGGCGATATC ACAGAGGGTA

      S  K  V  D  Y  Q  L  D  L  V  L  K  Q  T  S  S  I  P  M  M
2641  AGTAAAGTTG ACTATCAGCT GGACCTTGTC TTGAAACAGA CATCTTCTAT CCCCATGATG

      R  S  E  I  Q  Q  L  K  T  S  V  A  V  M  E  A  N  L  G  M
2701  CGGTCTGAAA TCCAGCAGCT GAAAACGTCT GTTGCGGTCA TGGAAGCCAA TTTGGGCATG

      M  K  I  L  D  P  G  C  A  N  V  S  S  L  S  D  L  R  A  V
2761  ATGAAGATCC TGGACCCTGG TTGTGCCAAC GTTTCATCTC TAAGTGATCT ACGGGCAGTT

      A  R  S  H  P  V  L  I  S  G  P  G  D  P  S  P  Y  V  T  Q
2821  GCCCGATCCC ACCCGGTTTT AATTTCTGGC CCCGGAGACC CATCTCCTTA TGTGACCCAA

      G  G  E  M  A  L  N  K  L  S  Q  P  V  Q  H  P  S  E  L  I
2881  GGGGGCGAAA TGGCACTCAA TAAACTTTCG CAACCGGTGC AACACCCCTC TGAATTGATT

      K  P  A  T  A  S  G  P  D  I  G  V  E  K  D  T  V  R  A  L
2941  AAACCCGCCA CGGCAAGCGG GCCTGATATA GGAGTGGAGA AAGACACTGT CCGTGCATTG

      I  M  S  R  P  M  H  P  S  S  S  A  R  L  L  S  K  L  D  A
3001  ATCATGTCAC GCCCTATGCA TCCGAGCTCT TCAGCTAGGC TCTTGAGCAA ACTGGACGCA

      A  G  S  I  E  E  I  R  K  I  K  R  L  A  L  N  G  *
3061  GCCGGATCGA TTGAGGAAAT CAGAAAAATC AAGCGCCTTG CACTGAATGG CTAATCACCA

3121  CCGCAACCCG CAGCAGATCC CTGTCCACCC AGCACCACAC GGTATCTGCA CCAAGCTCCT

                                   PacI            FseI
3181  CTCTGCAAAT CCAAGGTCCA ACACCCTTAA TTAAGTCTGT CTGGCCGGCC CGAGCGACAA

3241  CCCTGTCCTG CTTCCTCTGC CCCACTAAAT GATCGCGCAG CTGCAATCAA TTCAGCTATA

        (GE)        (GS)              M protein (SEQ ID NO:7)  M  D  S
3301  TTAAGGATTA AGAAAAAATA CGGGTAGAAT CGGAGTGCCC CGATTGTGCC AAGATGGACT
```

Figure 4d

```
      S  R  T   I  G  L   Y  F  D   S  T  L   P  S  S   N  L  L   A  F
3361  CATCTAGGAC AATCGGGCTG TACTTTGATT CTACCCTTCC TTCTAGCAAC CTGCTAGCAT

      P  I  V   L  Q  D   T  G  D   G  K  K   Q  I  A   P  Q  Y   R  I
3421  TCCCGATAGT CCTACAAGAC ACAGGGGACG GGAAGAAGCA AATCGCCCCG CAATACAGGA

      Q  R  L   D  S  W   T  D  S   K  E  D   S  V  F   I  T  T   Y  G
3481  TCCAGCGTCT TGACTCGTGG ACAGACAGCA AAGAAGACTC GGTATTCATC ACCACCTATG

      F  I  F   Q  V  G   N  E  E   A  T  V   G  M  I   N  D  N   P  K
3541  GATTCATCTT TCAGGTTGGG AATGAAGAAG CCACTGTCGG CATGATCAAT GATAATCCCA

      R  E  L   L  S  T   A  M  L   C  L  G   S  V  P   N  V  G   D  L
3601  AGCGCGAGTT ACTTTCCACT GCCATGCTAT GCCTAGGGAG TGTACCAAAT GTCGGAGATC

      V  E  L   A  R  A   C  L  T   M  V  V   T  C  K   K  S  A   T  N
3661  TTGTTGAGCT GGCAAGGGCC TGCCTCACTA TGGTGGTAAC ATGCAAGAAG AGTGCAACTA

      T  E  R   M  V  F   S  V  V   Q  A  P   Q  V  L   Q  S  C   R  V
3721  ACACCGAGAG AATGGTCTTC TCAGTAGTGC AGGCACCCCA GGTGCTGCAA AGCTGTAGGG

      V  A  N   K  Y  S   S  V  N   A  V  K   H  V  K   A  P  E   K  I
3781  TTGTGGCAAA CAAATACTCG TCGGTGAATG CAGTCAAGCA CGTGAAAGCA CCAGAGAAGA

      P  G  S   G  T  L   E  Y  K   V  N  F   V  S  L   T  V  V   P  R
3841  TTCCTGGGAG CGGAACCCTA GAGTACAAAG TGAACTTTGT CTCTCTGACC GTGGTGCCAA

      K  D  V   Y  K  I   P  T  A   A  L  K   V  S  G   S  S  L   Y  N
3901  GAAAGGACGT CTACAAGATA CCAACTGCAG CACTTAAGGT CTCTGGCTCA AGTCTGTACA

      L  A  L   N  V  T   I  D  V   E  V  D   P  K  S   P  L  V   K  S
3961  ATCTTGCGCT CAATGTCACT ATTGATGTGG AGGTAGACCC GAAGAGCCCG TTGGTCAAAT

      L  S  K   S  D  S   G  Y  Y   A  N  L   F  L  H   I  G  L   M  S
4021  CCCTTTCCAA GTCCGACAGT GGGTACTATG CTAATCTCTT CTTACATATT GGGCTTATGT

      T  V  D   K  K  G   K  K  V   T  F  D   K  L  E   R  K  I   R  R
4081  CCACTGTAGA TAAGAAGGGG AAGAAAGTGA CATTTGACAA GCTGGAAAGG AAGATAAGGA

      L  D  L   S  V  G   L  S  D   V  L  G   P  S  V   L  V  K   A  R
4141  GACTTGATCT ATCTGTAGGG CTTAGTGACG TGCTCGGACC TTCCGTGCTT GTAAAGGCGA

      G  A  R   T  K  L   L  A  P   F  F  S   S  S  G   T  A  C   Y  P
4201  GAGGTGCACG GACTAAGCTG CTGGCACCTT TCTTCTCTAG CAGTGGGACA GCCTGCTATC

      I  A  N   A  S  P   Q  V  A   K  I  L   W  S  Q   T  A  Y   L  R
4261  CCATAGCAAA TGCCTCTCCT CAGGTGGCCA AGATACTCTG GAGCCAAACC GCGTACCTGC

      S  V  K   V  I  I   Q  A  G   T  Q  R   A  V  A   V  T  A   D  H
4321  GGAGTGTAAA AGTCATTATC CAAGCGGGCA CCCAGCGTGC TGTCGCAGTG ACCGCCGACC

      E  V  T   S  T  K   L  E  K   G  H  T   I  A  K   Y  N  P   F  K
4381  ACGAGGTTAC CTCTACTAAG CTGGAGAAGG GGCATACCAT TGCCAAATAC AATCCCTTCA
```

Figure 4e

```
         K  *
4441  AGAAATAGGC TGCATCTCTG AGATTGCACT CCGCCCATCT TCCCGGATCA CCATGACACT
                                                            (GE)        (GS)
4501  AAATAATGAT CTGTCTTGAT TACTTATAGT TAGTTCGCCT GTCTATCAAA TTAGAAAAAA

                                    F protein (SEQ ID NO:9)  M   G  S  R  S
4561  CACGGGTAGA AGATTCTGGA TCCCGGTTGG CGCCTTCAAG GTGCAAGATG GGCTCCAGAT

       S  T  R  I  P  V  P  L  M  L  T  V  R  V  M  L  A  L  S  C
4621  CTTCTACCAG GATCCCAGTA CCTCTTATGC TGACCGTCCG AGTCATGTTG GCACTGAGTT

       V  C  P  T  S  A  L  D  G  R  P  L  A  A  A  G  I  V  V  T
4681  GCGTCTGTCC GACCAGCGCC CTTGATGGCA GGCCTCTTGC AGCTGCAGGG ATTGTGGTAA

       G  D  K  A  V  N  I  Y  T  S  S  Q  T  G  S  I  I  I  K  L
4741  CAGGAGACAA AGCAGTCAAC ATATACACCT CATCTCAGAC AGGGTCAATC ATAATCAAGT

       L  P  N  M  P  K  D  K  E  A  C  A  K  A  P  L  E  A  Y  N
4801  TACTCCCAAA TATGCCCAAG GATAAAGAGG CGTGTGCAAA AGCCCCGTTG GAGGCATACA

       R  T  L  T  T  L  L  T  P  L  G  D  S  I  R  R  I  Q  E  S
4861  ACAGGACATT GACTACTTTG CTCACCCCCC TTGGTGATTC TATCCGTAGG ATACAAGAGT

       V  T  T  S  G  G  G  K  Q  G  R  L  I  G  A  I  I  G  G  V
4921  CTGTGACCAC GTCCGGAGGA GGGAAACAGG GACGTCTTAT AGGCGCCATT ATCGGTGGTG

       A  L  G  V  A  T  A  A  Q  I  T  A  A  S  A  L  I  Q  A  N
4981  TAGCTCTCGG GGTTGCAACC GCTGCACAGA TAACAGCAGC CTCGGCTCTG ATACAAGCCA

       Q  N  A  A  N  I  L  R  L  K  E  S  I  A  A  T  N  E  A  V
5041  ATCAAAATGC TGCCAACATA CTCCGGCTAA AAGAGAGCAT TGCTGCAACC AATGAGGCTG

       H  E  V  T  N  G  L  S  Q  L  A  V  A  V  G  K  M  Q  Q  F
5101  TGCACGAGGT CACTAATGGA TTATCACAAC TAGCAGTGGC AGTTGGGAAG ATGCAGCAAT

       V  N  D  Q  F  N  K  T  A  Q  E  L  D  C  I  K  I  T  Q  Q
5161  TTGTTAATGA CCAGTTTAAT AAAACAGCTC AGGAATTGGA CTGTATAAAA ATTACACAGC

       V  G  V  E  L  N  L  Y  L  T  E  L  T  T  V  F  G  P  Q  I
5221  AGGTTGGTGT AGAACTCAAC CTGTACCTAA CTGAATTGAC TACAGTATTC GGGCCACAAA

       T  S  P  A  L  T  Q  L  T  I  Q  A  L  Y  N  L  A  G  G  N
5281  TCACTTCCCC TGCCTTAACT CAGCTGACTA TCCAGGCGCT TTACAATCTA GCTGGTGGGA

       M  D  Y  L  L  T  K  L  G  V  G  N  N  Q  L  S  S  L  I  S
5341  ATATGGATTA CTTGTTGACT AAGTTAGGTG TGGGGAACAA CCAACTCAGC TCATTAATTA

       S  G  L  I  T  G  N  P  I  L  Y  D  S  Q  T  Q  L  L  G  I
5401  GTAGTGGCCT GATCACCGGC AACCCTATTC TGTACGACTC ACAGACTCAA CTCTTGGGTA

       Q  V  T  L  P  S  V  G  N  L  N  N  M  R  A  T  Y  L  E  T
5461  TACAGGTAAC CCTACCCTCA GTCGGGAACC TAAATAATAT GCGTGCCACC TACCTGGAAA
```

Figure 4f

```
      L  S  V   S  T  T   K  G  F  A   S  A  L   V  P  K   V  V  T  Q
5521  CCTTGTCTGT AAGTACAACC AAAGGATTTG CCTCAGCACT TGTCCCAAAA GTAGTGACAC

      V  G  S   V  I  E   E  L  D  T   S  Y  C   I  E  T   D  L  D  L
5581  AGGTCGGTTC CGTGATAGAA GAGCTTGACA CCTCGTACTG TATAGAGACC GATTTGGATC

      Y  C  T   R  I  V   T  F  P  M   S  P  G   I  Y  S   C  L  S  G
5641  TATATTGTAC AAGAATAGTG ACATTCCCTA TGTCTCCTGG TATTTATTCC TGTTTGAGTG

      N  T  S   A  C  M   Y  S  K  T   E  G  A   L  T  T   P  Y  M  T
5701  GCAATACATC TGCTTGCATG TACTCAAAGA CTGAAGGCGC ACTCACTACG CCGTATATGA

      L  K  G   S  V  I   A  N  C  K   M  T  T   C  R  C   A  D  P  P
5761  CCCTCAAAGG CTCAGTTATT GCTAACTGTA AGATGACAAC ATGTAGATGT GCAGACCCCC

      G  I  I   S  Q  N   Y  G  E  A   V  S  L   I  D  R   Q  S  C  N
5821  CGGGTATCAT ATCGCAAAAT TATGGAGAAG CTGTGTCTCT AATAGATAGG CAATCATGCA

      I  L  S   L  D  G   I  T  L  R   L  S  G   E  F  D   A  T  Y  Q
5881  ATATCTTATC CTTAGACGGG ATAACTTTGA GGCTCAGTGG GGAATTTGAT GCAACTTATC

      K  N  I   S  I  Q   D  S  Q  V   I  V  T   G  N  L   D  I  S  T
5941  AAAAGAATAT CTCAATACAA GATTCTCAAG TAATAGTGAC AGGCAATCTT GATATCTCGA

      E  L  G   N  V  N   N  S  I  S   N  A  L   D  K  L   E  E  S  N
6001  CTGAGCTTGG GAATGTCAAC AACTCGATAA GTAATGCTTT GGATAAGTTA GAGGAAAGCA

      S  K  L   D  K  V   N  V  K  L   T  S  T   S  A  L   I  T  Y  I
6061  ACAGCAAACT AGATAAGGTC AATGTCAAAC TGACCAGCAC ATCCGCTCTT ATTACCTATA

      V  L  T   V  I  S   L  V  C  G   I  L  S   L  V  L   A  C  Y  L
6121  TCGTTTTAAC TGTCATATCT CTTGTATGTG GTATACTTAG CCTGGTTCTA GCATGCTACC

      M  Y  K   Q  K  A   Q  Q  K  T   L  L  W   L  G  N   N  T  L  D
6181  TGATGTACAA GCAAAAGGCG CAACAGAAGA CCTTGTTGTG GCTTGGGAAT AATACCCTAG

      Q  M  R   A  T  T   K  M  *
6241  ACCAGATGAG GGCCACTACA AAAATGTGAA TGCGGATGAG AGGCAGAAAC ATCCCCAATA
                                                  (GE)
6301  GCAGTTTGTG TGTAAAGTCT GACAGCCTGT TAATTAGAAG AATTAAGAAA AAACTACCGG
                          (GS)
6361  ATGTAGATGA CCAAAGGGCG ATATACGGGT AGAACGGTCG GGGAGGCCGT CCCTCAATCG

                                      HN protein (SEQ ID NO:11) M  D
6421  GGAGCCGGGC CTCACAACAT CCGTTCTACC GCATCACCAA TAGCAGTTTT CAGTCATGGA

      R  A  V   S  Q  V   A  L  E  N   D  E  R   E  A  K   N  T  W  R
6481  CCGCGCAGTT AGCCAAGTTG CGCTAGAGAA TGATGAAAGA GAGGCAAAGA ATACATGGCG

      L  V  F   R  I  A   I  L  L  S   T  V  V   T  L  A   I  S  A  A
6541  CTTGGTATTC CGGATCGCAA TCCTACTCTC AACGGTGGTG ACCTTAGCCA TCTCTGCAGC
```

Figure 4g

```
      A  L  A   Y  S  M  E   A  S  T   P  S  D   L  V  G  I   P  T  A
6601  CGCCCTTGCA TATAGCATGG AGGCCAGCAC ACCTAGCGAT CTTGTAGGCA TACCGACTGC

      I  S  R   A  E  E  K   I  T  S   A  L  G   S  N  Q  D   V  V  D
6661  GATCTCTAGA GCAGAGGAAA AGATTACATC TGCACTCGGT TCCAATCAAG ATGTAGTAGA

      R  I  Y   K  Q  V  A   L  E  S   P  L  A   L  L  N  T   E  S  T
6721  TAGGATATAT AAGCAGGTGG CCCTCGAATC TCCACTGGCA TTGCTAAACA CCGAATCTAC

      I  M  N   A  I  T  S   L  S  Y   R  I  N   G  A  A  N   S  S  G
6781  AATTATGAAC GCAATAACGT CTCTCTCTTA TCGAATCAAT GGGGCCGCAA ATAGCAGCGG

      C  G  A   P  I  H  D   P  D  Y   I  G  G   I  G  K  E   L  I  V
6841  ATGTGGAGCA CCCATTCATG ATCCAGATTA TATTGGAGGA ATAGGTAAAG AACTTATTGT

      D  D  A   S  D  V  T   S  Y  Y   P  S  A   F  Q  E  H   L  N  F
6901  AGATGATGCT AGCGACGTCA CATCATACTA TCCCTCTGCG TTCCAAGAAC ACCTGAACTT

      I  P  A   P  T  T  G   S  G  C   T  R  I   P  S  F  D   M  S  A
6961  TATCCCGGCG CCTACTACAG GATCAGGTTG CACTCGGATA CCCTCATTTG ACATGAGCGC

      T  H  Y   C  Y  T  H   N  V  I   L  S  G   C  R  D  H   S  H  S
7021  TACCCACTAC TGTTATACTC ACAATGTGAT ATTATCTGGC TGCAGAGATC ACTCGCACTC

      H  Q  Y   L  A  L  G   V  L  R   T  S  A   T  G  R  V   F  F  S
7081  ACATCAATAT TTAGCACTTG GTGTGCTTCG GACATCTGCA ACAGGGAGGG TATTCTTTTC

      T  L  R   S  I  N  L   D  D  T   Q  N  R   K  S  C  S   V  S  A
7141  CACTCTGCGT TCCATCAATC TGGATGACAC CCAAAATCGG AAGTCTTGCA GTGTGAGTGC

      T  P  L   G  C  D  M   L  C  S   K  V  T   E  T  E  E   E  D  Y
7201  AACCCCCTTG GGTTGTGATA TGCTGTGCTC TAAAGTCACA GAGACTGAAG AAGAGGATTA

      N  S  A   I  P  T  S   M  V  H   G  R  L   G  F  D  G   Q  Y  H
7261  TAACTCAGCT ATCCCCACGT CGATGGTACA TGGAAGGTTA GGGTTCGACG GCCAATACCA

      E  K  D   L  D  V  T   T  L  F   E  D  W   V  A  N  Y   P  G  V
7321  CGAGAAGGAC CTAGATGTCA CAACACTATT CGAGGACTGG GTGGCAAACT ACCCAGGAGT

      G  G  G   S  F  I  D   N  R  V   W  F  P   V  Y  G  G   L  K  P
7381  AGGGGGCGGG TCTTTTATTG ACAACCGCGT ATGGTTCCCA GTTTACGGAG GGCTAAAACC

      N  S  P   S  D  T  A   Q  E  G   K  Y  V   I  Y  K  R   Y  N  D
7441  CAATTCGCCC AGTGACACCG CACAAGAAGG GAAATATGTA ATATACAAGC GATACAATGA

      T  C  P   D  E  Q  D   Y  Q  I   Q  M  A   K  S  S  Y   K  P  G
7501  CACATGTCCA GATGAGCAAG ATTATCAGAT TCAAATGGCT AAGTCTTCAT ATAAGCCTGG

      R  F  G   G  K  R  V   Q  Q  A   I  L  S   I  K  V  S   T  S  L
7561  GCGGTTTGGA GGGAAACGCG TACAGCAGGC CATCTTATCT ATCAAAGTGT CAACATCCTT

      G  E  D   P  V  L  T   V  P  P   N  T  V   T  L  M  G   A  E  G
7621  GGGCGAGGAC CCGGTACTGA CTGTACCGCC CAACACAGTA ACACTCATGG GGGCCGAAGG
```

Figure 4h

```
      R  V  L   T  V  G  T   S  H  F   L  Y  Q   R  G  S  S   Y  F  S
7681  CAGAGTTCTC ACAGTAGGGA CATCTCATTT CCTTTATCAG CGAGGGTCAT CATACTTCTC

      P  A  L   L  Y  P  M   I  V  S   N  K  T   A  T  L  H   S  P  Y
7741  CCCTGCCCTA CTATATCCTA TGATAGTCAG CAACAAAACA GCCACTCTTC ATAGTCCTTA

      T  F  N   A  F  T  R   P  G  S   V  P  C   Q  A  S  A   R  C  P
7801  TACATTCAAT GCCTTCACTC GACCAGGTAG TGTCCCTTGC CAGGCTTCAG CAAGATGCCC

      N  S  C   V  T  G  V   Y  T  D   P  Y  P   L  V  F  Y   R  N  H
7861  TAACTCATGT GTTACCGGAG TCTATACTGA TCCATATCCC TTGGTCTTCT ATAGGAACCA

      T  L  R   G  V  F  G   T  M  L   D  D  K   Q  A  R  L   N  P  V
7921  CACCTTGCGA GGGGTATTCG GGACGATGCT TGATGATAAA CAAGCAAGAC TCAACCCTGT

      S  A  V   F  D  S  I   S  R  S   R  I  T   R  V  S  S   S  S  T
7981  ATCTGCAGTA TTTGACAGCA TATCCCGCAG TCGCATAACC CGGGTGAGTT CAAGCAGCAC

      K  A  A   Y  T  T  S   T  C  F   K  V  V   K  T  N  K   T  Y  C
8041  CAAGGCAGCA TACACAACAT CAACATGTTT TAAAGTTGTA AAGACCAATA AAACCTATTG

      L  S  I   A  E  I  S   N  T  L   F  G  E   F  R  I  V   P  L  L
8101  TCTCAGCATT GCCGAAATAT CCAATACCCT CTTCGGGGAA TTCAGAATCG TCCCTTTACT

      V  E  I   L  K  D  D   G  V  R   E  A  R   S  S  R  L   S  Q  L
8161  AGTTGAGATT CTCAAGGATG ATGGGGTTAG AGAAGCCAGG TCTAGCCGGT TGAGTCAACT

      R  E  G   W  K  D  D   I  V  S   P  I  F   C  D  A  K   N  Q  T
8221  GCGAGAGGGT TGGAAAGATG ACATTGTATC ACCTATCTTT TGCGACGCCA AGAATCAAAC

      E  Y  R   R  E  L  E   S  Y  A   A  S  W   P  *
8281  TGAATACCGG CGCGAGCTCG AGTCCTACGC TGCCAGTTGG CCATAATCAG CTAGTGCTAA
                                       (GE)
8341  TGTGATTAGA TTAAGTCTTG TCGGTAGTCA CTTGATTAAG AAAAAATGTG GGTGGTAGCG

                                                  L protein (SEQ ID NO:13)
                                       (GS)             M  A   S  S  G  P
8401  GGATATAAGG CAAAACAACT CAAGGAGGAT AGCACGGGTA GGACATGGCG AGCTCCGGTC

      E  R  A   E  H  Q   I  I  L  P   E  S  H   L  S  S   P  L  V  K
8461  CCGAGAGGGC GGAGCATCAG ATTATCCTAC CAGAGTCACA CCTGTCTTCA CCATTAGTCA

      H  K  L   L  Y  Y   W  K  L  T   G  L  P   L  P  D   E  C  D  F
8521  AGCACAAACT ACTCTATTAC TGGAAATTAA CTGGGCTACC ACTCCCTGAC GAGTGTGACT

      D  H  L   I  L  S   R  Q  W  K   K  I  L   E  S  A   S  P  D  T
8581  TCGACCACCT CATTCTCAGC CGACAATGGA AGAAAATACT TGAATCGGCC TCCCCTGACA

      E  R  M   I  K  L   G  R  A  V   H  Q  T   L  N  H   N  S  K  I
8641  CTGAGAGAAT GATAAAACTT GGAAGGGCAG TGCACCAGAC TCTCAACCAC AATTCCAAGA

      T  G  V   L  H  P   R  C  L  E   E  L  A   S  I  E   V  P  D  S
8701  TAACCGGAGT ACTCCATCCC AGGTGTTTAG AAGAATTGGC TAGTATTGAG GTTCCTGACT
```

Figure 4i

```
      T  N  K   F  R  K   I  E  K  K   I  Q  I   H  N  T   R  Y  G  E
8761  CAACCAACAA GTTTCGGAAG ATCGAGAAGA AAATCCAAAT TCACAACACA AGGTATGGAG

      L  F  T   R  L  C   T  H  V  E   K  K  L   L  G  S   S  W  S  N
8821  AACTGTTCAC AAGACTGTGC ACGCATGTAG AGAAGAAATT GTTGGGATCA TCTTGGTCTA

      N  V  P   R  S  E   E  F  N  S   I  R  T   D  P  A   F  W  F  H
8881  ATAATGTCCC CCGGTCAGAA GAGTTCAACA GCATCCGTAC AGATCCGGCA TTCTGGTTTC

      S  K  W   S  T  T   K  F  A  W   L  H  I   K  Q  I   Q  R  H  L
8941  ACTCAAAATG GTCCACAACT AAGTTTGCAT GGCTCCATAT AAAACAGATT CAAAGGCATC

      I  V  A   A  R  T   R  S  A  A   N  K  L   V  T  L   T  H  K  V
9001  TGATTGTGGC AGCAAGAACA AGGTCCGCAG CCAACAAATT GGTGACGCTG ACCCATAAGG

      G  Q  V   F  V  T   P  E  L  V   I  V  T   H  T  D   E  N  K  F
9061  TAGGCCAAGT CTTTGTTACT CCTGAGCTTG TCATTGTGAC ACATACAGAT GAGAACAAGT

      T  C  L   T  Q  E   L  V  L  M   Y  A  D   M  M  E   G  R  D  M
9121  TCACGTGTCT TACCCAGGAA CTTGTGTTGA TGTATGCAGA TATGATGGAG GGCAGAGATA

      V  N  I   I  S  S   T  A  A  H   L  R  S   L  S  E   K  I  D  D
9181  TGGTCAACAT AATATCATCC ACGGCGGCAC ATCTCAGGAG CCTATCAGAG AAAATTGATG

      I  L  R   L  V  D   A  L  A  K   D  L  G   N  Q  V   Y  D  V  V
9241  ACATTCTGCG GTTAGTAGAT GCCCTGGCAA AAGATCTGGG TAATCAAGTC TACGATGTTG

      A  L  M   E  G  F   A  Y  G  A   V  Q  L   L  E  P   S  G  T  F
9301  TAGCACTCAT GGAGGGATTT GCATACGGCG CCGTCCAGCT GCTTGAGCCG TCAGGTACAT

      A  G  D   F  F  A   F  N  L  Q   E  L  K   D  T  L   I  G  L  L
9361  TCGCAGGGGA TTTCTTCGCA TTCAACCTGC AGGAGCTCAA AGACACTTTG ATCGGCCTCC

      P  K  D   I  A  E   S  V  T  H   A  I  A   T  V  F   S  G  L  E
9421  TTCCTAAGGA TATAGCAGAA TCTGTGACTC ACGCAATAGC CACTGTATTC TCTGGCTTAG

      Q  N  Q   A  A  E   M  L  C  L   L  R  L   W  G  H   P  L  L  E
9481  AACAAAATCA AGCGGCTGAG ATGCTGTGCC TGTTGCGTCT ATGGGGCCAC CCATTACTTG

      S  R  I   A  A  K   A  V  R  S   Q  M  C   A  P  K   M  V  D  F
9541  AGTCCCGTAT TGCGGCAAAA GCAGTAAGGA GCCAAATGTG CGCACCAAAA ATGGTAGACT

      D  M  I   L  Q  V   L  S  F  F   K  G  T   I  I  N   G  Y  R  K
9601  TTGATATGAT CCTCCAGGTA TTGTCTTTCT TTAAAGGAAC AATCATCAAC GGATACAGAA

      K  N  A   G  V  W   P  R  V  K   V  D  T   I  Y  G   K  V  I  G
9661  AGAAGAATGC AGGTGTTTGG CCACGTGTCA AAGTAGATAC GATATACGGG AAGGTCATTG

      Q  L  H   A  D  S   A  E  I  S   H  D  I   M  L  R   E  Y  K  S
9721  GGCAGCTACA CGCTGATTCA GCGGAGATTT CACACGATAT CATGTTGAGA GAGTACAAGA

      L  S  A   L  E  F   E  P  C  I   E  Y  D   P  I  T   N  L  S  M
9781  GTTTATCTGC GCTTGAATTC GAGCCATGTA TAGAATACGA CCCTATCACC AATCTGAGCA
```

Figure 4j

```
      F  L  K   D  K  A   I  A  H  P   K  D  N   W  L  A   A  F  R  R
9841  TGTTTCTAAA AGACAAGGCG ATCGCACACC CGAAAGACAA CTGGCTCGCC GCGTTTAGGC

      N  L  L   S  E  D   Q  K  K  H   V  K  E   A  T  S   T  N  R  L
9901  GAAACCTTCT CTCTGAGGAC CAGAAGAAAC ATGTAAAGGA GGCAACCTCT ACTAACCGTC

      L  I  E   F  L  E   S  N  D  F   D  P  Y   K  E  M   E  Y  L  T
9961  TCTTGATAGA GTTCTTAGAG TCAAATGATT TTGATCCATA TAAGGAGATG GAATATCTGA

      T  L  E   Y  L  R   D  D  N  V   A  V  S   Y  S  L   K  E  K  E
10021 CGACCCTTGA GTACCTAAGA GATGACAATG TGGCAGTATC ATACTCGCTC AAGGAGAAGG

      V  K  V   N  G  R   I  F  A  K   L  T  K   K  L  R   N  C  Q  V
10081 AAGTGAAGGT TAATGGGCGG ATTTTTGCTA AGCTAACAAA GAAATTAAGG AACTGTCAAG

      M  A  E   G  I  L   A  D  Q  I   A  P  F   F  Q  G   N  G  V  I
10141 TGATGGCGGA AGGGATCTTA GCTGACCAGA TTGCACCTTT CTTTCAAGGG AATGGGGTCA

      Q  D  S   I  S  L   T  K  S  M   L  A  M   S  Q  L   S  F  N  S
10201 TTCAGGATAG CATATCTTTA ACCAAGAGTA TGCTAGCGAT GAGTCAATTG TCTTTCAACA

      N  K  K   R  I  T   D  C  K  E   R  V  A   S  N  R   N  H  D  Q
10261 GCAATAAGAA ACGTATCACT GACTGCAAAG AAAGAGTAGC CTCAAACCGC AATCACGATC

      K  S  K   N  R  R   R  V  A  T   F  I  T   T  D  L   Q  K  Y  C
10321 AAAAGAGCAA GAATCGTCGG AGAGTTGCCA CTTTTATAAC GACTGACCTG CAAAAGTACT

      L  N  W   R  Y  Q   T  I  K  L   F  A  H   A  I  N   Q  L  M  G
10381 GTCTTAATTG GAGATATCAG ACAATCAAAC TGTTCGCTCA TGCCATCAAT CAGCTGATGG

      L  P  H   F  F  E   W  I  H  L   R  L  M   D  T  T   M  F  V  G
10441 GCTTACCTCA CTTCTTCGAA TGGATTCATC TAAGACTAAT GGATACTACG ATGTTTGTAG

      D  P  F   N  P  P   S  D  P  T   D  C  D   L  S  R   V  P  N  D
10501 GAGACCCTTT CAATCCCCCA AGTGACCCAA CTGACTGTGA TCTCTCAAGA GTCCCAAATG

      D  I  Y   I  V  S   A  R  G  G   I  E  G   L  C  Q   K  L  W  T
10561 ATGACATATA TATTGTCAGT GCTAGAGGGG GTATTGAGGG ATTATGTCAG AAGCTATGGA

       M  I  S   I  A  A   I  Q  L  A   A  A  R   S  H  C   R  V  A  C
10621 CAATGATCTC AATTGCTGCA ATCCAACTTG CTGCAGCAAG ATCACATTGT CGCGTCGCCT

       M  V  Q   G  D  N   Q  V  I  A   V  T  R   E  V  R   S  D  D  S
10681 GTATGGTACA GGGTGACAAT CAAGTAATAG CTGTAACGAG AGAGGTAAGG TCAGATGACT

      P  E  M   V  L  T   Q  L  H  Q   A  S  D   N  F  F   K  E  L  I
10741 CCCCGGAAAT GGTGTTAACA CAATTGCATC AAGCCAGTGA TAATTTCTTC AAGGAATTGA

      H  V  N   H  L  I   G  H  N  L   K  D  R   E  T  I   R  S  D  T
10801 TTCATGTTAA TCATTTGATT GGCCATAATT TGAAGGATCG TGAAACAATC AGATCAGACA

      F  F  I   Y  S  K   R  I  F  K   D  G  A   I  L  S   Q  V  L  K
10861 CATTCTTCAT ATACAGCAAA CGAATATTCA AAGATGGAGC AATACTCAGT CAAGTCCTCA
```

Figure 4k

```
      N  S  S   K  L  V   L  I  S  G   D  L  S   E  N  T   V  M  S  C
10921 AAAATTCATC TAAATTAGTG CTAATATCAG GCGACCTTAG TGAAAACACC GTAATGTCCT

      A  N  I   A  S  T   I  A  R  L   C  E  N   G  L  P   K  D  F  C
10981 GTGCCAACAT TGCATCTACT ATAGCACGGC TGTGCGAGAA CGGGCTTCCA AAGGATTTCT

      Y  Y  L   N  Y  L   M  S  C  V   Q  T  Y   F  D  S   E  F  S  I
11041 GTTATTACTT AAACTACCTG ATGAGTTGCG TGCAGACATA CTTTGATTCT GAGTTTTCCA

      T  N  S   S  H  P   D  S  N  Q   S  W  I   E  D  I   S  F  V  H
11101 TCACTAACAG CTCGCACCCC GATTCTAACC AGTCGTGGAT TGAAGACATC TCTTTTGTGC

      S  Y  V   L  T  P   A  Q  L  G   G  L  S   N  L  Q   Y  S  R  L
11161 ACTCATATGT CCTGACCCCT GCCCAGCTAG GGGGACTGAG CAACCTCCAA TACTCAAGGC

      Y  T  R   N  I  G   D  P  G  T   T  A  F   A  E  I   K  R  L  E
11221 TCTACACGAG GAACATCGGT GACCCGGGAA CTACTGCTTT TGCAGAGATC AAGCGATTAG

      A  V  G   L  L  S   P  S  I  M   T  N  I   L  T  R   P  P  G  N
11281 AAGCAGTGGG GTTACTAAGT CCTAGTATTA TGACTAACAT CTTAACTAGG CCGCCTGGAA

      G  D  W   A  S  L   C  N  D  P   Y  S  F   N  F  E   T  V  A  S
11341 ATGGAGATTG GGCCAGTCTG TGTAACGACC CTTACTCTTT CAATTTTGAG ACTGTCGCGA

      P  N  I   V  L  K   K  H  T  Q   R  V  L   F  E  T   C  S  N  P
11401 GTCCAAATAT TGTCCTTAAG AAACATACAC AAAGAGTCCT ATTTGAAACT TGTTCAAATC

      L  L  S   G  V  H   T  E  D  N   E  A  E   E  K  A   L  A  E  F
11461 CCTTATTATC TGGCGTGCAT ACAGAGGATA ATGAGGCAGA AGAGAAGGCG TTGGCTGAAT

      L  L  N   Q  E  V   I  H  P  R   V  A  H   A  I  M   E  A  S  S
11521 TTTTACTCAA TCAAGAAGTA ATTCATCCAC GTGTCGCACA TGCTATCATG GAAGCAAGCT

      I  G  R   R  K  Q   I  Q  G  L   V  D  T   T  N  T   V  I  K  I
11581 CTATAGGTAG GAGGAAGCAG ATTCAAGGGC TTGTTGACAC AACAAACACC GTAATCAAGA

      A  L  T   R  R  P   L  G  I  K   R  L  M   R  I  V   N  Y  S  S
11641 TTGCATTGAC TAGGAGGCCA CTTGGCATCA AGAGGCTGAT GCGGATAGTT AACTACTCGA

       M  H  A   M  L  F   R  D  D  V   F  S  S   N  R  S   N  H  P  L
11701 GCATGCATGC AATGCTGTTT AGAGACGATG TTTTCTCATC TAACAGGTCT AACCACCCCT

      V  S  S   N  M  C   S  L  T  L   A  D  Y   A  R  N   R  S  W  S
11761 TAGTTTCCTC TAATATGTGT TCTCTGACGC TAGCAGACTA TGCACGGAAT AGAAGCTGGT

      P  L  T   G  G  R   K  I  L  G   V  S  N   P  D  T   I  E  L  V
11821 CACCATTGAC GGGGGGTAGA AAGATACTGG GTGTATCTAA TCCTGATACT ATAGAACTTG

      E  G  E   I  L  S   V  S  G  G   C  T  R   C  D  S   G  D  E  Q
11881 TAGAGGGTGA GATCCTTAGC GTCAGCGGAG GATGCACAAG ATGTGACAGC GGAGATGAAC

      F  T  W   F  H  L   P  S  N  I   E  L  T   D  D  T   S  K  N  P
11941 AATTCACTTG GTTCCATCTT CCGAGCAATA TAGAACTGAC CGATGACACC AGCAAGAATC
```

Figure 41

```
      P  M  R   V  P  Y   L  G  S  K   T  Q  E   R  R  A   A  S  L  A
12001 CTCCGATGAG AGTGCCGTAC CTCGGGTCAA AGACTCAAGA GAGGAGGGCC GCCTCGCTTG

      K  I  A   H  M  S   P  H  V  K   A  A  L   R  A  S   S  V  L  I
12061 CGAAAATAGC TCATATGTCA CCACATGTGA AAGCTGCTCT AAGGGCATCA TCCGTGTTGA

      W  A  Y   G  D  N   E  V  N  W   T  A  A   L  K  I   A  R  S  R
12121 TCTGGGCTTA TGGAGACAAC GAAGTAAATT GGACTGCTGC TCTTAAAATT GCAAGATCTC

      C  N  I   N  S  E   Y  L  R  L   L  S  P   L  P  T   A  G  N  L
12181 GGTGCAATAT AAACTCAGAG TATCTTCGAC TATTGTCCCC CTTACCCACA GCTGGGAATC

      Q  H  R   L  D  D   G  I  T  Q   M  T  F   T  P  A   S  L  Y  R
12241 TCCAACATAG ACTGGATGAC GGCATAACTC AGATGACATT CACCCCTGCA TCTCTCTACA

      V  S  P   Y  I  H   I  S  N  D   S  Q  R   L  F  T   E  E  G  V
12301 GGGTGTCACC TTATATTCAC ATATCCAATG ATTCTCAAAG GTTATTCACG GAAGAAGGAG

      K  E  G   N  V  V   Y  Q  Q  I   M  L  L   G  L  S   L  I  E  S
12361 TCAAAGAGGG AAATGTAGTT TATCAGCAAA TCATGCTCTT GGGTTTATCT CTAATCGAAT

      L  F  P   M  T  T   T  R  T  Y   D  E  I   T  L  H   L  H  S  K
12421 CACTCTTCCC GATGACGACA ACCAGGACAT ACGATGAGAT CACATTGCAC CTCCACAGTA

      F  S  C   C  I  R   E  A  P  V   A  V  P   F  E  L   L  G  M  A
12481 AATTTAGCTG CTGTATCAGG GAAGCACCGG TTGCAGTTCC TTTCGAGTTA CTCGGGATGG

      P  E  L   R  T  V   T  S  N  K   F  M  Y   D  P  S   P  V  S  E
12541 CACCAGAACT AAGGACAGTG ACCTCAAATA AGTTTATGTA TGATCCTAGT CCTGTATCGG

      G  D  F   A  R  L   D  L  A  I   F  K  S   Y  E  L   N  L  E  S
12601 AGGGTGACTT TGCGAGACTT GACTTAGCTA TCTTTAAGAG TTATGAGCTT AATCTAGAAT

      Y  P  T   I  E  L   M  N  I  L   S  I  S   S  G  K   L  I  G  Q
12661 CATATCCCAC AATAGAGCTA ATGAACATTC TTTCAATATC CAGCGGGAAG TTAATCGGCC

      S  V  V   S  Y  D   E  D  T  S   I  K  N   D  A  I   I  V  Y  D
12721 AGTCTGTGGT TTCTTATGAT GAAGATACCT CCATAAAGAA TGACGCCATA ATAGTGTATG

      N  T  R   N  W  I   S  E  A  Q   N  S  D   V  V  R   L  F  E  Y
12781 ACAACACCCG GAATTGGATC AGCGAAGCTC AGAATTCAGA TGTGGTCCGC CTATTCGAGT

      A  A  L   E  V  L   L  D  C  S   Y  Q  L   Y  Y  L   R  V  R  G
12841 ATGCAGCACT TGAAGTGCTT CTCGACTGTT CTTATCAGCT CTACTATCTG AGAGTAAGAG

      L  D  N   I  V  L   Y  M  S  D   L  Y  K   N  M  P   G  I  L  L
12901 GCCTAGACAA TATCGTGTTG TATATGAGTG ACTTATATAA GAATATGCCA GGAATTCTAC

      S  N  I   A  A  T   I  S  H  P   I  I  H   S  R  L   H  A  V  G
12961 TTTCCAACAT TGCAGCTACA ATATCTCATC CCATCATTCA TTCAAGATTG CATGCAGTAG

      L  V  N   H  D  G   S  H  Q  L   A  D  T   D  F  I   E  M  S  A
13021 GCCTGGTCAA TCACGACGGG TCACACCAAC TTGCAGACAC AGATTTCATC GAAATGTCTG
```

Figure 4m

```
       K  L  L   V  S  C   T  R  R  V   V  S  G   L  Y  A   G  N  K  Y
13081 CAAAACTATT AGTCTCTTGC ACTCGACGCG TGGTCTCAGG TTTATATGCA GGGAATAAGT

       D  L  L   F  P  S   V  L  D  D   N  L  S   E  K  M   L  Q  L  I
13141 ATGATCTGCT GTTCCCGTCT GTCTTAGATG ATAACCTGAG TGAGAAGATG CTTCAGCTGA

       S  R  L   C  C  L   Y  T  V  L   F  A  T   T  R  E   I  P  K  I
13201 TATCTCGGTT ATGCTGCCTG TATACGGTGC TCTTTGCTAC AACAAGAGAG ATCCCGAAAA

       R  G  L   S  A  E   E  K  C  S   V  L  T   E  Y  L   L  S  D  A
13261 TAAGAGGCTT ATCTGCAGAA GAGAAGTGTT CAGTACTTAC TGAGTACCTA CTGTCAGATG

       V  K  P   L  L  S   S  E  Q  V   S  S  I   M  S  P   N  I  V  T
13321 CTGTGAAACC ATTACTTAGT TCTGAGCAAG TGAGCTCTAT CATGTCTCCT AACATAGTTA

       F  P  A   N  L  Y   Y  M  S  R   K  S  L   N  L  I   R  E  R  E
13381 CGTTCCCAGC TAATCTATAT TACATGTCTC GGAAGAGCCT TAATTTGATT AGGGAAAGAG

       D  R  D   T  I  L   A  L  L  F   P  Q  E   P  L  L   E  F  P  L
13441 AGGACAGGGA CACTATCTTG GCATTGTTGT TCCCCCAAGA GCCACTACTT GAGTTCCCCT

       V  Q  D   I  G  A   R  V  K  D   P  F  T   R  Q  P   A  A  F  L
13501 TAGTACAAGA TATTGGCGCT CGAGTGAAAG ATCCATTCAC CCGACAACCT GCGGCGTTTT

       Q  E  L   D  L  S   A  P  A  R   Y  D  A   F  T  L   S  Q  V  H
13561 TACAAGAATT AGATTTGAGC GCTCCAGCAA GGTATGACGC ATTTACACTT AGTCAGGTTC

       S  E  H   T  S  P   N  P  E  D   D  Y  L   V  R  Y   L  F  R  G
13621 ATTCTGAACA CACATCACCA AATCCGGAGG ACGACTACTT AGTACGATAC CTGTTCAGAG

       I  G  T   A  S  S   S  W  Y  K   A  S  H   L  L  S   V  P  E  V
13681 GAATAGGGAC CGCGTCCTCC TCTTGGTATA AGGCATCTCA CCTTCTTTCT GTACCTGAGG

       R  C  A   R  H  G   N  S  L  Y   L  A  E   G  S  G   A  I  M  S
13741 TCAGATGTGC AAGGCACGGG AATTCCTTAT ACTTGGCAGA AGGAAGCGGA GCCATTATGA

       L  L  E   L  H  V   P  H  E  T   I  Y  Y   N  T  L   F  S  N  E
13801 GTCTTCTCGA ACTGCATGTG CCGCATGAGA CTATCTATTA CAATACGCTC TTCTCAAACG

        M  N  P   P  Q  R   H  F  G  P   T  P  T   Q  F  L   N  S  V  V
13861 AGATGAACCC CCCACAGCGG CATTTCGGAC CGACCCCAAC ACAGTTTCTG AATTCAGTTG

       Y  R  N   L  Q  A   E  V  P  C   K  D  G   F  V  Q   E  F  R  P
13921 TTTATAGGAA TCTACAGGCG GAGGTACCAT GTAAGGATGG ATTTGTCCAG GAGTTCCGTC

       L  W  R   E  N  T   E  E  S  D   L  T  S   D  K  A   V  G  Y  I
13981 CATTATGGAG AGAGAATACA GAAGAAAGCG ATCTGACCTC AGATAAAGCA GTGGGTTACA

       T  S  A   V  P  Y   R  S  V  S   L  L  H   C  D  I   E  I  P  P
14041 TCACATCTGC AGTGCCCTAC CGGTCTGTAT CATTGCTGCA CTGTGACATT GAGATTCCTC

       G  S  N   Q  S  L   L  D  Q  L   A  T  N   L  S  L   I  A  M  H
14101 CAGGATCCAA TCAAAGCTTA CTGGATCAAC TGGCTACCAA TCTGTCTCTG ATTGCCATGC
```

Figure 4n

S V R E G G V V I I K V L Y A M G Y Y F
14161 ATTCTGTAAG GGAGGGCGGG GTCGTGATCA TCAAAGTGTT GTATGCAATG GGATATTACT

H L L M N L F T P C S T K G Y I L S N G
14221 TCCATCTACT CATGAACTTG TTCACTCCGT GTTCTACGAA AGGATATATT CTCTCTAATG

Y A C R G D M E C Y L V F V M G Y R G G
14281 GCTATGCATG TAGAGGGGAT ATGGAGTGTT ACCTGGTATT TGTCATGGGC TATCGAGGTG

P T F V H E V V R M A K T L V Q R H G T
14341 GGCCTACATT TGTACATGAG GTAGTGAGGA TGGCAAAAAC TCTAGTGCAG CGGCACGGTA

L L S K S D E I T L T R L F T S Q R Q R
14401 CACTTTTGTC CAAATCAGAT GAGATCACAC TGACTAGGTT ATTTACCTCA CAGCGGCAGC

V T D I L S S P L P R L I K F L R K N I
14461 GTGTAACAGA CATCCTATCC AGTCCTTTAC CGAGACTAAT AAAGTTCTTG AGAAAGAATA

D T A L I E A G G Q P V R P F C A E S L
14521 TCGATACTGC GCTAATTGAA GCCGGGGGAC AACCCGTCCG TCCATTCTGT GCAGAGAGCT

V R T L A D T T Q M T Q I I A S H I D T
14581 TGGTGAGGAC ACTAGCGGAC ACAACTCAGA TGACCCAGAT CATCGCTAGT CACATTGACA

V I R S V I Y M E A E G D L A D T V F L
14641 CAGTCATTCG ATCTGTGATC TACATGGAGG CTGAGGGTGA TCTCGCCGAC ACAGTGTTCT

F T P Y N L S T D G K K R T S L K Q C T
14701 TATTTACCCC CTACAATCTC TCTACAGACG GTAAAAAGAG AACATCACTT AAACAGTGCA

R Q I L E V T I L G L R V E N L N K V G
14761 CAAGGCAGAT CTTAGAGGTC ACAATATTGG GTCTTAGAGT TGAAAATCTC AATAAAGTAG

D V V S L V L K G M I S L E D L I P L R
14821 GTGATGTAGT CAGTCTAGTA CTTAAAGGTA TGATTTCTCT GGAGGACCTG ATCCCTCTAA

T Y L K R S T C P K Y L K S V L G I T K
14881 GAACATACTT GAAGCGTAGT ACCTGCCCTA AGTATTTGAA GTCTGTTCTA GGTATTACTA

L K E M F T D T S L L Y L T R A Q Q K F
14941 AACTCAAAGA AATGTTTACA GACACCTCTT TATTATACTT GACTCGTGCT CAACAAAAAT

Y M K T I G N A V K G Y Y S N C D S *
15001 TCTACATGAA AACTATAGGC AACGCAGTCA AGGGATACTA CAGTAACTGT GACTCTTAAA (GE)
15061 GATAATCACA TATTAATAGG CTCCTTTTCT AGTTAACTGA GCCCTTGTTG ATTTAATGAT

15121 ACTATATTAG AAAAAAGTTG CACTCCGATC CTTTAGGACT CGTGTTCGAA TTCAAATAAT

15181 TGTCTTAGAA AAAAGTTGCG CGTAATTGTT CTTGAATGTA GTCTTGTCAT TCACCAAATC

HDV ribozyme
15241 TTTGTTTGGT GGGTCGGCAT *GGCATCTCCA CCTCCTCGCG GTCCGACCTG GGCATCCGAA*

Figure 4o

T7 terminator

15301 *GGAGGACGCA CGTCCACTCG GATGGCTAAG GGAG*CTAGCA TAACCCCTTG GGGCCTCTAA

15361 ACGGGTCTTG AGGGGTTTTT TGCTGAAAGG AGGAACTATA CGGCCGC

Genome sequence of Avinew NDV strain with cloning sites: SEQ ID NO:24
NP protein: SEQ ID NO:3
P protein: SEQ ID NO:5
M protein: SEQ ID NO:7
F protein: SEQ ID NO:9
HN protein: SEQ ID NO:11
L protein: SEQ ID NO:13

Egg Allantoic fluid

1. Marker
2. vAVW02
3. vAVW01
4. vAVW01
5. Negative control
6. Marker

Infected Cells lysate

1. Marker
2. Negative control
3. vAVW01
4. vAVW02
5. vAVW02

Figure 12A

| SEQ ID NO: | Type | Gene Description |
|---|---|---|
| 1 | DNA | Genome sequence of avinew NDV strain (15186bp) |
| 2 | DNA | NP gene of avinew NDV strain (122-1588bp of SEQ ID NO:1) (1467bp) |
| 3 | Protein | NP protein of avinew NDV strain (489aa) |
| 4 | DNA | P gene of avinew NDV strain (1887-3071bp of SEQ ID NO:1) (1185bp) |
| 5 | Protein | P protein of avinew NDV strain (395aa) |
| 6 | DNA | M gene of avinew NDV strain (3290-4381bp of SEQ ID NO:1) (1092bp) |
| 7 | Protein | M protein of avinew NDV strain (364aa) |
| 8 | DNA | F gene of avinew NDV strain (4544-6202bp of SEQ ID NO:1) (1659bp) |
| 9 | Protein | F protein of avinew NDV strain (553aa) |
| 10 | DNA | HN gene of avinew NDV strain (6412-8259bp of SEQ ID NO:1) (1848bp) |
| 11 | Protein | HN protein of avinew NDV strain (616aa) |
| 12 | DNA | L gene of avinew NDV strain (8381-14992bp of SEQ ID NO:1) (6612bp) |
| 13 | Protein | L protein of avinew NDV strain (2204aa) |
| 14 | DNA | Gene coding for HA of H5N1 A/Duck/Laos/3295/2006 (ABG67978) with modified cleavage site, codon-optimized |
| 15 | Protein | HA protein of H5N1 A/Duck/Laos/3295/2006 (ABG67978) with modified cleavage site |
| 16 | DNA | Gene coding for HA of H5N1 A/Turkey/Turkey/1/2005 (ABQ58921) with modified cleavage site, codon-optimized |
| 17 | Protein | HA protein of H5N1 A/Turkey/Turkey/1/2005 (ABQ58921) with modified cleavage site |
| 18 | DNA | Gene coding for HA of H5N1 A/chicken/Indonesia/7/2003 with modified cleavage site, codon-optimized |
| 19 | Protein | HA protein of H5N1 A/chicken/Indonesia/7/2003 with modified cleavage site |
| 20 | DNA | Gene coding for HA of H5N1 A/chicken/West Java/PWT-WIJ/2006 strain (EU124148) with modified cleavage site, codon-optimized |

Figure 12B

| SEQ ID NO: | Type | Gene Description |
|---|---|---|
| 21 | Protein | HA protein of H5N1 A/chicken/West Java/PWT-WIJ/2006 strain (EU124148) with modified cleavage site |
| 22 | DNA | Gene coding for HA of H9N2 A/chicken/Iran/AV1221/1998 strain, codon-optimized |
| 23 | Protein | HA protein of H9N2 A/chicken/Iran/AV1221/1998 strain, codon-optimized |
| 24 | DNA | Genome sequence of avinew NDV strain with modification (cloning sites) 15407bp |
| 25 | Peptide | highly pathogenic avian influenza sequence (multiple basic amino acids |
| 26 | Peptide | low pathogenic avian influenza sequence |

Blood sampling

Day 0 — Day 21 — Day 35 day-old chicks

Vaccination
($10^5$ $EID_{50}$ IO/IN)

Challenge (6 log10 H5N1 Hungary/06 IO)

AI H5N1 protection in SPF chicks after 1 vaccination

Post-Challenge Survival of Chickens Immunized with AVINEW and AVINEW Expressing H5

AIV Shedding from Immunized Chickens

A. ORAL SWABS

B. CLOACAL SWABS

C: ORAL SWABS

D: CLOACAL SWABS

H5N1 cl2.2. antigen

Kinetics of NDV HI titres (log2) after two vaccinations with AVINEW (G1), vAVW02 (G2) and vAVW03 (G3) at D0 and D21

Kinetics of AI H5N1 HI titres (log2) after two vaccinations with vAVW02 (G2) or vAVW03 (G3) at D0 and D21

Kinetics of AI H5N1 SN titres (log2) after two vaccinations
with vAVW02 (G2) or vAVW03 (G3) at D0 and D21

NDV HI titers (A) and AIV SN titers induced by 1 or 2 eye drop administrations of vAVW03

Duck Study 3: Kinetic of virus load (A and B) and of percentage of positive samples (C and D) in oropharyngeal (A and C) and cloacal (B and D) swabs after HPAI H5N1 challenge at Day 28

Duck Study 3: Kinetic of virus load (A and B) and of percentage of positive samples (C and D) in oropharyngeal (A and C) and cloacal (B and D) swabs after HPAI H5N1 challenge at Day 42

Figure 25A

```
                         1                                                50
SEQ ID NO:15      (1)  --MEKIVLLLAIVSLVKSDQICIGYHANNSTEQVDTIMEKNVTVTHAQDI
SEQ ID NO:17      (1)  --MEKIVLLLAIVSLVKSDQICIGYHANNSTEQVDTIMEKNVTVTHAQDI
SEQ ID NO:19      (1)  --MEKIVLLLAIVSLVKSDQICIGYHANNSTEQVDTIMEKNVTVTHAQDI
SEQ ID NO:21      (1)  --MEKIVLLLAIVSLVKSDQICIGYHANNSTEQVDTIMEKNVTVTHAQDI
SEQ ID NO:23      (1)  METISLITILLVVTASNADKICIGYQSTNSTETVDTLTETNVPVTHAKEL

                       51                                               100
SEQ ID NO:15     (49)  LEKTHNGKLCDLDGVKPLILRDCSVAGWLLGNPMCDEFINVPEWSYIVEK
SEQ ID NO:17     (49)  LEKTHNGKLCDLDGVKPLILRDCSVAGWLLGNPMCDEFLNVPEWSYIVEK
SEQ ID NO:19     (49)  LEKTHNGKLCDLDGVKPLILRDCSVAGWLLGNPMCDEFINVPEWSYIVEK
SEQ ID NO:21     (49)  LEKTHNGKLCDLDGVKPLILRDCSVAGWLLGNPMCDEFIKVQEWSYIVEK
SEQ ID NO:23     (51)  LHTEHNGMLCATNLGHPLILDTCTIEGLIYGNPSCDLLLGGREWSYIVER

                       101                                              150
SEQ ID NO:15     (99)  ANPANDLCYPGNFNDYEELKHLLSRINHFEKIQIIPKSSWSDHEASSGVS
SEQ ID NO:17     (99)  INPANDLCYPGNFNDYEELKHLLSRINHFEKIQIIPKSSWSDHEASAGVS
SEQ ID NO:19     (99)  ANPANDLCYPGNLNDYEELKHLLSRINHFEKIQIIPKSSWSDHEASSGVS
SEQ ID NO:21     (99)  ASPTNDLCYPGSFNDYEELKHLLSRIKHFEKIRIIPKSDWSDHEASLGVS
SEQ ID NO:23    (101)  SSAVNGTCYPGNVENLEELRTLFSSASSYQRIQIFPDTIWN--VTYTGTS

                       151                                              200
SEQ ID NO:15    (149)  SACPYQGTPSFFRNVVWLIKKNNTYPTIKRSYNNTNQEDLLILWGIHHSN
SEQ ID NO:17    (149)  SACPYQGRSSFFRNVVWLIKKDNAYPTIKRSYNNTNQEDLLVLWGIHHPN
SEQ ID NO:19    (149)  SACPYQGKSSFFRNVVWLIKKNSAYPTIKRSYNNTNQEDLLVLWGIHHPN
SEQ ID NO:21    (149)  SACPYLGSPSFFRNVVWLIKKNSTYPTIKKSYKNTNQEDLLVLWGIHHSN
SEQ ID NO:23    (149)  KACSG----SFYRSMRWLTQKSGSYPVQDAQYTNNRGKSILFVWGIHHPP

                        201                                              250
SEQ ID NO:15    (199)  DAAEQTKLYQNPTTYISVGTSTLNQRLVPKIATRSKVNGQSGRMDFFWTI
SEQ ID NO:17    (199)  DAAEQTRLYQNPTTYISVGTSTLNQRLVPKIATRSKVNGQSGRMEFFWTI
SEQ ID NO:19    (199)  DAAEQTRLYQNPTTYISVGTSTLNQRLVPKIAIRSKVNGQSGRMEFFWTI
SEQ ID NO:21    (199)  NVEEQTRLYQNPITYISIGTSTLNQRLVPKIATRSKVHGQSGRMDFFWTI
SEQ ID NO:23    (195)  TDTAQTNLYIRNDTTTSVTTEDLNRIFKPMIGPRPLVNGQQGRINYYWSV

                       251                                              300
SEQ ID NO:15    (249)  LKPNDAINFESNGNFIAPEYAYKIVKKGDSAIIKSEVEYGNCNTKCQTPI
SEQ ID NO:17    (249)  LKPNDAINFESNGNFIAPENAYKIVKKGDSTIMKSELEYGNCNTKCQTPI
SEQ ID NO:19    (249)  LKPNDAINFESNGNFIAPEYAYKIVKKGDSAIMKSELEYGNCNTKCQTPM
SEQ ID NO:21    (249)  LNPNDTINFESNGNFIAPEYAYKIVKKGDSAIMKSELEYGDCNTKCQTPM
SEQ ID NO:23    (245)  LKPGQTLRVRSNGNLIAPWYGHVLSGGSHGRILKTDLNSGNCVVQCQTEK

                       301                                              350
SEQ ID NO:15    (299)  GAINSSMPFHNIHPLTIGECPKYVKSNKLVLATGLRNSPLRE----TRGL
SEQ ID NO:17    (299)  GAINSSMPFHNIHPLTIGECPKYVKSSRLVLATGLRNSPQRE----TRGL
SEQ ID NO:19    (299)  GAINSSMPFHNIHPLTIGECPKYVKSNRLVLATGLRNSPQRERRRKKRGL
SEQ ID NO:21    (299)  GAINSSMPFHNIHPLTIGECPKYVKSNRLVLATGLRNSPQRE----TRGL
SEQ ID NO:23    (295)  GGLNSTLPFHNISKYAFGNCPKYVRVKSLKLAVGLRNVPARS----SRGL
```

Figure 25B

```
                         351                                              400
SEQ ID NO:15   (345)  FGAIAGFIEGGWQGMVDGWYGYHHSNEQGSGYAADKESTQKAIDGVTNKV
SEQ ID NO:17   (345)  FGAIAGFIEGGWQGMVDGWYGYHHSNEQGSGYAADKESTQKAIDGVTNKV
SEQ ID NO:19   (349)  FGAIAGFIEGGWQGMVDGWYGYHHSNEQGSGYAADKESTQKAIDGVTNKV
SEQ ID NO:21   (345)  FGAIAGFIEGGWQGMVDGWYGYHHSNEQGSGYAADKESTQKAIDGVTNKV
SEQ ID NO:23   (341)  FGAIAGFIEGGWPGLVAGWYGFQHSNDQGVGMAADRDSTQKAIDKITSKV

                         401                                              450
SEQ ID NO:15   (395)  NSIIDKMNTQFEAVGREFNNLERRIENLNKKMEDGFLDVWTYNAELLVLM
SEQ ID NO:17   (395)  NSIIDKMNTQFEAVGREFNNLERRIENLNKKMEDGFLDVWTYNAELLVLM
SEQ ID NO:19   (399)  NSIIDKMNTQFEAVGREFNNLERRIENLNKKMEDGFLDVWTYNAELLVLM
SEQ ID NO:21   (395)  NSIIDKMNTQFEAVGREFNNLERRIENLNKKMEDGFLDVWTYNAELLVLM
SEQ ID NO:23   (391)  NNIVDKMNKQYEIIDHEFSEVETRLNMINNKIDDQIQDVWAYNAELLVLL

                         451                                              500
SEQ ID NO:15   (445)  ENERTLDFHDSNVKNLYDKVRLQLRDNAKELGNGCFEFYHKCDNECMESV
SEQ ID NO:17   (445)  ENERTLDFHDSNVKNLYDKVRLQLRDNAKELGNGCFEFYHRCDNECMESV
SEQ ID NO:19   (449)  ENERTLDFHDSNVKNLYDKVRLQLRDNAKELGNGCFEFYHKCDNECMESI
SEQ ID NO:21   (445)  ENERTLDFHDSNVKNLYDKVRLQLRDNAKELGNGCFEFYHKCDNECMESI
SEQ ID NO:23   (441)  ENQKTLDEHDANVNNLYNKVKRALGSNAMEDGKGCFELYHKCDDQCMETI

                         501                                              550
SEQ ID NO:15   (495)  RNGTYDYPQYSEEARLKREEISGVKLESIGTYQILSIYSTVASSLALAIM
SEQ ID NO:17   (495)  RNGTYDYPQYSEEARLKREEISGVKLESIGTYQILSIYSTVASSLALAIM
SEQ ID NO:19   (499)  RNGTYNYPQYSEEARLKREEISGVKLESIGTYQILSIYSTVASSLALAIM
SEQ ID NO:21   (495)  RNGTYNYPQYSEEARLKREEISGVKLESIGTYQILSIYSTVASSLALAIM
SEQ ID NO:23   (491)  RNGTYNRRKYKEESRLERQKIEGVKLESEGTYKILTIYSTVASSLVLAMG

                         551                 571
SEQ ID NO:15   (545)  VAGLSLWMCSNGSLQCRICIK
SEQ ID NO:17   (545)  VAGLSLWMCSNGSLQCRICI-
SEQ ID NO:19   (549)  MAGLSLWMCSNGSLQCRICI-
SEQ ID NO:21   (545)  MAGLSLWMCSNGSLQCRICI-
SEQ ID NO:23   (541)  FAAFLFWAMSNGSCRCNICI-
```

Figure 25C

Sequence Identity Percentage

| SEQ ID NO | 15 | 17 | 19 | 21 | 23 |
|---|---|---|---|---|---|
| 15 | | 97 | 97 | 94 | 51 |
| 17 | | | 97 | 93 | 52 |
| 19 | | | | 95 | 52 |
| 21 | | | | | 52 |
| 23 | | | | | |

Figure 26A

```
                     1                                                50
SEQ ID NO:14    (1)  -----------------------------ATGGAAAAGATCGTGCTGCTG
SEQ ID NO:16    (1)  -----------------------------ATGGAAAAGATCGTGCTGCTG
SEQ ID NO:18    (1)  -----------------------------ATGGAGAAAATCGTGCTGCTG
SEQ ID NO:20    (1)  -----------------------------ATGGAAAAGATCGTGCTGCTG
SEQ ID NO:22    (1)  ATCGCGATATCCGTTAAGTTTGTATCGTAATGGAGACCATCAGCCTGATC

                     51                                              100
SEQ ID NO:14   (22)  ------CTGGCCATCGTGAGCCTGGTGAAGAGCGACCAGATCTGCATCGG
SEQ ID NO:16   (22)  ------CTGGCCATCGTGAGCCTGGTGAAGAGCGACCAGATCTGCATCGG
SEQ ID NO:18   (22)  ------CTGGCCATCGTGAGCCTGGTGAAAAGCGATCAGATCTGCATCGG
SEQ ID NO:20   (22)  ------CTGGCCATCGTGTCCCTGGTGAAGAGCGACCAGATCTGCATCGG
SEQ ID NO:22   (51)  ACCATCCTGCTGGTCGTGACCGCCAGCAACGCCGACAAGATCTGCATCGG

                     101                                             150
SEQ ID NO:14   (66)  CTACCACGCCAACAACAGCACCGAGCAGGTGGACACCATCATGGAAAAGA
SEQ ID NO:16   (66)  CTACCACGCCAACAACAGCACCGAGCAGGTGGACACCATCATGGAAAAGA
SEQ ID NO:18   (66)  CTACCACGCCAACAACAGCACAGAGCAAGTGGACACAATCATGGAAAAGA
SEQ ID NO:20   (66)  CTACCACGCCAACAACAGCACCGAGCAGGTGGACACCATTATGGAAAAGA
SEQ ID NO:22  (101)  CTACCAGAGCACCAACAGCACCGAGACCGTGGACACCCTGACCGAGACCA

                     151                                             200
SEQ ID NO:14  (116)  ATGTGACCGTGACCCACGCCCAGGACATCCTGGAAAAGACCCACAACGGC
SEQ ID NO:16  (116)  ATGTGACCGTGACCCACGCCCAGGACATCCTGGAAAAGACCCACAACGGC
SEQ ID NO:18  (116)  ACGTGACCGTGACACACGCCCAGGACATCCTGGAAAAGACACACAACGGG
SEQ ID NO:20  (116)  ACGTGACCGTGACCCATGCTCAGGACATCCTGGAAAAGACCCACAACGGC
SEQ ID NO:22  (151)  ACGTGCCCGTGACCCACGCCAAGGAACTGCTGCACACCGAGCACAACGGC

                     201                                             250
SEQ ID NO:14  (166)  AAGCTGTGCGACCTGGACGGCGTGAAGCCCCTGATCCTGAGGGACTGCAG
SEQ ID NO:16  (166)  AAGCTGTGCGACCTGGACGGCGTGAAGCCCCTGATCCTGAGGGACTGCAG
SEQ ID NO:18  (166)  AAGCTGTGCGATCTGGATGGAGTGAAGCCTCTGATCCTGAGAGATTGCAG
SEQ ID NO:20  (166)  AAGCTGTGCGACCTGGACGGCGTGAAGCCCCTGATCCTGAGAGACTGCAG
SEQ ID NO:22  (201)  ATGCTGTGCGCCACCAACCTGGGCCACCCTCTGATCCTGGACACCTGCAC

                     251                                             300
SEQ ID NO:14  (216)  CGTGGCCGGCTGGCTGCTGGGCAACCCCATGTGCGACGAGTTCATCAACG
SEQ ID NO:16  (216)  CGTGGCCGGCTGGCTGCTGGGCAACCCCATGTGCGACGAGTTTCTGAACG
SEQ ID NO:18  (216)  CGTGGCCGGATGGCTGCTGGGGAACCCAATGTGCGACGAATTCATCAACG
SEQ ID NO:20  (216)  CGTGGCCGGCTGGCTGCTGGGCAACCCCATGTGCGACGAGTTCATCAAGG
SEQ ID NO:22  (251)  CATCGAGGGCCTGATCTACGGCAACCCCAGCTGCGACCTGCTGCTGGGCG

                     301                                             350
SEQ ID NO:14  (266)  TGCCCGAGTGGAGCTACATCGTGGAGAAGGCCAACCCCGCCAACGACCTG
SEQ ID NO:16  (266)  TGCCCGAGTGGAGCTACATCGTGGAGAAGATCAACCCCGCCAACGACCTG
SEQ ID NO:18  (266)  TGCCCGAATGGAGCTACATCGTGGAGAAGGCCAACCCAGCCAACGACCTG
SEQ ID NO:20  (266)  TGCAGGAATGGTCCTACATCGTCGAGAAGGCCAGCCCCACCAACGACCTG
SEQ ID NO:22  (301)  GCAGGGAGTGGAGCTACATCGTGGAGCGGAGCAGCGCCGTGAACGGCACC
```

Figure 26B

```
                    351                                                400
SEQ ID NO:14  (316) TGCTACCCCGGCAACTTCAACGACTACGAGGAACTGAAGCACCTGCTGTC
SEQ ID NO:16  (316) TGCTACCCCGGCAACTTCAACGACTACGAGGAACTGAAGCACCTGCTGTC
SEQ ID NO:18  (316) TGCTACCCAGGGAACCTGAACGACTACGAAGAACTGAAACACCTGCTGAG
SEQ ID NO:20  (316) TGCTACCCCGGCAGCTTCAACGACTACGAGGAACTGAAGCACCTGCTGTC
SEQ ID NO:22  (351) TGCTACCCCGGCAACGTGGAGAACCTGGAGGAGCTGCGGACCCTGTTCAG

                    401                                                450
SEQ ID NO:14  (366) CAGGATCAACCACTTCGAGAAGATCCAGATCATCCCCAAGAGCAGCTGGT
SEQ ID NO:16  (366) CAGGATCAACCACTTCGAGAAGATCCAGATCATCCCCAAGAGCAGCTGGT
SEQ ID NO:18  (366) CAGAATCAACCACTTTGAGAAAATCCAGATCATCCCCAAAAGCAGCTGGT
SEQ ID NO:20  (366) CAGAATCAAGCACTTCGAGAAGATCCGCATCATCCCCAAGAGCGATTGGA
SEQ ID NO:22  (401) CAGCGCCTCCTCTTACCAGCGGATCCAGATCTTCCCCGACACCATCTGGA

                    451                                                500
SEQ ID NO:14  (416) CCGACCATGAGGCCTCTAGCGGCGTGAGCAGCGCCTGCCCATACCAGGGC
SEQ ID NO:16  (416) CCGACCACGAGGCCTCTGCTGGCGTGAGCAGCGCCTGCCCATACCAGGGC
SEQ ID NO:18  (416) CCGATCACGAAGCCAGCAGCGGAGTGAGCAGCGCCTGCCCATACCAGGGA
SEQ ID NO:20  (416) GCGACCACGAGGCCAGCCTGGGCGTGAGCAGCGCCTGCCCCTACCTGGGC
SEQ ID NO:22  (451) ------ACGTGACCTACACCGGCACCAGCAAGGCCTGC------------

                    501                                                550
SEQ ID NO:14  (466) ACCCCCAGCTTTTTCCGCAACGTGGTGTGGCTGATCAAGAAGAACAACAC
SEQ ID NO:16  (466) CGCAGCAGCTTCTTCCGCAACGTGGTGTGGCTGATCAAGAAGGACAACGC
SEQ ID NO:18  (466) AAGTCCAGCTTTTTTAGAAACGTGGTGTGGCTGATCAAAAAGAACAGCGC
SEQ ID NO:20  (466) AGCCCCAGCTTCTTCAGAAACGTGGTGTGGCTGATCAAGAAGAACAGCAC
SEQ ID NO:22  (483) AGCGGCAGCTTCTACCGGAGCATGCGGTGGCTGACCCAGAAGAGCGGCAG

                    551                                                600
SEQ ID NO:14  (516) CTACCCCACCATCAAGCGCAGCTACAACAACACCAACCAGG--AAGATC-
SEQ ID NO:16  (516) CTACCCCACCATCAAGCGCAGCTACAACAACACCAACCAGG--AAGATC-
SEQ ID NO:18  (516) CTACCCAACAATCAAGAGAAGCTACAACAACACCAACCAGG--AAGATC-
SEQ ID NO:20  (516) CTACCCCACCATCAAGAAGAGCTACAAGAACACCAACCAGG--AAGATC-
SEQ ID NO:22  (533) CTACCCCG---TGCAGGACGCCCAGTACACCAACAACCGGGGCAAGAGCA

                    601                                                650
SEQ ID NO:14  (563) TGCTGATCCTGTGGGGCATCCACCACAGCAACGACGCCGCCGAGCAGACC
SEQ ID NO:16  (563) TGCTGGTCCTGTGGGGCATCCACCACCCCAACGACGCCGCCGAGCAGACC
SEQ ID NO:18  (563) TGCTGGTGCTGTGGGGGATCCACCACCCTAACGATGCCGCCGAGCAGACA
SEQ ID NO:20  (563) TGCTGGTCCTGTGGGGCATCCACCACAGCAACAACGTGGAGGAACAGACC
SEQ ID NO:22  (580) TCCTGTTCGTGTGGGGCATCCACCACCCCCCCACCGACACCGCCCAGACC

                    651                                                700
SEQ ID NO:14  (613) AAGCTGTAC---CAGAACCCCACCACCTACATCAGCGTTGGCACAAGCAC
SEQ ID NO:16  (613) AGGCTGTAC---CAGAACCCCACCACCTACATCAGCGTCGGCACCTCTAC
SEQ ID NO:18  (613) AGGCTGTAC---CAGAACCCAACCACCTACATCTCCGTGGGGACAAGCAC
SEQ ID NO:20  (613) AGACTGTAC---CAGAACCCCATCACCTACATCAGCATCGGCACCAGCAC
SEQ ID NO:22  (630) AACCTGTACATCCGGAACGACACCACC---ACCTCCGTGACCACCGAGGA

                    701                                                750
SEQ ID NO:14  (660) CCTCAACCAGAGGCTGGTGCCCAAGATCGCCACCCGCAGCAAGGTGAACG
SEQ ID NO:16  (660) CCTGAATCAGAGGCTGGTGCCCAAGATCGCCACCCGCAGCAAGGTGAACG
SEQ ID NO:18  (660) ACTGAACCAGAGACTGGTGCCAAAAATCGCCATCAGATCCAAAGTGAACG
SEQ ID NO:20  (660) CCTGAACCAGAGACTGGTGCCCAAGATCGCCACCCGCAGCAAGGTGCACG
SEQ ID NO:22  (677) CCTGAACCGGATCTTCAAGCCCATGATCGGCCCCAGGCCCCTCGTGAACG
```

Figure 26C

```
                          751                                              800
SEQ ID NO:14     (710)   GCCAGAGCGGCAGGATGGACTTCTTCTGGACCATCCTGAAGCCCAACGAC
SEQ ID NO:16     (710)   GCCAGAGCGGCAGGATGGAATTCTTCTGGACCATCCTGAAGCCCAACGAT
SEQ ID NO:18     (710)   GGCAGAGCGGAAGAATGGAGTTCTTCTGGACAATCCTGAAACCCAACGAT
SEQ ID NO:20     (710)   GCCAGAGCGGCAGAATGGACTTCTTCTGGACCATCCTGAACCCCAACGAC
SEQ ID NO:22     (727)   GCCAGCAGGGCCGGATCAACTACTACTGGAGCGTGCTGAAGCCCGGCCAG

                          801                                              850
SEQ ID NO:14     (760)   GCCATCAACTTCGAGAGCAACGGCAACTTTATCGCCCCCGAGTACGCCTA
SEQ ID NO:16     (760)   GCCATCAACTTCGAGAGCAACGGCAACTTTATCGCCCCCGAGAACGCCTA
SEQ ID NO:18     (760)   GCCATCAACTTCGAGAGCAACGGAAACTTCATCGCCCCAGAATACGCCTA
SEQ ID NO:20     (760)   ACCATCAACTTCGAGAGCAACGGCAACTTTATCGCCCCCGAGTACGCCTA
SEQ ID NO:22     (777)   ACCCTGAGAGTGCGGAGCAACGGCAACCTGATCGCCCCTTGGTACGGCCA

                          851                                              900
SEQ ID NO:14     (810)   CAAGATCGTGAAGAAGGGCGACAGCGCCATCATCAAGAGCGAGGTGGAGT
SEQ ID NO:16     (810)   CAAGATCGTGAAGAAGGGCGACAGCACCATCATGAAGAGCGAGCTGGAAT
SEQ ID NO:18     (810)   CAAAATCGTGAAGAAAGGGGACAGCGCCATCATGAAAAGCGAACTGGAAT
SEQ ID NO:20     (810)   CAAGATCGTGAAGAAGGGCGACAGCGCCATCATGAAGAGCGAGCTGGAAT
SEQ ID NO:22     (827)   CGTGCTGTCCGGCGGCAGCCACGGCCGGATCCTGAAAACCGACCTGAACA

                          901                                              950
SEQ ID NO:14     (860)   ACGGCAACTGCAACACCAAGTGCCAGACCCCCATCGGCGCCATCAACAGC
SEQ ID NO:16     (860)   ACGGCAACTGCAACACCAAGTGCCAGACCCCCATCGGCGCCATCAACAGC
SEQ ID NO:18     (860)   ACGGCAACTGCAACACCAAGTGCCAGACCCCAATGGGGGCCATCAACAGC
SEQ ID NO:20     (860)   ACGGCGACTGCAACACCAAGTGCCAGACCCCCATGGGCGCCATCAACAGC
SEQ ID NO:22     (877)   GCGGCAACTGCGTGGTGCAGTGCCAGACCGAGAAGGGCGGCCTGAACAGC

                          951                                             1000
SEQ ID NO:14     (910)   AGCATGCCCTTCCACAACATCCACCCCCTGACCATCGGCGAGTGCCCCAA
SEQ ID NO:16     (910)   AGCATGCCCTTCCACAACATCCACCCCCTGACCATCGGCGAGTGCCCCAA
SEQ ID NO:18     (910)   AGCATGCCATTCCACAACATCCACCCTCTGACCATCGGGGAATGCCCCAA
SEQ ID NO:20     (910)   AGCATGCCCTTCCACAACATCCACCCCCTGACCATCGGCGAGTGCCCTAA
SEQ ID NO:22     (927)   ACCCTGCCCTTCCACAACATCAGCAAGTACGCCTTCGGCAACTGCCCTAA

                          1001                                            1050
SEQ ID NO:14     (960)   GTACGTGAAGAGCAACAAGCTGGTGCTGGCCACCGGCCTGAGGAACAGCC
SEQ ID NO:16     (960)   GTACGTGAAGAGCAGCAGGCTGGTGCTGGCCACCGGCCTGAGGAACAGCC
SEQ ID NO:18     (960)   ATACGTGAAAAGCAACAGACTGGTGCTGGCCACCGGGCTGAGAAACAGCC
SEQ ID NO:20     (960)   GTACGTGAAGAGCAACAGACTGGTGCTGGCCACCGGCCTGAGAAACAGCC
SEQ ID NO:22     (977)   GTACGTGCGCGTGAAGAGCCTGAAGCTGGCCGTGGGCCTGAGGAACGTGC

                          1051                                            1100
SEQ ID NO:14    (1010)   CCCTGCGCGAGACAAGGGGCCTGTTCGGCGCTATCGCCGGCTTCATCGAG
SEQ ID NO:16    (1010)   CCCAGCGCGAGACAAGGGGCCTGTTCGGCGCTATCGCCGGCTTCATCGAG
SEQ ID NO:18    (1010)   CTCAGAGAGAGACCAGAGGACTGTTTGGAGCCATCGCCGGCTTTATCGAG
SEQ ID NO:20    (1010)   CCCAGAGAGAGACAAGAGGCCTGTTCGGCGCTATCGCCGGCTTCATCGAG
SEQ ID NO:22    (1027)   CCGCCAGAAGCAGCAGGGGCCTGTTCGGCGCCATCGCCGGCTTCATCGAG

                          1101                                            1150
SEQ ID NO:14    (1060)   GGCGGCTGGCAGGGCATGGTGGACGGGTGGTACGGCTACCACCACTCCAA
SEQ ID NO:16    (1060)   GGCGGCTGGCAGGGCATGGTGGACGGGTGGTACGGCTACCATCACTCTAA
SEQ ID NO:18    (1060)   GGAGGATGGCAGGGAATGGTGGATGGCTGGTACGGATACCACCACAGCAA
SEQ ID NO:20    (1060)   GGCGGCTGGCAGGGCATGGTGGACGGGTGGTACGGCTACCACCACTCCAA
SEQ ID NO:22    (1077)   GGCGGCTGGCCTGGACTGGTGGCCGGGTGGTACGGCTTCCAGCACAGCAA
```

Figure 26D

```
                        1151                                              1200
SEQ ID NO:14   (1110)   CGAGCAGGGCAGCGGCTACGCCGCCGACAAAGAGAGCACCCAGAAGGCCA
SEQ ID NO:16   (1110)   CGAACAAGGCAGCGGCTACGCCGCCGACAAAGAGAGCACCCAGAAGGCCA
SEQ ID NO:18   (1110)   CGAGCAGGGGAGCGGATACGCCGCCGACAAAGAATCCACCCAGAAGGCCA
SEQ ID NO:20   (1110)   CGAGCAGGGCAGCGGCTACGCCGCCGACAAAGAGAGCACCCAGAAGGCCA
SEQ ID NO:22   (1127)   CGACCAGGGCGTGGGCATGGCCGCCGACCGGGACAGCACCCAGAAGGCCA

                        1201                                              1250
SEQ ID NO:14   (1160)   TCGACGGCGTCACCAACAAGGTGAACAGCATCATCGACAAGATGAACACC
SEQ ID NO:16   (1160)   TCGACGGCGTCACCAACAAGGTGAACAGCATCATCGACAAGATGAACACC
SEQ ID NO:18   (1160)   TCGACGGCGTGACCAACAAAGTGAACAGCATCATCGACAAAATGAACACC
SEQ ID NO:20   (1160)   TCGACGGCGTCACCAACAAAGTGAACAGCATCATCGACAAGATGAACACC
SEQ ID NO:22   (1177)   TCGACAAGATCACCAGCAAAGTGAACAACATCGTGGACAAGATGAACAAG

                        1251                                              1300
SEQ ID NO:14   (1210)   CAGTTCGAGGCCGTGGGCCGCGAGTTCAACAACCTGGAAAGGCGCATCGA
SEQ ID NO:16   (1210)   CAGTTCGAGGCCGTGGGCCGCGAGTTCAACAACCTGGAAAGGCGCATCGA
SEQ ID NO:18   (1210)   CAGTTTGAGGCCGTGGGAAGGGAGTTTAACAACCTGGAAAGGAGAATCGA
SEQ ID NO:20   (1210)   CAGTTCGAGGCCGTGGGCAGAGAGTTCAACAACCTGGAACGCAGAATCGA
SEQ ID NO:22   (1227)   CAGTACGAGATCATCGACCACGAGTTCAGCGAGGTGGAGACCCGGCTGAA

                        1301                                              1350
SEQ ID NO:14   (1260)   GAACCTGAACAAGAAAATGGAAGATGGCTTCCTGGACGTGTGGACCTACA
SEQ ID NO:16   (1260)   GAACCTGAACAAGAAAATGGAAGATGGCTTCCTGGACGTGTGGACCTACA
SEQ ID NO:18   (1260)   GAACCTGAACAAGAAGATGGAGGACGGATTCCTGGATGTGTGGACCTACA
SEQ ID NO:20   (1260)   GAACCTGAACAAGAAAATGGAAGATGGCTTCCTGGACGTGTGGACCTACA
SEQ ID NO:22   (1277)   CATGATCAACAACAAGATCGACGACCAGATCCAGGACGTGTGGGCCTACA

                        1351                                              1400
SEQ ID NO:14   (1310)   ACGCCGAGCTGCTGGTGCTGATGGAAAACGAGAGGACCCTGGACTTCCAC
SEQ ID NO:16   (1310)   ACGCCGAGCTGCTCGTGCTGATGGAAAACGAGAGGACCCTGGACTTCCAC
SEQ ID NO:18   (1310)   ACGCCGAACTGCTGGTGCTGATGGAAAACGAGAGAACCCTGGACTTTCAC
SEQ ID NO:20   (1310)   ACGCCGAGCTGCTGGTGCTGATGGAAAACGAGAGAACCCTGGACTTCCAC
SEQ ID NO:22   (1327)   ACGCCGAGCTGCTCGTGCTGCTGGAGAACCAGAAAACCCTGGACGAGCAC

                        1401                                              1450
SEQ ID NO:14   (1360)   GATAGCAACGTGAAGAACCTGTACGACAAAGTGCGCCTGCAGCTGAGGGA
SEQ ID NO:16   (1360)   GACAGCAACGTGAAGAACCTGTACGACAAAGTGCGCCTGCAGCTGAGGGA
SEQ ID NO:18   (1360)   GACAGCAACGTGAAGAACCTGTACGACAAAGTGAGGCTGCAGCTGAGGGA
SEQ ID NO:20   (1360)   GACAGCAACGTGAAGAACCTGTACGACAAAGTGCGCCTGCAGCTGAGAGA
SEQ ID NO:22   (1377)   GACGCCAACGTGAACAATCTGTACAACAAAGTGAAGCGGGCCCTGGGCAG

                        1451                                              1500
SEQ ID NO:14   (1410)   CAACGCCAAAGAGCTGGGCAACGGCTGCTTCGAGTTCTACCACAAGTGCG
SEQ ID NO:16   (1410)   CAACGCCAAAGAGCTGGGCAACGGCTGCTTCGAGTTCTACCACCGCTGCG
SEQ ID NO:18   (1410)   TAACGCCAAGGAGCTGGGCAACGGCTGCTTCGAGTTCTACCACAAATGCG
SEQ ID NO:20   (1410)   CAACGCCAAAGAGCTGGGCAACGGCTGCTTCGAGTTCTACCACAAGTGCG
SEQ ID NO:22   (1427)   CAACGCCATGGAGGACGGCAAGGGCTGCTTCGAGCTGTACCACAAGTGCG

                        1501                                              1550
SEQ ID NO:14   (1460)   ACAACGAGTGCATGGAAAGCGTGAGGAACGGCACCTACGACTACCCCCAG
SEQ ID NO:16   (1460)   ACAACGAGTGCATGGAAAGCGTGAGGAACGGCACCTACGACTACCCCCAG
SEQ ID NO:18   (1460)   ATAACGAATGCATGGAAAGCATCAGAAACGGAACCTACAACTACCCCCAG
SEQ ID NO:20   (1460)   ACAACGAGTGCATGGAAAGCATCAGAAACGGCACCTACAACTACCCCCAG
SEQ ID NO:22   (1477)   ACGACCAGTGCATGGAGACAATCAGAAACGGCACCTACAACCGGCGGAAG
```

Figure 26E

```
                      1551                                              1600
SEQ ID NO:14  (1510)  TACAGCGAGGAAGCCAGGCTGAAGCGCGAAGAGATCAGCGGAGTGAAGCT
SEQ ID NO:16  (1510)  TACAGCGAGGAAGCCAGGCTGAAGCGCGAAGAGATCAGCGGAGTGAAGCT
SEQ ID NO:18  (1510)  TACAGCGAAGAAGCCAGACTGAAAAGAGAAGAAATCTCCGGAGTGAAACT
SEQ ID NO:20  (1510)  TACAGCGAGGAAGCCAGACTGAAGAGAGAGGAAATCAGCGGAGTCAAGCT
SEQ ID NO:22  (1527)  TACAAGGAAGAGAGCCGGCTGGAGCGGCAGAAAATCGAGGGCGTGAAGCT

                      1601                                              1650
SEQ ID NO:14  (1560)  GGAAAGCATCGGCACCTACCAGATCCTGAGCATCTACAGCACCGTGGCCT
SEQ ID NO:16  (1560)  GGAAAGCATCGGCACCTACCAGATCCTGAGCATCTACAGCACCGTGGCTA
SEQ ID NO:18  (1560)  GGAATCCATCGGAACCTACCAGATCCTGAGCATCTACAGCACAGTGGCCT
SEQ ID NO:20  (1560)  GGAATCCATCGGCACCTACCAGATCCTGAGCATCTACAGCACCGTGGCCA
SEQ ID NO:22  (1577)  GGAGAGCGAGGGCACCTATAAGATCCTGACCATCTACAGCACCGTGGCCT

                      1651                                              1700
SEQ ID NO:14  (1610)  CTAGCCTGGCTCTGGCCATCATGGTGGCCGGACTGAGCCTGTGGATGTGC
SEQ ID NO:16  (1610)  GCTCTCTGGCCCTGGCCATCATGGTGGCCGGACTGAGCCTGTGGATGTGC
SEQ ID NO:18  (1610)  CCTCCCTGGCCCTGGCCATCATGATGGCCGGACTGAGCCTGTGGATGTGC
SEQ ID NO:20  (1610)  GCAGCCTGGCCCTGGCTATTATGATGGCAGGACTGAGCCTGTGGATGTGC
SEQ ID NO:22  (1627)  CCAGCCTGGTGCTGGCCATGGGCTTCGCCGCCTTTCTGTTCTGGGCCATG

                      1701                                              1750
SEQ ID NO:14  (1660)  AGCAACGGCAGCCTGCAGTGCAGGATCTGCATCAAGTGA-----------
SEQ ID NO:16  (1660)  AGCAACGGCAGCCTGCAGTGCAGGATCTGCATCTGATGA-----------
SEQ ID NO:18  (1660)  TCCAACGGAAGCCTGCAGTGCAGAATCTGCATCTGA--------------
SEQ ID NO:20  (1660)  AGCAACGGCAGCCTGCAGTGCAGAATCTGCATCTGA--------------
SEQ ID NO:22  (1677)  TCCAACGGCTCCTGCCGGTGCAACATCTGCATCTGATGACTCGAGTCTAG

                      1751
SEQ ID NO:14  (1699)  --
SEQ ID NO:16  (1699)  --
SEQ ID NO:18  (1696)  --
SEQ ID NO:20  (1696)  --
SEQ ID NO:22  (1727)  AA
```

Figure 26F

Sequence Identity Percentage

| SEQ ID NO: | 14 | 16 | 18 | 20 | 22 |
|---|---|---|---|---|---|
| 14 | | 97% | 89% | 94% | 69% |
| 16 | | | 88% | 93% | 69% |
| 18 | | | | 88% | 66% |
| 20 | | | | | 68% |
| 22 | | | | | |

SEQUENCE LISTING

```
<160> NUMBER OF SEQ ID NOS: 26

<210> SEQ ID NO 1
<211> LENGTH: 15186
<212> TYPE: DNA
<213> ORGANISM: artificial sequence
<220> FEATURE:
<223> OTHER INFORMATION: NDV genome sequence

<400> SEQUENCE: 1

accaaacaga gaatccgtga ggtacgatag aaggcgaagg agcaatcgaa gtcgtacggg     60

tagaaggtgt gaatctcgag tgcgagcccg aagctcaaac tcgagagagc cttctgccaa    120

aatgtcttct gtattcgatg agtacgagca gctcctcgcg gctcagactc gccccaatgg    180

agctcatggc ggaggagaga aggggagcac cttaaaggta gaagtcccgg tattcactct    240

caacagtgat gacccagaag atagatggaa ctttgcagtg ttttgtcttc ggattgctgt    300

tagcgaggat gccaacaaac cacttaggca aggtgctctc atatctctct tatgttccca    360

ctctcaagtg atgaggaacc atgttgccct tgcggggaaa cagaatgagg ccacactggc    420

tgttcttgag atcgatggtt ttaccaacgg cgtgccccag ttcaacaaca ggagtggagt    480

gtctgaagag agagcacaga gatttatgat gatagcaggg tctctccctc gggcatgcag    540

caacggtacc ccgttcgtca cagctggggt tgaagatgat gcaccagaag acattactga    600

taccctggag aggatcctct ctatccaggc tcaagtatgg gtcacggtgg caaaggccat    660

gactgcatat gagacagcag atgagtcaga aacaagaaga atcaataagt acatgcagca    720

aggcagggtc cagaagaagt acatcctcca ccccgtatgc aggagcgcaa tccaactcac    780

aatcagacag tctctggcgg tccgcatctt tttggttagc gagcttaaga gaggccgcaa    840

cacggcaggt gggacctcca cctattacaa cttggtgggg gatgtagact catacatcag    900

gaacactggg ctaactgcat tcttcctgac acttaaatat ggaattaaca ccaagacatc    960

agcccttgca cttagcagcc tctcaggcga tatccagaaa atgaagcagc tcatgcgctt   1020

gtatcggatg aaaggagata atgcgccgta catgacattg ctcggtgaca gtgaccagat   1080

gagctttgca cctgccgagt atgcacaact ttactccttt gccatgggta tggcatcagt   1140

cctagataaa ggaactagca aataccaatt tgccagggac tttatgagca catcattctg   1200

gagacttgga gtagagtacg ctcaggctca aggaagtagc atcaatgagg atatggccgc   1260

cgagctaaag ctaaccccag cagcaaggag aggcctggca gctgctgccc aaagagtgtc   1320

tgaggagacc agcagcatgg acatgcccac ccaacaagcc ggggtcctca ctggactcag   1380

cgacggaggc tcccaagccc cccaaggtgc actgaacaga tcacaagggc aaccggacac   1440

cggggatggg gagacccaat ttctggatct gatgagagcg gtggcaaata gcatgagaga   1500

agcgccaaac tctgcgcagg gcacccctca accggggcct cccccaaccc ctgggccctc   1560

tcaagacaat gacaccgact gggggtactg accgacagca cccagtttgc ttctatgagg   1620

tcatcccaat tcctctgccc acaccccacc cctcaatccg caatcccgca tggccaaacc   1680

cacaaacgaa cccccctgtc tccctcctct cccccagccc cacaacccca cctgcccagg   1740

gcaacatagg tacaatgcga cccactaata atcaatacag ggccaaagaa attagaaaaa   1800

agtacgggta gaagggagac attcagagat cagggcgagt cacccgggtc tctgctctcc   1860
```

-continued

```
cttctaccta gtggattagg atggagatgg ccacctttac agatgcggag atcgacgagc   1920
tatttgagac cagtggaact gtcattgaca gcataattac ggcccaggga aaaccagtag   1980
agactgttgg aaggagtgca atcccacaag gcaaaactaa ggctttgagc gcagcatggg   2040
agaagcatgg gagcatccag tcaccagcca gccaagacac ccctgatcga caggacagat   2100
cagataaaca actgtccaca cccgagcaag cgagtccaaa cgacagcccc ccagccacat   2160
ccactgacca gcctcccact caggctgcag atgaggccgg cgatacacag ctcaagaccg   2220
gagcaagcaa ctctctgctg tcgatgcttg ataaactcag caataagtca tctaatgcta   2280
aaaagggccc agggtcgagc cctcaagaaa ggcatcatca acgtctgact caacaacagg   2340
ggagtcaaca aagccgcgga aacagccaag agagaccgca gaaccaggcc aaggccatcc   2400
ctggaaacca ggtcacagac gcgaacacag catatcatgg acaatgggag gagtcacaac   2460
tatcagctgg tgcaacccat catgctctcc gatcagagca gagccaagac aatactcctg   2520
cacctgtgga tcatgtccag ctacctgtcg actttgtgca ggcgatgatg tctatgatgg   2580
aggcgatatc acagagggta agtaaagttg actatcagct ggaccttgtc ttgaaacaga   2640
catcttctat ccccatgatg cggtctgaaa tccagcagct gaaaacgtct gttgcggtca   2700
tggaagccaa tttgggcatg atgaagatcc tggaccctgg ttgtgccaac gtttcatctc   2760
taagtgatct acgggcagtt gcccgatccc acccggtttt aatttctggc cccggagacc   2820
catctcctta tgtgacccaa gggggcgaaa tggcactcaa taaactttcg caaccggtgc   2880
aacacccctc tgaattgatt aaacccgcca cggcaagcgg gcctgatata ggagtggaga   2940
aagacactgt ccgtgcattg atcatgtcac gccctatgca tccgagctct tcagctaggc   3000
tcttgagcaa actggacgca gccggatcga ttgaggaaat cagaaaaatc aagcgccttg   3060
cactgaatgg ctaatcacca ccgcaacccg cagcagatcc ctgtccaccc agcaccacac   3120
ggtatctgca ccaagctcct ctctgcaaac ccaaggtcca acaccccgag cgacaaccct   3180
gtcctgcttc ctctgcccca ctaaatgatc gcgcagctgc aatcaattca gctatattaa   3240
ggattaagaa aaaatacggg tagaatcgga gtgccccgat tgtgccaaga tggactcatc   3300
taggacaatc gggctgtact ttgattctac ccttccttct agcaacctgc tagcattccc   3360
gatagtccta caagacacag gggacgggaa gaagcaaatc gccccgcaat acaggatcca   3420
gcgtcttgac tcgtggacag acagcaaaga agactcggta ttcatcacca cctatggatt   3480
catctttcag gttgggaatg aagaagccac tgtcggcatg atcaatgata atcccaagcg   3540
cgagttactt tccactgcca tgctatgcct agggagtgta ccaaatgtcg gagatcttgt   3600
tgagctggca agggcctgcc tcactatggt ggtaacatgc aagaagagtg caactaacac   3660
cgagagaatg gtcttctcag tagtgcaggc accccaggtg ctgcaaagct gtagggttgt   3720
ggcaaacaaa tactcgtcgg tgaatgcagt caagcacgtg aaagcaccag agaagattcc   3780
tgggagcgga accctagagt acaaagtgaa ctttgtctct ctgaccgtgg tgccaagaaa   3840
ggacgtctac aagataccaa ctgcagcact taaggtctct ggctcaagtc tgtacaatct   3900
tgcgctcaat gtcactattg atgtggaggt agacccgaag agcccgttgg tcaaatccct   3960
ttccaagtcc gacagtgggt actatgctaa tctcttctta catattgggc ttatgtccac   4020
tgtagataag aaggggaaga aagtgacatt tgacaagctg gaaaggaaga taaggagact   4080
tgatctatct gtagggctta gtgacgtgct cggaccttcc gtgcttgtaa aggcgagagg   4140
tgcacggact aagctgctgg cacctttctt ctctagcagt gggacagcct gctatcccat   4200
agcaaatgcc tctcctcagg tggccaagat actctggagc caaaccgcgt acctgcggag   4260
```

-continued

```
tgtaaaagtc attatccaag cgggcaccca gcgtgctgtc gcagtgaccg ccgaccacga   4320
ggttacctct actaagctgg agaaggggca taccattgcc aaatacaatc ccttcaagaa   4380
ataggctgca tctctgagat tgcactccgc ccatcttccc ggatcaccat gacactaaat   4440
aatgatctgt cttgattact tatagttagt tcgcctgtct atcaaattag aaaaaacacg   4500
ggtagaagat tctggatccc ggttggcgcc ttcaaggtgc aagatgggct ccagatcttc   4560
taccaggatc ccagtacctc ttatgctgac cgtccgagtc atgttggcac tgagttgcgt   4620
ctgtccgacc agcgcccttg atggcaggcc tcttgcagct gcagggattg tggtaacagg   4680
agacaaagca gtcaacatat acacctcatc tcagacaggg tcaatcataa tcaagttact   4740
cccaaatatg cccaaggata aagaggcgtg tgcaaaagcc ccgttggagg catacaacag   4800
gacattgact actttgctca cccccccttgg tgattctatc cgtaggatac aagagtctgt   4860
gaccacgtcc ggaggaggga aacagggacg tcttataggc gccattatcg gtggtgtagc   4920
tctcggggtt gcaaccgctg cacagataac agcagcctcg gctctgatac aagccaatca   4980
aaatgctgcc aacatactcc ggctaaaaga gagcattgct gcaaccaatg aggctgtgca   5040
cgaggtcact aatggattat cacaactagc agtggcagtt gggaagatgc agcaatttgt   5100
taatgaccag tttaataaaa cagctcagga attggactgt ataaaaatta cacagcaggt   5160
tggtgtagaa ctcaacctgt acctaactga attgactaca gtattcgggc cacaaatcac   5220
ttcccctgcc ttaactcagc tgactatcca ggcgctttac aatctagctg gtgggaatat   5280
ggattacttg ttgactaagt taggtgtggg gaacaaccaa ctcagctcat taattagtag   5340
tggcctgatc accggcaacc ctattctgta cgactcacag actcaactct tgggtataca   5400
ggtaacccta ccctcagtcg ggaacctaaa taatatgcgt gccacctacc tggaaacctt   5460
gtctgtaagt acaaccaaag gatttgcctc agcacttgtc ccaaaagtag tgacacaggt   5520
cggttccgtg atagaagagc ttgacacctc gtactgtata gagaccgatt tggatctata   5580
ttgtacaaga atagtgacat tccctatgtc tcctggtatt tattcctgtt tgagtggcaa   5640
tacatctgct tgcatgtact caaagactga aggcgcactc actacgccgt atatgaccct   5700
caaaggctca gttattgcta actgtaagat gacaacatgt agatgtgcag accccccggg   5760
tatcatatcg caaaattatg gagaagctgt gtctctaata gataggcaat catgcaatat   5820
cttatcctta gacgggataa ctttgaggct cagtggggaa tttgatgcaa cttatcaaaa   5880
gaatatctca atacaagatt ctcaagtaat agtgacaggc aatcttgata tctcgactga   5940
gcttgggaat gtcaacaact cgataagtaa tgctttggat aagttagagg aaagcaacag   6000
caaactagat aaggtcaatg tcaaactgac cagcacatcc gctcttatta cctatatcgt   6060
tttaactgtc atatctcttg tatgtggtat acttagcctg gttctagcat gctacctgat   6120
gtacaagcaa aaggcgcaac agaagacctt gttgtggctt gggaataata ccctagacca   6180
gatgagggcc actacaaaaa tgtgaatgcg gatgagaggc agaaacatcc ccaatagcag   6240
tttgtgtgta aagtctgaca gcctgttaat tagaagaatt aagaaaaaac taccggatgt   6300
agatgaccaa agggcgatat acgggtagaa cggtcgggga ggccgtccct caatcgggag   6360
ccgggcctca caacatccgt tctaccgcat caccaatagc agttttcagt catggaccgc   6420
gcagttagcc aagttgcgct agagaatgat gaaagagagg caaagaatac atggcgcttg   6480
gtattccgga tcgcaatcct actctcaacg gtggtgacct tagccatctc tgcagccgcc   6540
cttgcatata gcatggaggc cagcacacct agcgatcttg taggcatacc gactgcgatc   6600
```

-continued

```
tctagagcag aggaaaagat tacatctgca ctcggttcca atcaagatgt agtagatagg   6660
atatataagc aggtggccct cgaatctcca ctggcattgc taaacaccga atctacaatt   6720
atgaacgcaa taacgtctct ctcttatcga atcaatgggg ccgcaaatag cagcggatgt   6780
ggagcaccca ttcatgatcc agattatatt ggaggaatag gtaaagaact tattgtagat   6840
gatgctagcg acgtcacatc atactatccc tctgcgttcc aagaacacct gaactttatc   6900
ccggcgccta ctacaggatc aggttgcact cggataccct catttgacat gagcgctacc   6960
cactactgtt atactcacaa tgtgatatta tctggctgca gagatcactc gcactcacat   7020
caatatttag cacttggtgt gcttcggaca tctgcaacag ggagggtatt cttttccact   7080
ctgcgttcca tcaatctgga tgacacccaa aatcggaagt cttgcagtgt gagtgcaacc   7140
cccttgggtt gtgatatgct gtgctctaaa gtcacagaga ctgaagaaga ggattataac   7200
tcagctatcc ccacgtcgat ggtacatgga aggttagggt tcgacggcca ataccacgag   7260
aaggacctag atgtcacaac actattcgag gactgggtgg caaactaccc aggagtaggg   7320
ggcgggtctt ttattgacaa ccgcgtatgg ttcccagttt acggagggct aaaacccaat   7380
tcgcccagtg acaccgcaca agaagggaaa tatgtaatat acaagcgata caatgacaca   7440
tgtccagatg agcaagatta tcagattcaa atggctaagt cttcatataa gcctgggcgg   7500
tttggaggga aacgcgtaca gcaggccatc ttatctatca aagtgtcaac atccttgggc   7560
gaggacccgg tactgactgt accgcccaac acagtaacac tcatgggggc cgaaggcaga   7620
gttctcacag tagggacatc tcatttcctt tatcagcgag ggtcatcata cttctcccct   7680
gccctactat atcctatgat agtcagcaac aaaacagcca ctcttcatag tccttataca   7740
ttcaatgcct tcactcgacc aggtagtgtc ccttgccagg cttcagcaag atgccctaac   7800
tcatgtgtta ccggagtcta tactgatcca tatcccttgg tcttctatag gaaccacacc   7860
ttgcgagggg tattcgggac gatgcttgat gataaacaag caagactcaa ccctgtatct   7920
gcagtatttg acagcatatc ccgcagtcgc ataacccggg tgagttcaag cagcaccaag   7980
gcagcataca caacatcaac atgttttaaa gttgtaaaga ccaataaaac ctattgtctc   8040
agcattgccg aaatatccaa taccctcttc ggggaattca gaatcgtccc tttactagtt   8100
gagattctca aggatgatgg ggttagagaa gccaggtcta gccggttgag tcaactgcga   8160
gagggttgga aagatgacat tgtatcacct atcttttgcg acgccaagaa tcaaactgaa   8220
taccggcgcg agctcgagtc ctacgctgcc agttggccat aatcagctag tgctaatgtg   8280
attagattaa gtcttgtcgg tagtcacttg attaagaaaa aatgtgggtg gtagcgggat   8340
ataaggcaaa acaactcaag gaggatagca cgggtaggac atggcgagct ccggtcccga   8400
gagggcggag catcagatta tcctaccaga gtcacacctg tcttcaccat tagtcaagca   8460
caaactactc tattactgga aattaactgg gctaccactc cctgacgagt gtgacttcga   8520
ccacctcatt ctcagccgac aatggaagaa aatacttgaa tcggcctccc ctgacactga   8580
gagaatgata aaacttggaa gggcagtgca ccagactctc aaccacaatt ccaagataac   8640
cggagtactc catcccaggt gtttagaaga attggctagt attgaggttc ctgactcaac   8700
caacaagttt cggaagatcg agaagaaaat ccaaattcac aacacaaggt atggagaact   8760
gttcacaaga ctgtgcacgc atgtagagaa gaaattgttg ggatcatctt ggtctaataa   8820
tgtcccccgg tcagaagagt tcaacagcat ccgtacagat ccggcattct ggtttcactc   8880
aaaatggtcc acaactaagt ttgcatggct ccatataaaa cagattcaaa ggcatctgat   8940
tgtggcagca agaacaaggt ccgcagccaa caaattggtg acgctgaccc ataaggtagg   9000
```

-continued

```
ccaagtcttt gttactcctg agcttgtcat tgtgacacat acagatgaga acaagttcac    9060
gtgtcttacc caggaacttg tgttgatgta tgcagatatg atggagggca gagatatggt    9120
caacataata tcatccacgg cggcacatct caggagccta tcagagaaaa ttgatgacat    9180
tctgcggtta gtagatgccc tggcaaaaga tctgggtaat caagtctacg atgttgtagc    9240
actcatggag ggatttgcat acggcgccgt ccagctgctt gagccgtcag gtacattcgc    9300
aggggatttc ttcgcattca acctgcagga gctcaaagac actttgatcg gcctccttcc    9360
taaggatata gcagaatctg tgactcacgc aatagccact gtattctctg gcttagaaca    9420
aaatcaagcg gctgagatgc tgtgcctgtt gcgtctatgg ggccacccat tacttgagtc    9480
ccgtattgcg gcaaaagcag taaggagcca aatgtgcgca ccaaaaatgg tagactttga    9540
tatgatcctc caggtattgt ctttctttaa aggaacaatc atcaacggat acagaaagaa    9600
gaatgcaggt gtttggccac gtgtcaaagt agatacgata tacgggaagg tcattgggca    9660
gctacacgct gattcagcgg agatttcaca cgatatcatg ttgagagagt acaagagttt    9720
atctgcgctt gaattcgagc catgtataga atacgaccct atcaccaatc tgagcatgtt    9780
tctaaaagac aaggcgatcg cacacccgaa agacaactgg ctcgccgcgt ttaggcgaaa    9840
ccttctctct gaggaccaga agaaacatgt aaaggaggca acctctacta accgtctctt    9900
gatagagttc ttagagtcaa atgattttga tccatataag gagatggaat atctgacgac    9960
ccttgagtac ctaagagatg acaatgtggc agtatcatac tcgctcaagg agaaggaagt   10020
gaaggttaat gggcggattt ttgctaagct aacaaagaaa ttaaggaact gtcaagtgat   10080
ggcggaaggg atcttagctg accagattgc acctttcttt caagggaatg ggtcattca    10140
ggatagcata tctttaacca agagtatgct agcgatgagt caattgtctt tcaacagcaa   10200
taagaaacgt atcactgact gcaaagaaag agtagcctca aaccgcaatc acgatcaaaa   10260
gagcaagaat cgtcggagag ttgccacttt tataacgact gacctgcaaa agtactgtct   10320
taattggaga tatcagacaa tcaaactgtt cgctcatgcc atcaatcagc tgatgggctt   10380
acctcacttc ttcgaatgga ttcatctaag actaatggat actacgatgt ttgtaggaga   10440
ccctttcaat cccccaagtg acccaactga ctgtgatctc tcaagagtcc caaatgatga   10500
catatatatt gtcagtgcta gagggggtat tgagggatta tgtcagaagc tatggacaat   10560
gatctcaatt gctgcaatcc aacttgctgc agcaagatca cattgtcgcg tcgcctgtat   10620
ggtacagggt gacaatcaag taatagctgt aacgagagag gtaaggtcag atgactcccc   10680
ggaaatggtg ttaacacaat tgcatcaagc cagtgataat ttcttcaagg aattgattca   10740
tgttaatcat ttgattggcc ataatttgaa ggatcgtgaa acaatcagat cagacacatt   10800
cttcatatac agcaaacgaa tattcaaaga tggagcaata ctcagtcaag tcctcaaaaa   10860
ttcatctaaa ttagtgctaa tatcaggcga ccttagtgaa aacaccgtaa tgtcctgtgc   10920
caacattgca tctactatag cacggctgtg cgagaacggg cttccaaagg atttctgtta   10980
ttacttaaac tacctgatga gttgcgtgca gacatacttt gattctgagt tttccatcac   11040
taacagctcg caccccgatt ctaaccagtc gtggattgaa gacatctctt ttgtgcactc   11100
atatgtcctg acccctgccc agctaggggg actgagcaac ctccaatact caaggctcta   11160
cacgaggaac atcggtgacc cgggaactac tgcttttgca gagatcaagc gattagaagc   11220
agtggggtta ctaagtccta gtattatgac taacatctta actaggccgc ctggaaatgg   11280
agattgggcc agtctgtgta acgaccctta ctctttcaat tttgagactg tcgcgagtcc   11340
```

-continued

```
aaatattgtc cttaagaaac atacacaaag agtcctattt gaaacttgtt caaatccctt  11400
attatctggc gtgcatacag aggataatga ggcagaagag aaggcgttgg ctgaattttt  11460
actcaatcaa gaagtaattc atccacgtgt cgcacatgct atcatggaag caagctctat  11520
aggtaggagg aagcagattc aagggcttgt tgacacaaca aacaccgtaa tcaagattgc  11580
attgactagg aggccacttg gcatcaagag gctgatgcgg atagttaact actcgagcat  11640
gcatgcaatg ctgtttagag acgatgtttt ctcatctaac aggtctaacc accccttagt  11700
ttcctctaat atgtgttctc tgacgctagc agactatgca cggaatagaa gctggtcacc  11760
attgacgggg ggtagaaaga tactgggtgt atctaatcct gatactatag aacttgtaga  11820
gggtgagatc cttagcgtca gcggaggatg cacaagatgt gacagcggag atgaacaatt  11880
cacttggttc catcttccga gcaatataga actgaccgat gacaccagca agaatcctcc  11940
gatgagagtg ccgtacctcg ggtcaaagac tcaagagagg agggccgcct cgcttgcgaa  12000
aatagctcat atgtcaccac atgtgaaagc tgctctaagg gcatcatccg tgttgatctg  12060
ggcttatgga gacaacgaag taaattggac tgctgctctt aaaattgcaa gatctcggtg  12120
caatataaac tcagagtatc ttcgactatt gtcccccctta cccacagctg ggaatctcca  12180
acatagactg gatgacggca taactcagat gacattcacc cctgcatctc tctacagggt  12240
gtcaccttat attcacatat ccaatgattc tcaaaggtta ttcacggaag aaggagtcaa  12300
agagggaaat gtagtttatc agcaaatcat gctcttgggt ttatctctaa tcgaatcact  12360
cttcccgatg acgacaacca ggacatacga tgagatcaca ttgcacctcc acagtaaatt  12420
tagctgctgt atcagggaag caccggttgc agttcctttc gagttactcg ggatggcacc  12480
agaactaagg acagtgacct caaataagtt tatgtatgat cctagtcctg tatcggaggg  12540
tgactttgcg agacttgact tagctatctt taagagttat gagcttaatc tagaatcata  12600
tcccacaata gagctaatga acattctttc aatatccagc gggaagttaa tcggccagtc  12660
tgtggtttct tatgatgaag atacctccat aaagaatgac gccataatag tgtatgacaa  12720
cacccggaat tggatcagcg aagctcagaa ttcagatgtg gtccgcctat tcgagtatgc  12780
agcacttgaa gtgcttctcg actgttctta tcagctctac tatctgagag taagaggcct  12840
agacaatatc gtgttgtata tgagtgactt atataagaat atgccaggaa ttctactttc  12900
caacattgca gctacaatat ctcatcccat cattcattca agattgcatg cagtaggcct  12960
ggtcaatcac gacgggtcac accaacttgc agacacagat ttcatcgaaa tgtctgcaaa  13020
actattagtc tcttgcactc gacgcgtggt ctcaggttta tatgcaggga ataagtatga  13080
tctgctgttc ccgtctgtct tagatgataa cctgagtgag aagatgcttc agctgatatc  13140
tcggttatgc tgcctgtata cggtgctctt tgctacaaca agagagatcc cgaaaataag  13200
aggcttatct gcagaagaga agtgttcagt acttactgag tacctactgt cagatgctgt  13260
gaaaccatta cttagttctg agcaagtgag ctctatcatg tctcctaaca tagttacgtt  13320
cccagctaat ctatattaca tgtctcggaa gagccttaat ttgattaggg aaagagagga  13380
cagggacact atcttggcat tgttgttccc ccaagagcca ctacttgagt tcccccttagt  13440
acaagatatt ggcgctcgag tgaaagatcc attcacccga caacctgcgg cgtttttaca  13500
agaattagat ttgagcgctc cagcaaggta tgacgcattt acacttagtc aggttcattc  13560
tgaacacaca tcaccaaatc cggaggacga ctacttagta cgatacctgt tcagaggaat  13620
agggaccgcg tcctcctctt ggtataaggc atctcacctt ctttctgtac ctgaggtcag  13680
atgtgcaagg cacgggaatt ccttatactt ggcagaagga agcggagcca ttatgagtct  13740
```

tctcgaactg catgtgccgc atgagactat ctattacaat acgctcttct caaacgagat 13800 gaaccccccca cagcggcatt tcggaccgac cccaacacag tttctgaatt cagttgttta 13860
taggaatcta caggcggagg taccatgtaa ggatggattt gtccaggagt tccgtccatt 13920
atggagagag aatacagaag aaagcgatct gacctcagat aaagcagtgg gttacatcac 13980
atctgcagtg ccctaccggt ctgtatcatt gctgcactgt gacattgaga ttcctccagg 14040
atccaatcaa agcttactgg atcaactggc taccaatctg tctctgattg ccatgcattc 14100
tgtaagggag ggcggggtcg tgatcatcaa agtgttgtat gcaatgggat attacttcca 14160
tctactcatg aacttgttca ctccgtgttc tacgaaagga tatattctct ctaatggcta 14220
tgcatgtaga ggggatatgg agtgttacct ggtatttgtc atgggctatc gaggtgggcc 14280
tacatttgta catgaggtag tgaggatggc aaaaactcta gtgcagcggc acggtacact 14340
tttgtccaaa tcagatgaga tcacactgac taggttattt acctcacagc ggcagcgtgt 14400
aacagacatc ctatccagtc ctttaccgag actaataaag ttcttgagaa agaatatcga 14460
tactgcgcta attgaagccg gggacaacc cgtccgtcca ttctgtgcag agagcttggt 14520
gaggacacta gcggacacaa ctcagatgac ccagatcatc gctagtcaca ttgacacagt 14580
cattcgatct gtgatctaca tggaggctga gggtgatctc gccgacacag tgttcttatt 14640
taccccctac aatctctcta cagacggtaa aaagagaaca tcacttaaac agtgcacaag 14700
gcagatctta gaggtcacaa tattgggtct tagagttgaa aatctcaata aagtaggtga 14760
tgtagtcagt ctagtactta aaggtatgat ttctctggag gacctgatcc ctctaagaac 14820
atacttgaag cgtagtacct gccctaagta tttgaagtct gttctaggta ttactaaact 14880
caaagaaatg tttacagaca cctctttatt atacttgact cgtgctcaac aaaaattcta 14940
catgaaaact ataggcaacg cagtcaaggg atactacagt aactgtgact cttaaagata 15000
atcacatatt aataggctcc ttttctagtt aactgagccc ttgttgattt aatgatacta 15060
tattagaaaa aagttgcact ccgatccttt aggactcgtg ttcgaattca aataattgtc 15120
ttagaaaaaa gttgcgcgta attgttcttg aatgtagtct tgtcattcac caaatctttg 15180
tttggt 15186

<210> SEQ ID NO 2
<211> LENGTH: 1467
<212> TYPE: DNA
<213> ORGANISM: artificial sequence
<220> FEATURE:
<223> OTHER INFORMATION: NP gene of NDV avinew

<400> SEQUENCE: 2
atgtcttctg tattcgatga gtacgagcag ctcctcgcgg ctcagactcg ccccaatgga 60
gctcatggcg gaggagagaa ggggagcacc ttaaaggtag aagtcccggt attcactctc 120
aacagtgatg acccagaaga tagatggaac tttgcagtgt tttgtcttcg gattgctgtt 180
agcgaggatg ccaacaaacc acttaggcaa ggtgctctca tatctctctt atgttcccac 240
tctcaagtga tgaggaacca tgttgccctt gcggggaaac agaatgaggc cacactggct 300
gttcttgaga tcgatggttt taccaacggc gtgccccagt tcaacaacag gagtggagtg 360
tctgaagaga gagcacagag atttatgatg atagcagggt ctctccctcg ggcatgcagc 420
aacggtaccc cgttcgtcac agctggggtt gaagatgatg caccagaaga cattactgat 480
accctggaga ggatcctctc tatccaggct caagtatggg tcacggtggc aaaggccatg 540

```
actgcatatg agacagcaga tgagtcagaa acaagaagaa tcaataagta catgcagcaa    600

ggcagggtcc agaagaagta catcctccac cccgtatgca ggagcgcaat ccaactcaca    660

atcagacagt ctctggcggt ccgcatcttt ttggttagcg agcttaagag aggccgcaac    720

acggcaggtg ggacctccac ctattacaac ttggtggggg atgtagactc atacatcagg    780

aacactgggc taactgcatt cttcctgaca cttaaatatg gaattaacac caagacatca    840

gcccttgcac ttagcagcct ctcaggcgat atccagaaaa tgaagcagct catgcgcttg    900

tatcggatga aaggagataa tgcgccgtac atgacattgc tcggtgacag tgaccagatg    960

agctttgcac ctgccgagta tgcacaactt tactcctttg ccatgggtat ggcatcagtc   1020

ctagataaag gaactagcaa ataccaattt gccagggact ttatgagcac atcattctgg   1080

agacttggag tagagtacgc tcaggctcaa ggaagtagca tcaatgagga tatggccgcc   1140

gagctaaagc taaccccagc agcaaggaga ggcctggcag ctgctgccca aagagtgtct   1200

gaggagacca gcagcatgga catgcccacc caacaagccg ggtcctcac tggactcagc    1260

gacggaggct cccaagcccc ccaaggtgca ctgaacagat cacaagggca accggacacc   1320

ggggatgggg agacccaatt tctggatctg atgagagcgg tggcaaatag catgagagaa   1380

gcgccaaact ctgcgcaggg cacccctcaa ccggggcctc ccccaacccc tgggccctct   1440

caagacaatg acaccgactg ggggtac                                       1467
```

<210> SEQ ID NO 3
<211> LENGTH: 489
<212> TYPE: PRT
<213> ORGANISM: artificial sequence
<220> FEATURE:
<223> OTHER INFORMATION: NP protein of NDV avinew

<400> SEQUENCE: 3

```
Met Ser Ser Val Phe Asp Glu Tyr Glu Gln Leu Leu Ala Ala Gln Thr
1               5                   10                  15

Arg Pro Asn Gly Ala His Gly Gly Gly Glu Lys Gly Ser Thr Leu Lys
            20                  25                  30

Val Glu Val Pro Val Phe Thr Leu Asn Ser Asp Asp Pro Glu Asp Arg
        35                  40                  45

Trp Asn Phe Ala Val Phe Cys Leu Arg Ile Ala Val Ser Glu Asp Ala
    50                  55                  60

Asn Lys Pro Leu Arg Gln Gly Ala Leu Ile Ser Leu Leu Cys Ser His
65                  70                  75                  80

Ser Gln Val Met Arg Asn His Val Ala Leu Ala Gly Lys Gln Asn Glu
                85                  90                  95

Ala Thr Leu Ala Val Leu Glu Ile Asp Gly Phe Thr Asn Gly Val Pro
            100                 105                 110

Gln Phe Asn Asn Arg Ser Gly Val Ser Glu Glu Arg Ala Gln Arg Phe
        115                 120                 125

Met Met Ile Ala Gly Ser Leu Pro Arg Ala Cys Ser Asn Gly Thr Pro
    130                 135                 140

Phe Val Thr Ala Gly Val Glu Asp Asp Ala Pro Glu Asp Ile Thr Asp
145                 150                 155                 160

Thr Leu Glu Arg Ile Leu Ser Ile Gln Ala Gln Val Trp Val Thr Val
                165                 170                 175

Ala Lys Ala Met Thr Ala Tyr Glu Thr Ala Asp Glu Ser Glu Thr Arg
            180                 185                 190

Arg Ile Asn Lys Tyr Met Gln Gln Gly Arg Val Gln Lys Lys Tyr Ile
```

```
        195                 200                 205

Leu His Pro Val Cys Arg Ser Ala Ile Gln Leu Thr Ile Arg Gln Ser
    210                 215                 220

Leu Ala Val Arg Ile Phe Leu Val Ser Glu Leu Lys Arg Gly Arg Asn
225                 230                 235                 240

Thr Ala Gly Gly Thr Ser Thr Tyr Tyr Asn Leu Val Gly Asp Val Asp
                245                 250                 255

Ser Tyr Ile Arg Asn Thr Gly Leu Thr Ala Phe Phe Leu Thr Leu Lys
            260                 265                 270

Tyr Gly Ile Asn Thr Lys Thr Ser Ala Leu Ala Leu Ser Ser Leu Ser
        275                 280                 285

Gly Asp Ile Gln Lys Met Lys Gln Leu Met Arg Leu Tyr Arg Met Lys
    290                 295                 300

Gly Asp Asn Ala Pro Tyr Met Thr Leu Leu Gly Asp Ser Asp Gln Met
305                 310                 315                 320

Ser Phe Ala Pro Ala Glu Tyr Ala Gln Leu Tyr Ser Phe Ala Met Gly
                325                 330                 335

Met Ala Ser Val Leu Asp Lys Gly Thr Ser Lys Tyr Gln Phe Ala Arg
            340                 345                 350

Asp Phe Met Ser Thr Ser Phe Trp Arg Leu Gly Val Glu Tyr Ala Gln
        355                 360                 365

Ala Gln Gly Ser Ser Ile Asn Glu Asp Met Ala Ala Glu Leu Lys Leu
    370                 375                 380

Thr Pro Ala Ala Arg Arg Gly Leu Ala Ala Ala Ala Gln Arg Val Ser
385                 390                 395                 400

Glu Glu Thr Ser Ser Met Asp Met Pro Thr Gln Gln Ala Gly Val Leu
                405                 410                 415

Thr Gly Leu Ser Asp Gly Gly Ser Gln Ala Pro Gln Gly Ala Leu Asn
            420                 425                 430

Arg Ser Gln Gly Gln Pro Asp Thr Gly Asp Gly Glu Thr Gln Phe Leu
        435                 440                 445

Asp Leu Met Arg Ala Val Ala Asn Ser Met Arg Glu Ala Pro Asn Ser
    450                 455                 460

Ala Gln Gly Thr Pro Gln Pro Gly Pro Pro Pro Thr Pro Gly Pro Ser
465                 470                 475                 480

Gln Asp Asn Asp Thr Asp Trp Gly Tyr
                485


<210> SEQ ID NO 4
<211> LENGTH: 1185
<212> TYPE: DNA
<213> ORGANISM: artificial sequence
<220> FEATURE:
<223> OTHER INFORMATION: P gene of NDV Avinew

<400> SEQUENCE: 4

atggccacct ttacagatgc ggagatcgac gagctatttg agaccagtgg aactgtcatt      60

gacagcataa ttacggccca gggaaaacca gtagagactg ttggaaggag tgcaatccca     120

caaggcaaaa ctaaggcttt gagcgcagca tgggagaagc atgggagcat ccagtcacca     180

gccagccaag acacccctga tcgacaggac agatcagata aacaactgtc cacacccgag     240

caagcgagtc caaacgacag ccccccagcc acatccactg accagcctcc cactcaggct     300

gcagatgagg ccggcgatac acagctcaag accggagcaa gcaactctct gctgtcgatg     360

cttgataaac tcagcaataa gtcatctaat gctaaaaagg gcccagggtc gagccctcaa     420
```

```
gaaaggcatc atcaacgtct gactcaacaa caggggagtc aacaaagccg cggaaacagc    480

caagagagac cgcagaacca ggccaaggcc atccctggaa accaggtcac agacgcgaac    540

acagcatatc atggacaatg ggaggagtca caactatcag ctggtgcaac ccatcatgct    600

ctccgatcag agcagagcca agacaatact cctgcacctg tggatcatgt ccagctacct    660

gtcgactttg tgcaggcgat gatgtctatg atggaggcga tatcacagag ggtaagtaaa    720

gttgactatc agctggacct tgtcttgaaa cagacatctt ctatccccat gatgcggtct    780

gaaatccagc agctgaaaac gtctgttgcg gtcatggaag ccaatttggg catgatgaag    840

atcctggacc ctggttgtgc caacgtttca tctctaagtg atctacgggc agttgcccga    900

tcccacccgg ttttaatttc tggccccgga gacccatctc cttatgtgac ccaagggggc    960

gaaatggcac tcaataaact ttcgcaaccg gtgcaacacc cctctgaatt gattaaaccc   1020

gccacggcaa gcgggcctga tataggagtg gagaaagaca ctgtccgtgc attgatcatg   1080

tcacgcccta tgcatccgag ctcttcagct aggctcttga gcaaactgga cgcagccgga   1140

tcgattgagg aaatcagaaa aatcaagcgc cttgcactga atggc                   1185
```

<210> SEQ ID NO 5
<211> LENGTH: 395
<212> TYPE: PRT
<213> ORGANISM: artificial sequence
<220> FEATURE:
<223> OTHER INFORMATION: P protein of NDV Avinew

<400> SEQUENCE: 5

```
Met Ala Thr Phe Thr Asp Ala Glu Ile Asp Glu Leu Phe Glu Thr Ser
1               5                   10                  15

Gly Thr Val Ile Asp Ser Ile Ile Thr Ala Gln Gly Lys Pro Val Glu
            20                  25                  30

Thr Val Gly Arg Ser Ala Ile Pro Gln Gly Lys Thr Lys Ala Leu Ser
        35                  40                  45

Ala Ala Trp Glu Lys His Gly Ser Ile Gln Ser Pro Ala Ser Gln Asp
    50                  55                  60

Thr Pro Asp Arg Gln Asp Arg Ser Asp Lys Gln Leu Ser Thr Pro Glu
65                  70                  75                  80

Gln Ala Ser Pro Asn Asp Ser Pro Pro Ala Thr Ser Thr Asp Gln Pro
                85                  90                  95

Pro Thr Gln Ala Ala Asp Glu Ala Gly Asp Thr Gln Leu Lys Thr Gly
            100                 105                 110

Ala Ser Asn Ser Leu Leu Ser Met Leu Asp Lys Leu Ser Asn Lys Ser
        115                 120                 125

Ser Asn Ala Lys Lys Gly Pro Gly Ser Ser Pro Gln Glu Arg His His
    130                 135                 140

Gln Arg Leu Thr Gln Gln Gln Gly Ser Gln Gln Ser Arg Gly Asn Ser
145                 150                 155                 160

Gln Glu Arg Pro Gln Asn Gln Ala Lys Ala Ile Pro Gly Asn Gln Val
                165                 170                 175

Thr Asp Ala Asn Thr Ala Tyr His Gly Gln Trp Glu Glu Ser Gln Leu
            180                 185                 190

Ser Ala Gly Ala Thr His His Ala Leu Arg Ser Glu Gln Ser Gln Asp
        195                 200                 205

Asn Thr Pro Ala Pro Val Asp His Val Gln Leu Pro Val Asp Phe Val
    210                 215                 220
```

```
Gln Ala Met Met Ser Met Met Glu Ala Ile Ser Gln Arg Val Ser Lys
225                 230                 235                 240

Val Asp Tyr Gln Leu Asp Leu Val Leu Lys Gln Thr Ser Ser Ile Pro
                245                 250                 255

Met Met Arg Ser Glu Ile Gln Gln Leu Lys Thr Ser Val Ala Val Met
            260                 265                 270

Glu Ala Asn Leu Gly Met Met Lys Ile Leu Asp Pro Gly Cys Ala Asn
        275                 280                 285

Val Ser Ser Leu Ser Asp Leu Arg Ala Val Ala Arg Ser His Pro Val
    290                 295                 300

Leu Ile Ser Gly Pro Gly Asp Pro Ser Pro Tyr Val Thr Gln Gly Gly
305                 310                 315                 320

Glu Met Ala Leu Asn Lys Leu Ser Gln Pro Val Gln His Pro Ser Glu
                325                 330                 335

Leu Ile Lys Pro Ala Thr Ala Ser Gly Pro Asp Ile Gly Val Glu Lys
            340                 345                 350

Asp Thr Val Arg Ala Leu Ile Met Ser Arg Pro Met His Pro Ser Ser
        355                 360                 365

Ser Ala Arg Leu Leu Ser Lys Leu Asp Ala Ala Gly Ser Ile Glu Glu
    370                 375                 380

Ile Arg Lys Ile Lys Arg Leu Ala Leu Asn Gly
385                 390                 395
```

<210> SEQ ID NO 6
<211> LENGTH: 1092
<212> TYPE: DNA
<213> ORGANISM: artificial sequence
<220> FEATURE:
<223> OTHER INFORMATION: M gene of NDV Avinew

<400> SEQUENCE: 6

```
atggactcat ctaggacaat cgggctgtac tttgattcta cccttccttc tagcaacctg     60

ctagcattcc cgatagtcct acaagacaca ggggacggga agaagcaaat cgccccgcaa    120

tacaggatcc agcgtcttga ctcgtggaca gacagcaaag aagactcggt attcatcacc    180

acctatggat tcatctttca ggttgggaat gaagaagcca ctgtcggcat gatcaatgat    240

aatcccaagc gcgagttact ttccactgcc atgctatgcc tagggagtgt accaaatgtc    300

ggagatcttg ttgagctggc aagggcctgc ctcactatgg tggtaacatg caagaagagt    360

gcaactaaca ccgagagaat ggtcttctca gtagtgcagg caccccaggt gctgcaaagc    420

tgtagggttg tggcaaacaa atactcgtcg gtgaatgcag tcaagcacgt gaaagcacca    480

gagaagattc ctgggagcgg aaccctagag tacaaagtga actttgtctc tctgaccgtg    540

gtgccaagaa aggacgtcta caagatacca actgcagcac ttaaggtctc tggctcaagt    600

ctgtacaatc ttgcgctcaa tgtcactatt gatgtggagg tagacccgaa gagcccgttg    660

gtcaaatccc tttccaagtc cgacagtggg tactatgcta atctcttctt acatattggg    720

cttatgtcca ctgtagataa gaaggggaag aaagtgacat ttgacaagct ggaaaggaag    780

ataaggagac ttgatctatc tgtagggctt agtgacgtgc tcggaccttc cgtgcttgta    840

aaggcgagag gtgcacggac taagctgctg gcacctttct tctctagcag tgggacagcc    900

tgctatccca tagcaaatgc ctctcctcag gtggccaaga tactctggag ccaaaccgcg    960

tacctgcgga gtgtaaaagt cattatccaa gcgggcaccc agcgtgctgt cgcagtgacc   1020

gccgaccacg aggttacctc tactaagctg gagaaggggc ataccattgc caaatacaat   1080
```

-continued

```
cccttcaaga aa                                                         1092


<210> SEQ ID NO 7
<211> LENGTH: 364
<212> TYPE: PRT
<213> ORGANISM: artificial sequence
<220> FEATURE:
<223> OTHER INFORMATION: M protein of NDV Avinew

<400> SEQUENCE: 7

Met Asp Ser Ser Arg Thr Ile Gly Leu Tyr Phe Asp Ser Thr Leu Pro
1               5                   10                  15

Ser Ser Asn Leu Leu Ala Phe Pro Ile Val Leu Gln Asp Thr Gly Asp
            20                  25                  30

Gly Lys Lys Gln Ile Ala Pro Gln Tyr Arg Ile Gln Arg Leu Asp Ser
        35                  40                  45

Trp Thr Asp Ser Lys Glu Asp Ser Val Phe Ile Thr Thr Tyr Gly Phe
    50                  55                  60

Ile Phe Gln Val Gly Asn Glu Glu Ala Thr Val Gly Met Ile Asn Asp
65                  70                  75                  80

Asn Pro Lys Arg Glu Leu Leu Ser Thr Ala Met Leu Cys Leu Gly Ser
                85                  90                  95

Val Pro Asn Val Gly Asp Leu Val Glu Leu Ala Arg Ala Cys Leu Thr
            100                 105                 110

Met Val Val Thr Cys Lys Lys Ser Ala Thr Asn Thr Glu Arg Met Val
        115                 120                 125

Phe Ser Val Val Gln Ala Pro Gln Val Leu Gln Ser Cys Arg Val Val
    130                 135                 140

Ala Asn Lys Tyr Ser Ser Val Asn Ala Val Lys His Val Lys Ala Pro
145                 150                 155                 160

Glu Lys Ile Pro Gly Ser Gly Thr Leu Glu Tyr Lys Val Asn Phe Val
                165                 170                 175

Ser Leu Thr Val Val Pro Arg Lys Asp Val Tyr Lys Ile Pro Thr Ala
            180                 185                 190

Ala Leu Lys Val Ser Gly Ser Ser Leu Tyr Asn Leu Ala Leu Asn Val
        195                 200                 205

Thr Ile Asp Val Glu Val Asp Pro Lys Ser Pro Leu Val Lys Ser Leu
    210                 215                 220

Ser Lys Ser Asp Ser Gly Tyr Tyr Ala Asn Leu Phe Leu His Ile Gly
225                 230                 235                 240

Leu Met Ser Thr Val Asp Lys Lys Gly Lys Lys Val Thr Phe Asp Lys
                245                 250                 255

Leu Glu Arg Lys Ile Arg Arg Leu Asp Leu Ser Val Gly Leu Ser Asp
            260                 265                 270

Val Leu Gly Pro Ser Val Leu Val Lys Ala Arg Gly Ala Arg Thr Lys
        275                 280                 285

Leu Leu Ala Pro Phe Phe Ser Ser Ser Gly Thr Ala Cys Tyr Pro Ile
    290                 295                 300

Ala Asn Ala Ser Pro Gln Val Ala Lys Ile Leu Trp Ser Gln Thr Ala
305                 310                 315                 320

Tyr Leu Arg Ser Val Lys Val Ile Ile Gln Ala Gly Thr Gln Arg Ala
                325                 330                 335

Val Ala Val Thr Ala Asp His Glu Val Thr Ser Thr Lys Leu Glu Lys
            340                 345                 350

Gly His Thr Ile Ala Lys Tyr Asn Pro Phe Lys Lys
```

355 360

<210> SEQ ID NO 8
<211> LENGTH: 1659
<212> TYPE: DNA
<213> ORGANISM: artificial sequence
<220> FEATURE:
<223> OTHER INFORMATION: F gene of NDV Avinew

<400> SEQUENCE: 8
atgggctcca gatcttctac caggatccca gtacctctta tgctgaccgt ccgagtcatg 60
ttggcactga gttgcgtctg tccgaccagc gcccttgatg gcaggcctct tgcagctgca 120
gggattgtgg taacaggaga caaagcagtc aacatataca cctcatctca gacagggtca 180
atcataatca agttactccc aaatatgccc aaggataaag aggcgtgtgc aaaagccccg 240
ttggaggcat acaacaggac attgactact ttgctcaccc cccttggtga ttctatccgt 300
aggatacaag agtctgtgac cacgtccgga ggagggaaac agggacgtct tataggcgcc 360
attatcggtg gtgtagctct cggggttgca accgctgcac agataacagc agcctcggct 420
ctgatacaag ccaatcaaaa tgctgccaac atactccggc taaaagagag cattgctgca 480
accaatgagg ctgtgcacga ggtcactaat ggattatcac aactagcagt ggcagttggg 540
aagatgcagc aatttgttaa tgaccagttt aataaaacag ctcaggaatt ggactgtata 600
aaaattacac agcaggttgg tgtagaactc aacctgtacc taactgaatt gactacagta 660
ttcgggccac aaatcacttc ccctgcctta actcagctga ctatccaggc gctttacaat 720
ctagctggtg ggaatatgga ttacttgttg actaagttag gtgtggggaa caaccaactc 780
agctcattaa ttagtagtgg cctgatcacc ggcaacccta ttctgtacga ctcacagact 840
caactcttgg gtatacaggt aaccctaccc tcagtcggga acctaaataa tatgcgtgcc 900
acctacctgg aaaccttgtc tgtaagtaca accaaaggat ttgcctcagc acttgtccca 960
aaagtagtga cacaggtcgg ttccgtgata gaagagcttg acacctcgta ctgtatagag 1020
accgatttgg atctatattg tacaagaata gtgacattcc ctatgtctcc tggtatttat 1080
tcctgtttga gtggcaatac atctgcttgc atgtactcaa agactgaagg cgcactcact 1140
acgccgtata tgaccctcaa aggctcagtt attgctaact gtaagatgac aacatgtaga 1200
tgtgcagacc ccccgggtat catatcgcaa aattatggag aagctgtgtc tctaatagat 1260
aggcaatcat gcaatatctt atccttagac gggataactt tgaggctcag tggggaattt 1320
gatgcaactt atcaaaagaa tatctcaata caagattctc aagtaatagt gacaggcaat 1380
cttgatatct cgactgagct tgggaatgtc aacaactcga taagtaatgc tttggataag 1440
ttagaggaaa gcaacagcaa actagataag gtcaatgtca aactgaccag cacatccgct 1500
cttattacct atatcgtttt aactgtcata tctcttgtat gtggtatact tagcctggtt 1560
ctagcatgct acctgatgta caagcaaaag gcgcaacaga agaccttgtt gtggcttggg 1620
aataataccc tagaccagat gagggccact acaaaaatg 1659

<210> SEQ ID NO 9
<211> LENGTH: 553
<212> TYPE: PRT
<213> ORGANISM: artificial sequence
<220> FEATURE:
<223> OTHER INFORMATION: F protein of NDV Avinew

<400> SEQUENCE: 9

Met Gly Ser Arg Ser Ser Thr Arg Ile Pro Val Pro Leu Met Leu Thr

-continued

```
1               5                   10                  15

Val Arg Val Met Leu Ala Leu Ser Cys Val Cys Pro Thr Ser Ala Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Ile Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Lys Gln Gly Arg Leu Ile Gly Ala Ile Ile Gly Gly Val Ala Leu Gly
        115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asn Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Ser Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Thr Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg Gln Ser Cys Asn Ile Leu Ser Leu Asp Gly Ile
            420                 425                 430
```

```
Thr Leu Arg Leu Ser Gly Glu Phe Asp Ala Thr Tyr Gln Lys Asn Ile
        435                 440                 445

Ser Ile Gln Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asp Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Val Ile Ser Leu
            500                 505                 510

Val Cys Gly Ile Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550


<210> SEQ ID NO 10
<211> LENGTH: 1848
<212> TYPE: DNA
<213> ORGANISM: artificial sequence
<220> FEATURE:
<223> OTHER INFORMATION: HN gene of NDV avinew

<400> SEQUENCE: 10

atggaccgcg cagttagcca agttgcgcta gagaatgatg aaagagaggc aaagaataca     60

tggcgcttgg tattccggat cgcaatccta ctctcaacgg tggtgacctt agccatctct    120

gcagccgccc ttgcatatag catggaggcc agcacaccta gcgatcttgt aggcataccg    180

actgcgatct ctagagcaga ggaaaagatt acatctgcac tcggttccaa tcaagatgta    240

gtagatagga tatataagca ggtggccctc gaatctccac tggcattgct aaacaccgaa    300

tctacaatta tgaacgcaat aacgtctctc tcttatcgaa tcaatggggc cgcaaatagc    360

agcggatgtg gagcacccat tcatgatcca gattatattg gaggaatagg taaagaactt    420

attgtagatg atgctagcga cgtcacatca tactatccct ctgcgttcca agaacacctg    480

aactttatcc cggcgcctac tacaggatca ggttgcactc ggataccctc atttgacatg    540

agcgctaccc actactgtta tactcacaat gtgatattat ctggctgcag agatcactcg    600

cactcacatc aatatttagc acttggtgtg cttcggacat ctgcaacagg gagggtattc    660

ttttccactc tgcgttccat caatctggat gacacccaaa atcggaagtc ttgcagtgtg    720

agtgcaaccc ccttgggttg tgatatgctg tgctctaaag tcacagagac tgaagaagag    780

gattataact cagctatccc cacgtcgatg gtacatggaa ggttagggtt cgacggccaa    840

taccacgaga aggacctaga tgtcacaaca ctattcgagg actgggtggc aaactaccca    900

ggagtagggg gcgggtcttt tattgacaac cgcgtatggt tcccagttta cggagggcta    960

aaacccaatt cgcccagtga caccgcacaa gaagggaaat atgtaatata caagcgatac   1020

aatgacacat gtccagatga gcaagattat cagattcaaa tggctaagtc ttcatataag   1080

cctgggcggt ttggagggaa acgcgtacag caggccatct tatctatcaa agtgtcaaca   1140

tccttgggcg aggacccggt actgactgta ccgcccaaca cagtaacact catgggggcc   1200

gaaggcagag ttctcacagt agggacatct catttccttt atcagcgagg gtcatcatac   1260

ttctcccctg ccctactata tcctatgata gtcagcaaca aaacagccac tcttcatagt   1320
```

-continued

```
ccttatacat tcaatgcctt cactcgacca ggtagtgtcc cttgccaggc ttcagcaaga    1380

tgccctaact catgtgttac cggagtctat actgatccat atcccttggt cttctatagg    1440

aaccacacct tgcgaggggt attcgggacg atgcttgatg ataaacaagc aagactcaac    1500

cctgtatctg cagtatttga cagcatatcc cgcagtcgca taacccgggt gagttcaagc    1560

agcaccaagg cagcatacac aacatcaaca tgttttaaag ttgtaaagac caataaaacc    1620

tattgtctca gcattgccga aatatccaat accctcttcg gggaattcag aatcgtccct    1680

ttactagttg agattctcaa ggatgatggg gttagagaag ccaggtctag ccggttgagt    1740

caactgcgag agggttggaa agatgacatt gtatcaccta tcttttgcga cgccaagaat    1800

caaactgaat accggcgcga gctcgagtcc tacgctgcca gttggcca             1848
```

<210> SEQ ID NO 11
<211> LENGTH: 616
<212> TYPE: PRT
<213> ORGANISM: artificial sequence
<220> FEATURE:
<223> OTHER INFORMATION: HN protein of NDV Avinew

<400> SEQUENCE: 11

```
Met Asp Arg Ala Val Ser Gln Val Ala Leu Glu Asn Asp Glu Arg Glu
1               5                   10                  15

Ala Lys Asn Thr Trp Arg Leu Val Phe Arg Ile Ala Ile Leu Leu Ser
            20                  25                  30

Thr Val Val Thr Leu Ala Ile Ser Ala Ala Ala Leu Ala Tyr Ser Met
        35                  40                  45

Glu Ala Ser Thr Pro Ser Asp Leu Val Gly Ile Pro Thr Ala Ile Ser
    50                  55                  60

Arg Ala Glu Glu Lys Ile Thr Ser Ala Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Ser Thr Ile Met Asn Ala Ile Thr Ser Leu Ser Tyr
            100                 105                 110

Arg Ile Asn Gly Ala Ala Asn Ser Ser Gly Cys Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Tyr Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Glu Asp Tyr Asn Ser Ala Ile Pro Thr Ser Met Val His
            260                 265                 270
```

```
Gly Arg Leu Gly Phe Asp Gly Gln Tyr His Glu Lys Asp Leu Asp Val
        275                 280                 285

Thr Thr Leu Phe Glu Asp Trp Val Ala Asn Tyr Pro Gly Val Gly Gly
    290                 295                 300

Gly Ser Phe Ile Asp Asn Arg Val Trp Phe Pro Val Tyr Gly Gly Leu
305                 310                 315                 320

Lys Pro Asn Ser Pro Ser Asp Thr Ala Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Gln Met Ala Lys Ser Ser Tyr Lys Pro Gly Arg Phe Gly Gly Lys Arg
        355                 360                 365

Val Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Val Leu Thr Val Gly Thr Ser His Phe Leu Tyr Gln Arg
                405                 410                 415

Gly Ser Ser Tyr Phe Ser Pro Ala Leu Leu Tyr Pro Met Ile Val Ser
            420                 425                 430

Asn Lys Thr Ala Thr Leu His Ser Pro Tyr Thr Phe Asn Ala Phe Thr
        435                 440                 445

Arg Pro Gly Ser Val Pro Cys Gln Ala Ser Ala Arg Cys Pro Asn Ser
    450                 455                 460

Cys Val Thr Gly Val Tyr Thr Asp Pro Tyr Pro Leu Val Phe Tyr Arg
465                 470                 475                 480

Asn His Thr Leu Arg Gly Val Phe Gly Thr Met Leu Asp Asp Lys Gln
                485                 490                 495

Ala Arg Leu Asn Pro Val Ser Ala Val Phe Asp Ser Ile Ser Arg Ser
            500                 505                 510

Arg Ile Thr Arg Val Ser Ser Ser Ser Thr Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Ser Arg Leu Ser Gln Leu Arg Glu Gly Trp Lys Asp Asp Ile Val Ser
            580                 585                 590

Pro Ile Phe Cys Asp Ala Lys Asn Gln Thr Glu Tyr Arg Arg Glu Leu
        595                 600                 605

Glu Ser Tyr Ala Ala Ser Trp Pro
    610                 615
```

<210> SEQ ID NO 12
<211> LENGTH: 6612
<212> TYPE: DNA
<213> ORGANISM: artificial sequence
<220> FEATURE:
<223> OTHER INFORMATION: L gene of NDV Avinew

<400> SEQUENCE: 12

```
atggcgagct ccggtcccga gagggcggag catcagatta tcctaccaga gtcacacctg      60

tcttcaccat tagtcaagca caaactactc tattactgga aattaactgg gctaccactc     120
```

```
cctgacgagt gtgacttcga ccacctcatt ctcagccgac aatggaagaa aatacttgaa    180
tcggcctccc ctgacactga gagaatgata aaacttggaa gggcagtgca ccagactctc    240
aaccacaatt ccaagataac cggagtactc catcccaggt gtttagaaga attggctagt    300
attgaggttc ctgactcaac caacaagttt cggaagatcg agaagaaaat ccaaattcac    360
aacacaaggt atggagaact gttcacaaga ctgtgcacgc atgtagagaa gaaattgttg    420
ggatcatctt ggtctaataa tgtcccccgg tcagaagagt tcaacagcat ccgtacagat    480
ccggcattct ggtttcactc aaaatggtcc acaactaagt ttgcatggct ccatataaaa    540
cagattcaaa ggcatctgat tgtggcagca agaacaaggt ccgcagccaa caaattggtg    600
acgctgaccc ataaggtagg ccaagtcttt gttactcctg agcttgtcat tgtgacacat    660
acagatgaga acaagttcac gtgtcttacc caggaacttg tgttgatgta tgcagatatg    720
atggagggca gagatatggt caacataata tcatccacgg cggcacatct caggagccta    780
tcagagaaaa ttgatgacat tctgcggtta gtagatgccc tggcaaaaga tctgggtaat    840
caagtctacg atgttgtagc actcatggag ggatttgcat acggcgccgt ccagctgctt    900
gagccgtcag gtacattcgc aggggatttc ttcgcattca acctgcagga gctcaaagac    960
actttgatcg gcctccttcc taaggatata gcagaatctg tgactcacgc aatagccact   1020
gtattctctg gcttagaaca aaatcaagcg gctgagatgc tgtgcctgtt gcgtctatgg   1080
ggccacccat tacttgagtc ccgtattgcg gcaaaagcag taaggagcca aatgtgcgca   1140
ccaaaaatgg tagactttga tatgatcctc caggtattgt ctttctttaa aggaacaatc   1200
atcaacggat acagaaagaa gaatgcaggt gtttggccac gtgtcaaagt agatacgata   1260
tacgggaagg tcattgggca gctacacgct gattcagcgg agatttcaca cgatatcatg   1320
ttgagagagt acaagagttt atctgcgctt gaattcgagc catgtataga atacgaccct   1380
atcaccaatc tgagcatgtt tctaaaagac aaggcgatcg cacacccgaa agacaactgg   1440
ctcgccgcgt ttaggcgaaa ccttctctct gaggaccaga agaaacatgt aaaggaggca   1500
acctctacta accgtctctt gatagagttc ttagagtcaa atgattttga tccatataag   1560
gagatggaat atctgacgac ccttgagtac ctaagagatg acaatgtggc agtatcatac   1620
tcgctcaagg agaaggaagt gaaggttaat gggcggattt ttgctaagct aacaaagaaa   1680
ttaaggaact gtcaagtgat ggcggaaggg atcttagctg accagattgc acctttcttt   1740
caagggaatg gggtcattca ggatagcata tctttaacca agagtatgct agcgatgagt   1800
caattgtctt tcaacagcaa taagaaacgt atcactgact gcaaagaaag agtagcctca   1860
aaccgcaatc acgatcaaaa gagcaagaat cgtcggagag ttgccacttt tataacgact   1920
gacctgcaaa agtactgtct taattggaga tatcagacaa tcaaactgtt cgctcatgcc   1980
atcaatcagc tgatgggctt acctcacttc ttcgaatgga ttcatctaag actaatggat   2040
actacgatgt ttgtaggaga ccctttcaat cccccaagtg acccaactga ctgtgatctc   2100
tcaagagtcc caaatgatga catatatatt gtcagtgcta gagggggtat tgagggatta   2160
tgtcagaagc tatggacaat gatctcaatt gctgcaatcc aacttgctgc agcaagatca   2220
cattgtcgcg tcgcctgtat ggtacagggt gacaatcaag taatagctgt aacgagagag   2280
gtaaggtcag atgactcccc ggaaatggtg ttaacacaat tgcatcaagc cagtgataat   2340
ttcttcaagg aattgattca tgttaatcat ttgattggcc ataatttgaa ggatcgtgaa   2400
acaatcagat cagacacatt cttcatatac agcaaacgaa tattcaaaga tggagcaata   2460
```

-continued

```
ctcagtcaag tcctcaaaaa ttcatctaaa ttagtgctaa tatcaggcga ccttagtgaa   2520
aacaccgtaa tgtcctgtgc caacattgca tctactatag cacggctgtg cgagaacggg   2580
cttccaaagg atttctgtta ttacttaaac tacctgatga gttgcgtgca gacatacttt   2640
gattctgagt tttccatcac taacagctcg caccccgatt ctaaccagtc gtggattgaa   2700
gacatctctt ttgtgcactc atatgtcctg acccctgccc agctaggggg actgagcaac   2760
ctccaatact caaggctcta cacgaggaac atcggtgacc cgggaactac tgcttttgca   2820
gagatcaagc gattagaagc agtggggtta ctaagtccta gtattatgac taacatctta   2880
actaggccgc ctggaaatgg agattgggcc agtctgtgta acgaccctta ctctttcaat   2940
tttgagactg tcgcgagtcc aaatattgtc cttaagaaac atacacaaag agtcctattt   3000
gaaacttgtt caaatccctt attatctggc gtgcatacag aggataatga ggcagaagag   3060
aaggcgttgg ctgaattttt actcaatcaa gaagtaattc atccacgtgt cgcacatgct   3120
atcatggaag caagctctat aggtaggagg aagcagattc aagggcttgt tgacacaaca   3180
aacaccgtaa tcaagattgc attgactagg aggccacttg gcatcaagag gctgatgcgg   3240
atagttaact actcgagcat gcatgcaatg ctgtttagag acgatgtttt ctcatctaac   3300
aggtctaacc accccttagt ttcctctaat atgtgttctc tgacgctagc agactatgca   3360
cggaatagaa gctggtcacc attgacgggg ggtagaaaga tactgggtgt atctaatcct   3420
gatactatag aacttgtaga gggtgagatc cttagcgtca gcggaggatg cacaagatgt   3480
gacagcggag atgaacaatt cacttggttc catcttccga gcaatataga actgaccgat   3540
gacaccagca agaatcctcc gatgagagtg ccgtacctcg ggtcaaagac tcaagagagg   3600
agggccgcct cgcttgcgaa aatagctcat atgtcaccac atgtgaaagc tgctctaagg   3660
gcatcatccg tgttgatctg ggcttatgga gacaacgaag taaattggac tgctgctctt   3720
aaaattgcaa gatctcggtg caatataaac tcagagtatc ttcgactatt gtccccctta   3780
cccacagctg ggaatctcca acatagactg gatgacggca taactcagat gacattcacc   3840
cctgcatctc tctacagggt gtcaccttat attcacatat ccaatgattc tcaaaggtta   3900
ttcacggaag aaggagtcaa agagggaaat gtagtttatc agcaaatcat gctcttgggt   3960
ttatctctaa tcgaatcact cttcccgatg acgacaacca ggacatacga tgagatcaca   4020
ttgcacctcc acagtaaatt tagctgctgt atcagggaag caccggttgc agttcctttc   4080
gagttactcg ggatggcacc agaactaagg acagtgacct caaataagtt tatgtatgat   4140
cctagtcctg tatcggaggg tgactttgcg agacttgact tagctatctt taagagttat   4200
gagcttaatc tagaatcata tcccacaata gagctaatga acattctttc aatatccagc   4260
gggaagttaa tcggccagtc tgtggtttct tatgatgaag atacctccat aaagaatgac   4320
gccataatag tgtatgacaa cacccggaat tggatcagcg aagctcagaa ttcagatgtg   4380
gtccgcctat tcgagtatgc agcacttgaa gtgcttctcg actgttctta tcagctctac   4440
tatctgagag taagaggcct agacaatatc gtgttgtata tgagtgactt atataagaat   4500
atgccaggaa ttctactttc caacattgca gctacaatat ctcatcccat cattcattca   4560
agattgcatg cagtaggcct ggtcaatcac gacgggtcac accaacttgc agacacagat   4620
ttcatcgaaa tgtctgcaaa actattagtc tcttgcactc gacgcgtggt ctcaggttta   4680
tatgcaggga ataagtatga tctgctgttc ccgtctgtct tagatgataa cctgagtgag   4740
aagatgcttc agctgatatc tcggttatgc tgcctgtata cggtgctctt tgctacaaca   4800
agagagatcc cgaaaataag aggcttatct gcagaagaga agtgttcagt acttactgag   4860
```

```
tacctactgt cagatgctgt gaaaccatta cttagttctg agcaagtgag ctctatcatg   4920
tctcctaaca tagttacgtt cccagctaat ctatattaca tgtctcggaa gagccttaat   4980
ttgattaggg aaagagagga cagggacact atcttggcat tgttgttccc ccaagagcca   5040
ctacttgagt tccccttagt acaagatatt ggcgctcgag tgaaagatcc attcacccga   5100
caacctgcgg cgtttttaca agaattagat ttgagcgctc cagcaaggta tgacgcattt   5160
acacttagtc aggttcattc tgaacacaca tcaccaaatc cggaggacga ctacttagta   5220
cgatacctgt tcagaggaat agggaccgcg tcctcctctt ggtataaggc atctcacctt   5280
ctttctgtac ctgaggtcag atgtgcaagg cacgggaatt ccttatactt ggcagaagga   5340
agcggagcca ttatgagtct tctcgaactg catgtgccgc atgagactat ctattacaat   5400
acgctcttct caaacgagat gaaccccccca cagcggcatt tcggaccgac cccaacacag   5460
tttctgaatt cagttgttta taggaatcta caggcggagg taccatgtaa ggatggattt   5520
gtccaggagt tccgtccatt atggagagag aatacagaag aaagcgatct gacctcagat   5580
aaagcagtgg gttacatcac atctgcagtg ccctaccggt ctgtatcatt gctgcactgt   5640
gacattgaga ttcctccagg atccaatcaa agcttactgg atcaactggc taccaatctg   5700
tctctgattg ccatgcattc tgtaagggag ggcggggtcg tgatcatcaa agtgttgtat   5760
gcaatgggat attacttcca tctactcatg aacttgttca ctccgtgttc tacgaaagga   5820
tatattctct ctaatggcta tgcatgtaga ggggatatgg agtgttacct ggtatttgtc   5880
atgggctatc gaggtgggcc tacatttgta catgaggtag tgaggatggc aaaaactcta   5940
gtgcagcggc acggtacact tttgtccaaa tcagatgaga tcacactgac taggttattt   6000
acctcacagc ggcagcgtgt aacagacatc ctatccagtc ctttaccgag actaataaag   6060
ttcttgagaa agaatatcga tactgcgcta attgaagccg ggggacaacc cgtccgtcca   6120
ttctgtgcag agagcttggt gaggacacta gcggacacaa ctcagatgac ccagatcatc   6180
gctagtcaca ttgacacagt cattcgatct gtgatctaca tggaggctga gggtgatctc   6240
gccgacacag tgttcttatt tacccccctac aatctctcta cagacggtaa aaagagaaca   6300
tcacttaaac agtgcacaag gcagatctta gaggtcacaa tattgggtct tagagttgaa   6360
aatctcaata aagtaggtga tgtagtcagt ctagtactta aaggtatgat ttctctggag   6420
gacctgatcc ctctaagaac atacttgaag cgtagtacct gccctaagta tttgaagtct   6480
gttctaggta ttactaaact caaagaaatg tttacagaca cctctttatt atacttgact   6540
cgtgctcaac aaaaattcta catgaaaact ataggcaacg cagtcaaggg atactacagt   6600
aactgtgact ct                                                        6612
```

<210> SEQ ID NO 13
<211> LENGTH: 2204
<212> TYPE: PRT
<213> ORGANISM: artificial sequence
<220> FEATURE:
<223> OTHER INFORMATION: L protein of NDV Avinew

<400> SEQUENCE: 13

```
Met Ala Ser Ser Gly Pro Glu Arg Ala Glu His Gln Ile Ile Leu Pro
1               5                   10                  15

Glu Ser His Leu Ser Ser Pro Leu Val Lys His Lys Leu Leu Tyr Tyr
            20                  25                  30

Trp Lys Leu Thr Gly Leu Pro Leu Pro Asp Glu Cys Asp Phe Asp His
        35                  40                  45
```

```
Leu Ile Leu Ser Arg Gln Trp Lys Lys Ile Leu Glu Ser Ala Ser Pro
    50                  55                  60

Asp Thr Glu Arg Met Ile Lys Leu Gly Arg Ala Val His Gln Thr Leu
65                  70                  75                  80

Asn His Asn Ser Lys Ile Thr Gly Val Leu His Pro Arg Cys Leu Glu
                85                  90                  95

Glu Leu Ala Ser Ile Glu Val Pro Asp Ser Thr Asn Lys Phe Arg Lys
            100                 105                 110

Ile Glu Lys Lys Ile Gln Ile His Asn Thr Arg Tyr Gly Glu Leu Phe
        115                 120                 125

Thr Arg Leu Cys Thr His Val Glu Lys Lys Leu Leu Gly Ser Ser Trp
    130                 135                 140

Ser Asn Asn Val Pro Arg Ser Glu Glu Phe Asn Ser Ile Arg Thr Asp
145                 150                 155                 160

Pro Ala Phe Trp Phe His Ser Lys Trp Ser Thr Thr Lys Phe Ala Trp
                165                 170                 175

Leu His Ile Lys Gln Ile Gln Arg His Leu Ile Val Ala Ala Arg Thr
            180                 185                 190

Arg Ser Ala Ala Asn Lys Leu Val Thr Leu Thr His Lys Val Gly Gln
        195                 200                 205

Val Phe Val Thr Pro Glu Leu Val Ile Val Thr His Thr Asp Glu Asn
    210                 215                 220

Lys Phe Thr Cys Leu Thr Gln Glu Leu Val Leu Met Tyr Ala Asp Met
225                 230                 235                 240

Met Glu Gly Arg Asp Met Val Asn Ile Ile Ser Ser Thr Ala Ala His
                245                 250                 255

Leu Arg Ser Leu Ser Glu Lys Ile Asp Asp Ile Leu Arg Leu Val Asp
            260                 265                 270

Ala Leu Ala Lys Asp Leu Gly Asn Gln Val Tyr Asp Val Val Ala Leu
        275                 280                 285

Met Glu Gly Phe Ala Tyr Gly Ala Val Gln Leu Leu Glu Pro Ser Gly
    290                 295                 300

Thr Phe Ala Gly Asp Phe Phe Ala Phe Asn Leu Gln Glu Leu Lys Asp
305                 310                 315                 320

Thr Leu Ile Gly Leu Leu Pro Lys Asp Ile Ala Glu Ser Val Thr His
                325                 330                 335

Ala Ile Ala Thr Val Phe Ser Gly Leu Glu Gln Asn Gln Ala Ala Glu
            340                 345                 350

Met Leu Cys Leu Leu Arg Leu Trp Gly His Pro Leu Leu Glu Ser Arg
        355                 360                 365

Ile Ala Ala Lys Ala Val Arg Ser Gln Met Cys Ala Pro Lys Met Val
    370                 375                 380

Asp Phe Asp Met Ile Leu Gln Val Leu Ser Phe Phe Lys Gly Thr Ile
385                 390                 395                 400

Ile Asn Gly Tyr Arg Lys Lys Asn Ala Gly Val Trp Pro Arg Val Lys
                405                 410                 415

Val Asp Thr Ile Tyr Gly Lys Val Ile Gly Gln Leu His Ala Asp Ser
            420                 425                 430

Ala Glu Ile Ser His Asp Ile Met Leu Arg Glu Tyr Lys Ser Leu Ser
        435                 440                 445

Ala Leu Glu Phe Glu Pro Cys Ile Glu Tyr Asp Pro Ile Thr Asn Leu
    450                 455                 460
```

-continued

```
Ser Met Phe Leu Lys Asp Lys Ala Ile Ala His Pro Lys Asp Asn Trp
465                 470                 475                 480

Leu Ala Ala Phe Arg Arg Asn Leu Leu Ser Glu Asp Gln Lys Lys His
                485                 490                 495

Val Lys Glu Ala Thr Ser Thr Asn Arg Leu Leu Ile Glu Phe Leu Glu
            500                 505                 510

Ser Asn Asp Phe Asp Pro Tyr Lys Glu Met Glu Tyr Leu Thr Thr Leu
        515                 520                 525

Glu Tyr Leu Arg Asp Asp Asn Val Ala Val Ser Tyr Ser Leu Lys Glu
    530                 535                 540

Lys Glu Val Lys Val Asn Gly Arg Ile Phe Ala Lys Leu Thr Lys Lys
545                 550                 555                 560

Leu Arg Asn Cys Gln Val Met Ala Glu Gly Ile Leu Ala Asp Gln Ile
                565                 570                 575

Ala Pro Phe Phe Gln Gly Asn Gly Val Ile Gln Asp Ser Ile Ser Leu
            580                 585                 590

Thr Lys Ser Met Leu Ala Met Ser Gln Leu Ser Phe Asn Ser Asn Lys
        595                 600                 605

Lys Arg Ile Thr Asp Cys Lys Glu Arg Val Ala Ser Asn Arg Asn His
    610                 615                 620

Asp Gln Lys Ser Lys Asn Arg Arg Arg Val Ala Thr Phe Ile Thr Thr
625                 630                 635                 640

Asp Leu Gln Lys Tyr Cys Leu Asn Trp Arg Tyr Gln Thr Ile Lys Leu
                645                 650                 655

Phe Ala His Ala Ile Asn Gln Leu Met Gly Leu Pro His Phe Phe Glu
            660                 665                 670

Trp Ile His Leu Arg Leu Met Asp Thr Thr Met Phe Val Gly Asp Pro
        675                 680                 685

Phe Asn Pro Pro Ser Asp Pro Thr Asp Cys Asp Leu Ser Arg Val Pro
    690                 695                 700

Asn Asp Asp Ile Tyr Ile Val Ser Ala Arg Gly Gly Ile Glu Gly Leu
705                 710                 715                 720

Cys Gln Lys Leu Trp Thr Met Ile Ser Ile Ala Ala Ile Gln Leu Ala
                725                 730                 735

Ala Ala Arg Ser His Cys Arg Val Ala Cys Met Val Gln Gly Asp Asn
            740                 745                 750

Gln Val Ile Ala Val Thr Arg Glu Val Arg Ser Asp Asp Ser Pro Glu
        755                 760                 765

Met Val Leu Thr Gln Leu His Gln Ala Ser Asp Asn Phe Phe Lys Glu
    770                 775                 780

Leu Ile His Val Asn His Leu Ile Gly His Asn Leu Lys Asp Arg Glu
785                 790                 795                 800

Thr Ile Arg Ser Asp Thr Phe Phe Ile Tyr Ser Lys Arg Ile Phe Lys
                805                 810                 815

Asp Gly Ala Ile Leu Ser Gln Val Leu Lys Asn Ser Ser Lys Leu Val
            820                 825                 830

Leu Ile Ser Gly Asp Leu Ser Glu Asn Thr Val Met Ser Cys Ala Asn
        835                 840                 845

Ile Ala Ser Thr Ile Ala Arg Leu Cys Glu Asn Gly Leu Pro Lys Asp
    850                 855                 860

Phe Cys Tyr Tyr Leu Asn Tyr Leu Met Ser Cys Val Gln Thr Tyr Phe
865                 870                 875                 880

Asp Ser Glu Phe Ser Ile Thr Asn Ser Ser His Pro Asp Ser Asn Gln
```

```
                885                 890                 895

Ser Trp Ile Glu Asp Ile Ser Phe Val His Ser Tyr Val Leu Thr Pro
            900                 905                 910

Ala Gln Leu Gly Gly Leu Ser Asn Leu Gln Tyr Ser Arg Leu Tyr Thr
        915                 920                 925

Arg Asn Ile Gly Asp Pro Gly Thr Thr Ala Phe Ala Glu Ile Lys Arg
    930                 935                 940

Leu Glu Ala Val Gly Leu Leu Ser Pro Ser Ile Met Thr Asn Ile Leu
945                 950                 955                 960

Thr Arg Pro Pro Gly Asn Gly Asp Trp Ala Ser Leu Cys Asn Asp Pro
                965                 970                 975

Tyr Ser Phe Asn Phe Glu Thr Val Ala Ser Pro Asn Ile Val Leu Lys
            980                 985                 990

Lys His Thr Gln Arg Val Leu Phe  Glu Thr Cys Ser Asn  Pro Leu Leu
        995                 1000                1005

Ser Gly  Val His Thr Glu Asp  Asn Glu Ala Glu Glu  Lys Ala Leu
    1010                1015                1020

Ala Glu  Phe Leu Leu Asn Gln  Glu Val Ile His Pro  Arg Val Ala
    1025                1030                1035

His Ala  Ile Met Glu Ala Ser  Ser Ile Gly Arg Arg  Lys Gln Ile
    1040                1045                1050

Gln Gly  Leu Val Asp Thr Thr  Asn Thr Val Ile Lys  Ile Ala Leu
    1055                1060                1065

Thr Arg  Arg Pro Leu Gly Ile  Lys Arg Leu Met Arg  Ile Val Asn
    1070                1075                1080

Tyr Ser  Ser Met His Ala Met  Leu Phe Arg Asp Asp  Val Phe Ser
    1085                1090                1095

Ser Asn  Arg Ser Asn His Pro  Leu Val Ser Ser Asn  Met Cys Ser
    1100                1105                1110

Leu Thr  Leu Ala Asp Tyr Ala  Arg Asn Arg Ser Trp  Ser Pro Leu
    1115                1120                1125

Thr Gly  Gly Arg Lys Ile Leu  Gly Val Ser Asn Pro  Asp Thr Ile
    1130                1135                1140

Glu Leu  Val Glu Gly Glu Ile  Leu Ser Val Ser Gly  Gly Cys Thr
    1145                1150                1155

Arg Cys  Asp Ser Gly Asp Glu  Gln Phe Thr Trp Phe  His Leu Pro
    1160                1165                1170

Ser Asn  Ile Glu Leu Thr Asp  Asp Thr Ser Lys Asn  Pro Pro Met
    1175                1180                1185

Arg Val  Pro Tyr Leu Gly Ser  Lys Thr Gln Glu Arg  Arg Ala Ala
    1190                1195                1200

Ser Leu  Ala Lys Ile Ala His  Met Ser Pro His Val  Lys Ala Ala
    1205                1210                1215

Leu Arg  Ala Ser Ser Val Leu  Ile Trp Ala Tyr Gly  Asp Asn Glu
    1220                1225                1230

Val Asn  Trp Thr Ala Ala Leu  Lys Ile Ala Arg Ser  Arg Cys Asn
    1235                1240                1245

Ile Asn  Ser Glu Tyr Leu Arg  Leu Leu Ser Pro Leu  Pro Thr Ala
    1250                1255                1260

Gly Asn  Leu Gln His Arg Leu  Asp Asp Gly Ile Thr  Gln Met Thr
    1265                1270                1275

Phe Thr  Pro Ala Ser Leu Tyr  Arg Val Ser Pro Tyr  Ile His Ile
    1280                1285                1290
```

-continued

```
Ser Asn  Asp Ser Gln Arg Leu  Phe Thr Glu Glu Gly  Val Lys Glu
    1295                 1300                 1305

Gly Asn  Val Val Tyr Gln Gln  Ile Met Leu Leu Gly  Leu Ser Leu
    1310                 1315                 1320

Ile Glu  Ser Leu Phe Pro Met  Thr Thr Thr Arg Thr  Tyr Asp Glu
    1325                 1330                 1335

Ile Thr  Leu His Leu His Ser  Lys Phe Ser Cys Cys  Ile Arg Glu
    1340                 1345                 1350

Ala Pro  Val Ala Val Pro Phe  Glu Leu Leu Gly Met  Ala Pro Glu
    1355                 1360                 1365

Leu Arg  Thr Val Thr Ser Asn  Lys Phe Met Tyr Asp  Pro Ser Pro
    1370                 1375                 1380

Val Ser  Glu Gly Asp Phe Ala  Arg Leu Asp Leu Ala  Ile Phe Lys
    1385                 1390                 1395

Ser Tyr  Glu Leu Asn Leu Glu  Ser Tyr Pro Thr Ile  Glu Leu Met
    1400                 1405                 1410

Asn Ile  Leu Ser Ile Ser Ser  Gly Lys Leu Ile Gly  Gln Ser Val
    1415                 1420                 1425

Val Ser  Tyr Asp Glu Asp Thr  Ser Ile Lys Asn Asp  Ala Ile Ile
    1430                 1435                 1440

Val Tyr  Asp Asn Thr Arg Asn  Trp Ile Ser Glu Ala  Gln Asn Ser
    1445                 1450                 1455

Asp Val  Val Arg Leu Phe Glu  Tyr Ala Ala Leu Glu  Val Leu Leu
    1460                 1465                 1470

Asp Cys  Ser Tyr Gln Leu Tyr  Tyr Leu Arg Val Arg  Gly Leu Asp
    1475                 1480                 1485

Asn Ile  Val Leu Tyr Met Ser  Asp Leu Tyr Lys Asn  Met Pro Gly
    1490                 1495                 1500

Ile Leu  Leu Ser Asn Ile Ala  Ala Thr Ile Ser His  Pro Ile Ile
    1505                 1510                 1515

His Ser  Arg Leu His Ala Val  Gly Leu Val Asn His  Asp Gly Ser
    1520                 1525                 1530

His Gln  Leu Ala Asp Thr Asp  Phe Ile Glu Met Ser  Ala Lys Leu
    1535                 1540                 1545

Leu Val  Ser Cys Thr Arg Arg  Val Val Ser Gly Leu  Tyr Ala Gly
    1550                 1555                 1560

Asn Lys  Tyr Asp Leu Leu Phe  Pro Ser Val Leu Asp  Asp Asn Leu
    1565                 1570                 1575

Ser Glu  Lys Met Leu Gln Leu  Ile Ser Arg Leu Cys  Cys Leu Tyr
    1580                 1585                 1590

Thr Val  Leu Phe Ala Thr Thr  Arg Glu Ile Pro Lys  Ile Arg Gly
    1595                 1600                 1605

Leu Ser  Ala Glu Glu Lys Cys  Ser Val Leu Thr Glu  Tyr Leu Leu
    1610                 1615                 1620

Ser Asp  Ala Val Lys Pro Leu  Leu Ser Ser Glu Gln  Val Ser Ser
    1625                 1630                 1635

Ile Met  Ser Pro Asn Ile Val  Thr Phe Pro Ala Asn  Leu Tyr Tyr
    1640                 1645                 1650

Met Ser  Arg Lys Ser Leu Asn  Leu Ile Arg Glu Arg  Glu Asp Arg
    1655                 1660                 1665

Asp Thr  Ile Leu Ala Leu Leu  Phe Pro Gln Glu Pro  Leu Leu Glu
    1670                 1675                 1680
```

```
Phe Pro  Leu Val Gln Asp Ile  Gly Ala Arg Val Lys  Asp Pro Phe
    1685                 1690                 1695

Thr Arg  Gln Pro Ala Ala Phe  Leu Gln Glu Leu Asp  Leu Ser Ala
    1700                 1705                 1710

Pro Ala  Arg Tyr Asp Ala Phe  Thr Leu Ser Gln Val  His Ser Glu
    1715                 1720                 1725

His Thr  Ser Pro Asn Pro Glu  Asp Asp Tyr Leu Val  Arg Tyr Leu
    1730                 1735                 1740

Phe Arg  Gly Ile Gly Thr Ala  Ser Ser Ser Trp Tyr  Lys Ala Ser
    1745                 1750                 1755

His Leu  Leu Ser Val Pro Glu  Val Arg Cys Ala Arg  His Gly Asn
    1760                 1765                 1770

Ser Leu  Tyr Leu Ala Glu Gly  Ser Gly Ala Ile Met  Ser Leu Leu
    1775                 1780                 1785

Glu Leu  His Val Pro His Glu  Thr Ile Tyr Tyr Asn  Thr Leu Phe
    1790                 1795                 1800

Ser Asn  Glu Met Asn Pro Pro  Gln Arg His Phe Gly  Pro Thr Pro
    1805                 1810                 1815

Thr Gln  Phe Leu Asn Ser Val  Val Tyr Arg Asn Leu  Gln Ala Glu
    1820                 1825                 1830

Val Pro  Cys Lys Asp Gly Phe  Val Gln Glu Phe Arg  Pro Leu Trp
    1835                 1840                 1845

Arg Glu  Asn Thr Glu Glu Ser  Asp Leu Thr Ser Asp  Lys Ala Val
    1850                 1855                 1860

Gly Tyr  Ile Thr Ser Ala Val  Pro Tyr Arg Ser Val  Ser Leu Leu
    1865                 1870                 1875

His Cys  Asp Ile Glu Ile Pro  Pro Gly Ser Asn Gln  Ser Leu Leu
    1880                 1885                 1890

Asp Gln  Leu Ala Thr Asn Leu  Ser Leu Ile Ala Met  His Ser Val
    1895                 1900                 1905

Arg Glu  Gly Gly Val Val Ile  Ile Lys Val Leu Tyr  Ala Met Gly
    1910                 1915                 1920

Tyr Tyr  Phe His Leu Leu Met  Asn Leu Phe Thr Pro  Cys Ser Thr
    1925                 1930                 1935

Lys Gly  Tyr Ile Leu Ser Asn  Gly Tyr Ala Cys Arg  Gly Asp Met
    1940                 1945                 1950

Glu Cys  Tyr Leu Val Phe Val  Met Gly Tyr Arg Gly  Gly Pro Thr
    1955                 1960                 1965

Phe Val  His Glu Val Val Arg  Met Ala Lys Thr Leu  Val Gln Arg
    1970                 1975                 1980

His Gly  Thr Leu Leu Ser Lys  Ser Asp Glu Ile Thr  Leu Thr Arg
    1985                 1990                 1995

Leu Phe  Thr Ser Gln Arg Gln  Arg Val Thr Asp Ile  Leu Ser Ser
    2000                 2005                 2010

Pro Leu  Pro Arg Leu Ile Lys  Phe Leu Arg Lys Asn  Ile Asp Thr
    2015                 2020                 2025

Ala Leu  Ile Glu Ala Gly Gly  Gln Pro Val Arg Pro  Phe Cys Ala
    2030                 2035                 2040

Glu Ser  Leu Val Arg Thr Leu  Ala Asp Thr Thr Gln  Met Thr Gln
    2045                 2050                 2055

Ile Ile  Ala Ser His Ile Asp  Thr Val Ile Arg Ser  Val Ile Tyr
    2060                 2065                 2070

Met Glu  Ala Glu Gly Asp Leu  Ala Asp Thr Val Phe  Leu Phe Thr
```

```
    2075                2080                2085

Pro Tyr  Asn Leu Ser Thr Asp  Gly Lys Lys Arg Thr  Ser Leu Lys
    2090                2095                2100

Gln Cys  Thr Arg Gln Ile Leu  Glu Val Thr Ile Leu  Gly Leu Arg
    2105                2110                2115

Val Glu  Asn Leu Asn Lys Val  Gly Asp Val Val Ser  Leu Val Leu
    2120                2125                2130

Lys Gly  Met Ile Ser Leu Glu  Asp Leu Ile Pro Leu  Arg Thr Tyr
    2135                2140                2145

Leu Lys  Arg Ser Thr Cys Pro  Lys Tyr Leu Lys Ser  Val Leu Gly
    2150                2155                2160

Ile Thr  Lys Leu Lys Glu Met  Phe Thr Asp Thr Ser  Leu Leu Tyr
    2165                2170                2175

Leu Thr  Arg Ala Gln Gln Lys  Phe Tyr Met Lys Thr  Ile Gly Asn
    2180                2185                2190

Ala Val  Lys Gly Tyr Tyr Ser  Asn Cys Asp Ser
    2195                2200
```

<210> SEQ ID NO 14
<211> LENGTH: 1698
<212> TYPE: DNA
<213> ORGANISM: artificial sequence
<220> FEATURE:
<223> OTHER INFORMATION: codon-optimized HA gene coding for Influenza H5N1 A/Duck/Laos/3295/2006 (ABG67978)

<400> SEQUENCE: 14

```
atggaaaaga tcgtgctgct gctggccatc gtgagcctgg tgaagagcga ccagatctgc     60

atcggctacc acgccaacaa cagcaccgag caggtggaca ccatcatgga aaagaatgtg    120

accgtgaccc acgcccagga catcctggaa aagacccaca acggcaagct gtgcgacctg    180

gacggcgtga agcccctgat cctgagggac tgcagcgtgg ccggctggct gctgggcaac    240

cccatgtgcg acgagttcat caacgtgccc gagtggagct acatcgtgga gaaggccaac    300

cccgccaacg acctgtgcta ccccggcaac ttcaacgact acgaggaact gaagcacctg    360

ctgtccagga tcaaccactt cgagaagatc cagatcatcc ccaagagcag ctggtccgac    420

catgaggcct ctagcggcgt gagcagcgcc tgcccatacc agggcacccc cagctttttc    480

cgcaacgtgg tgtggctgat caagaagaac aacacctacc ccaccatcaa gcgcagctac    540

aacaacacca accaggaaga tctgctgatc ctgtggggca tccaccacag caacgacgcc    600

gccgagcaga ccaagctgta ccagaacccc accacctaca tcagcgttgg cacaagcacc    660

ctcaaccaga ggctggtgcc caagatcgcc acccgcagca aggtgaacgg ccagagcggc    720

aggatggact tcttctggac catcctgaag cccaacgacg ccatcaactt cgagagcaac    780

ggcaacttta tcgcccccga gtacgcctac aagatcgtga agaagggcga cagcgccatc    840

atcaagagcg aggtggagta cggcaactgc aacaccaagt gccagacccc catcggcgcc    900

atcaacagca gcatgccctt ccacaacatc caccccctga ccatcggcga gtgccccaag    960

tacgtgaaga gcaacaagct ggtgctggcc accggcctga ggaacagccc cctgcgcgag   1020

acaaggggcc tgttcggcgc tatcgccggc ttcatcgagg gcggctggca gggcatggtg   1080

gacgggtggt acggctacca ccactccaac gagcagggca gcggctacgc cgccgacaaa   1140

gagagcaccc agaaggccat cgacggcgtc accaacaagg tgaacagcat catcgacaag   1200

atgaacaccc agttcgaggc cgtgggccgc gagttcaaca acctggaaag gcgcatcgag   1260
```

-continued aacctgaaca agaaaatgga agatggcttc ctggacgtgt ggacctacaa cgccgagctg 1320
ctggtgctga tggaaaacga gaggaccctg gacttccacg atagcaacgt gaagaacctg 1380
tacgacaaag tgcgcctgca gctgagggac aacgccaaag agctgggcaa cggctgcttc 1440
gagttctacc acaagtgcga caacgagtgc atggaaagcg tgaggaacgg cacctacgac 1500
tacccccagt acagcgagga agccaggctg aagcgcgaag agatcagcgg agtgaagctg 1560
gaaagcatcg gcacctacca gatcctgagc atctacagca ccgtggcctc tagcctggct 1620
ctggccatca tggtggccgg actgagcctg tggatgtgca gcaacggcag cctgcagtgc 1680
aggatctgca tcaagtga 1698

<210> SEQ ID NO 15
<211> LENGTH: 565
<212> TYPE: PRT
<213> ORGANISM: artificial sequence
<220> FEATURE:
<223> OTHER INFORMATION: H5N1 A/Duck/Laos/3295/2006 (ABG67978) with modified cleavage site

<400> SEQUENCE: 15

Met Glu Lys Ile Val Leu Leu Leu Ala Ile Val Ser Leu Val Lys Ser
1 5 10 15

Asp Gln Ile Cys Ile Gly Tyr His Ala Asn Asn Ser Thr Glu Gln Val
20 25 30

Asp Thr Ile Met Glu Lys Asn Val Thr Val Thr His Ala Gln Asp Ile
35 40 45

Leu Glu Lys Thr His Asn Gly Lys Leu Cys Asp Leu Asp Gly Val Lys
50 55 60

Pro Leu Ile Leu Arg Asp Cys Ser Val Ala Gly Trp Leu Leu Gly Asn
65 70 75 80

Pro Met Cys Asp Glu Phe Ile Asn Val Pro Glu Trp Ser Tyr Ile Val
85 90 95

Glu Lys Ala Asn Pro Ala Asn Asp Leu Cys Tyr Pro Gly Asn Phe Asn
100 105 110

Asp Tyr Glu Glu Leu Lys His Leu Leu Ser Arg Ile Asn His Phe Glu
115 120 125

Lys Ile Gln Ile Ile Pro Lys Ser Ser Trp Ser Asp His Glu Ala Ser
130 135 140

Ser Gly Val Ser Ser Ala Cys Pro Tyr Gln Gly Thr Pro Ser Phe Phe
145 150 155 160

Arg Asn Val Val Trp Leu Ile Lys Lys Asn Asn Thr Tyr Pro Thr Ile
165 170 175

Lys Arg Ser Tyr Asn Asn Thr Asn Gln Glu Asp Leu Leu Ile Leu Trp
180 185 190

Gly Ile His His Ser Asn Asp Ala Ala Glu Gln Thr Lys Leu Tyr Gln
195 200 205

Asn Pro Thr Thr Tyr Ile Ser Val Gly Thr Ser Thr Leu Asn Gln Arg
210 215 220

Leu Val Pro Lys Ile Ala Thr Arg Ser Lys Val Asn Gly Gln Ser Gly
225 230 235 240

Arg Met Asp Phe Phe Trp Thr Ile Leu Lys Pro Asn Asp Ala Ile Asn
245 250 255

Phe Glu Ser Asn Gly Asn Phe Ile Ala Pro Glu Tyr Ala Tyr Lys Ile
260 265 270

Val Lys Lys Gly Asp Ser Ala Ile Ile Lys Ser Glu Val Glu Tyr Gly

-continued

```
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile Lys
                565


<210> SEQ ID NO 16
<211> LENGTH: 1698
<212> TYPE: DNA
<213> ORGANISM: artificial sequence
<220> FEATURE:
<223> OTHER INFORMATION: codon-optimzied gene coding for HA from
      Influenza H5N1 A/Turkey/Turkey/1/2005 (ABQ58921) with modified
      cleavage site

<400> SEQUENCE: 16

atggaaaaga tcgtgctgct gctggccatc gtgagcctgg tgaagagcga ccagatctgc      60

atcggctacc acgccaacaa cagcaccgag caggtggaca ccatcatgga aaagaatgtg     120

accgtgaccc acgcccagga catcctggaa aagacccaca acggcaagct gtgcgacctg     180

gacggcgtga agcccctgat cctgagggac tgcagcgtgg ccggctggct gctgggcaac     240

cccatgtgcg acgagtttct gaacgtgccc gagtggagct acatcgtgga gaagatcaac     300

cccgccaacg acctgtgcta ccccggcaac ttcaacgact acgaggaact gaagcacctg     360
```

-continued

```
ctgtccagga tcaaccactt cgagaagatc cagatcatcc ccaagagcag ctggtccgac    420

cacgaggcct ctgctggcgt gagcagcgcc tgcccatacc agggccgcag cagcttcttc    480

cgcaacgtgg tgtggctgat caagaaggac aacgcctacc ccaccatcaa gcgcagctac    540

aacaacacca accaggaaga tctgctggtc ctgtggggca tccaccaccc caacgacgcc    600

gccgagcaga ccaggctgta ccagaacccc accacctaca tcagcgtcgg cacctctacc    660

ctgaatcaga ggctggtgcc caagatcgcc acccgcagca aggtgaacgg ccagagcggc    720

aggatggaat tcttctggac catcctgaag cccaacgatg ccatcaactt cgagagcaac    780

ggcaacttta tcgcccccga gaacgcctac aagatcgtga agaagggcga cagcaccatc    840

atgaagagcg agctggaata cggcaactgc aacaccaagt gccagacccc catcggcgcc    900

atcaacagca gcatgccctt ccacaacatc cacccccctga ccatcggcga gtgccccaag    960

tacgtgaaga gcagcaggct ggtgctggcc accggcctga ggaacagccc ccagcgcgag   1020

acaaggggcc tgttcggcgc tatcgccggc ttcatcgagg gcggctggca gggcatggtg   1080

gacgggtggt acggctacca tcactctaac gaacaaggca gcggctacgc cgccgacaaa   1140

gagagcaccc agaaggccat cgacggcgtc accaacaagg tgaacagcat catcgacaag   1200

atgaacaccc agttcgaggc cgtgggccgc gagttcaaca acctggaaag gcgcatcgag   1260

aacctgaaca agaaaatgga agatggcttc ctggacgtgt ggacctacaa cgccgagctg   1320

ctcgtgctga tggaaaacga gaggaccctg gacttccacg acagcaacgt gaagaacctg   1380

tacgacaaag tgcgcctgca gctgagggac aacgccaaag agctgggcaa cggctgcttc   1440

gagttctacc accgctgcga caacgagtgc atggaaagcg tgaggaacgg cacctacgac   1500

taccccccagt acagcgagga agccaggctg aagcgcgaag agatcagcgg agtgaagctg   1560

gaaagcatcg gcacctacca gatcctgagc atctacagca ccgtggctag ctctctggcc   1620

ctggccatca tggtggccgg actgagcctg tggatgtgca gcaacggcag cctgcagtgc   1680

aggatctgca tctgatga                                                 1698
```

<210> SEQ ID NO 17
<211> LENGTH: 564
<212> TYPE: PRT
<213> ORGANISM: artificial sequence
<220> FEATURE:
<223> OTHER INFORMATION: HA protein from Influenza H5N1 A/Turkey/Turkey/1/2005 (ABQ58921) with modified cleavage site

<400> SEQUENCE: 17

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110
```

```
Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ala Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Ser Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Arg Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
```

```
    530                 535                 540

Val Ala Gly Leu Ser Leu Trp Met Cys Ser Asn Gly Ser Leu Gln Cys
545                 550                 555                 560

Arg Ile Cys Ile


<210> SEQ ID NO 18
<211> LENGTH: 1695
<212> TYPE: DNA
<213> ORGANISM: artificial sequence
<220> FEATURE:
<223> OTHER INFORMATION: codon-optimized HA gene coding for HA from
      Influenza H5N1 A/chicken/Indonesia/7/2003 with modified cleavage
      site

<400> SEQUENCE: 18

atggagaaaa tcgtgctgct gctggccatc gtgagcctgg tgaaaagcga tcagatctgc     60

atcggctacc acgccaacaa cagcacagag caagtggaca caatcatgga aaagaacgtg    120

accgtgacac acgcccagga catcctggaa aagacacaca acgggaagct gtgcgatctg    180

gatggagtga agcctctgat cctgagagat tgcagcgtgg ccggatggct gctggggaac    240

ccaatgtgcg acgaattcat caacgtgccc gaatggagct acatcgtgga gaaggccaac    300

ccagccaacg acctgtgcta cccagggaac ctgaacgact acgaagaact gaaacacctg    360

ctgagcagaa tcaaccactt tgagaaaatc cagatcatcc ccaaaagcag ctggtccgat    420

cacgaagcca gcagcggagt gagcagcgcc tgcccatacc agggaaagtc cagctttttt    480

agaaacgtgg tgtggctgat caaaaagaac agcgcctacc caacaatcaa gagaagctac    540

aacaacacca accaggaaga tctgctggtg ctgtggggga tccaccaccc taacgatgcc    600

gccgagcaga caaggctgta ccagaaccca accacctaca tctccgtggg gacaagcaca    660

ctgaaccaga gactggtgcc aaaaatcgcc atcagatcca aagtgaacgg gcagagcgga    720

agaatggagt tcttctggac aatcctgaaa cccaacgatg ccatcaactt cgagagcaac    780

ggaaacttca tcgccccaga atacgcctac aaaatcgtga agaaagggga cagcgccatc    840

atgaaaagcg aactggaata cggcaactgc aacaccaagt gccagacccc aatgggggcc    900

atcaacagca gcatgccatt ccacaacatc caccctctga ccatcgggga atgccccaaa    960

tacgtgaaaa gcaacagact ggtgctggcc accgggctga gaaacagccc tcagagagag   1020

accagaggac tgtttggagc catcgccggc tttatcgagg gaggatggca gggaatggtg   1080

gatggctggt acggatacca ccacagcaac gagcagggga gcggatacgc cgccgacaaa   1140

gaatccaccc agaaggccat cgacggcgtg accaacaaag tgaacagcat catcgacaaa   1200

atgaacaccc agtttgaggc cgtgggaagg gagtttaaca acctggaaag gagaatcgag   1260

aacctgaaca agaagatgga ggacggattc ctggatgtgt ggacctacaa cgccgaactg   1320

ctggtgctga tggaaaacga gagaaccctg gactttcacg acagcaacgt gaagaacctg   1380

tacgacaaag tgaggctgca gctgagggat aacgccaagg agctgggcaa cggctgcttc   1440

gagttctacc acaaatgcga taacgaatgc atggaaagca tcagaaacgg aacctacaac   1500

taccccccagt acagcgaaga agccagactg aaaagagaag aaatctccgg agtgaaactg   1560

gaatccatcg gaacctacca gatcctgagc atctacagca cagtggcctc ctccctggcc   1620

ctggccatca tgatggccgg actgagcctg tggatgtgct ccaacggaag cctgcagtgc   1680

agaatctgca tctga                                                     1695


<210> SEQ ID NO 19
```

```
<211> LENGTH: 568
<212> TYPE: PRT
<213> ORGANISM: artificial sequence
<220> FEATURE:
<223> OTHER INFORMATION: HA protein from Influenza H5N1 A/chicken/
      Indonesia/7/2003 with modified cleavage site

<400> SEQUENCE: 19

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Leu Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Ile Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
```

```
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

<210> SEQ ID NO 20
<211> LENGTH: 1695
<212> TYPE: DNA
<213> ORGANISM: artificial sequence
<220> FEATURE:
<223> OTHER INFORMATION: codon-optimized HA gene from Influenza H5N1 A/chicken/West Java/PWT-WIJ/2006 strain (EU124148) with modified cleavage site

<400> SEQUENCE: 20

```
atggaaaaga tcgtgctgct gctggccatc gtgtccctgg tgaagagcga ccagatctgc      60

atcggctacc acgccaacaa cagcaccgag caggtggaca ccattatgga aaagaacgtg     120

accgtgaccc atgctcagga catcctggaa aagacccaca acggcaagct gtgcgacctg     180

gacggcgtga agcccctgat cctgagagac tgcagcgtgg ccggctggct gctgggcaac     240

cccatgtgcg acgagttcat caaggtgcag gaatggtcct acatcgtcga gaaggccagc     300

cccaccaacg acctgtgcta ccccggcagc ttcaacgact acgaggaact gaagcacctg     360

ctgtccagaa tcaagcactt cgagaagatc cgcatcatcc ccaagagcga ttggagcgac     420

cacgaggcca gcctgggcgt gagcagcgcc tgcccctacc tgggcagccc cagcttcttc     480

agaaacgtgg tgtggctgat caagaagaac agcacctacc ccaccatcaa gaagagctac     540

aagaacacca accaggaaga tctgctggtc ctgtggggca tccaccacag caacaacgtg     600

gaggaacaga ccagactgta ccagaacccc atcacctaca tcagcatcgg caccagcacc     660

ctgaaccaga gactggtgcc caagatcgcc acccgcagca aggtgcacgg ccagagcggc     720

agaatggact tcttctggac catcctgaac cccaacgaca ccatcaactt cgagagcaac     780

ggcaacttta tcgcccccga gtacgcctac aagatcgtga agaagggcga cagcgccatc     840

atgaagagcg agctggaata cggcgactgc aacaccaagt gccagacccc catgggcgcc     900
```

-continued

```
atcaacagca gcatgccctt ccacaacatc cacccccctga ccatcggcga gtgccctaag    960

tacgtgaaga gcaacagact ggtgctggcc accggcctga gaaacagccc ccagagagag   1020

acaagaggcc tgttcggcgc tatcgccggc ttcatcgagg gcggctggca gggcatggtg   1080

gacgggtggt acggctacca ccactccaac gagcagggca gcggctacgc cgccgacaaa   1140

gagagcaccc agaaggccat cgacggcgtc accaacaaag tgaacagcat catcgacaag   1200

atgaacaccc agttcgaggc cgtgggcaga gagttcaaca acctggaacg cagaatcgag   1260

aacctgaaca agaaaatgga agatggcttc ctggacgtgt ggacctacaa cgccgagctg   1320

ctggtgctga tggaaaacga gagaaccctg gacttccacg acagcaacgt gaagaacctg   1380

tacgacaaag tgcgcctgca gctgagagac aacgccaaag agctgggcaa cggctgcttc   1440

gagttctacc acaagtgcga caacgagtgc atggaaagca tcagaaacgg cacctacaac   1500

taccccccagt acagcgagga agccagactg aagagagagg aaatcagcgg agtcaagctg   1560

gaatccatcg gcacctacca gatcctgagc atctacagca ccgtggccag cagcctggcc   1620

ctggctatta tgatggcagg actgagcctg tggatgtgca gcaacggcag cctgcagtgc   1680

agaatctgca tctga                                                    1695
```

<210> SEQ ID NO 21
<211> LENGTH: 564
<212> TYPE: PRT
<213> ORGANISM: artificial sequence
<220> FEATURE:
<223> OTHER INFORMATION: HA protein from Influenza H5N1 A/chicken/West Java/PWT-WIJ/2006 strain (EU124148) with modified cleavage site

<400> SEQUENCE: 21

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Lys Val Gln Glu Trp Ser Tyr Ile Val
                85                  90                  95

Glu Lys Ala Ser Pro Thr Asn Asp Leu Cys Tyr Pro Gly Ser Phe Asn
            100                 105                 110

Asp Tyr Glu Glu Leu Lys His Leu Leu Ser Arg Ile Lys His Phe Glu
        115                 120                 125

Lys Ile Arg Ile Ile Pro Lys Ser Asp Trp Ser Asp His Glu Ala Ser
    130                 135                 140

Leu Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Lys Asn Thr Asn Gln Glu Asp Leu Leu Val Leu Trp
            180                 185                 190

Gly Ile His His Ser Asn Asn Val Glu Glu Gln Thr Arg Leu Tyr Gln
        195                 200                 205
```

-continued

```
Asn Pro Ile Thr Tyr Ile Ser Ile Gly Thr Ser Thr Leu Asn Gln Arg
    210                 215                 220

Leu Val Pro Lys Ile Ala Thr Arg Ser Lys Val His Gly Gln Ser Gly
225                 230                 235                 240

Arg Met Asp Phe Phe Trp Thr Ile Leu Asn Pro Asn Asp Thr Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asp Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Met Ala Gly Leu Ser Leu Trp Met Cys Ser Asn Gly Ser Leu Gln Cys
545                 550                 555                 560

Arg Ile Cys Ile
```

<210> SEQ ID NO 22
<211> LENGTH: 1728
<212> TYPE: DNA
<213> ORGANISM: artificial sequence
<220> FEATURE:
<223> OTHER INFORMATION: codon-optimized gene coding for HA from
Influenza H9N2 A/chicken/Iran/AV1221/1998 strain

<400> SEQUENCE: 22

```
atcgcgatat ccgttaagtt tgtatcgtaa tggagaccat cagcctgatc accatcctgc     60
tggtcgtgac cgccagcaac gccgacaaga tctgcatcgg ctaccagagc accaacagca    120
ccgagaccgt ggacaccctg accgagacca acgtgcccgt gacccacgcc aaggaactgc    180
tgcacaccga gcacaacggc atgctgtgcg ccaccaacct gggccaccct ctgatcctgg    240
acacctgcac catcgagggc ctgatctacg gcaaccccag ctgcgacctg ctgctgggcg    300
gcagggagtg gagctacatc gtggagcgga gcagcgccgt gaacggcacc tgctaccccg    360
gcaacgtgga gaacctggag gagctgcgga ccctgttcag cagcgcctcc tcttaccagc    420
ggatccagat cttccccgac accatctgga acgtgaccta caccggcacc agcaaggcct    480
gcagcggcag cttctaccgg agcatgcggt ggctgaccca gaagagcggc agctaccccg    540
tgcaggacgc ccagtacacc aacaaccggg gcaagagcat cctgttcgtg tggggcatcc    600
accacccccc caccgacacc gcccagacca acctgtacat ccggaacgac accaccacct    660
ccgtgaccac cgaggacctg aaccggatct tcaagcccat gatcggcccc aggcccctcg    720
tgaacggcca gcagggccgg atcaactact actggagcgt gctgaagccc ggccagaccc    780
tgagagtgcg gagcaacggc aacctgatcg ccccttggta cggccacgtg ctgtccggcg    840
gcagccacgg ccggatcctg aaaaccgacc tgaacagcgg caactgcgtg gtgcagtgcc    900
agaccgagaa gggcggcctg aacagcaccc tgcccttcca caacatcagc aagtacgcct    960
tcggcaactg ccctaagtac gtgcgcgtga agagcctgaa gctggccgtg ggcctgagga   1020
acgtgcccgc cagaagcagc aggggcctgt tcggcgccat cgccggcttc atcgagggcg   1080
gctggcctgg actggtggcc gggtggtacg gcttccagca cagcaacgac cagggcgtgg   1140
gcatggccgc cgaccgggac agcacccaga aggccatcga caagatcacc agcaaagtga   1200
acaacatcgt ggacaagatg aacaagcagt acgagatcat cgaccacgag ttcagcgagg   1260
tggagacccg gctgaacatg atcaacaaca agatcgacga ccagatccag gacgtgtggg   1320
cctacaacgc cgagctgctc gtgctgctgg agaaccagaa aaccctggac gagcacgacg   1380
ccaacgtgaa caatctgtac aacaaagtga agcgggccct gggcagcaac gccatggagg   1440
acggcaaggg ctgcttcgag ctgtaccaca agtgcgacga ccagtgcatg gagacaatca   1500
gaaacggcac ctacaaccgg cggaagtaca aggaagagag ccggctggag cggcagaaaa   1560
tcgagggcgt gaagctggag agcgagggca cctataagat cctgaccatc tacagcaccg   1620
tggcctccag cctggtgctg gccatgggct tcgccgcctt tctgttctgg gccatgtcca   1680
acggctcctg ccggtgcaac atctgcatct gatgactcga gtctagaa                1728
```

```
<210> SEQ ID NO 23
<211> LENGTH: 560
<212> TYPE: PRT
<213> ORGANISM: artificial sequence
<220> FEATURE:
<223> OTHER INFORMATION: HA proein from Influenza H9N2 A/chicken/Iran/
      AV1221/1998 strain

<400> SEQUENCE: 23

Met Glu Thr Ile Ser Leu Ile Thr Ile Leu Leu Val Val Thr Ala Ser
1               5                   10                  15

Asn Ala Asp Lys Ile Cys Ile Gly Tyr Gln Ser Thr Asn Ser Thr Glu
            20                  25                  30

Thr Val Asp Thr Leu Thr Glu Thr Asn Val Pro Val Thr His Ala Lys
        35                  40                  45

Glu Leu Leu His Thr Glu His Asn Gly Met Leu Cys Ala Thr Asn Leu
```

```
    50                  55                  60

Gly His Pro Leu Ile Leu Asp Thr Cys Thr Ile Glu Gly Leu Ile Tyr
65                  70                  75                  80

Gly Asn Pro Ser Cys Asp Leu Leu Leu Gly Gly Arg Glu Trp Ser Tyr
                85                  90                  95

Ile Val Glu Arg Ser Ser Ala Val Asn Gly Thr Cys Tyr Pro Gly Asn
            100                 105                 110

Val Glu Asn Leu Glu Glu Leu Arg Thr Leu Phe Ser Ser Ala Ser Ser
        115                 120                 125

Tyr Gln Arg Ile Gln Ile Phe Pro Asp Thr Ile Trp Asn Val Thr Tyr
    130                 135                 140

Thr Gly Thr Ser Lys Ala Cys Ser Gly Ser Phe Tyr Arg Ser Met Arg
145                 150                 155                 160

Trp Leu Thr Gln Lys Ser Gly Ser Tyr Pro Val Gln Asp Ala Gln Tyr
                165                 170                 175

Thr Asn Asn Arg Gly Lys Ser Ile Leu Phe Val Trp Gly Ile His His
            180                 185                 190

Pro Pro Thr Asp Thr Ala Gln Thr Asn Leu Tyr Ile Arg Asn Asp Thr
        195                 200                 205

Thr Thr Ser Val Thr Thr Glu Asp Leu Asn Arg Ile Phe Lys Pro Met
    210                 215                 220

Ile Gly Pro Arg Pro Leu Val Asn Gly Gln Gln Gly Arg Ile Asn Tyr
225                 230                 235                 240

Tyr Trp Ser Val Leu Lys Pro Gly Gln Thr Leu Arg Val Arg Ser Asn
                245                 250                 255

Gly Asn Leu Ile Ala Pro Trp Tyr Gly His Val Leu Ser Gly Gly Ser
            260                 265                 270

His Gly Arg Ile Leu Lys Thr Asp Leu Asn Ser Gly Asn Cys Val Val
        275                 280                 285

Gln Cys Gln Thr Glu Lys Gly Gly Leu Asn Ser Thr Leu Pro Phe His
    290                 295                 300

Asn Ile Ser Lys Tyr Ala Phe Gly Asn Cys Pro Lys Tyr Val Arg Val
305                 310                 315                 320

Lys Ser Leu Lys Leu Ala Val Gly Leu Arg Asn Val Pro Ala Arg Ser
                325                 330                 335

Ser Arg Gly Leu Phe Gly Ala Ile Ala Gly Phe Ile Glu Gly Gly Trp
            340                 345                 350

Pro Gly Leu Val Ala Gly Trp Tyr Gly Phe Gln His Ser Asn Asp Gln
        355                 360                 365

Gly Val Gly Met Ala Ala Asp Arg Asp Ser Thr Gln Lys Ala Ile Asp
    370                 375                 380

Lys Ile Thr Ser Lys Val Asn Asn Ile Val Asp Lys Met Asn Lys Gln
385                 390                 395                 400

Tyr Glu Ile Ile Asp His Glu Phe Ser Glu Val Glu Thr Arg Leu Asn
                405                 410                 415

Met Ile Asn Asn Lys Ile Asp Asp Gln Ile Gln Asp Val Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
    450                 455                 460

Gly Ser Asn Ala Met Glu Asp Gly Lys Gly Cys Phe Glu Leu Tyr His
465                 470                 475                 480
```

```
Lys Cys Asp Asp Gln Cys Met Glu Thr Ile Arg Asn Gly Thr Tyr Asn
                485                 490                 495

Arg Arg Lys Tyr Lys Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Leu Ala Met Gly Phe Ala Ala Phe
    530                 535                 540

Leu Phe Trp Ala Met Ser Asn Gly Ser Cys Arg Cys Asn Ile Cys Ile
545                 550                 555                 560


<210> SEQ ID NO 24
<211> LENGTH: 15407
<212> TYPE: DNA
<213> ORGANISM: artificial sequence
<220> FEATURE:
<223> OTHER INFORMATION: NDV Avinew genome sequence containing cloning
      sites

<400> SEQUENCE: 24

ttcgccctta acagcggccg ctaatacgac tcactatagg accaaacaga gaatccgtga      60

ggtacgatag aaggcgaagg agcaatcgaa gtcgtacggg tagaaggtgt gaatctcgag     120

tgcgagcccg aagctcaaac tcgagagagc cttctgccaa aatgtcttct gtattcgatg     180

agtacgagca gctcctcgcg gctcagactc gccccaatgg agctcatggc ggaggagaga     240

aggggagcac cttaaaggta gaagtcccgg tattcactct caacagtgat gacccagaag     300

atagatggaa ctttgcagtg ttttgtcttc ggattgctgt tagcgaggat gccaacaaac     360

cacttaggca aggtgctctc atatctctct tatgttccca ctctcaagtg atgaggaacc     420

atgttgccct tgcggggaaa cagaatgagg ccacactggc tgttcttgag atcgatggtt     480

ttaccaacgg cgtgccccag ttcaacaaca ggagtggagt gtctgaagag agagcacaga     540

gatttatgat gatagcaggg tctctccctc gggcatgcag caacggtacc ccgttcgtca     600

cagctggggt tgaagatgat gcaccagaag acattactga taccctggag aggatcctct     660

ctatccaggc tcaagtatgg gtcacggtgg caaaggccat gactgcatat gagacagcag     720

atgagtcaga aacaagaaga atcaataagt acatgcagca aggcagggtc cagaagaagt     780

acatcctcca ccccgtatgc aggagcgcaa tccaactcac aatcagacag tctctggcgg     840

tccgcatctt tttggttagc gagcttaaga gaggccgcaa cacggcaggt gggacctcca     900

cctattacaa cttggtgggg gatgtagact catacatcag gaacactggg ctaactgcat     960

tcttcctgac acttaaatat ggaattaaca ccaagacatc agcccttgca cttagcagcc    1020

tctcaggcga tatccagaaa atgaagcagc tcatgcgctt gtatcggatg aaaggagata    1080

atgcgccgta catgacattg ctcggtgaca gtgaccagat gagctttgca cctgccgagt    1140

atgcacaact ttactccttt gccatgggta tggcatcagt cctagataaa ggaactagca    1200

aataccaatt tgccagggac tttatgagca catcattctg gagacttgga gtagagtacg    1260

ctcaggctca aggaagtagc atcaatgagg atatggccgc cgagctaaag ctaaccccag    1320

cagcaaggag aggcctggca gctgctgccc aaagagtgtc tgaggagacc agcagcatgg    1380

acatgcccac ccaacaagcc ggggtcctca ctggactcag cgacggaggc tcccaagccc    1440

cccaaggtgc actgaacaga tcacaagggc aaccggacac cggggatggg gagacccaat    1500

ttctggatct gatgagagcg gtggcaaata gcatgagaga agcgccaaac tctgcgcagg    1560
```

-continued

```
gcacccctca accggggcct cccccaaccc ctgggccctc tcaagacaat gacaccgact   1620
gggggtactg accgacagca cccagtttgc ttctatgagg tcatcccaat tcctctgccc   1680
acaccccacc cctcaatccg caatcccgca tggccaaacc cacaaacgaa ccccccctgtc   1740
tccctcctct cccccagccc cacaacccca cctgcccagg gcaacatagg tacaatgcga   1800
cccactaata atcaatacag ggccaaagaa attagaaaaa agtacgggta gaagggagac   1860
attcagagat cagggcgagt cacccgggtc tctgctctcc cttctaccta gtggattagg   1920
atggagatgg ccacctttac agatgcggag atcgacgagc tatttgagac cagtggaact   1980
gtcattgaca gcataattac ggcccaggga aaaccagtag agactgttgg aaggagtgca   2040
atcccacaag gcaaaactaa ggctttgagc gcagcatggg agaagcatgg gagcatccag   2100
tcaccagcca gccaagacac ccctgatcga caggacagat cagataaaca actgtccaca   2160
cccgagcaag cgagtccaaa cgacagcccc ccagccacat ccactgacca gcctcccact   2220
caggctgcag atgaggccgg cgatacacag ctcaagaccg gagcaagcaa ctctctgctg   2280
tcgatgcttg ataaactcag caataagtca tctaatgcta aaaagggccc agggtcgagc   2340
cctcaagaaa ggcatcatca acgtctgact caacaacagg ggagtcaaca aagccgcgga   2400
aacagccaag agagaccgca gaaccaggcc aaggccatcc ctggaaacca ggtcacagac   2460
gcgaacacag catatcatgg acaatgggag gagtcacaac tatcagctgg tgcaacccat   2520
catgctctcc gatcagagca gagccaagac aatactcctg cacctgtgga tcatgtccag   2580
ctacctgtcg actttgtgca ggcgatgatg tctatgatgg aggcgatatc acagagggta   2640
agtaaagttg actatcagct ggaccttgtc ttgaaacaga catcttctat ccccatgatg   2700
cggtctgaaa tccagcagct gaaaacgtct gttgcggtca tggaagccaa tttgggcatg   2760
atgaagatcc tggaccctgg ttgtgccaac gtttcatctc taagtgatct acgggcagtt   2820
gcccgatccc acccggtttt aatttctggc cccggagacc catctcctta tgtgacccaa   2880
gggggcgaaa tggcactcaa taaactttcg caaccggtgc aacacccctc tgaattgatt   2940
aaacccgcca cggcaagcgg gcctgatata ggagtggaga aagacactgt ccgtgcattg   3000
atcatgtcac gccctatgca tccgagctct tcagctaggc tcttgagcaa actggacgca   3060
gccggatcga ttgaggaaat cagaaaaatc aagcgccttg cactgaatgg ctaatcacca   3120
ccgcaacccg cagcagatcc ctgtccaccc agcaccacac ggtatctgca ccaagctcct   3180
ctctgcaaat ccaaggtcca acacccttaa ttaagtctgt ctggccggcc cgagcgacaa   3240
ccctgtcctg cttcctctgc cccactaaat gatcgcgcag ctgcaatcaa ttcagctata   3300
ttaaggatta agaaaaaata cgggtagaat cggagtgccc cgattgtgcc aagatggact   3360
catctaggac aatcgggctg tactttgatt ctacccttcc ttctagcaac ctgctagcat   3420
tcccgatagt cctacaagac acaggggacg ggaagaagca aatcgccccg caatacagga   3480
tccagcgtct tgactcgtgg acagacagca aagaagactc ggtattcatc accacctatg   3540
gattcatctt tcaggttggg aatgaagaag ccactgtcgg catgatcaat gataatccca   3600
agcgcgagtt actttccact gccatgctat gcctagggag tgtaccaaat gtcggagatc   3660
ttgttgagct ggcaagggcc tgcctcacta tggtggtaac atgcaagaag agtgcaacta   3720
acaccgagag aatggtcttc tcagtagtgc aggcacccca ggtgctgcaa agctgtaggg   3780
ttgtggcaaa caaatactcg tcggtgaatg cagtcaagca cgtgaaagca ccagagaaga   3840
ttcctgggag cggaacccta gagtacaaag tgaactttgt ctctctgacc gtggtgccaa   3900
gaaaggacgt ctacaagata ccaactgcag cacttaaggt ctctggctca agtctgtaca   3960
```

```
atcttgcgct caatgtcact attgatgtgg aggtagaccc gaagagcccg ttggtcaaat   4020

ccctttccaa gtccgacagt gggtactatg ctaatctctt cttacatatt gggcttatgt   4080

ccactgtaga taagaagggg aagaaagtga catttgacaa gctggaaagg aagataagga   4140

gacttgatct atctgtaggg cttagtgacg tgctcggacc ttccgtgctt gtaaaggcga   4200

gaggtgcacg gactaagctg ctggcacctt tcttctctag cagtgggaca gcctgctatc   4260

ccatagcaaa tgcctctcct caggtggcca agatactctg gagccaaacc gcgtacctgc   4320

ggagtgtaaa agtcattatc caagcgggca cccagcgtgc tgtcgcagtg accgccgacc   4380

acgaggttac ctctactaag ctggagaagg ggcataccat tgccaaatac aatcccttca   4440

agaaataggc tgcatctctg agattgcact ccgcccatct tcccggatca ccatgacact   4500

aaataatgat ctgtcttgat tacttatagt tagttcgcct gtctatcaaa ttagaaaaaa   4560

cacgggtaga agattctgga tcccggttgg cgccttcaag gtgcaagatg ggctccagat   4620

cttctaccag gatcccagta cctcttatgc tgaccgtccg agtcatgttg gcactgagtt   4680

gcgtctgtcc gaccagcgcc cttgatggca ggcctcttgc agctgcaggg attgtggtaa   4740

caggagacaa agcagtcaac atatacacct catctcagac agggtcaatc ataatcaagt   4800

tactcccaaa tatgcccaag gataaagagg cgtgtgcaaa agccccgttg gaggcataca   4860

acaggacatt gactactttg ctcacccccc ttggtgattc tatccgtagg atacaagagt   4920

ctgtgaccac gtccggagga gggaaacagg gacgtcttat aggcgccatt atcggtggtg   4980

tagctctcgg ggttgcaacc gctgcacaga taacagcagc ctcggctctg atacaagcca   5040

atcaaaatgc tgccaacata ctccggctaa aagagagcat tgctgcaacc aatgaggctg   5100

tgcacgaggt cactaatgga ttatcacaac tagcagtggc agttgggaag atgcagcaat   5160

ttgttaatga ccagtttaat aaaacagctc aggaattgga ctgtataaaa attacacagc   5220

aggttggtgt agaactcaac ctgtacctaa ctgaattgac tacagtattc gggccacaaa   5280

tcacttcccc tgccttaact cagctgacta tccaggcgct ttacaatcta gctggtggga   5340

atatggatta cttgttgact aagttaggtg tggggaacaa ccaactcagc tcattaatta   5400

gtagtggcct gatcaccggc aaccctattc tgtacgactc acagactcaa ctcttgggta   5460

tacaggtaac cctaccctca gtcgggaacc taaataatat gcgtgccacc tacctggaaa   5520

ccttgtctgt aagtacaacc aaaggatttg cctcagcact tgtcccaaaa gtagtgacac   5580

aggtcggttc cgtgatagaa gagcttgaca cctcgtactg tatagagacc gatttggatc   5640

tatattgtac aagaatagtg acattcccta tgtctcctgg tatttattcc tgtttgagtg   5700

gcaatacatc tgcttgcatg tactcaaaga ctgaaggcgc actcactacg ccgtatatga   5760

ccctcaaagg ctcagttatt gctaactgta agatgacaac atgtagatgt gcagaccccc   5820

cgggtatcat atcgcaaaat tatggagaag ctgtgtctct aatagatagg caatcatgca   5880

atatcttatc cttagacggg ataactttga ggctcagtgg ggaatttgat gcaacttatc   5940

aaaagaatat ctcaatacaa gattctcaag taatagtgac aggcaatctt gatatctcga   6000

ctgagcttgg gaatgtcaac aactcgataa gtaatgcttt ggataagtta gaggaaagca   6060

acagcaaact agataaggtc aatgtcaaac tgaccagcac atccgctctt attacctata   6120

tcgttttaac tgtcatatct cttgtatgtg gtatacttag cctggttcta gcatgctacc   6180

tgatgtacaa gcaaaaggcg caacagaaga ccttgttgtg gcttgggaat aataccctag   6240

accagatgag ggccactaca aaaatgtgaa tgcggatgag aggcagaaac atccccaata   6300
```

-continued

```
gcagtttgtg tgtaaagtct gacagcctgt taattagaag aattaagaaa aaactaccgg   6360
atgtagatga ccaaagggcg atatacgggt agaacggtcg gggaggccgt ccctcaatcg   6420
ggagccgggc ctcacaacat ccgttctacc gcatcaccaa tagcagtttt cagtcatgga   6480
ccgcgcagtt agccaagttg cgctagagaa tgatgaaaga gaggcaaaga atacatggcg   6540
cttggtattc cggatcgcaa tcctactctc aacggtggtg accttagcca tctctgcagc   6600
cgcccttgca tatagcatgg aggccagcac acctagcgat cttgtaggca taccgactgc   6660
gatctctaga gcagaggaaa agattacatc tgcactcggt tccaatcaag atgtagtaga   6720
taggatatat aagcaggtgg ccctcgaatc tccactggca ttgctaaaca ccgaatctac   6780
aattatgaac gcaataacgt ctctctctta tcgaatcaat ggggccgcaa atagcagcgg   6840
atgtggagca cccattcatg atccagatta tattggagga ataggtaaag aacttattgt   6900
agatgatgct agcgacgtca catcatacta tccctctgcg ttccaagaac acctgaactt   6960
tatcccggcg cctactacag gatcaggttg cactcggata ccctcatttg acatgagcgc   7020
tacccactac tgttatactc acaatgtgat attatctggc tgcagagatc actcgcactc   7080
acatcaatat ttagcacttg gtgtgcttcg gacatctgca acagggaggg tattcttttc   7140
cactctgcgt tccatcaatc tggatgacac ccaaaatcgg aagtcttgca gtgtgagtgc   7200
aaccccccttg ggttgtgata tgctgtgctc taaagtcaca gagactgaag aagaggatta   7260
taactcagct atccccacgt cgatggtaca tggaaggtta gggttcgacg gccaatacca   7320
cgagaaggac ctagatgtca caacactatt cgaggactgg gtggcaaact acccaggagt   7380
agggggcggg tcttttattg acaaccgcgt atggttccca gtttacggag ggctaaaacc   7440
caattcgccc agtgacaccg cacaagaagg gaaatatgta atatacaagc gatacaatga   7500
cacatgtcca gatgagcaag attatcagat tcaaatggct aagtcttcat ataagcctgg   7560
gcggtttgga gggaaacgcg tacagcaggc catcttatct atcaaagtgt caacatcctt   7620
gggcgaggac ccggtactga ctgtaccgcc caacacagta acactcatgg gggccgaagg   7680
cagagttctc acagtaggga catctcattt cctttatcag cgagggtcat catacttctc   7740
ccctgcccta ctatatccta tgatagtcag caacaaaaca gccactcttc atagtcctta   7800
tacattcaat gccttcactc gaccaggtag tgtcccttgc caggcttcag caagatgccc   7860
taactcatgt gttaccggag tctatactga tccatatccc ttggtcttct ataggaacca   7920
caccttgcga ggggtattcg ggacgatgct tgatgataaa caagcaagac tcaaccctgt   7980
atctgcagta tttgacagca tatcccgcag tcgcataacc cgggtgagtt caagcagcac   8040
caaggcagca tacacaacat caacatgttt taaagttgta aagaccaata aaacctattg   8100
tctcagcatt gccgaaatat ccaataccct cttcggggaa ttcagaatcg tccctttact   8160
agttgagatt ctcaaggatg atggggttag agaagccagg tctagccggt tgagtcaact   8220
gcgagagggt tggaaagatg acattgtatc acctatcttt tgcgacgcca agaatcaaac   8280
tgaataccgg cgcgagctcg agtcctacgc tgccagttgg ccataatcag ctagtgctaa   8340
tgtgattaga ttaagtcttg tcggtagtca cttgattaag aaaaaatgtg ggtggtagcg   8400
ggatataagg caaaacaact caaggaggat agcacgggta ggacatggcg agctccggtc   8460
ccgagagggc ggagcatcag attatcctac cagagtcaca cctgtcttca ccattagtca   8520
agcacaaact actctattac tggaaattaa ctgggctacc actccctgac gagtgtgact   8580
tcgaccacct cattctcagc cgacaatgga agaaaatact tgaatcggcc tcccctgaca   8640
ctgagagaat gataaaactt ggaagggcag tgcaccagac tctcaaccac aattccaaga   8700
```

```
taaccggagt actccatccc aggtgtttag aagaattggc tagtattgag gttcctgact   8760
caaccaacaa gtttcggaag atcgagaaga aaatccaaat tcacaacaca aggtatggag   8820
aactgttcac aagactgtgc acgcatgtag agaagaaatt gttgggatca tcttggtcta   8880
ataatgtccc ccggtcagaa gagttcaaca gcatccgtac agatccggca ttctggtttc   8940
actcaaaatg gtccacaact aagtttgcat ggctccatat aaaacagatt caaaggcatc   9000
tgattgtggc agcaagaaca aggtccgcag ccaacaaatt ggtgacgctg acccataagg   9060
taggccaagt ctttgttact cctgagcttg tcattgtgac acatacagat gagaacaagt   9120
tcacgtgtct tacccaggaa cttgtgttga tgtatgcaga tatgatggag ggcagagata   9180
tggtcaacat aatatcatcc acggcggcac atctcaggag cctatcagag aaaattgatg   9240
acattctgcg gttagtagat gccctggcaa aagatctggg taatcaagtc tacgatgttg   9300
tagcactcat ggagggattt gcatacggcg ccgtccagct gcttgagccg tcaggtacat   9360
tcgcagggga tttcttcgca ttcaacctgc aggagctcaa agacactttg atcggcctcc   9420
ttcctaagga tatagcagaa tctgtgactc acgcaatagc cactgtattc tctggcttag   9480
aacaaaatca agcggctgag atgctgtgcc tgttgcgtct atggggccac ccattacttg   9540
agtcccgtat tgcggcaaaa gcagtaagga gccaaatgtg cgcaccaaaa atggtagact   9600
ttgatatgat cctccaggta ttgtctttct ttaaaggaac aatcatcaac ggatacagaa   9660
agaagaatgc aggtgtttgg ccacgtgtca aagtagatac gatatacggg aaggtcattg   9720
ggcagctaca cgctgattca gcggagattt cacacgatat catgttgaga gagtacaaga   9780
gtttatctgc gcttgaattc gagccatgta tagaatacga ccctatcacc aatctgagca   9840
tgtttctaaa agacaaggcg atcgcacacc cgaaagacaa ctggctcgcc gcgtttaggc   9900
gaaaccttct ctctgaggac cagaagaaac atgtaaagga ggcaacctct actaaccgtc   9960
tcttgataga gttcttagag tcaaatgatt ttgatccata taaggagatg gaatatctga  10020
cgacccttga gtacctaaga gatgacaatg tggcagtatc atactcgctc aaggagaagg  10080
aagtgaaggt taatgggcgg atttttgcta agctaacaaa gaaattaagg aactgtcaag  10140
tgatggcgga agggatctta gctgaccaga ttgcaccttt ctttcaaggg aatggggtca  10200
ttcaggatag catatcttta accaagagta tgctagcgat gagtcaattg tctttcaaca  10260
gcaataagaa acgtatcact gactgcaaag aaagagtagc ctcaaaccgc aatcacgatc  10320
aaaagagcaa gaatcgtcgg agagttgcca cttttataac gactgacctg caaaagtact  10380
gtcttaattg gagatatcag acaatcaaac tgttcgctca tgccatcaat cagctgatgg  10440
gcttacctca cttcttcgaa tggattcatc taagactaat ggatactacg atgtttgtag  10500
gagacccttt caatcccccca agtgacccaa ctgactgtga tctctcaaga gtcccaaatg  10560
atgacatata tattgtcagt gctagagggg gtattgaggg attatgtcag aagctatgga  10620
caatgatctc aattgctgca atccaacttg ctgcagcaag atcacattgt cgcgtcgcct  10680
gtatggtaca gggtgacaat caagtaatag ctgtaacgag agaggtaagg tcagatgact  10740
ccccggaaat ggtgttaaca caattgcatc aagccagtga taatttcttc aaggaattga  10800
ttcatgttaa tcatttgatt ggccataatt tgaaggatcg tgaaacaatc agatcagaca  10860
cattcttcat atacagcaaa cgaatattca aagatggagc aatactcagt caagtcctca  10920
aaaattcatc taaattagtg ctaatatcag gcgaccttag tgaaaacacc gtaatgtcct  10980
gtgccaacat tgcatctact atagcacggc tgtgcgagaa cgggcttcca aaggatttct  11040
```

-continued gttattactt aaactacctg atgagttgcg tgcagacata ctttgattct gagttttcca 11100
tcactaacag ctcgcacccc gattctaacc agtcgtggat tgaagacatc tcttttgtgc 11160
actcatatgt cctgacccct gcccagctag ggggactgag caacctccaa tactcaaggc 11220
tctacacgag gaacatcggt gacccgggaa ctactgcttt tgcagagatc aagcgattag 11280
aagcagtggg gttactaagt cctagtatta tgactaacat cttaactagg ccgcctggaa 11340
atggagattg ggccagtctg tgtaacgacc cttactcttt caattttgag actgtcgcga 11400
gtccaaatat tgtccttaag aaacatacac aaagagtcct atttgaaact tgttcaaatc 11460
ccttattatc tggcgtgcat acagaggata atgaggcaga agagaaggcg ttggctgaat 11520
ttttactcaa tcaagaagta attcatccac gtgtcgcaca tgctatcatg gaagcaagct 11580
ctataggtag gaggaagcag attcaagggc ttgttgacac aacaaacacc gtaatcaaga 11640
ttgcattgac taggaggcca cttggcatca agaggctgat gcggatagtt aactactcga 11700
gcatgcatgc aatgctgttt agagacgatg ttttctcatc taacaggtct aaccacccct 11760
tagtttcctc taatatgtgt tctctgacgc tagcagacta tgcacggaat agaagctggt 11820
caccattgac ggggggtaga aagatactgg gtgtatctaa tcctgatact atagaacttg 11880
tagagggtga gatccttagc gtcagcggag gatgcacaag atgtgacagc ggagatgaac 11940
aattcacttg gttccatctt ccgagcaata tagaactgac cgatgacacc agcaagaatc 12000
ctccgatgag agtgccgtac ctcgggtcaa agactcaaga gaggagggcc gcctcgcttg 12060
cgaaaatagc tcatatgtca ccacatgtga aagctgctct aagggcatca tccgtgttga 12120
tctgggctta tggagacaac gaagtaaatt ggactgctgc tcttaaaatt gcaagatctc 12180
ggtgcaatat aaactcagag tatcttcgac tattgtcccc cttacccaca gctgggaatc 12240
tccaacatag actggatgac ggcataactc agatgacatt cacccctgca tctctctaca 12300
gggtgtcacc ttatattcac atatccaatg attctcaaag gttattcacg gaagaaggag 12360
tcaaagaggg aaatgtagtt tatcagcaaa tcatgctctt gggtttatct ctaatcgaat 12420
cactcttccc gatgacgaca accaggacat acgatgagat cacattgcac ctccacagta 12480
aatttagctg ctgtatcagg gaagcaccgg ttgcagttcc tttcgagtta ctcgggatgg 12540
caccagaact aaggacagtg acctcaaata agtttatgta tgatcctagt cctgtatcgg 12600
agggtgactt tgcgagactt gacttagcta tctttaagag ttatgagctt aatctagaat 12660
catatcccac aatagagcta atgaacattc tttcaatatc cagcgggaag ttaatcggcc 12720
agtctgtggt ttcttatgat gaagatacct ccataaagaa tgacgccata atagtgtatg 12780
acaacacccg gaattggatc agcgaagctc agaattcaga tgtggtccgc ctattcgagt 12840
atgcagcact tgaagtgctt ctcgactgtt cttatcagct ctactatctg agagtaagag 12900
gcctagacaa tatcgtgttg tatatgagtg acttatataa gaatatgcca ggaattctac 12960
tttccaacat tgcagctaca atatctcatc ccatcattca ttcaagattg catgcagtag 13020
gcctggtcaa tcacgacggg tcacaccaac ttgcagacac agatttcatc gaaatgtctg 13080
caaaactatt agtctcttgc actcgacgcg tggtctcagg tttatatgca gggaataagt 13140
atgatctgct gttcccgtct gtcttagatg ataacctgag tgagaagatg cttcagctga 13200
tatctcggtt atgctgcctg tatacggtgc tctttgctac aacaagagag atcccgaaaa 13260
taagaggctt atctgcagaa gagaagtgtt cagtacttac tgagtaccta ctgtcagatg 13320
ctgtgaaacc attacttagt tctgagcaag tgagctctat catgtctcct aacatagtta 13380
cgttcccagc taatctatat tacatgtctc ggaagagcct taatttgatt agggaaagag 13440
aggacaggga cactatcttg gcattgttgt tcccccaaga gccactactt gagttcccct 13500
tagtacaaga tattggcgct cgagtgaaag atccattcac ccgacaacct gcggcgtttt 13560
tacaagaatt agatttgagc gctccagcaa ggtatgacgc atttacactt agtcaggttc 13620
attctgaaca cacatcacca aatccggagg acgactactt agtacgatac ctgttcagag 13680
gaatagggac cgcgtcctcc tcttggtata aggcatctca ccttctttct gtacctgagg 13740
tcagatgtgc aaggcacggg aattccttat acttggcaga aggaagcgga gccattatga 13800
gtcttctcga actgcatgtg ccgcatgaga ctatctatta caatacgctc ttctcaaacg 13860
agatgaaccc cccacagcgg catttcggac cgaccccaac acagtttctg aattcagttg 13920
tttataggaa tctacaggcg gaggtaccat gtaaggatgg atttgtccag gagttccgtc 13980
cattatggag agagaataca gaagaaagcg atctgacctc agataaagca gtgggttaca 14040
tcacatctgc agtgccctac cggtctgtat cattgctgca ctgtgacatt gagattcctc 14100
caggatccaa tcaaagctta ctggatcaac tggctaccaa tctgtctctg attgccatgc 14160
attctgtaag ggagggcggg gtcgtgatca tcaaagtgtt gtatgcaatg ggatattact 14220
tccatctact catgaacttg ttcactccgt gttctacgaa aggatatatt ctctctaatg 14280
gctatgcatg tagaggggat atggagtgtt acctggtatt tgtcatgggc tatcgaggtg 14340
ggcctacatt tgtacatgag gtagtgagga tggcaaaaac tctagtgcag cggcacggta 14400
cacttttgtc caaatcagat gagatcacac tgactaggtt atttacctca cagcggcagc 14460
gtgtaacaga catcctatcc agtcctttac cgagactaat aaagttcttg agaaagaata 14520
tcgatactgc gctaattgaa gccgggggac aacccgtccg tccattctgt gcagagagct 14580
tggtgaggac actagcggac acaactcaga tgacccagat catcgctagt cacattgaca 14640
cagtcattcg atctgtgatc tacatggagg ctgagggtga tctcgccgac acagtgttct 14700
tatttacccc ctacaatctc tctacagacg gtaaaaagag aacatcactt aaacagtgca 14760
caaggcagat cttagaggtc acaatattgg gtcttagagt tgaaaatctc aataaagtag 14820
gtgatgtagt cagtctagta cttaaaggta tgatttctct ggaggacctg atccctctaa 14880
gaacatactt gaagcgtagt acctgcccta agtatttgaa gtctgttcta ggtattacta 14940
aactcaaaga aatgtttaca gacacctctt tattatactt gactcgtgct caacaaaaat 15000
tctacatgaa aactataggc aacgcagtca agggatacta cagtaactgt gactcttaaa 15060
gataatcaca tattaatagg ctccttttct agttaactga gcccttgttg atttaatgat 15120
actatattag aaaaaagttg cactccgatc ctttaggact cgtgttcgaa ttcaaataat 15180
tgtcttagaa aaaagttgcg cgtaattgtt cttgaatgta gtcttgtcat tcaccaaatc 15240
tttgtttggt gggtcggcat ggcatctcca cctcctcgcg gtccgacctg ggcatccgaa 15300
ggaggacgca cgtccactcg gatggctaag ggagctagca taaccccttg ggcctctaa 15360 acgggtcttg aggggttttt tgctgaaagg aggaactata cggccgc 15407

<210> SEQ ID NO 25
<211> LENGTH: 8
<212> TYPE: PRT
<213> ORGANISM: artificial sequence
<220> FEATURE:
<223> OTHER INFORMATION: highly pathogenic avian influenza sequence - multiple basic amino acids

<400> SEQUENCE: 25

Arg Glu Arg Arg Arg Lys Lys Arg

-continued

```
1               5


<210> SEQ ID NO 26
<211> LENGTH: 4
<212> TYPE: PRT
<213> ORGANISM: artificial sequence
<220> FEATURE:
<223> OTHER INFORMATION: low pathogenic avian influenza sequence

<400> SEQUENCE: 26

Arg Glu Thr Arg
1
```

NEWCASTLE DISEASE VIRUS VECTORED AVIAN VACCINES

INCORPORATION BY REFERENCE

This application claims benefit of U.S. provisional application Ser. No. 61/166,481 filed Apr. 3, 2009.

FIELD OF THE INVENTION

The present invention encompasses NDV-vectored avian vaccines or compositions, in particular avian influenza vaccines. The vaccine may be an engineered avian vaccine.

BACKGROUND OF THE INVENTION

Several studies in recent years have highlighted the potential of Newcastle disease virus (NDV) to be used as a vaccine vector for avian diseases (Krishnamurthy et al., Virology 278, 168-182, 2000; Huang et al., J. Gen. Virol. 82, 1729-1736, 2001; Nakaya et al., J. Virol. 75, 11868-11873, 2001; Park et al. PNAS 103, 8203-8208, 2006; Veits et al PNAS 103, 8197-8202, 2006; Ge et al. J. Virol. 81, 150-158, 2007; Romer-Oberdörfer et al. Vaccine 26, 2307-2313, 2008).

NDV belongs to the Paramyxovirinae family and the *Avulavirus* genus. NDV replicates in respiratory and gastrointestinal tracts, in the oviduct, and for some isolates, in the nerve system. The transmission is aerogenic and by oral and fecal routes. NDV causes a highly contagious and fatal disease affecting all species of birds, and can infect some mammalian species. The disease can vary from clinically unapparent to highly virulent forms, depending on the virus strain and the host species. The continuous spectrum of virulence displayed by NDV strains enabled the grouping of them into three different pathotypes: lentogenic, mesogenic, and velogenic (Alexander, D. J., Diseases of Poultry, Iowa State Uni. Press, Ames Iowa, 541-569, 1997). Lentogenic strains do not usually cause disease in adult chickens and are widely used as live vaccines in poultry industries in the United States and other countries. Viruses of intermediate virulence are termed mesogenic, while viruses that cause high mortality are termed velogenic. The disease has a worldwide distribution and remains a constant major threat to commercial poultry production.

The NDV genome is a non-segmented negative strand of RNA of approximately 15 kb. The genomic RNA contains six genes that encode the following proteins in the order of: the nucleocapsid protein (NP), phosphoprotein (P), matrix protein (M), fusion protein (F), haemagglutinin-neuramimidase (FIN) and large polymerase protein (L). Two additional proteins, V and W, of unknown function are produced by RNA editing during P gene transcription (Steward et al., 1993, Journal of General Virology 74:2539-2547).

The development of methods to recover non-segmented negative RNA viruses entirely from cloned cDNA, established in recent years, opened up the possibility of genetically manipulating this virus group, including NDV (Conzelmann, K. K., Ann. Rev. Genet. 32, 123-162, 1998; Roberts and Rose, Virology 247, 1-6, 1998). This unique molecular genetic methodology, termed "reverse genetics," provides a means not only to investigate the functions of various virus-encoded genes (Palese et al., PNAS 93, 11354-11358, 1996; Nagai, Y., Rev. Med. Virol. 9, 83-99, 1999) but also to allow the use of these viruses to express heterologous genes (Bukreyev et al., J. Virol. 70, 6634-6641, 1996; Mebatsion et al., PNAS 93, 7310-7314, 1996; Schnell et al., PNAS 93, 11359-11365, 1996; Hasan et al., J. Gen. Virol. 78, 2813-2820, 1997; He et al., Virology 237, 249-260, 1997; Sakai et al., FEBS Lett. 45, 221-226, 1999). This provides a new method of generating improved vaccines and vaccine vectors.

The recovery systems from cloned cDNA, based on a lentogenic vaccine strain (LaSota) of NDV, were reported simultaneously by two independent groups in 1999 (Peeters et al., 1999; Romer-Oberdorfer et al., 1999). In the first reported system, the full-length NDV cDNA from LaSota strain (ATCC-VR699) was assembled in pOLTV5 transcription vector containing a T7 DNA-dependent-RNA polymerase promoter. Individual clones of the NDV transcriptase complex (NP, P, and L) were cloned in a eukaryotic expression vector. The cotransfection protocol generated several infective centers in infected monolayers (Peeters et al., J. Virol. 73, 5001-5009, 1999). The second system reported for recovery of a lentogenic NDV from cloned cDNA essentially used the same strategy of assembling the full-length antigenomic expression plasmid and support plasmids (Romer-Oberdorfer et al., Journal of General Virology, 80, 2987-2995, 1999). Other systems were developed recently to recover a lentogenic Hitchner B1 (Nakaya et al., 2001) or LaSota strain of NDV (Huang et al., 2001). The only system available for the recovery of recombinant mesogenic NDV was described by Krishnamurthy et al. (2000). This system utilized the vaccinia virus recombinant (MVA) and HEP-2 cells for transfection. The full length clone of the mesogenic strain Beaudette C and the support plasmids (N, P, and L) from the same strain were used for transfection. An additional transcriptional unit encoding the CAT reporter gene was placed between the HN and L genes. The growth of the rNDV expressing the CAT gene was delayed and the virus was attenuated. The CAT reporter gene was stably expressed for several passages in cell culture.

Avian influenza (AIV), sometimes called avian flu, and commonly recognized as bird flu refers to influenza caused by influenza viruses adapted to birds. AIV is a segmented, single-strand, negative sense RNA virus belonging to the family of Orthomyxoviridae, and is classified as a type A influenza virus. Type A virus is the most frequent cause of animal and human influenza. This type occurs in numerous strains or subtypes that are differentiated mainly on the basis of two surface lipid-enveloped membrane proteins, hemagglutinin (HA) and neuraminidase (NA). HA, facilitates entry of the virus into host cells, and NA assists in the release of progeny virus from infected cells (de Jong et al., J Clin Virol. 35(1):2-13, 2006). Influenza type A viruses are divided into subtypes based on their specific HA and NA content. There are 16 different HA subtypes, and 9 different NA subtypes. Many different combinations of HA and NA proteins are possible. Subtypes of influenza A virus are named according to their HA and NA surface proteins. For example, an "H7N2 virus" designates an influenza A subtype that has an HA protein of the H7 subtype and an NA protein from the N2 subtype. Similarly an "H5N1" virus has an HA of the H5 subtype and an NA from the N1 subtype. The H5N1 subtype has specifically been associated with recent outbreaks in Asia, Russia, the Middle East, Europe and Africa (Olsen et al., Science 21; 312(5772):384-8, 2006).

Influenza A viruses can infect humans, pigs, horses, seals, whales, poultry, cats, dogs, ferrets and other animals, but wild birds are their natural host. Aquatic birds constitute the main influenza reservoir from which virus lineages evolved and adapted to their host, e.g., human, swine and equine influenza. Host specificity is not absolute and cross-species transmission may occur as illustrated by the ability of highly pathogenic avian influenza (HPAI) H5N1 subtype to infect human, feline, canine and porcine species.

The highly pathogenic Influenza A virus subtype H5N1 virus is an emerging avian influenza virus of global concern as a potential pandemic threat. H5N1 has killed millions of poultry in a growing number of countries throughout Asia, Europe and Africa. Unlike type B influenza, type A influenza undergoes antigenic shift (at least two different strains of virus combine to form a new subtype) and epidemiologists, infectious disease investigators, and other health experts are acutely concerned that the co-existence of human flu viruses and avian flu viruses (especially H5N1) may provide an opportunity for genetic material to be exchanged between species-specific viruses, possibly creating a new virulent influenza strain that is easily transmissible and lethal to humans (Food Safety Research Information Office. "A Focus on Avian Influenza". Created May 2006, Updated November 2007).

Since the first H5N1 outbreak occurred in 1997, there has been an increasing number of HPAI H5N1 bird-to-human transmissions leading to clinically severe and fatal human infections. However, because there is a significant species barrier that exists between birds and humans, the virus does not easily cross over to humans. Although millions of birds have become infected with the virus since its discovery, only about 200 humans have died from Avian Flu in Indonesia, Laos, Vietnam, Romania, China, Turkey and Russia combined.

Considering the susceptibility of animals, including humans, to AIV, a means of preventing AIV infection and protecting animals is essential. Accordingly, there is a need for an effective vaccine against influenza.

Citation or identification of any document in this application is not an admission that such document is available as prior art to the present invention.

SUMMARY OF THE INVENTION

The invention is based, in part, on Applicants' discovery that the AIV hemagglutinin gene expressed by the enterotropic AVINEW® strain of Newcastle Disease Virus (NDV) was highly immunogenic in avians.

The present invention relates to an NDV-vectored avian vaccine or composition that may comprise an effective amount of an engineered NDV vector with inherent enteric tropism that harbors and expresses certain avian antigens, more specifically an avian influenza antigen, and a pharmaceutically or veterinarily acceptable carrier, excipient, or vehicle. The enterotropic NDV may be the NDV strain of the AVINEW® modified live vaccine commercialized by Merial Limited.

The avian influenza antigen may be a hemagglutinin. The avian influenza HA antigen may be an HA from the H5 subtype.

The invention also relates to a method of vaccinating an avian comprising administering to the avian an effective amount of a vaccine which may comprise an effective amount of a recombinant NDV vector and a pharmaceutically or veterinarily acceptable carrier, excipient, or vehicle. The administering may be by in ovo, eye drop, spray, drinking water or parenteral (subcutaneous, intramuscular, transdermal) administration.

The invention relates to a method for modifying the genome of Avinew NDV to produce engineered Avinew NDV, wherein the method comprises the introduction into the Avinew NDV genome an isolated polynucleotide in a nonessential region of the Avinew NDV genome. The nonessential region may be an open reading frame encoding a nonessential protein or a non-essential part of an open reading frame; or an untranslated (or non-coding) region located upstream the NP gene, or between two genes (intergenic regions), or downstream from the L gene of the Avinew NDV genome.

The invention further relates to administration of the vaccine or composition using prime-boost protocol. The invention relates to priming the avian with an avian influenza vaccine prior to administration of the vaccine of the present invention that may comprise an effective amount of an engineered NDV vector and a pharmaceutically or veterinarily acceptable carrier, excipient, or vehicle. Alternatively, the invention further relates to priming with the vaccine of the present invention (the engineered NDV vector expressing at least one avian influenza antigen and a pharmaceutically or veterinarily acceptable carrier) prior to administration of an avian influenza vaccine.

The invention further encompasses a kit for performing a method of eliciting or inducing an immune response that may comprise any one of the recombinant influenza immunological compositions or vaccines, or inactivated immunological compositions or vaccines, and instructions for performing the method.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may be best understood in conjunction with the accompanying drawings, in which:

FIGS. 4*a*-4*o* provide the sequence of the insert of the plasmid pIV0291. Italics refer to non AVINEW® sequence and underlined italics refer to an internal PacI-FseI insertion between the P and the M genes, italics refer to HDV ribozyme (3' end) and underlined italics refer to T7 promoter (5' end) and terminator (3' end). The start sequences of transcription (GS=Gene Start) and the transcription termination sequences (GE=Gene End) are indicated in the map and the sequences are underlined. An encircled T (position 3190 in FIG. 4c) refers to a surrounded nucleotide (before PacI-FseI insertion): this is a T (position 3190 of SEQ ID NO:24) in the assembled AVINEW® genome into the transcription vector (T comes from the primer used for creating the PacI and FseI restriction sites). In the consensus AVINEW® genome (SEQ ID NO:1), the nucleotide at the corresponding position 3150 is a C.

FIGS. 12A and 12B are a table showing the SEQ ID NO assigned to DNA and protein sequences.

FIGS. 25A, 25B and 25C provide the sequence alignment between the avian influenza HA proteins and sequence identity percentage at the amino acid level.

FIGS. 26A, 26B, 26C, 26D, 26E and 26F provide the sequence alignment between the avian influenza HA proteins and sequence identity percentage at the nucleic acid level.

DETAILED DESCRIPTION

Figure 1A:
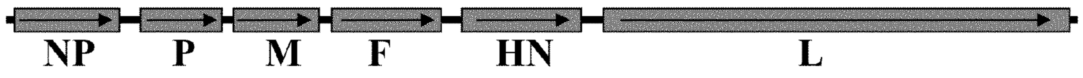
FIG. 1A depicts a genetic map of the full length NDV genome.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

In the present invention, AVINEW vaccine strain is used as the vector. AVINEW is a live NDV vaccine (Merial Limited) that is widely used worldwide. This vaccine strain is naturally avirulent and presents a double respiratory and enteric tropism. Furthermore, the AVINEW strain belongs to a NDV genogroup (Class II, Genotype I) that may infect ducks. In contrast to LaSota, whose tropism is essentially directed to the respiratory tract, it does not induce respiratory side reactions.

The present invention relates to an avian vaccine that may comprise an effective amount of an engineered NDV vector and a pharmaceutically or veterinarily acceptable carrier, excipient, or vehicle.

The present invention encompasses any engineered NDV vector expressing a protein, polypeptide, antigen, epitope or immunogen that elicits an immunogenic response in an animal, such as an avian. The protein, polypeptide, antigen, epitope or immunogen may be an influenza protein, polypeptide, antigen, epitope or immunogen, such as, but not limited to, a protein, polypeptide, peptide or fragment(s) thereof, that elicit, induce or stimulate a response in an animal, such as an avian.

By "animal" is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

In one embodiment, the avian influenza immunological composition or vaccine comprises an engineered vector and a pharmaceutical or veterinary acceptable excipient, carrier or vehicle. The engineered vector may be an NDV expression vector which may comprise a polynucleotide encoding an influenza protein, polypeptide, antigen, epitope or immunogen. The influenza protein, polypeptide, antigen, epitope or immunogen, may be a hemagglutinin, matrix protein, neuraminidase, nonstructural protein, nucleoprotein, polymerase, or any fragment thereof.

In another embodiment, the influenza protein, polypeptide, antigen, epitope or immunogen may be derived from an avian infected with influenza or an avian influenza strain. The avian influenza protein, antigen, epitope or immunogen may be a hemagglutinin (HA) such as, but not limited to, HA precursor, H1, H2, H3, H4, H5, H6, H7, H8, H9, H10, H11, H12, H13, H14, H15, or H16 protein, matrix protein (such as, but not limited to, matrix protein M1 or M2), neuraminidase (such as, but not limited to, NA1, NA2, NA3, NA4, NA5, NA6, NA7, NA8, or NA9), nonstructural (NS) protein (such as, but not limited to, N1 or NS2), nucleoprotein (NP) and polymerase (such as, but not limited to, PA polymerase, PB1 polymerase 1 or PB2 polymerase 2).

The avian influenza antigen may be a hemagglutinin, such as an H5 HA. In one embodiment, the H5 is isolated from the H5N1 A/turkey/Turkey/1/2005 (clade 2.2), A/chicken/Indonesia/7/2003 (clade 2.1), the A/duck/Laos/3295/2006 (clade 2.3), the A/chicken/West Java/PWT-WIJ/2006 (clade 2.1) strains.

In another embodiment, the avian influenza protein, polypeptide, antigen, epitope or immunogen may be derived from an avian infected with influenza or an avian influenza strain derived from a recent isolate of any subtype.

As used herein, the term "antigen" or "immunogen" means a substance that induces a specific immune response in a host animal. The antigen may comprise a whole organism, killed, attenuated or live; a subunit or portion of an organism; a recombinant vector containing an insert expressing an epitope, polypeptide, peptide, protein, or fragment thereof with immunogenic properties; a piece or fragment of nucleic acid capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope, also known as antigenic determinant, is the part of a macromolecule recognized by the immune system and able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term epitope is the part of a macromolecule recognized by the immune system and able to induce an immune reaction of the humoral type (B cells) and/or cellular type (T cells). The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708, 871; Geysen et al., 1984; Geysen et al., 1986, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in the PCT Application Serial No. PCT/US2004/022605 incorporated herein by reference in its entirety.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, preferably at least about 5 amino acids, more preferably at least about 10-15 amino acids, and most preferably about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of an influenza protein or polyprotein. A polynucleotide encoding a fragment of the total protein or polyprotein, more advantageously, comprises or consists essentially of or consists of a minimum of 15 nucleotides, advantageously about 30-45 nucleotides, and preferably about 45-75, at least 57, 87 or 150 consecutive or contiguous nucleotides of the sequence encoding the total protein or polyprotein. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999), and in PCT Application Serial No. PCT/US2004/022605 all of which are incorporated herein by reference in their entireties can be used in the practice of the invention, without undue experimentation. Other documents cited and incorporated herein may also be consulted for methods for determining epitopes of an immunogen or antigen and thus nucleic acid molecules that encode such epitopes.

A "polynucleotide" is a polymeric form of nucleotides of any length that contains deoxyribonucleotides, ribonucleotides, and analogs in any combination. Polynucleotides may have three-dimensional structure, and may perform any function, known or unknown. The term "polynucleotide" includes double-, single-stranded, and triple-stranded helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The term "codon optimization" refers to the process of optimally configuring the nucleic acid sequence encoding a protein, polypeptide, antigen, epitope, domain or fragment for expression/translation in a selected host. In general, gene expression levels depend on many factors, such as promoter sequences and regulatory elements. One of the most important factors is the adaptation of the codon usage of the transcript gene to the typical codon usage of the host (Lithwich, G. and Margalit, H., Genome Res. 13, 2665-2673, 2003). Therefore, highly expressed genes in prokaryotic genomes under translational selection have a pronounced codon usage bias. This is because they use a small subset of codons that are recognized by the most abundant tRNA species (Ikemura, T., J. Mol. Biol. 151, 389-409, 1981). The force that modulates this codon adaptation is called translational selection and its strength is important in fast-growing bacteria (Rocha, E. P., Genome Res. 14, 2279-2286, 2004; Sharp, P. M. et al., Nucleic Acids Res. 33, 1141-1153). If a gene contains codons that are rarely used by the host, its expression level will not be maximal. This may be one of the limitations of heterologous protein expression (Gustafsson, C. et al., Trends Biotechnol. 22, 346-353, 2004) and the development of DNA vaccines (Ivory, C. and Chadee, K., Genet. Vaccines Ther. 2, 17, 2004). A high number of synthetic genes have been re-designed to increase their expression level. The Synthetic Gene Database (SGDB) (Wu G. et al., Nucleic Acids Res. 35, D76-D79, 2007) contains information from more than 200 published experiments on synthetic genes. In the design process of a nucleic acid sequence that will be inserted into a new host to express a certain protein in optimal amounts, codon usage optimization is usually one of the first steps (Gustafsson, C., Trends Biotechnol. 22, 346-353, 2004). Codon usage optimization basically involves altering the rare codons in the target gene so that they more closely reflect the codon usage of the host without modifying the amino acid sequence of the encoded protein (Gustafsson, C., Trends Biotechnol. 22, 346-353, 2004). The information usually used for the optimization process is therefore the DNA or protein sequence to be optimized and a codon usage table (reference set) of the host.

There are several public web servers and stand-alone applications that allow some kind of codon optimization by anyone skilled in the art. '*GeneDesign*' (Richardson, S. M. et al., Genome Res. 16, 550-556, 2006), '*Synthetic Gene Designer*' (Wu G. et al., Protein Expr. Purif. 47, 441-445, 2006) and '*Gene Designer*' (Villalobos, A. et al., BMC Bioinformatics 7, 285, 2006) are packages that provide a platform for synthetic gene design, including a codon optimization step. With regard to the methods for codon usage optimization available in each server or program, the first programs developed used only the 'one amino acid-one codon' approach. More recent programs and servers now include further methods to create some codon usage variability. This variability reflects the codon usage variability of natural highly expressed genes and enables additional criteria to be introduced (such as the avoidance of restriction sites) in the optimization process. Most applications and web servers described herein provide three methods of codon optimization: a complete optimization of all codons, an optimization based on the relative codon usage frequencies of the reference set that uses a Monte Carlo approach and a novel approaches designed to maximize the optimization with the minimum changes between the query and optimized sequences. In one embodiment herein, the sequences encoding the protein complement of NDV are codon optimized for expression in avian cells, in a preferred embodiment the nucleic acid sequences that encode NDV P, L and NP are codon optimized for expression in avian cells. In yet another embodiment, the nucleic acid sequence encoding the recombinant protein, antigen, peptide, polypeptide, fragment, domain, or epitope is codon optimized for expression in avian. In another embodiment, the codon optimized sequences encode AIV proteins, antigens, peptides, polypeptides, fragments, domains, or epitopes for avian expression. In yet another embodiment, the codon optimized sequences encode AIV HA and/or N proteins, antigens, peptides, polypeptides, fragments, domains, or epitopes for avian expression.

The following are non-limiting examples of polynucleotides: a gene or gene fragment, exons, introns, mRNA, tRNA, rRNA, siRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The invention further comprises a complementary strand to a polynucleotide encoding an influenza protein, antigen, epitope or immunogen. The complementary strand can be polymeric and of any length, and can contain deoxyribonucleotides, ribonucleotides, and analogs in any combination thereof.

The terms “protein”, “peptide”, “polypeptide” and “polypeptide fragment” are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An “isolated” polynucleotide or polypeptide is one that is substantially free of the materials with which it is associated in its native environment. By substantially free, is meant at least 50%, at least 70%, at least 80%, at least 90%, or at least 95% free of these materials.

Hybridization reactions can be performed under conditions of different “stringency.” Conditions that increase stringency of a hybridization reaction are well known. See for example, “Molecular Cloning: A Laboratory Manual”, second edition (Sambrook et al., 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the influenza polypeptides and functionally equivalent fragments thereof that may enhance, decrease or not significantly affect inherent properties of the polypeptides encoded thereby. These functionally equivalent variants, derivatives, and fragments display the ability to retain influenza activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the influenza polynucleotide or polypeptide of interest.

In one aspect, the present invention provides influenza polypeptides, particularly avian influenza polypeptides. In another aspect, the present invention provides a polypeptide having a sequence as set forth in SEQ ID NO: 15, 17, 19, 21, or 23, and variant or fragment thereof.

In another aspect, the present invention provides a polypeptide having at least 70%, at least 75%, at least 80%, at least 85%, at least 90%, at least 95%, 96%, 97%, 98% or 99% sequence identity to an avian HA polypeptide of the invention, particularly to the polypeptides having a sequence as set forth in SEQ ID NO: 15, 17, 19, 21, or 23.

In yet another aspect, the present invention provides fragments and variants of the influenza polypeptides identified above (SEQ ID NO: 15, 17, 19, 21 and 23) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 15, 17, 19, 21, or 23.

An immunogenic fragment of an influenza polypeptide includes at least 8, 10, 15, or consecutive amino acids, at least 21 amino acids, at least 23 amino acids, at least 25 amino acids, or at least 30 amino acids of an influenza polypeptide having a sequence as set forth in SEQ ID NO: 2, 4, 5, 8, 10, 12, or 14, or variants thereof. In another embodiment, a fragment of an influenza polypeptide includes a specific antigenic epitope found on a full-length influenza polypeptide.

In another aspect, the present invention provides a polynucleotide encoding an influenza HA polypeptide, such as a polynucleotide encoding a polypeptide having a sequence as set forth in SEQ ID NO: 15, 17, 19, 21, or 23. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 15, 17, 19, 21, or 23, or a conservative variant, an allelic variant, a homolog or an immunogenic fragment comprising at least eight or at east ten consecutive amino acids of one of these polypeptides, or a combination of these polypeptides. The polynucleotide encoding the influenza HA polypeptide may be codon-optimized for expression in a specific animal species. The HA protein may be modified at the cleavage site from a highly pathogenic avian influenza sequence (multiple basic amino acids: RERRRKKR-SEQ ID NO:25) to a low pathogenic avian influenza sequence (RETR-SEQ ID NO:26).

In another aspect, the present invention provides a polynucleotide having a nucleotide sequence as set forth in SEQ ID NO: 14, 16, 18, 21, 22, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 14, 16, 18, 21, 22, or a variant thereof.

For the purposes of the present invention, sequence identity or homology is determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin et al., 1990 modified as in Karlin et al., 1993.

Another example of a mathematical algorithm used for comparison of sequences is the algorithm of Myers et al., 1988. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson et al., 1988.

In general, comparison of amino acid sequences is accomplished by aligning an amino acid sequence of a polypeptide of a known structure with the amino acid sequence of a polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence identity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}$=8; $N_{dif}$=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur et al., 1983, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Vector NTI Software™, Invitrogen Inc. CA, USA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

And, without undue experimentation, the skilled artisan can consult with many other programs or references for determining percent homology.

The invention further encompasses the influenza polynucleotides contained in a vector molecule or an expression vector and operably linked to a promoter element and optionally to an enhancer.

A "vector" refers to a recombinant DNA or RNA plasmid, bacteriophage, or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes vectors for cloning as well as viral vectors.

The term "engineered" or "recombinant" means a polynucleotide of semisynthetic, or synthetic origin that either does not occur in nature or is linked to another polynucleotide in an arrangement not found in nature.

"Heterologous" means derived from a genetically distinct entity from the rest of the entity to which it is being compared. For example, a polynucleotide may be incorporated by genetic engineering techniques into a plasmid or vector derived from a different source, and is thus a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an influenza polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. an influenza peptide, advantageously, in the vector, an ATG is placed at 5' of the reading frame and a stop codon is placed at 3'. Other elements for controlling expression may be present, such as enhancer sequences, stabilizing sequences, such as intron and or untranslated 5' or 3' sequences and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450; 6,312,683, and 6,596,279; U.S. patent application Ser. No. 920,197, filed Oct. 16, 1986; WO 90/01543; W091/11525; WO 94/16716; WO 96/39491; WO 98/33510; EP 265785; EP 0 370 573; Andreansky et al., 1996; Ballay et al., 1993; Felgner et al., 1994; Frolov et al., 1996; Graham, 1990; Grunhaus et al., 1992; Ju et al., 1998; Kitson et al., 1991; McClements et al., 1996; Moss, 1996; Paoletti, 1996; Pennock et al., 1984; Richardson (Ed), 1995; Smith et al., 1983; Robertson et al., 1996; Robinson et al., 1997; and Roizman, 1996. The herein cited and incorporated herein by reference documents, in addition to providing examples of vectors useful in the practice of the invention, can also provide sources for non-influenza peptides or fragments thereof to be expressed by vector or vectors in, or included in, the compositions of the invention.

The present invention also relates to preparations comprising vectors, such as expression vectors, e.g., prophylactic or therapeutic compositions. The preparations can comprise, consist essentially of, or consist of one or more vectors, e.g., expression vectors, such as in vivo expression vectors, comprising, consisting essentially or consisting of (and advantageously expressing) one or more of influenza polypeptides, antigens, epitopes or immunogens. The vector contains and expresses a polynucleotide that comprises, consists essentially of, or consists of a polynucleotide coding for (and advantageously expressing) an influenza antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of an influenza polypeptide, antigen, epitope or immunogen (e.g., hemagglutinin, neuraminidase, nucleoprotein) or a fragment thereof.

According to another embodiment, the vector or vectors in the preparation comprise, or consist essentially of, or consist of polynucleotide(s) encoding one or more proteins or fragment(s) thereof of an influenza polypeptide, antigen, epitope or immunogen, the vector or vectors expressing the polynucleotide(s). The inventive preparation comprises, consists essentially of, or consists of, at least two vectors comprising, consisting essentially of, or consisting of, and advantageously also expressing, in vivo under appropriate conditions or suitable conditions or in a suitable host cell, polynucleotides from different influenza isolates encoding the same proteins and/or for different proteins. Preparations containing one or more vectors comprising, consisting essentially of or consisting of polynucleotides encoding, and advantageously expressing, in vivo, an influenza polypeptide, antigen, fusion protein or an epitope thereof. The invention is also directed at mixtures of vectors that contain, consist essentially of, or consist of coding for, and express, different influenza proteins, polypeptides, antigens, epitopes or immunogens, e.g., an influenza polypeptide, antigen, epitope or immunogen from different species such as, but not limited to, humans, horses, pigs, seals, whales, in addition to avian species including chicken, turkeys, ducks and geese.

The term plasmid covers any DNA transcription unit comprising a polynucleotide according to the invention and the elements necessary for its in vivo expression in a cell or cells of the desired host or target; and, in this regard, it is noted that a supercoiled plasmid and all of its topoisomers, open-circular plasmid, as well as linear forms of the plasmid, are intended to be within the scope of the invention.

Each plasmid comprises or contains or consists essentially of, in addition to the heterologous polynucleotide encoding a recombinant protein, antigen, epitope or immunogen, optionally fused with a polynucleotide encoding an heterologous peptide sequence, variant, analog or fragment, operably linked to a promoter or under the control of a promoter or dependent upon a promoter. In general, it is advantageous to employ a strong promoter that is functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter segment, which may or may not be associated with the enhancer segment. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter is either of a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e g, akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., 1979).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Advantageous host cells include, but are not limited to, baby hamster kidney (BHK) cells, colon carcinoma (Caco-2) cells, COS7 cells, MCF-7 cells, MCF-10A cells, Madin-Darby canine kidney (MDCK) lines, mink lung (MvlLu) cells, MRC-5 cells, U937 cells and VERO cells. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In one embodiment of the present invention, the vector is a Newcastle Disease Virus (NDV) vector. Newcastle disease virus also designated as avian paramyxovirus 1 (APMV1, family Paramyxoviridae, subfamily Paramyxovirinae, genus *Avulavirus*) is an avian pathogen whose naturally occurring strains exhibit a wide range of disease severity. NDV is particularly advantageous as a vaccine vector for veterinary use because the vector itself serves as a needed poultry vaccine. NDV strain pathotypes are asymptomatic enteric (e.g., Ulster 2C, Queensland V4), lentogenic (e.g., Hitchner B1, F (e.g., Asplin), La Sota), mesogenic (e.g., strain H, Mukteswar, Roakin, Beaudette C) or velogenic (e.g., Texas GB, NY parrot 70181, Italien, Milano, Herts 33/56). Advantages of avian influenza vector vaccines based on the NDV vector include, but are not limited to, (1) induce a broad immunity, including humoral, cellular and mucosal responses (2) do not express NP and M proteins and therefore is compatible with the DIVA (differentiate infected from vaccinated animals) strategy, (3) induce rapid onset of immunity, (4) bivalent and (5) production poses less risk for the environment than inactivated vaccines in case of accidental release.

Certain characteristics of NDV suggest that recombinant NDV (rNDV) or engineered NDV expressing a foreign viral protein would be very good vaccine candidates. NDV grows to very high titers in many cell lines and eggs, and it elicits strong humoral and cellular immune responses in vivo. NDV naturally infects via respiratory and alimentary tract mucosal surfaces, so it is especially useful to deliver protective antigens of respiratory disease pathogens such as AIV. In addition, commercially available live NDV vaccines are widely used in the United States and most other countries. Vaccines based on live NDV recombinants may also have advantages over other live recombinant vaccine vectors. First, the foreign protein is expressed with only a few NDV proteins. In contrast, pox and herpes virus vectors express a large number of additional proteins from their large-size genomes. For the generation of specific immune responses in vaccine applications, it may be advantageous to have only a limited number of proteins expressed. Second, NDV replicates in the cytoplasm of the infected cells without a DNA phase, which eliminates the problem of integration of viral genome into the host cell DNA. The virus does not undergo detectable genetic recombination Another application of reverse genetics is to develop a more effective and better NDV vaccine as described herein. Current NDV vaccines utilize naturally occurring lentogenic strains, such as the Hitchner B1 and LaSota. As encountered with other live attenuated vaccines, the current NDV vaccines may still cause disease due to reversion to virulence. The choice of the NDV vaccine strain as the vector is important since first data reported with the Hitchner B1 NDV strain were disappointing. Later, data obtained with the LaSota NDV strain was encouraging and vaccine candidates based on this strain are being used in the field in China and Mexico.

The invention herein, describes the applicant's use of the NDV AVINEW® vaccine strain as the vector for delivery of recombinant-derived antigens to avians. More specifically the antigens may be avian influenza virus (AIV) antigens. AVINEW® is a live NDV vaccine developed by Merial Ltd. that is used worldwide. This vaccine strain is naturally avirulent and presents a double respiratory and enteric tropism. The divergent tropism in avians may afford unique biological characteristics to recombinant NDV (rNDV) or engineered NDV vaccines that utilize the AVINEW® backbone for gene delivery in avians with respect to interference from Maternally-Derived Antibodies (MDA) to NDV itself. Such resistance to MDA may allow active immunization of commercial and wild-type avians that may inherently have significant levels of NDV-specific MDAs and otherwise be recalcitrant to more conventional recombinant NDV immunization.

Furthermore, the AVINEW® strain belongs to a NDV genogroup or type (Class 2, genotype I) that may infect ducks. In contrast to LaSota, whose tropism is essentially directed to the respiratory tract, the AVINEW® strain does not induce respiratory side reactions.

In one embodiment, the NDV vector is NDV AVINEW®. The NDV vector may also be the vector of U.S. Pat. No. 5,118,502, in particular the strain deposited as ATCC No. VR 2239.

One embodiment of the invention provides the genomic DNA sequence and encoded protein sequences of AVINEW. The genomic DNA sequence of AVINEW NDV strain has a polynucleotide sequence as set forth in SEQ ID NO:1. The AVINEW genomic cDNA sequence (SEQ ID NO:1) is different from the VG/GA sequence (GenBank Accession No. EU289028). The sequence identity between AVINEW (SEQ ID NO:1) and VG/GA (EU289028) genomic sequences is 89.6%. The amino acid sequence identity between the proteins of the Avinew strain and the VG/GA strain is: 95.9% for NP protein (SEQ ID NO:3 of Avinew and GenBank No. ABZ80386), 89.7% for P protein (SEQ ID NO:5 of Avinew v. GenBank ABZ80387), 94.2% for M protein (SEQ ID NO:7 of Avinew v. GenBank No. ABZ80388), 92.4% for F protein (SEQ ID NO:9 of Avinew v. GenBank No. ABZ80389), 88.1% for HN protein (SEQ ID NO:11 of Avinew v. GenBank No. ABZ80390), and 96.9% for L protein (SEQ ID NO:13 of Avinew v. GenBank No. ABZ80391). The nucleic acid sequence identity between the genes of the Avinew train and the VG/GA strain is: 90.6% for NP gene (SEQ ID NO:2 of Avinew v. 122-1591 bp of EU289028), 88.6% for P gene (SEQ ID NO:4 of Avinew v. 1887-3074 bp of EU289028), 90.1% for M gene (SEQ ID NO:6 of Avinew v. 3290-4384 bp of EU289028), 90.0% for F gene (SEQ ID NO:8 of Avinew v. 4544-6205 bp of EU289028), 84.7% for FIN gene (SEQ ID NO:10 of Avinew v. 6412-8145 bp of EU289028), and 90.9% for L gene (SEQ ID NO:12 of Avinew v. 8381-14995 bp of EU289028). Comparison of the complete genomic and individual gene sequences with other available NDV reference sequences showed that the AVINEW NDV strain is genetically closely related to the Australian lentogenic strains 98-1154 and the Queensland V4. The sequence of the NDV 98-1154 complete genome is depicted in GenBank AY935491. The sequence identity between ANIVEW (SEQ ID NO:1) and AY935491 genomic sequences is 98.8%. The amino acid sequence identity between the proteins of the Avinew strain and the VG/GA strain is: 99.8% for NP protein (SEQ ID NO:3 of Avinew v. GenBank No. AAX45376), 97.7% for P protein (SEQ ID NO:5 of Avinew v. GenBank No. AAX45377), 98.4% for M protein (SEQ ID NO:7 of Avinew v. GenBank No. AAX45378), 98.7% for F protein (SEQ ID NO: 9 of Avinew v. GenBank No. AAX45379), 92.4% for FIN protein (SEQ ID NO:11 of Avinew v. GenBank No. AAX45380), and 99.5% for L protein (SEQ ID NO:13 of Avinew v. GenBank No. AAX45381). The nucleic acid sequence identity between the genes of the Avinew train and the VG/GA strain is: 99.0% for NP gene (SEQ ID NO:2 of Avinew v. 122-1591 bp of AY935491), 98.2% for P gene (SEQ ID NO:4 of Avinew v. 1887-3074 bp of AY935491), 98.6% for M gene (SEQ ID NO:6 of Avinew v. 3290-4384 bp of AY935491), 98.8% for F gene (SEQ ID NO:8 of Avinew v. 4544-6205 bp of AY935491), 93.1% for HN gene (SEQ ID NO:10 of Avinew v. 6412-8154 bp of AY935491), and 98.8% for L gene (SEQ ID NO:12 of Avinew v. 8381-14995 bp of AY935491). Only partial sequences are available in GenBank for Queensland V4.

In another embodiment, the invention provides a polynucleotide having a sequence as set forth in SEQ ID NO:1, 2, 4, 6, 8, 10, 12, or 24, and variant or fragment thereof. The invention further comprises a complementary strand to a polynucleotide described herein. In yet another embodiment, the invention provides a polypeptide having a sequence as set forth in SEQ ID NO:3, 5, 7, 9, 11, or 13, and variant or fragment thereof.

In another aspect, the present invention provides a genomic cDNA of AVINEW having the sequence as set forth in SEQ ID NO:1 or SEQ ID NO:24. In yet another embodiment, the polynucleotide is a reverse complementary strand of the polynucleotide having the sequence as set forth in SEQ ID NO:1 or SEQ ID NO:24. In yet another embodiment, the polynucleotide or a reverse complementary strand of a polynucleotide of the present invention has at least 70%, at least 75%, at least 80%, at least 85%, at least 90%, at least 95%, 96%, 97%, 98% or 99% sequence identity to a polypeptide having a sequence as set forth in SEQ ID NO:1 or SEQ ID NO:24.

In one embodiment, the present invention provides a fragment of polynucleotide encoding an AVINEW polypeptide, such as a polynucleotide encoding a polypeptide having a sequence as set forth in SEQ ID NO: 3, 5, 7, 9, 11, or 13. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 3, 5, 7, 9, 11, or 13, or a conservative variant, an allelic variant, a homolog or an immunogenic fragment comprising at least eight or at east ten consecutive amino acids of one of these polypeptides, or a combination of these polypeptides.

In another aspect, the present invention provides a polynucleotide having a nucleotide sequence as set forth in SEQ ID NO:1, 2, 4, 6, 8, 10, 12, or 24, or a variant thereof. In yet another embodiment, the polynucleotide is a reverse complementary strand of the polynucleotide having the sequence as set forth in SEQ ID NO:1, 2, 4, 6, 8, 10, 12, or 24. In yet another aspect, the present invention provides a polynucleotide or a reverse complementary strand of a polynucleotide having at least 70%, at least 75%, at least 80%, at least 85%, at least 90%, at least 95%, 96%, 97%, 98% or 99% sequence identity to one of a polynucleotide having a sequence as set forth in SEQ ID NO:1, 2, 4, 6, 8, 10, 12, or 24, or a variant thereof.

In one aspect, the present invention relates to a pharmaceutical composition or vaccine for inducing an immunological response in a host animal inoculated with the vaccine or composition, the composition including a pharmaceutical acceptable carrier and a modified AVINEW recombinant virus. In yet another aspect of the invention, the engineered AVINEW virus includes, within a non-essential region of the virus genome, a heterologous DNA sequence which encodes an antigenic protein derived from a pathogen wherein the vaccine when administered to a host, is capable of inducing an immunological response specific to the protein encoded by the pathogen.

The term "nonessential region" refers to a region of a virus genome which is not essential for replication and propagation of the virus in tissue culture and whose deletion or inactivation may reduce virulence in a variety of animal systems. Any nonessential region or portion thereof can be deleted from the AVINEW genome or a foreign sequence can be inserted in it, and the viability and stability of the engineered AVINEW resulting from the deletion or insertion can be used to ascertain whether a deleted region or portion thereof is indeed nonessential. In another embodiment, the nonessential region of the AVINEW genome is the region between P gene and M gene, or the region between M gene and F gene of AVINEW genome. In yet another embodiment, the nonessential region may be in the region of 3075 nt-3289 nt or 4385 nt-4543 nt of SEQ ID NO:1, 3115 nt-3353 nt or 4449 nt-4607 nt of SEQ ID NO:24.

One aspect of the invention relates to NDV vectors expressing avian antigens. The antigen may be avian influenza antigen. The avian influenza antigen may be a hemagglutinin, such as H5 HA.

NDV vectors expressing avian influenza genes, such as a construct of NDV expressing a H5 subtype avian influenza virus (AIV) hemagglutinin (HA) with both a wild-type and mutated HA open reading frame (ORF) from the HPAIV wild bird isolate, A/Bar-headed goose/Qinghai/3/2005 (H5N1) inserted into the intergenic region between the P and M genes of the LaSota NDV vaccine strain (e.g., Ge et al., Journal of Virology, January 2007, vol. 81, no. 1, pp. 105-158), a complete cDNA clone of the Newcastle disease virus (NDV) vaccine strain Hitchner B1 expressing an influenza virus submitted to GenBank under accession number AF375823 (see, e.g., Nakaya et al., Journal of Virology, December 2001, pp. 11868-11873), a NDV recombinant (NDVH5Vm) which expresses the H5 protein of HPAIV A/chicken/Vietnam/P41/05 (H5N1) (see, e.g., Römer-Oberdörfer et al., Vaccine. 2008 May 2; 26(19):2307-13. Epub 2008 Mar. 18), rNDV-AIV-H7 constructed using a lentogenic paramyxovirus type 1 vector (NDV B1 strain) with insertion of the hemagglutinin (HA) gene from avian influenza virus (AIV) A/chicken/NY/13142-5/94 (H7N2) (see, e.g., Swayne et al., Avian Diseases 47:1047-1050, 2003), a NDV-expressing avian influenza virus (AIV) hemagglutinin (HA) of subtype H5 constructed by reverse genetics (see, e.g., Veits et al., PNAS, May 23, 2006, vol. 103, no. 21, pp. 8197-8202) and a recombinant NDV-H5 expressing the HA gene of AIV A/chicken/Vietnam/P41/2005 (H5N1) based on lentogenic NDV vaccine strain Clone 30 (see, e.g., Veits et al., Vaccine (2008) 26, 1688-1696) are also contemplated for the present invention.

In yet another embodiment of the present invention, an avian influenza virus expressing NDV genes, such as a chimeric avian influenza virus that expresses the ectodomain of the hemagglutinin-neuraminidase gene of NDV instead of the neuraminidase protein of the H5N1 avian influenza virus or a bivalent vaccine expressing the ectodomain of an H7 avian influenza virus hemagglutinin into a fusogenic and attenuated NDV gene (containing only its ectodomain, with the transmembrane and cytoplasmic domains derived from the F protein of NDV) (see, e.g., Park et al., PNAS, May 23, 2006, vol. 103, no. 21, pp. 8203-8308) are also contemplated.

In one embodiment, the invention provides for the administration of a therapeutically effective amount of a formulation for the delivery and expression of a protein, antigen, epitope or immunogen in a target cell. Determination of the prophylactically or therapeutically effective amount is routine experimentation for one of ordinary skill in the art. In another embodiment, the formulation comprises an expression vector comprising a polynucleotide that expresses an influenza antigen, epitope or immunogen and a pharmaceutically or veterinarily acceptable carrier, vehicle or excipient. In another embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be sterile water, a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

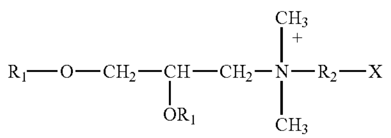

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

In another embodiment, pharmaceutically or veterinarily acceptable carrier, excipient, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (Tween 80®), available from AppliChem, Inc., Cheshire, Conn.) and sorbitan esters (e.g., sorbitan monooleate (Span 80®), available from Sigma Aldrich, St. Louis, Mo.). In addition, with respect to a water-in-oil emulsion, see also U.S. Pat. No. 6,919,084, e.g., Example 8 thereof, incorporated herein by reference. In some embodiments, the antigen-containing aqueous phase comprises a saline solution comprising one or more buffering agents. An example of a suitable buffering solution is phosphate buffered saline. In an advantageous embodiment, the water-in-oil emulsion may be a water/oil/water (W/O/W) triple emulsion (see, e.g., U.S. Pat. No. 6,358,500, incorporated herein by reference). Examples of other suitable emulsions are described in U.S. Pat. No. 7,371,395, incorporated herein by reference.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of cross linked acrylic or methacrylic acid, especially cross linked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers cross linked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are cross linked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or cross linked ethylene-maleic anhydride copolymers and they are, for example, cross linked by divinyl ether. Reference is also made to J. Fields et al., 1960.

With regard to structure, the acrylic or methacrylic acid polymers and EMA are preferably formed by basic units having the following formula:

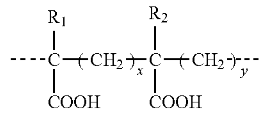

in which:

R1 and R2, which can be the same or different, represent H or CH3 x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between 0.01 and 1.5% w/v, 0.05 to 1% w/v or 0.1 to 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α(IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, an avian cytokine for preparations to be administered to an avian).

In another embodiment, the composition of the present invention may be prepared using the chemical or physical procedure as described by Stauffer et al. (Recent Patents on Anti-Infective Drug Discovery, 1, 291-296, 2006). Some of the inactivation techniques are summarized in the table below.

| Chemical | Physical | Combined |
|---|---|---|
| Ascorbic Acid | | Ascorbic Acid + UV |
| b-Propiolactone | Heat | Beta Propiolactone + UV |
| b-aminophenylketone | Pressure | Formalin + Heat |
| diethylpyrocarbonate | UV | Formalin + UV |
| Ethylenimine | Non Ionic Detergents | Heat + Low Pressure |
| Formalin/Formaldehyde | | Pressure + Heat or Cold |
| Phenol | | Psoralen + UV |

In one embodiment, the administration of the vaccine is to an avian, such as chickens, ducks, geese, turkeys, guinea fowl, partridges or ostriches. Chickens include, but are not limited to commercial layers, breeders, broilers, fancy chickens, and game hens. Ducks include, but are not limited to, Pekin ducks, Muscovy ducks, mule ducks and wild ducks. In an embodiment wherein the avian is a duck or avian larger than a chicken, larger doses may be contemplated. For example, in an embodiment wherein the administration is by eye drop, a dose approximating about 1 chicken dose, 2 chicken doses, 3 chicken doses, 4 chicken doses, 5 chicken doses, 6 chicken doses, 7 chicken doses, 8 chicken doses, 9 chicken doses and advantageously 10 chicken doses with the dosage up to about 20 to up to about 100 chicken doses if needed. For ease of reference, 5.5 $\log_{10}$ 50% Egg Infective Dose ($EID_{50}$) is approximately 1 chicken dose.

In another embodiment, the dosage may be in mean embryo infectious doses ($EID_{50}$). In one embodiment, the dosage may be about $10^1$ $EID_{50}$, about $10^2$ EID50, $10^3$ $EID_{50}$, about $10^4$ $EID_{50}$, about $10^5$ $EID_{50}$, about $10^6$ $EID_{50}$, about $10^7$ $EID_{50}$, or about $10^8$ $EID_{50}$.

The immunological composition and/or vaccine according to the invention comprise or consist essentially of or consist of an effective quantity to elicit a protective or therapeutic response of one or more expression vectors and/or polypeptides as discussed herein; and, an effective quantity can be determined from this disclosure, including the documents incorporated herein, and the knowledge in the art, without undue experimentation.

Advantageously, when the antigen is hemagglutinin, the dosage is measured in hemagglutination units (HAUs) or in micrograms. In an advantageous embodiment, the dosage may be about 100 hemagglutination units (HAU)/dose, about 1000 HAU/dose or about 10000 HAU/dose. In certain embodiments, the dosage is between 1 and 100 μg. The dosage volume may be between about 0.02 ml and 2 ml, advantageously between 0.03 ml and 1 ml, more advantageously between 0.03 ml and 0.5 ml and in an especially advantageous embodiment, the volume may be about 0.03 ml to about 0.3 ml.

The vaccines of the present invention may be administered to avian in ovo, via drinking water, sprays, aerosols, intranasal instillation, eye drop, beak-dipping, by wing-web stabbing, transdermal, subcutaneous or intramuscular injection. Advantageously, the vaccines are administered by subcutaneous, in ovo, eye drop, spray or drinking water.

In yet another embodiment, the vaccine may be administered in ovo 1 to 3 days before hatching, or to a 1 day old, 2 day old, 3 day old, 4 day old, 5 day old, 6 day old, 7 day old, 8 day old, 9 day old, 10 day old, 11 day old, 12 day old, 13 day old, 14 day old, 15 day old, 16 day old, 17 day old, 18 day old, 19 day old, 20 day old or 21 day old chicken.

In one embodiment of the invention, a prime-boost regimen can be employed, which is comprised of at least one primary administration and at least one booster administration using at least one common protein, polypeptide, antigen, epitope or immunogen. The immunological composition or vaccine used in primary administration is different in nature from those used as a booster. However, it is noted that the same composition can be used as the primary administration and the boost. This administration protocol is called "prime-boost".

In another aspect of the prime-boost protocol of the invention, a composition comprising the engineered avian influenza Avinew NDV vaccine or composition is administered followed by the administration of vaccine or composition comprising a recombinant viral vector that contains and expresses an avian influenza antigen in vivo, or an inactivated viral vaccine or composition comprising the avian influenza antigen, or a vaccine or composition comprising an avian influenza subunit (protein), or a DNA plasmid vaccine or composition that contains or expresses an avian influenza antigen. Likewise, a prime-boost protocol may comprise the administration of vaccine or composition comprising a recombinant viral vector that contains and expresses an avian influenza antigen in vivo, or an inactivated viral vaccine or composition comprising the avian influenza antigen, or a vaccine or composition comprising an avian influenza subunit (protein), or a DNA plasmid vaccine or composition that contains or expresses an avian influenza antigen, followed by the administration of a composition comprising the engineered avian influenza Avinew NDV vaccine or composition. It is further noted that both the primary and the secondary administrations may comprise the composition comprising the engineered avian influenza Avinew NDV vaccine or composition.

A prime-boost protocol comprises at least one prime-administration and at least one boost administration using at least one common antigen. The vaccine or composition used in prime-administration may be different in nature from those used as a later booster vaccine or composition. The prime-administration may comprise one or more administrations. Similarly, the boost administration may comprise one or more administrations.

The various administrations are preferably carried out about 1 to about 6 weeks apart, or about 2 to about 4 weeks apart. Repeated booster every 2 to 6 weeks or an annual booster is also contemplated. The animals are preferably at least one day old at the time of the first administration.

The immunological composition and/or vaccine contains per dose from about $10^4$ to about $10^{11}$, advantageously from about $10^5$ to about $10^{10}$ and more advantageously from about $10^6$ to about $10^9$ viral particles of recombinant adenovirus expressing an influenza antigen, epitope or immunogen. In the case of immunological composition and/or vaccine based on a poxvirus, a dose can be between about $10^2$ pfu and about $10^9$ pfu. The immunological composition and/or vaccine contains per dose from about $10^2$ to about $10^7$, advantageously from about $10^3$ to about $10^5$ pfu of poxvirus or herpesvirus recombinant expressing the influenza antigen, epitope or immunogen.

In an embodiment wherein the avian immunological composition or vaccine is an inactivated avian virus, the inactivated avian virus may be derived from various seed viruses used in the production of the oil-emulsion vaccines may include Ulster 2C, B1, LaSota or Roakin. An inactivated avian influenza virus may also be classical inactivated (whole virus beta-propiolactone (BPL)-inactivated vaccine (H5N9-It) containing the H5N9 Eurasian isolate A/chicken/Italy 22A/98 propagated on embryonated SPF eggs. Other inactivated vaccines, adjuvanted, include commercially available whole virus preparations (Fort Dodge Animal Health, Intervet International, Merial Italia) based on field viruses of subtypes H5N2 and H5N9 or a recombinant H5N3 virus derived by genetic engineering (the latter contains a modified HA gene of A/chicken/Vietnam/C58/04 (H5N1), the neuraminidase gene of A/duck/Germany/1215/73 (H2N3) and the internal genes of A/PR/8/34 (H1N1).

The viral vector may be an attenuated avipox expression vector. In one embodiment, the avipox expression vector may be a fowlpox vector, for example, TROVAC®. In another embodiment, the avipox expression vector may be a canarypox vector, for example, ALVAC®. The influenza antigen, epitope or immunogen may be a hemagglutinin, such as H5. The fowlpox vector may be vFP89 (see, US 2008/0107681 and US 2008/0107687) or vFP2211 (see, US 2008/0107681 and US 2008/0107687). The canarypox vector may be vCP2241 (see, US 2008/0107681 and US 2008/0107687). Other viruses that may be used in methods of the invention include, but are not limited to, vaccinia viruses, such as an attenuated vaccinia virus, for instance NYVAC, adenoviruses and herpesviruses.

The efficacy of the vaccines may be tested about 2 to 4 weeks after the last immunization by challenging animals, such as an avian, with a virulent strain of influenza, for example, the influenza H5N1, H5N8 or H5N9 strains. Both homologous and heterologous strains may be used for challenge to test the efficacy of the vaccine. The animal may be challenged by spray, intra-nasally, eye drop, oculo-nasal, 1M, intra-tracheally, and/or orally. The challenge viral may be about $10^3$ to about $10^8$ $EID_{50}$ in a volume depending upon the route of administration. For example, if the administration is by spray, a virus suspension is aerosolized to generate about 1 to 100 μl an droplets, if the administration is intra-nasal, intra-tracheal or oral, the volume of the challenge virus is about 0.05 to about 5 ml. The dose volume of compositions for target species, e.g., the dose volume of avian compositions, may be about 50 μl for in ovo, about 20 to about 50 μl for eye drop, about 0.25 ml to about 1 ml for spray. Animals may be observed daily for 14 days following challenge for clinical signs and mortality. In addition, the groups of animals may be euthanized and evaluated for pathological findings. Oropharyngeal, tracheal or cloacal swabs may be collected from all animals post challenge for virus detection. The presence or absence of viral antigens in tissues may be evaluated by immunohistochemistry, viral isolation or titration, or nucleic acid detection such as reverse-transcriptase polymerase chain reaction (RT-PCR). Blood samples may be collected post-challenge and may be analyzed for the presence of anti-influenza H5N1 virus-specific antibody.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each immunization protocol, without any undue experimentation.

The present invention contemplates at least one administration to an animal of an efficient amount of the therapeutic composition made according to the invention. This administration may be via various routes including, but not limited to, intramuscular (IM), intradermal (ID) or subcutaneous (SC) injection or via intranasal, in ovo, or oral administration. The therapeutic composition according to the invention can also be administered by a needleless apparatus (as, for example with a Pigjet, Dermojet, Biojector, Vetjet or Vitajet apparatus (Bioject, Oreg., USA)). In one embodiment, the animal is an avian.

Another embodiment of the invention is a kit for performing a method of inducing an immunological or protective response against influenza in an animal comprising a recombinant NDV immunological composition or vaccine or an inactivated influenza immunological composition or vaccine and instructions for performing the method of delivery in an effective amount for eliciting an immune response in the animal.

The invention is further illustrated by the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1

Development of Reverse Genetics of the AVINEW® (NDV) Strain and Generation of NDV Mutants Expressing Heterologous Genes The aim of this Example was to develop the reverse genetics of the AVINEW NDV strain to generate engineered NDV mutants expressing heterologous genes.

Figure 1B:
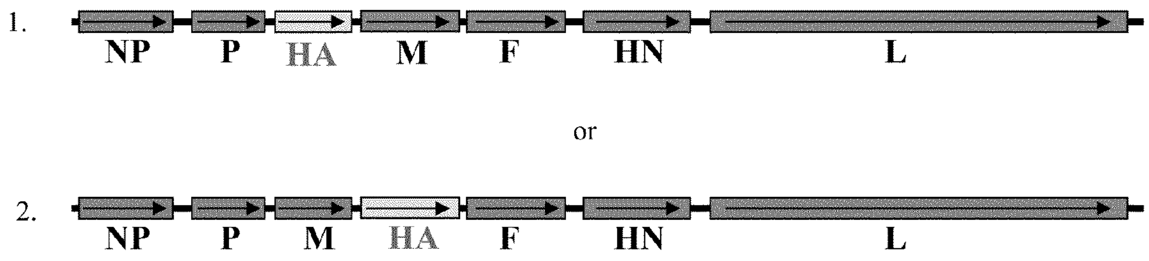
FIG. 1B depicts a map illustrating the genetic map of two engineered NDV with influenza HA insertion into 2 representative transgene insertion sites into the full length NDV genome.

The NDV is a negative RNA virus that contains 6 major genes (NP, P, M, F, HN and L) as depicted in FIG. 1A. The generation of genetically modified NDV virus needs a reverse genetics system. A reverse genetic system has been developed by Applicants based on the AVINEW vaccine strain of NDV. This system permits generation of modified Newcastle Disease Viruses expressing a foreign gene, such as the hemagglutinin (HA) of influenza as depicted in FIG. 1B.

Example 1.1

Figure 1C:
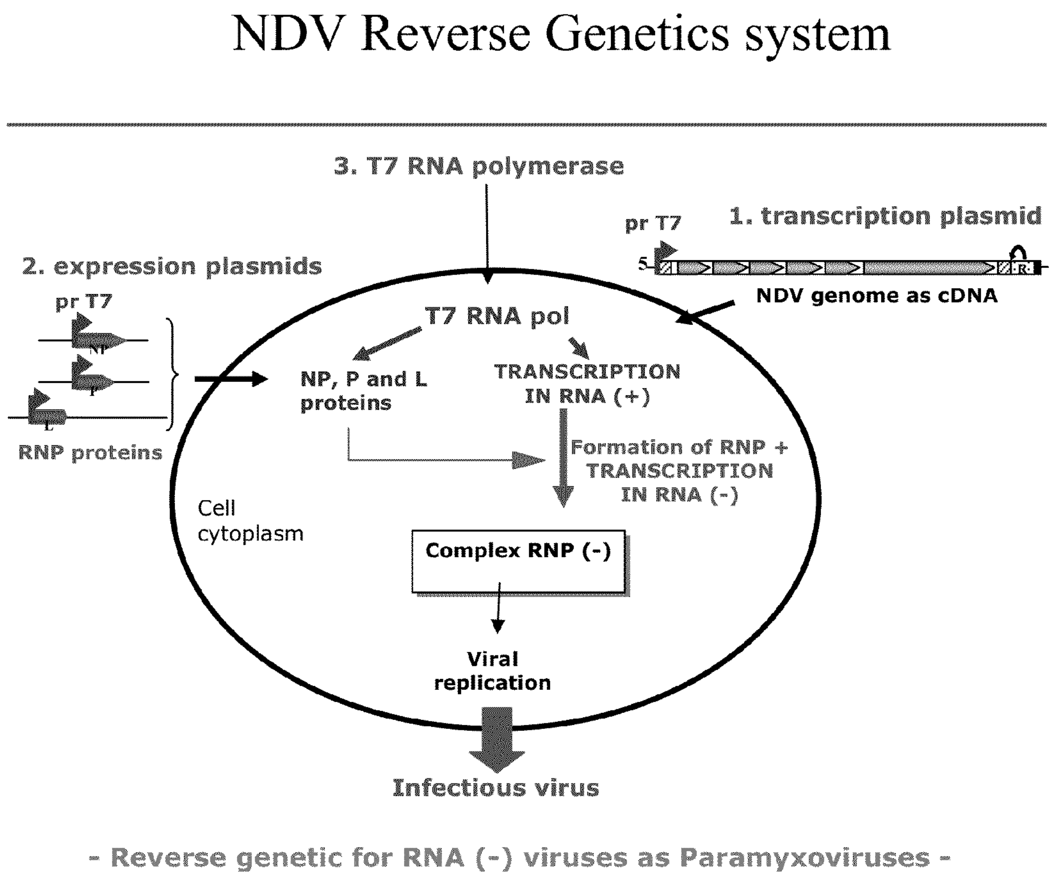
FIG. 1C is an example of flow diagram of the NDV reverse genetics system, depicting the way to recover engineered NDV infectious particles using NDV reverse genetics.
Figure 2:
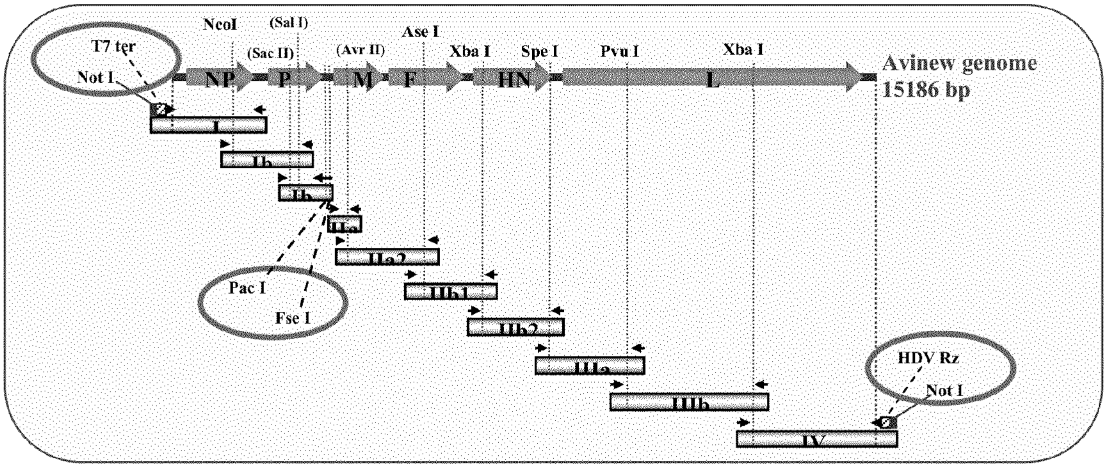
FIG. 2 depicts a schematic representation of the cloning of the AVINEW whole genome into a transcription plasmid for reverse genetics development and insertion of unique restriction sites (PacI & FseI) allowing easy cloning of transgenes between the P and M genes.

Cloning of the Whole AVINEW NDV Genome into a Transcription Plasmid and Sequence Analysis For the purpose of sequencing the genome of AVINEW NDV strain, the whole genome of the AVINEW strain needs to be cloned into a plasmid that is designated as a "transcription plasmid" (see 1. in FIG. 1C). The transcription plasmid allows generating a positive RNA corresponding to the entire genome of the AVINEW strain of NDV. The strategy for AVINEW genome cloning by successively joining a set of 10 overlapping cDNAs fragments amplified from the AVINEW extracted RNA by reverse transcriptase polymerase chain reaction (RT-PCR) is shown in FIG. 2. This final plasmid designated pIV029 (see FIG. 3) contains the complete genome sequence of AVINEW that is under the control of T7 RNA polymerase transcription signals (T7 promoter located upstream) and is terminated by Hepatitis Delta Virus (HDV) ribozyme that is used to cleave the RNA at the authentic NDV genomic terminus followed by T7 terminator. Restriction sites were inserted between P and M genes to permit the insertion of a transgene (see FIGS. 2 & 3).

The entire genome of the AVINEW® strain was sequenced. The AVINEW® genome is 15186 bp in length which is, as expected based on the nucleocapsid protein binding motif, a multiple of 6 nucleotides.

Figure 3:
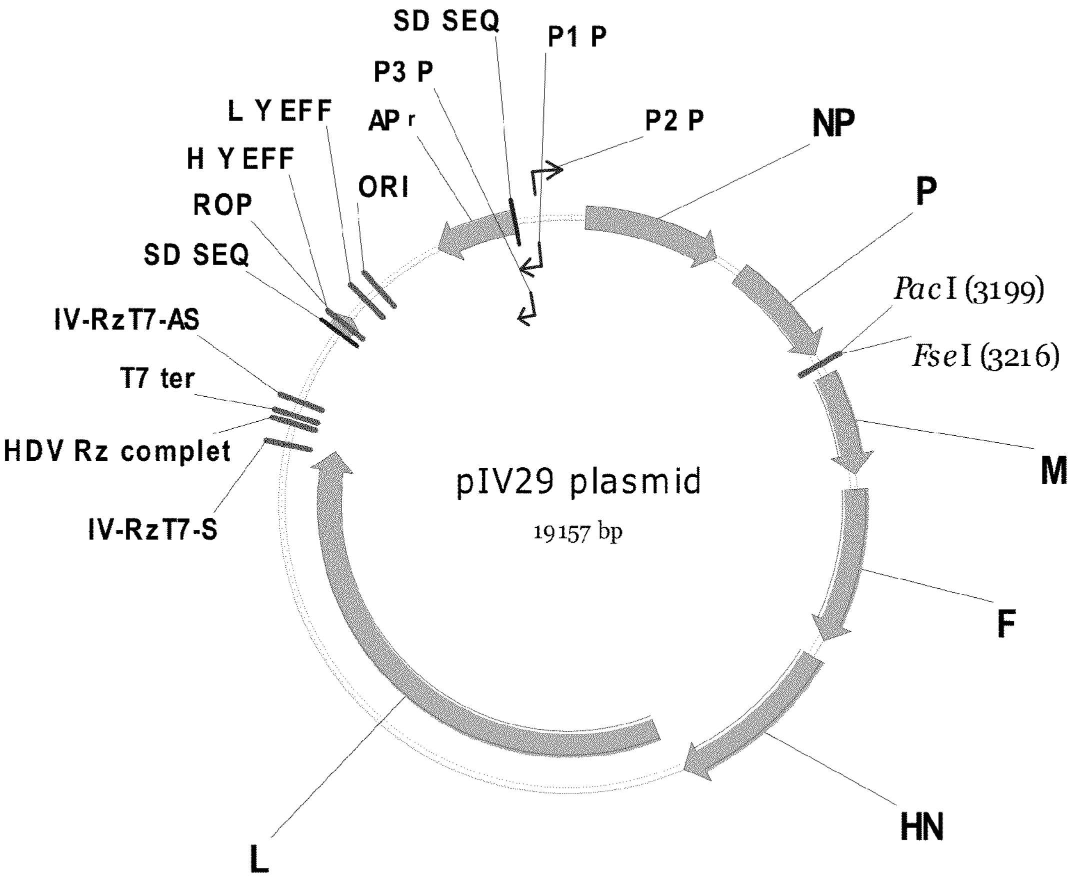
FIG. 3 depicts the plasmid map of the plasmid pIV029.

The annotated sequence of the insert of pIV029 is presented in FIGS. 4A-40 and a plasmid map is presented in FIG. 3. In FIGS. 4A-40, the 6 open reading frames (ORF) of the Avinew strain (NP, P, M, F, HN and L) are translated into their amino acid sequence. Each ORF is flanked by "gene start" upstream and "gene stop" downstream sequences that are indicated with GS and GE. The T7 promoter and T7 terminator sequences are indicated.

Example 1.2

Construction of the Expression Plasmids Containing the NP, P and L Genes of AVINEW NDV In the reverse genetics system, plasmids designated "expression plasmids" that encode the nucleocapsid (NP), phosphoprotein (P) and large polymerase protein (L) under the control of the T7 RNA polymerase promoter need to be constructed (see FIG. 1C). These three proteins are associated with viral RNA to form the RiboNucleoProteins (RNPs) which represent the smallest infectious unit of NDV. The complex composed of NP, P, and L proteins presents RNA dependent RNA polymerase activity.

The expression plasmids pIV32 (FIG. 5), pIV33 (FIG. 6) and pIV34 (FIG. 7) were constructed and contain the NP, P and L genes of AVINEW, respectively, under the control of the T7 RNA polymerase promoter and Foot and Mouth Disease Virus (FMDV) Internal Ribosome Entry Site (IRES).

Example 1.2.1

Figure 5:
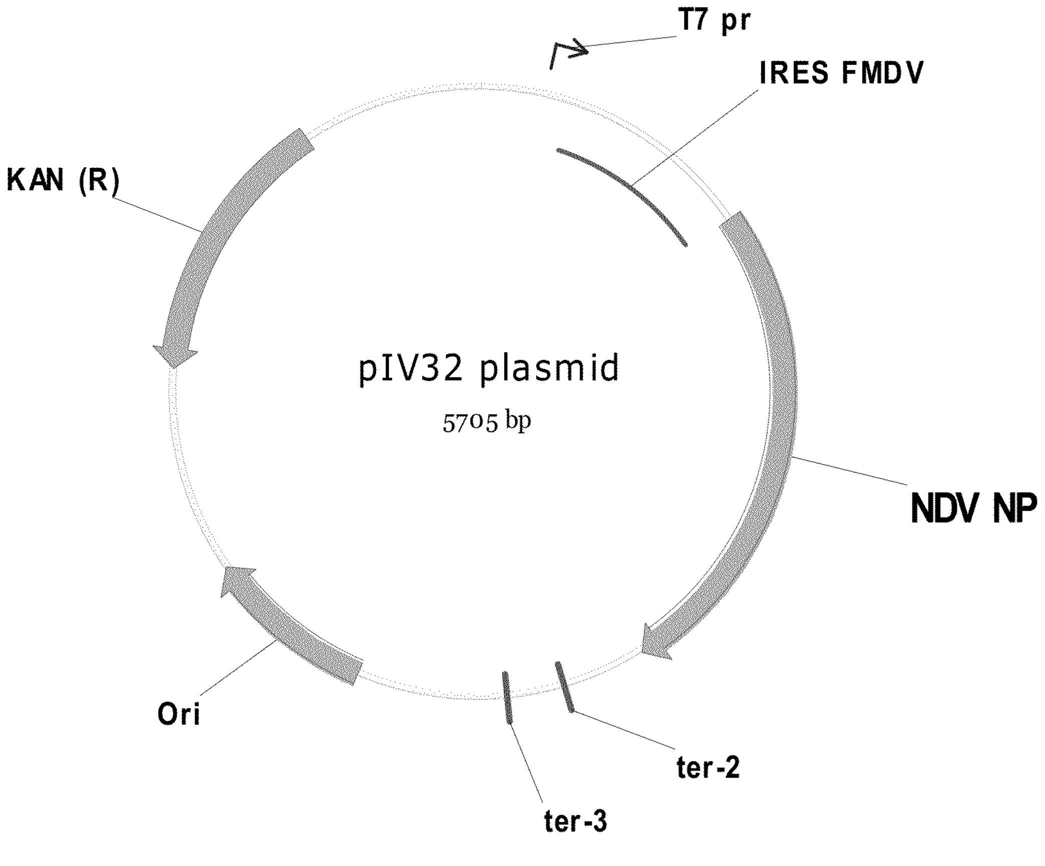
FIG. 5 depicts the plasmid map of the plasmid pIV32.

Construction of the Expression Plasmids PIV32 Containing the NP Gene of AVINEW NDV The map of expression plasmid pIV32 is shown in FIG. 5. This plasmid contained the nucleotide sequence encoding the open reading frame (ORF) of the nucleocapsid (NP) gene of the Newcastle Disease Virus AVINEW® vaccine strain under the control of T7 RNA polymerase promoter and Foot and Mouth Disease Virus (FMDV) Internal Ribosome Entry Site (IRES). The NDV ORF NP (1467 bp, SEQ ID NO:2) encodes a 489 amino acid polypeptide (SEQ ID NO:3). Protein NP is the major structural component of the nucleocapsid. The protein is approximately 58 kDa. Total of 2600 NP molecules tightly encapsidate the genomic RNA. NP interacts with several other viral encoded proteins, all of which are involved in controlling replication (NP-NP, NP-P, NP-(PL), and NP-V). NP associated with NDV genomic RNA and proteins P and L constitute the NDV ribonucleoprotein (RNP) complex, which is the infectious form of NDV genome.

Example 1.2.2

Figure 6:
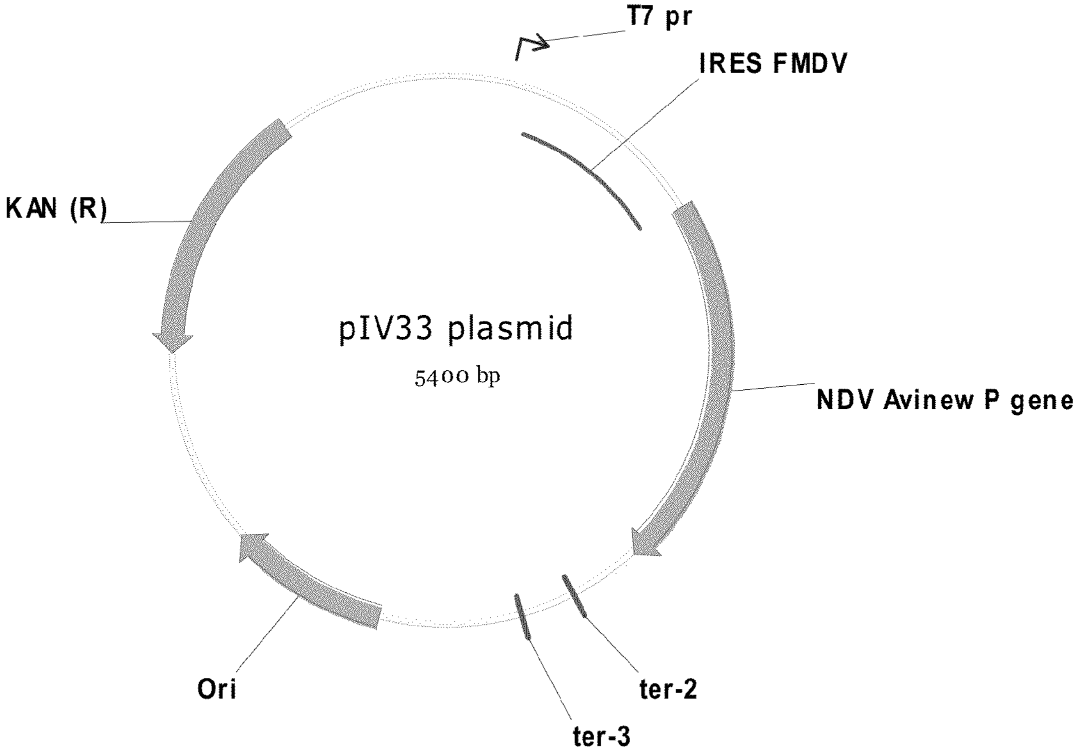
FIG. 6 depicts the plasmid map of the plasmid pIV33.

Construction of the Expression Plasmid pIV33 Containing the P Gene of AVINEW NDV The map of expression plasmid pIV33 is shown in FIG. 6. This plasmid contained the nucleotide sequence encoding the ORF of the phosphoprotein (P) gene of the Newcastle Disease Virus AVINEW® vaccine strain under the control of T7 RNA polymerase promoter and Foot and Mouth Disease Virus (FMDV) Internal Ribosome Entry Site (IRES). This plasmid was designed for generation of recombinant NDV AVINEW® as a vaccine vector using reverse genetic methodology.

The NDV ORF P (1185 bp, SEQ ID NO:4) encodes a 395 amino acid polypeptide: the structural phosphoprotein (P) (SEQ ID NO:5). This protein has a molecular weight of 53 to 56 kDa as determined by SDS-PAGE. Protein P is essential for the activity of the RNA polymerase complex, which it forms with the large subunit L. Although all the catalytic activities of the polymerase are associated with the L subunit, its function requires specific interactions with P. P associated with proteins L and NP and with NDV genomic RNA constitute the NDV ribonucleoprotein (RNP) complex, which is the infectious form of NDV genome.

In addition, the P gene encodes protein V (unknown function) with an apparent molecular weight of 36 to 38 kDa on SDS-PAGE. The P and V proteins share the same amino terminus, but they diverge at their C-termini. This difference is generated by an RNA-editing mechanism in which one non-templated G residue is inserted into P-gene-derived mRNA. The unedited transcript codes for the P protein while the edited transcript codes for the V protein. Being phosphoproteins, both P and V are rich in serine and threonine residues over their whole lengths. In addition, the V protein is rich in cysteine residues at the C-terminus. As well, the P gene encodes protein W (unknown function), with an apparent molecular weight of 28 to 33 kDa on SDS-PAGE. This protein is also produced by a RNA-editing mechanism in which two instead of one non-template G residues are inserted into P-gene-derived mRNA.

Example 1.2.3

Figure 7:
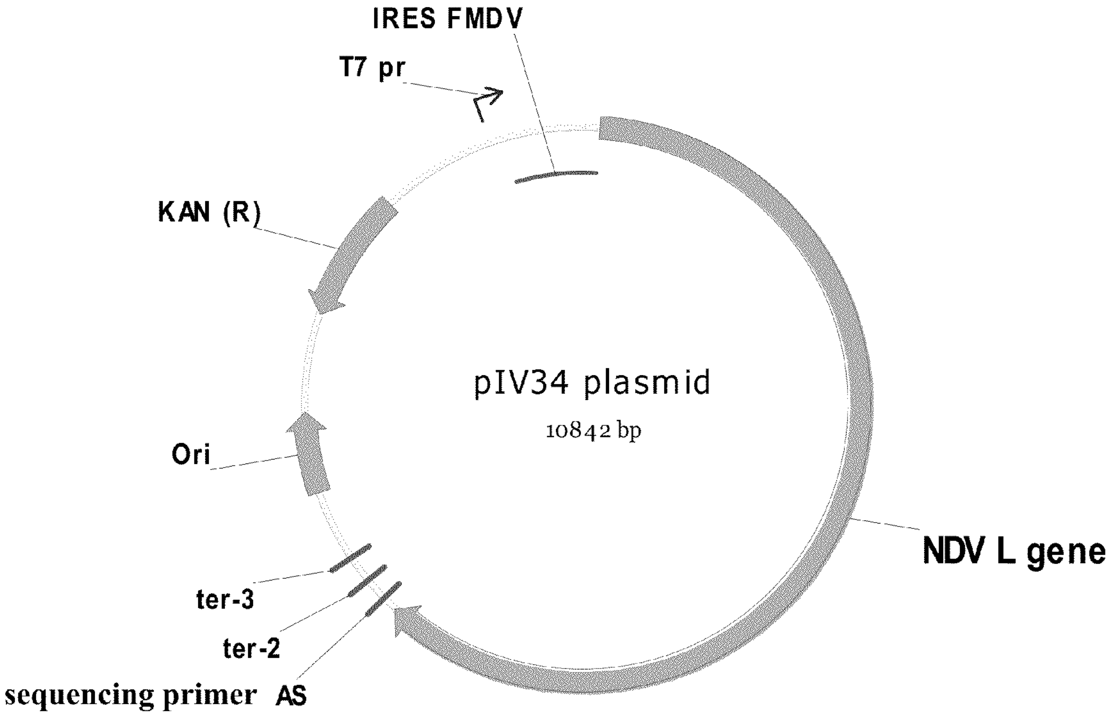
FIG. 7 depicts the plasmid map of the plasmid pIV034.

Construction of the Expression Plasmids pIV034 Containing the L Gene of AVINEW NDV The map of expression plasmid pIV34 is shown in FIG. 7. This plasmid contained the nucleotide sequence encoding the ORF of the large polymerase protein (L) gene of the Newcastle Disease Virus AVINEW® vaccine strain under control of T7 RNA polymerase promoter and Foot and Mouth Disease Virus (FMDV) Internal Ribosome Entry Site (IRES). This plasmid is designed for generation of recombinant NDV AVINEW® as a vaccine vector using reverse genetic methodology.

The NDV L gene (6612 bp, SEQ ID NO:12) encodes a 2204 amino acid polypeptide, which is the L protein (SEQ ID NO:13). Paramyxoviridae, like other non-segmented negative strand RNA viruses, have an RNA-dependent RNA polymerase composed of two subunits, a large protein L and a phosphoprotein P. The L protein confers the RNA polymerase activity on the complex while the P protein acts as a transcription factor. Protein L associated with proteins P and NP and with NDV genomic RNA constitutes the NDV ribonucleoprotein (RNP) complex, which is the infectious form of NDV genome.

Example 1.3

Figure 8:
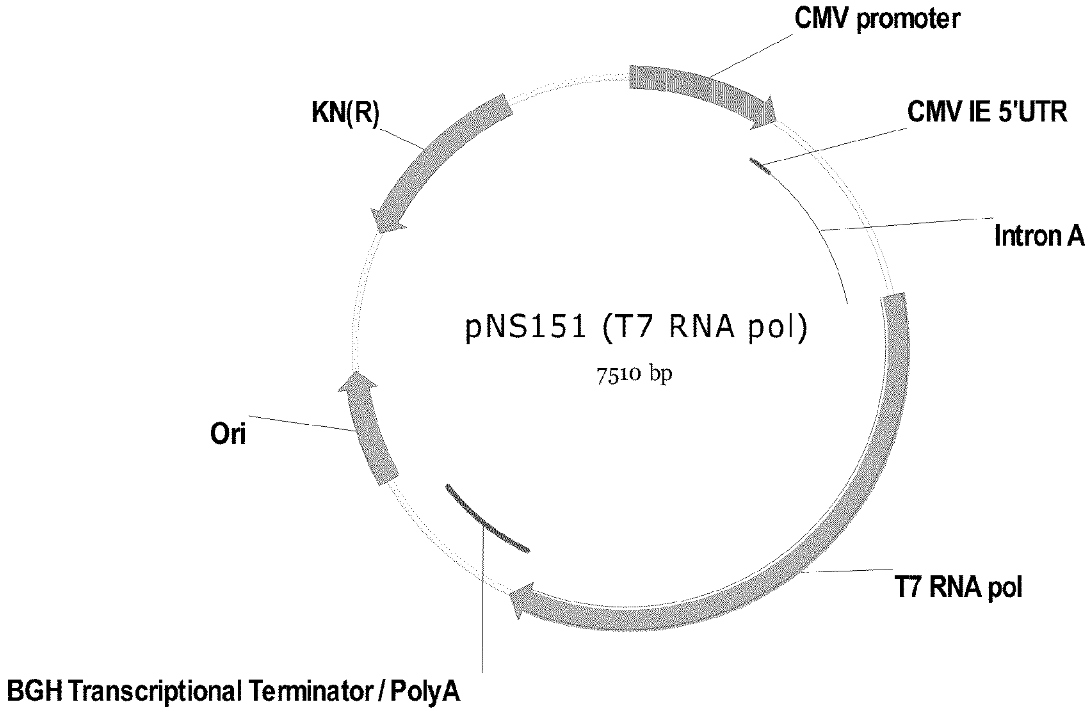
FIG. 8 depicts the plasmid map of the plasmid pNS151.

Construction of the Expression Plasmid Allowing Expression of the T7 RNA Polymerase The reverse genetics system requires the T7 RNA polymerase to be expressed in cells where the NDV virus will be regenerated (see FIG. 1C). Different systems can be used to express the T7 RNA polymerase including the use of a recombinant virus (e.g. an avipox) as a vector, the use of cells that constitutively express the enzyme or the transient expression using an expression plasmid. The latter solution was chosen and an expression plasmid (designated pNS151) encoding the T7 RNA polymerase under the HCMV IE promoter was constructed. The T7 RNA polymerase allows not only the transcription/expression of NP, P and L proteins from the expression plasmids described above, but also transcribes the NDV genome (present in the transcription plasmid) into a positive sense RNA. A map of the plasmid is shown in FIG. 8.

Example 1.4

Recovery of NDV Virus Using the Reverse Genetics System

The above-described five plasmids (one transcription plasmid containing the NDV genome, three expression plasmids expressing NDV NP, P and L, and the expression plasmid expressing the T7 polymerase) were co-transfected together into Chinese hamster ovary (CHO) cells. FIG. 1C is a schematic representation that explains the mechanism of the reverse genetics system. As the scheme shows that upon entry of the cell, T7 RNA polymerase is expressed which then transcribe the NDV genome from the transcription plasmid into a positive sense RNA (RNA(+)) genome as well as the NP, P and L genes from the individual expression plasmids. The NP, P and L protein transcripts are then translated as expressed NP, P and L proteins which then assemble and form RNPs with genomic RNA(+). This RNP complex synthesizes a negative sense RNA genome (RNA(−)) which then initiates the normal replication cycle of NDV virus facilitating the generation of infectious particles. Trypsin or other exogenous proteases such as provided by egg allantoic clued may be added in the medium to cleave the F protein of generated viruses.

Using this system, the infectious particles of AVINEW NDV were successfully obtained. Briefly, the different plasmids (pIV029, pIV32, pIV33, pIV034 and pNS151) required were transfected into CHO cells. After 72 hours, the CHO supernatants were inoculated in 10-day-old embryonated eggs to amplify the virus. After 3 days, the allantoic fluid was harvested and checked for hemagglutination activity (HA) using chicken red blood cells. The obtained reverse genetics AVINEW mutant was designated vAVW01. It contains the same sequence as the AVINEW parental virus except for the two unique restriction sites (PacI & FseI) introduced between the P and M genes (see FIG. 2).

Example 1.5

Figure 9:
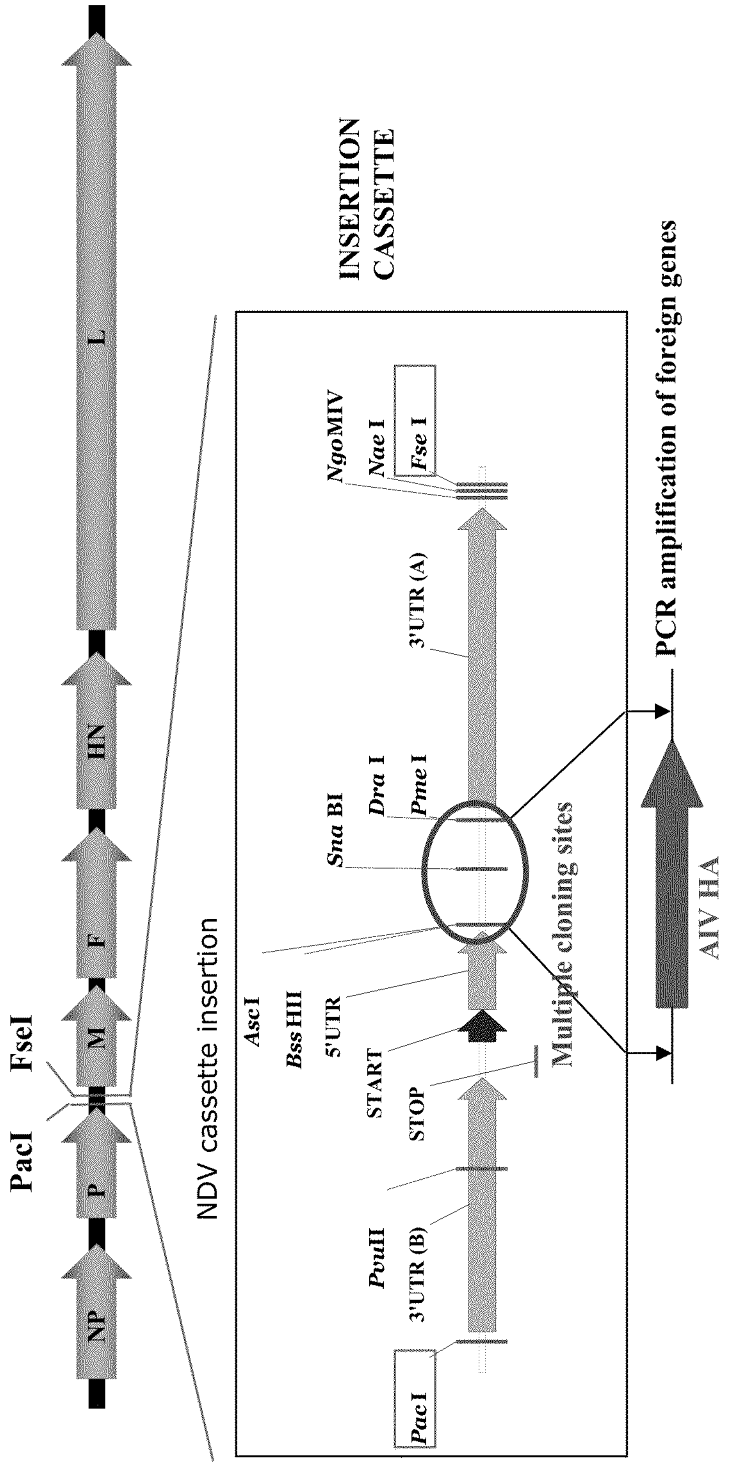
FIG. 9 depicts the schematic method to introduce the AIV HA gene into the NDV genome via an NDV insertion cassette.

Generation of NDV Virus Expressing Foreign Genes Using the Reverse Genetics System To generate modified NDV viruses expressing a foreign antigen, a locus of insertion needs to be chosen. Different loci can be chosen including upstream of NP gene and between 2 genes. In this example, the site between the P and M genes of AVINEW® NDV was chosen to insert a foreign gene as shown in FIG. 9. The foreign gene needs to be inserted along with the required "start" and "stop" transcription sequences and the number of inserted nucleotides needs to be designed such that the total number of nucleotides in the modified NDV genome remains a multiple of six.

Figure 10:
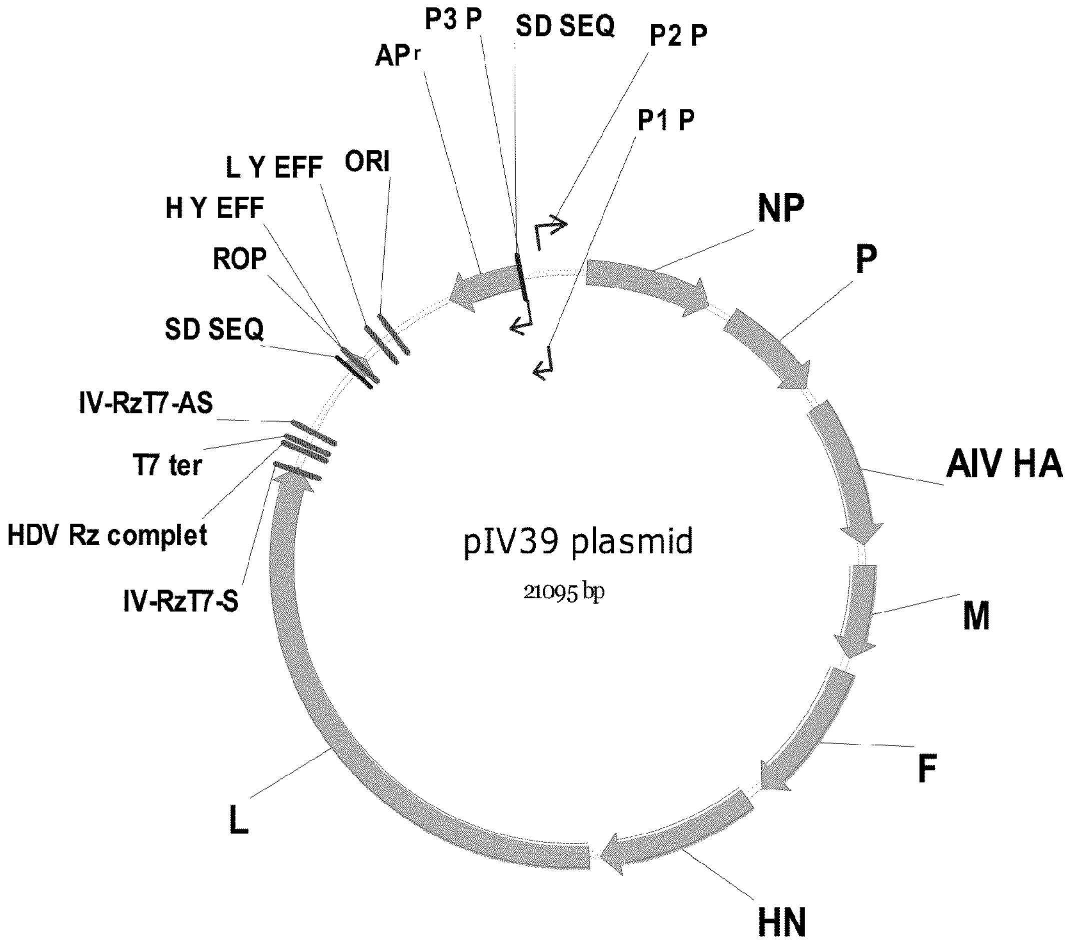
FIG. 10 depicts the plasmid map of the plasmid pIV039.

This example details the generation of AVINEW mutants expressing the hemagglutinin (HA) gene from avian influenza. The HA gene was first inserted into a transfer plasmid that allows the insertion of the foreign gene and flanking sequences into the PacI and FseI unique restriction sites of pIV029. The structure of the transfer plasmid is depicted in FIG. 9 (within the box). It contains from left to right the PacI site, the 3'UTR of P downstream from the PacI site, the gene end (or STOP) sequence of P, the P/M intergene, the gene start (or START) sequence of M, the 5' UTR of M, multiple cloning sites, the 3'UTR of P (upstream from the PacI site) and the FseI site. The HA gene was cloned into the multiple cloning site of the transfer plasmid as depicted in FIG. 9 and then the whole PacI/FseI insert was cloned into the same restriction sites of pIV029 (FIG. 3) to generate the transcription plasmid containing the foreign gene. An example (pIV039) of such transcription plasmid is shown in FIG. 10. In this example, a synthetic gene coding for the amino acid sequence of the HA gene of the A/chicken/Indonesia/7/2003 highly pathogenic H5N1 avian influenza virus modified at the cleavage site was inserted into the transcription plasmid.

The transcription plasmid pIV039 was used together with the 4 additional expression plasmids required for the generation of AVINEW mutants by reverse genetics (see example 1.4) to generate an AVINEW® mutant designated vAVW02 expressing the HA gene from the A/chicken/Indonesia/7/2003 highly pathogenic (HP) H5N1 avian influenza (AI) virus.

The same method was used to generate different AVINEW mutants expressing an HA gene from different HPAI H5N1 or low pathogenic AI (LPAI) H9N2. The sequences of the insert HA genes from different H5N1 and H9N2 AI isolates are assigned SEQ ID NO as shown in FIG. 12, and both the DNA and protein sequences are included in the Sequence Listing. The content of the electronically submitted Sequence Listing filed with the application is incorporated herein by reference in its entirety.

The procedure described above was successfully used for the recovery of infectious AVINEW mutants expressing an HA gene from different HPAI H5N1 or low pathogenic AI (LPAI) H9N2 (see Table 1).

TABLE 1

Different Avinew mutants generated and expressing a synthetic HA gene from different avian influenza isolates. All HA genes from HPAI H5N1 were mutated at the cleavage site in order to match the sequence of the cleavage site of LPAI H5 isolates

| Name | Insert | Avian influenza strain | HA subtype and clade of AI |
|---|---|---|---|
| vAVW01 | — | — | — |
| vAVW02 | H5 | A/chicken/Indonesia/7/2003 | H5N1 clade 2.1 |
| vAVW03 | H5 | A/turkey/Turkey/1/2005 | H5N1 clade 2.2 |
| vAVW04 | H5 | A/Duck/Laos/3295/2006 | H5N1 clade 2.3 |
| vAVW05 | H9 | A/chicken/Iran/AV1221/1998 | H9N2 |
| vAVW06 | H9 | A/chicken/Iran/AV1221/1998 (mutated) | H9N2 |
| vAVW09 | H5 | A/chicken/WestJava/PWT-WIJ/2006 | H5N1 clade 2.1 |

Example 1.6

Production and Characterization of NDV Virus Expressing Foreign Genes Using the Reverse Genetics System All engineered AVINEW mutants were amplified by subsequent passage on embryonated eggs and characterized. The recombinant viruses grew to titers similar to the original AVINEW® virus (8 to 10 log 10 EID50/ml) suggesting that the foreign gene insertion did not have a significant impact on the replication of the virus in embryonated eggs. An example of infectious titers obtained in the $2^{nd}$ or $3^{rd}$ passage on embryonated eggs is shown in Table 2.

Figure 11A:
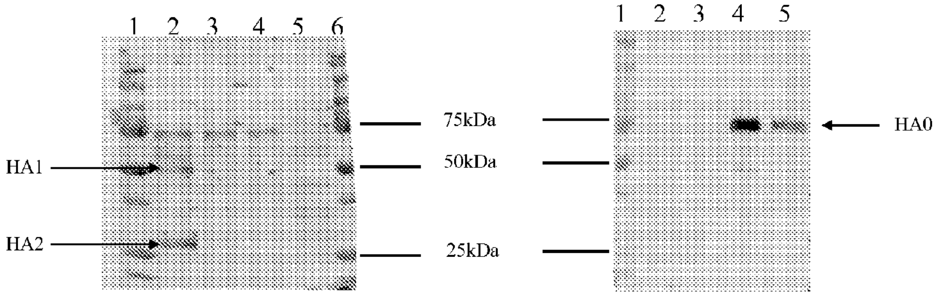
FIGS. 11A and 11B depict HA expression by the engineered NDV vAVW02. The vAVW01 that does not contain insert is used as a negative control. HA expression is detected by Western blot in the allantoic fluid of virus-inoculated embryonated eggs (left panel in FIG. 11A) or from an infected CHO cell lysate (right panel of FIG. 11A) or by immunofluorescence in infected CHO cells (FIG. 11B) using an anti-H5 positive chicken serum on infected CHO cells.
Figure 11B:
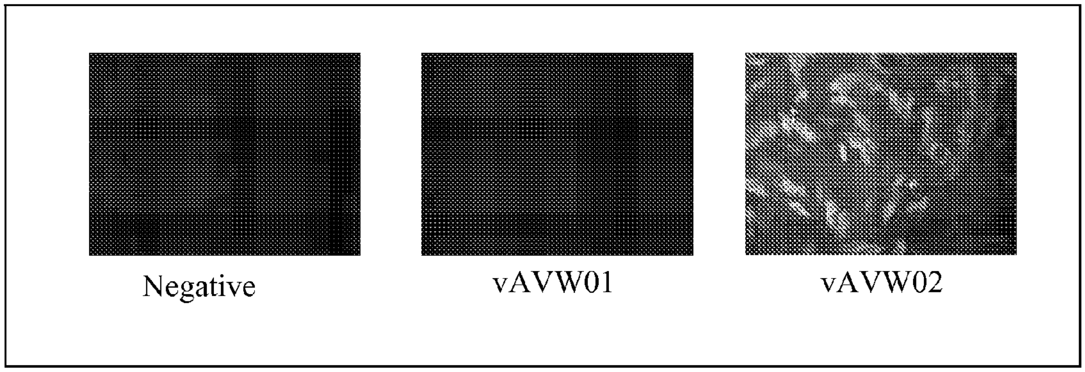

Expression of the H5 transgene was confirmed by indirect immunofluorescence on infected CHO cells and by immunoblot (Western Blot or WB) on allantoic fluids and on CHO infected cells lysates (see FIGS. 11A and 11B for vAVW02 as an example). The electrophoretic profile of the H5 was as expected. Due to the presence of proteases in the allantoic fluid, the proper HA cleavage products, namely HA1 (50 kDa) and HA2 (28 kDa), were detected. In CHO cells infected (in absence of trypsin) with the egg-grown viruses, applicants detected only the HA0 form (75 kDa) (FIG. 11A).

The expression of the foreign HA protein at the surface of the NDV virion was confirmed by immunoelectron microscopy using vAVW02 as an example (see FIG. 11B).

TABLE 2

Yield and control of expression of Avinew mutants generated and expressing a synthetic HA gene from different avian influenza isolates.

| Name | Insert | Titers in EID50/ml | HA expression detected by IF in CHO cells | HA expression detected by WB in allantoic fluid from infected eggs or in CHO-infected lysate |
|---|---|---|---|---|
| vAVW01 | — | 9.8 | Negative | Negative |
| vAVW02 | H5 | 9.1 | Positive | Positive |
| vAVW03 | H5 | 8.2 | Positive | Positive |
| vAVW04 | H5 | 8.7 | Positive | Positive |
| vAVW05 | H9 | 8.8 | Positive | Not tested |
| vAVW06 | H9 | 9.2 | Positive | Not tested |
| vAVW09 | H5 | 9.1 | Positive | Not tested |

Example 2

Figure 14:
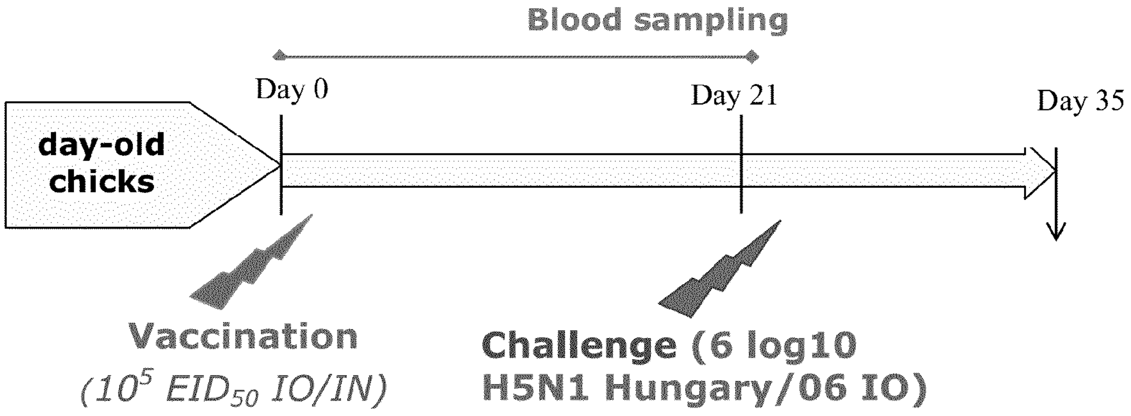
FIG. 14 depicts a vaccination/challenge timeline and protocol for evaluation of avian influenza protection induced by engineered NDV in SPF chickens.
Figure 15:
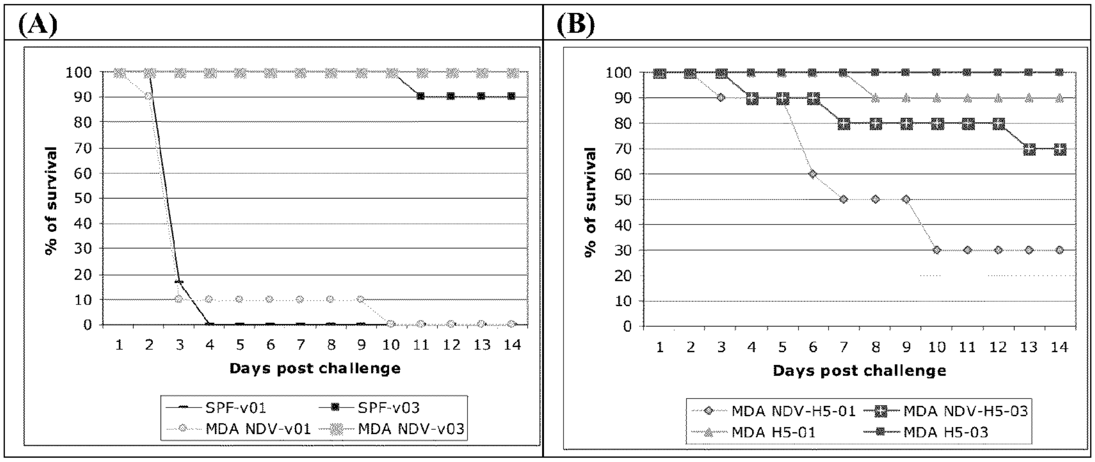
FIG. 15 shows the kinetics charts of mortality of chickens with no MDA (SPF) or NDV MDAs (21A), or NDV and H5 MDAs or H5 only MDAs (21B) vaccinated at day-of-age with either vAVW01 (v01 or 01; no inserted gene) or vAVW03 (v03 or 03; AI HA insert).

Chicken study 1: Protection against Newcastle disease and ND and AI HI Titers Induced by Engineered AVINEW Mutants in Chickens The aim of this study was to verify that the insertion of a foreign gene into the genome of the AVINEW strain did not decrease the ability to protect chickens against Newcastle disease (ND). The vaccination scheme is shown in FIG. 14. The percentage of protection induced by the AVINEW vaccine and 2 engineered AVINEW mutants (vAVW01 that does not contain any insert (see Table 1) and vAVW03 that contains a HPAI H5N1 HA insert) is shown in FIG. 15. Similar levels of ND protection were induced by the two tested doses of the 3 vaccines demonstrating that, in the tested conditions, there is no negative impact of the HA insertion on the ability of the vector to protect against a velogenic NDV challenge with the Herts33 strain.

Example 3

Protection Against H5N1 HPAI Induced by Engineered AVINEW Mutants in SPF Chickens with or without Maternally-Derived Antibodies (MDA) Against NDV and/or AI

Example 3.1

Chicken study 2: Protection Against an Hungarian (2006) H5N1 HPAI Isolate Induced by One Administration of Engineered AVINEW Mutants in SPF Chickens The efficacy of the engineered AVINEW mutant vAVW03 against an HPAI H5N1 challenge was evaluated in SPF (specific pathogen free) chickens. Eight one-day-old SPF chickens were vaccinated with $10^5$ EID50 by eye drop (ED) and intra-nasal (IN) route (D0). The H5N1 challenge (6 log 10 of the H5N1 clade 2.2 A/duck/Hungary/11804/2006 isolate per bird) was performed 4 (D28) and 6 (D42) weeks after vaccination. Chickens were followed up for 2 weeks after challenge. Results are shown in Table 3 and Table A.

TABLE 3

Chicken study 2: Results of clinical protection from a vaccination-challenge study evaluating the protective efficacy induced by the engineered vAVW03 mutant against an HPAI H5N1 (A/duck/Hungary/11804/2006) challenge in SPF chicks

| | Vaccination (D0) | | H5N1 | Protection |
|---|---|---|---|---|
| Group | Vaccine | Dose (EID50) | Challenge | (MTD)[a] |
| 1 | — | — | D28 | 0% (3.0) |
| 2 | vAVW03 | 5 log10 | D28 | 100% |
| 3 | — | — | D42 | 0% (3.5) |
| 4 | vAVW03 | 5 log10 | D42 | 75% (8.0) |

[a]MTD: mean time to death in days

TABLE A

Chicken study 2: Results of protection against shedding from a vaccination-challenge study evaluating the protective efficacy induced by the engineered vAVW03 mutant against an HPAI H5N1 (A/duck/Hungary/11804/2006) challenge in SPF chicks

| | Vaccination (D0) | | H5N1 | Oral shedding[a] | | | Cloacal shedding[a] | | |
|---|---|---|---|---|---|---|---|---|---|
| Group | Vaccine | Dose (EID50) | Chall. | 2 dpc | 4 dpc | 7 dpc | 2 dpc | 4 dpc | 7 dpc |
| 1 | — | — | D28 | 8/8 | — | — | 8/8 | — | — |
| 2 | vAVW03 | 5 log10 | D28 | 3/8 | 2/8 | 2/8 | 0/8 | 0/8 | 0/8 |
| 3 | — | — | D42 | 8/8 | — | — | 7/8 | — | — |
| 4 | vAVW03 | 5 log10 | D42 | 4/8 | 4/8 | 2/8 | 0/8 | 2/8 | 1/8 |

[a]Shedding was evaluated using real time PCR from oral and cloacal swabs taken 2, 4 and 7 days post-challenge (dpc)

Full and partial (75%) clinical protections were induced at D28 and D42, respectively. The number of chickens shedding detectable amount of challenge virus was reduced in the vaccinated groups. Furthermore the levels of shedding in the vaccinated groups (2 and 4) at 2 dpc were more than 3 log 10 and about 2 log 10 lower than that in the control groups after challenge at D28 and D42, respectively. Altogether, these results indicate that the Avinew vector expressing an HPAI HA gene is protective in SPF chickens.

Example 3.A

Chicken Study A: Protection Against an Egyptian (2006) H5N1 HPAI Isolate Induced by One Administration of Engineered AVINEW Mutants in SPF Chickens The efficacy of the engineered AVINEW mutant vAVW03 against an Egyptian HPAI H5N1 challenge was evaluated in SPF (specific pathogen free) chickens. Ten one-day-old SPF chickens were vaccinated with $10^6$ EID50 by eye drop (ED) and intra-nasal (IN) route (D0). The H5N1 challenge (6 log 10 of the H5N1 clade 2.2 A/chicken/Egypt/06959-NLQP/2006 isolate per bird) was performed 3 (D21) weeks after vaccination. Chickens were followed up for 2 weeks after challenge. Results are shown in Table B.

TABLE B

Chicken study A: Results of clinical protection from a vaccination-challenge study evaluating the protective efficacy induced by the engineered vAVW03 mutant against an HPAI H5N1 (A/chicken/Egypt/06959-NLQP/2006) challenge in SPF chicks

| | Vaccination (DO) | | Protection after challenge |
|---|---|---|---|
| Group | Vaccine | Dose (EID50) | at D21 |
| 1 | — | — | 0% |
| 2 | vAVW03 | 6 log10 | 90% |

Excellent (90%) clinical protections were induced at D21 against this Egyptian HPAI H5N1 isolate confirming that the Avinew vector expressing an HPAI HA gene induces protection in SPF chickens.

Example 3.B

Chicken Study B: Protection Against an Hungarian (2006) H5N1 HPAI Isolate Induced by 1 or 2 Administrations of an Engineered AVINEW Mutants or a Prime-Boost Regimen in SPF Chickens The efficacy of the engineered AVINEW mutant vAVW03 after one, two administrations or a prime-boost regime with an inactivated vaccine against a Hugarian (2006) HPAI H5N1 challenge was evaluated in SPF (specific pathogen free) chickens. Eight one-day-old SPF chicks per group were vaccinated with $10^5$ EID50 by eye drop (ED) and intra-nasal (IN) route at D0 (groups 2, 3 and 4) and at D14 (group 3). Chickens from group 3 received an inactivated vaccine made with the H5N9 A/chicken/Italy/A22/1998 LPAI isolate (0.5 ml/chick). The H5N1 challenge (6 log 10 of the H5N1 clade 2.2 A/duck/Hungary/11804/2006 isolate per chicken) was performed 4 (D42) weeks after the second vaccination. Chickens were followed up for 2 weeks after challenge. Results are shown in Table C.

TABLE C

Chicken study B:
Results of protection from a vaccination-challenge study evaluating the protective efficacy induced by different vaccination scheme including the vAVW03 mutant against an HPAI H5N1 (A/duck/Hungary/11804/2006) challenge in SPF chickens.

| | Vaccination at | | # birds protected/ total (MTD*) after challenge | Number of chickens/total shedding virus (real time RT-PCR) 2dpc-4 dpc** | |
|---|---|---|---|---|---|
| | | | | Oral | Cloacal |
| Group | D0 | D14 | at D42 | swab | swab |
| 1 | — | — | 0/8 (3.8) | 8/8-0/0 | 8/8-0/0 |
| 2 | vAVW03 | — | 7/8 (6) | 5/8-2/8 | 0/8-0/8 |
| 3 | vAVW03 | vAVW03 | 7/8 (6) | 3/8-2/8 | 0/8-0/8 |
| 4 | vAVW03 | Inact. H5N9** | 8/8 | 0/8-1/8 | 0/8-0/8 |

*MTD, mean time to death in days
**dpc, day post-challenge
***the inactivated (or killed) AI H5N9 vaccine was prepared with the H5N9 A/chicken/Italy/A22/1998 LPAI isolate Excellent clinical protections were induced in the 3 vaccinated groups. Reduction in the number of shedding chickens as well as in the level of shedding of challenge virus was also induced by vaccination. The best protective performances were obtained in chickens from group 4 that received the prime-boost regimen. These results confirm that the Avinew vector expressing an HPAI HA gene induces protection in SPF chickens and indicates that the level of protection may be improved by a prime-boost strategy.

Example 3.C

Chicken study C: Protection Against a Variant Egyptian (2008) H5N1 HPAI Isolate Induced by Different Vaccination Schemes Including an Engineered AVINEW Mutants in SPF Chickens The efficacy of the engineered AVINEW mutant vAVW03 included in different vaccination schemes (see Table D) against an HPAI H5N1 challenge using a variant Egyptian isolate from 2008 (A/chicken/Egypt/1709-6/2008) was evaluated in one-day-old SPF (specific pathogen free) chickens. The vaccination scheme is shown in Table D. The vAVW03 vaccine was administered at a dose of $10^6$ $EID_{50}$/100 μL by the intra-ocular (50 μL) and intra-nasal (50 μL) routes at D0 (groups 2 and 3) and at D14 (groups 2 and 4). Chickens from group 3 received an inactivated vaccine made with the reverse genetics H5N1 strain that contains the HA (modified at the cleavage site) and NA from the H5N1 clade 2.3 A/duck/Anhui/1/2006 LPAI isolate (0.5 ml/chick). Chickens from group 4 received at D0 a commercial dose (approximately 3.5 log 10 TCID50/2004) by the subcutaneous route (nape of the neck) of the fowlpox recombinant vFP89 expressing the HA from the H5N8 HPAI A/turkey/Ireland/1378/1983 isolate (TROVAC-AIV H5 vaccine, see US 2008/0107681 and US 2008/0107687) diluted in Marek's disease vaccine diluent (Merial's proprietary material). The H5N1 challenge (5 log 10 of the H5N1 clade 2.2 A/chicken/Egypt/1709-6/2008 isolate per bird) was performed 2 weeks after the second vaccination (D28). Chickens were followed up for 10 days after challenge. Results are shown in Table D.

TABLE D

Chicken study C: Results of clinical protection from a vaccination-challenge study evaluating the protective efficacy induced by different vaccination scheme including the vAVW03 mutant against an HPAI H5N1 (A/chicken/Egypt/1709-6/2008) challenge in SPF chickens.

| Group | Number of chickens | Vaccination at D0 | Vaccination at D14 | Mean ± SD HI titers (log2) using H5N1 antigen* D28 | # chickens protected/total (MTD**) after challenge at D28 |
|---|---|---|---|---|---|
| 1 | 10 | — | — | — | 0/10 (3) |
| 2 | 14 | vAVW03 | vAVW03 | 3.3 ± 0.7 | 13/14 (6) |
| 3 | 14 | vAVW03 | Inact. Re5 | 9.1 ± 1.5 | 14/14 |
| 4 | 14 | vFP89 | vAVW03 | 4.4 ± 1.3 | 14/14 |

*the H5N1 antigen was prepared from the A/turkey/Turkey/1/2005 antigen; SD standard deviation

**MTD, mean time to death in days

The HI titers induced by the different vaccination schemes are shown in Table D. As expected, the higher HI titers were obtained in group 3 after the boost with an inactivated vaccine. Excellent clinical protections (93-100%) were induced in the 3 vaccinated groups. It's worth mentioning that the A/chicken/Egypt/1709-6/2008 isolate (HA protein sequence available in GenBank: ACD65000.1) is one of the H5N1 antigenic variants that emerged recently in Egypt and against which commercial inactivated H5 vaccines provide less protection than against older Egyptian strains. These results confirm that the Avinew vector expressing an HPAI HA gene induces protection in SPF chickens against an antigenic variant H5N1 Egyptian isolate.

Example 3.2

Chicken Study 3: Protection Against H5N1 HPAI Induced by Engineered AVINEW Mutants in Chickens with and without NDV and/or AI MDA The goal of the study was to evaluate the level of HPAI H5N1 protection induced by the AVINEW mutant vAVW03 expressing an H5N1 HPAI HA gene in SPF chickens and to evaluate the possible interference of maternally-derived antibodies (MDA) against the NDV vector and/or against AI.

In order to evaluate the effect of MDA on AI protection, SPF breeders had to be immunized with different vaccination schemes as shown in Table 4. There were 3 groups of breeders: the first group (G1) was vaccinated against NDV (3 administrations of AVINEW and 1 administration of inactivated (or killed) vaccine) and AI (3 administrations of an inactivated vaccine based on the H5N9 A/chicken/Italy/A22/1998 LPAI isolate); the second group (G4) was vaccinated against NDV only (same immunization scheme as group 1) and the third group (G5) was vaccinated with AI only (two administrations of an inactivated vaccine based on an H5N1 mutant containing the HA and NA genes from the A/goose/Guandong/1996 isolate) (see details in Table 4).

TABLE 4

Vaccination scheme of the SPF breeders used to produce one-day-old chickens with ND and/or AI MDAs

| Breeders group | Breeders vaccines | Weeks 0 | 3 | 4 | 6 | 8 | 9 | 16 | MDA in the progeny |
|---|---|---|---|---|---|---|---|---|---|
| G1 | ND L + K* | L | | L | | L | | K | H5N9 + ND |
| | AI H5N9 K** | | K | | K | | | K | |

TABLE 4-continued

Vaccination scheme of the SPF breeders used to produce one-day-old chickens with ND and/or AI MDAs

| Breeders group | Breeders vaccines | Weeks 0 | 3 | 4 | 6 | 8 | 9 | 16 | MDA in the progeny |
|---|---|---|---|---|---|---|---|---|---|
| G4 | ND L + K | L | | L | | L | | K | ND |
| | — | | | | | | | | |
| G5 | — | | | | | | | | H5N1 |
| | AI H5N1 K*** | | | | | | K | K | |

*L = Live NDV vaccine AVINEW; K = killed NDV vaccine (Gallimune 407)

**the inactivated (or killed) AI H5N9 vaccine was prepared with the H5N9 A/chicken/Italy/A22/1998 LPAI isolate

***the inactivated (or killed) AI H5N1 vaccine was prepared with an AI mutant containing the HA and NA genes from the H5N1 A/goose/Guandong/1996 HPAI isolate Chickens were hatched from eggs laid by these immunized breeders and the HPAI H5N1 efficacy induced by vAVW03 in these chicks with MDA was compared with that induced in SPF chickens without MDA.

Figure 13:
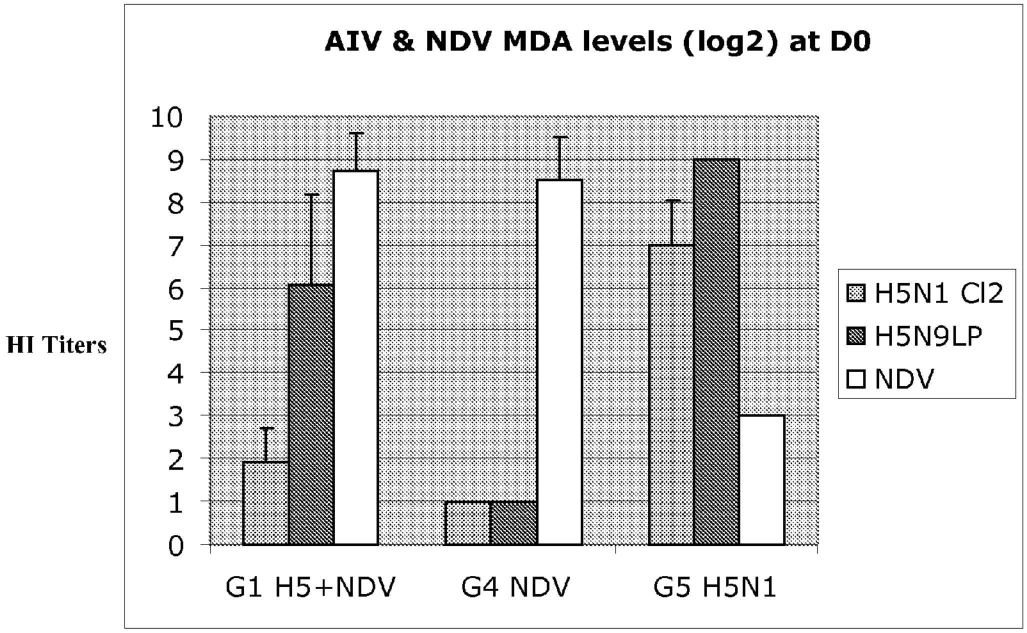
FIG. 13 depicts anti-NDV and anti-AI (against either H5N1 Cl2 or H5N9LP antigens) Maternally Derived Antibody (MDA) HI titers in the one-day-old chicken progeny of different groups of vaccinated SPF layers.

FIG. 13 shows the mean NDV and AI HI titers (in log 2) observed in one-day-old chickens hatched from the immunized breeders described in Table 4. NDV titers were very high in both groups from ND-vaccinated breeders (G1 & G4). The AI HI titers measured with H5N1 clade 2.2 (A/duck/Hungary/11804/2006) and H5N9 (A/chicken/Italy/A22/1998) antigens were higher in the chicken progeny of G5 breeders vaccinated with an inactivated H5N1 vaccine. These results confirmed the presence of the expected MDA in the serums of day-old chicks hatched from the vaccinated SPF breeders.

FIG. 14 depicts a timeline for the immunization and challenge protocol of SPF chickens with or without MDA. One-day-old chickens from regular SPF flocks or from vaccinated SPF breeders were immunized by the oculonasal route with $10^5$ EID50 of either vAVW03 expressing the HA gene from the A/turkey/Turkey/1/2005 HPAI H5N1 isolate (10 animals) or with vAVW01 that did not contain any HA insert and was used as a control (10 animals). Three weeks post-vaccination, all chickens were challenged with 6 log 10 of the HPAI H5N1 A/duck/Hungary/11804/2006 isolate by the intraocular route. Chickens were observed for clinical signs and mortality during two weeks after challenge. Table 5 summarizes the vaccination scheme and the avian influenza protection results.

TABLE 5

AI protection induced by an AVINEW ® mutant (vAVW03) expressing H5N1 HA in SPF chickens and chickens with various MDAs

| Group | MDA | Breeders | Vaccine | Mortality | MDT* | % protection |
|---|---|---|---|---|---|---|
| 1 | — | SPF | vAVW01 | 10/10 | 3.8 | 0% |
| 2 | — | SPF | vAVW03 | 1/10 | 11 | 90% |
| 3 | H5N9 + ND | G1 | vAVW01 | 7/10 | 7.3 | 30% |
| 4 | H5N9 + ND | G1 | vAVW03 | 2/9 | 10 | 78% |
| 5 | ND | G4 | vAVW01 | 10/10 | 3.6 | 0% |
| 6 | ND | G4 | vAVW03 | 0/10 | — | 100% |
| 7 | H5N1 | G5 | vAVW01 | 1/10 | 8 | 90% |
| 8 | H5N1 | G5 | vAVW03 | 0/10 | — | 100% |

*MDT = mean death time in days

Figure 16:
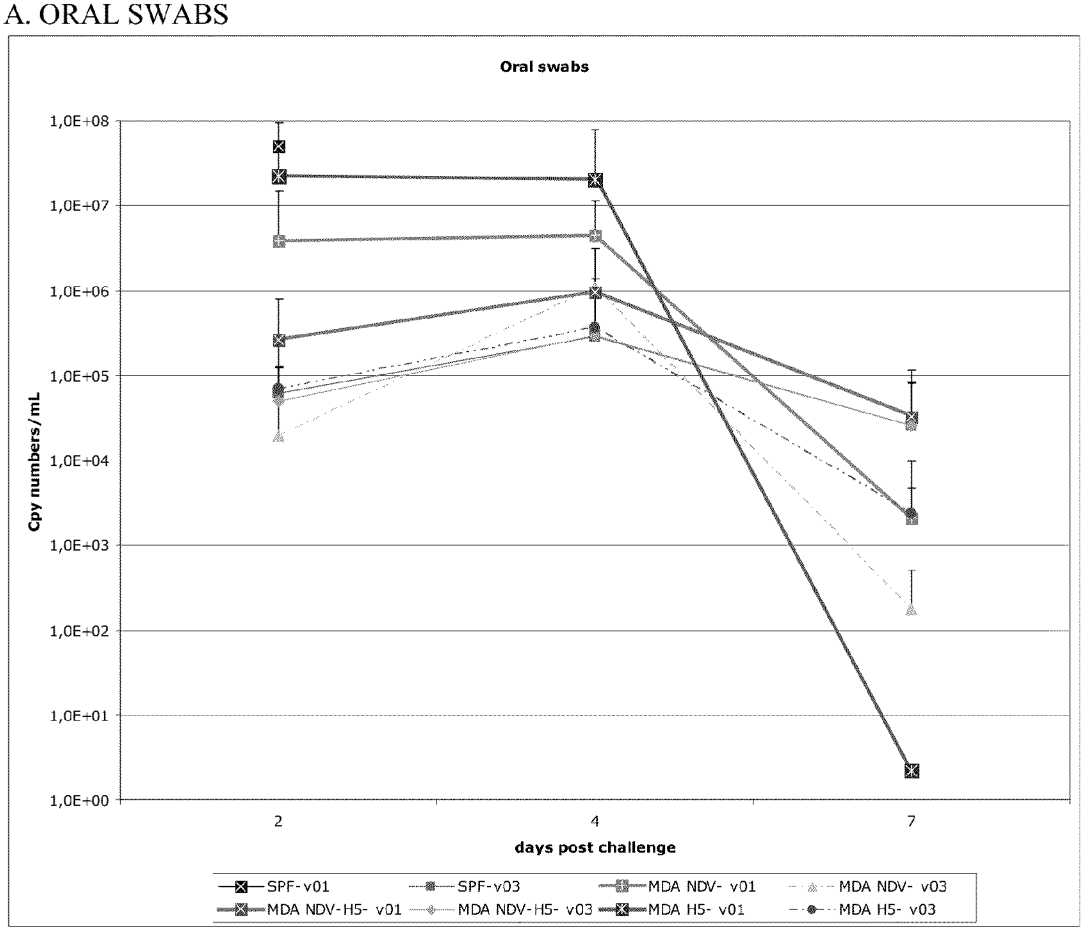
FIG. 16 depicts a comparison of AIV shedding from oral (A & C) and cloacal (B & D) swabs in chickens without (SPF) or with MDAs vaccinated with vAVW01 or vAVW03. The results in C and D are expressed as the ratio in log 10 between mean levels of HPAI H5N1 challenge shedding of vAVW01-immunized chickens and those of vAVW03-immunized chickens at different time points after challenge.
Figure 16:
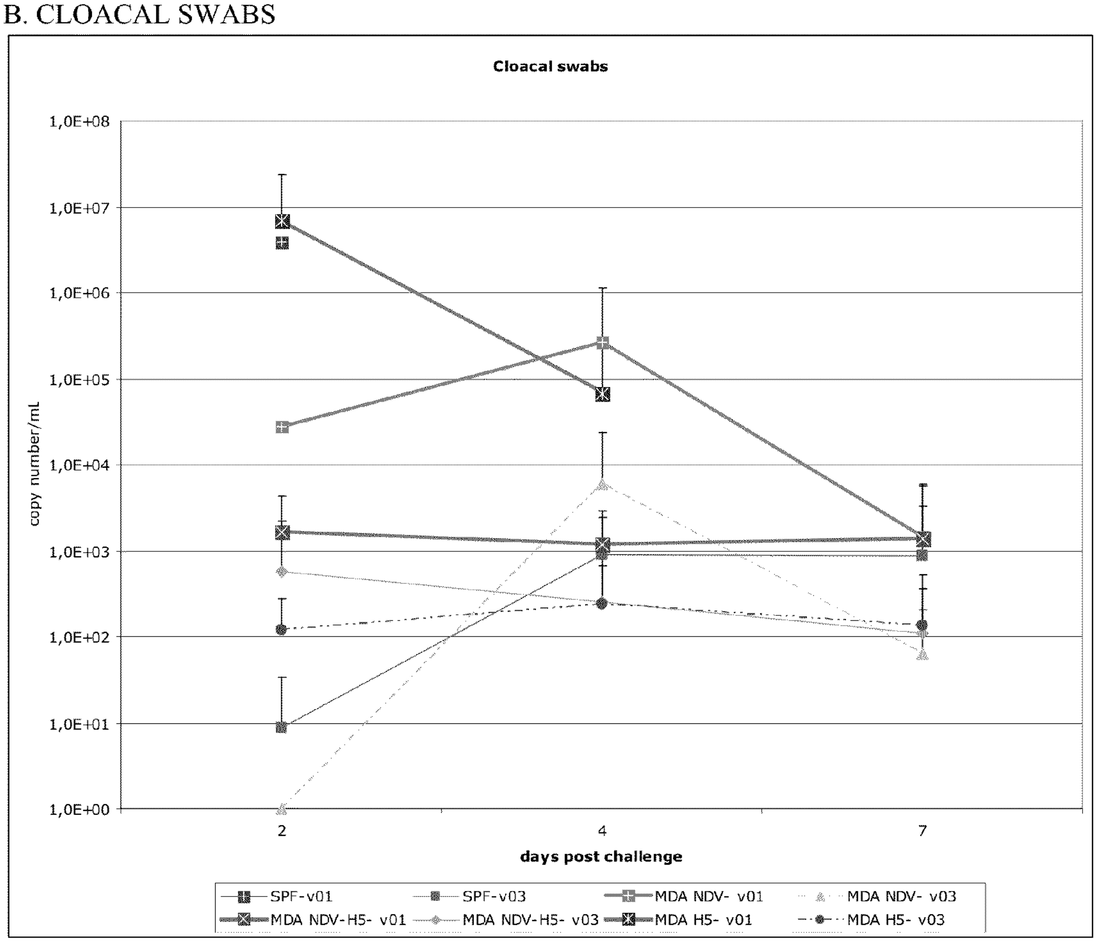
Figure 16:
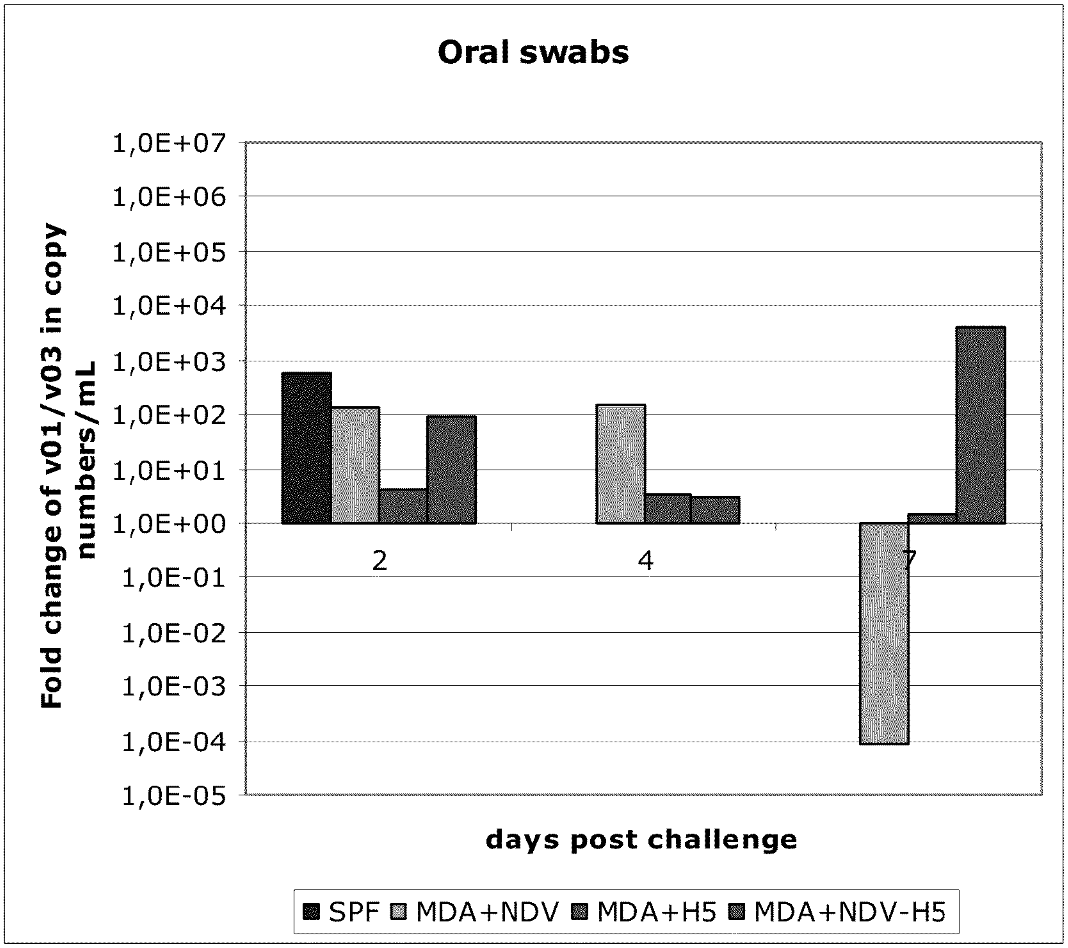
Figure 16:
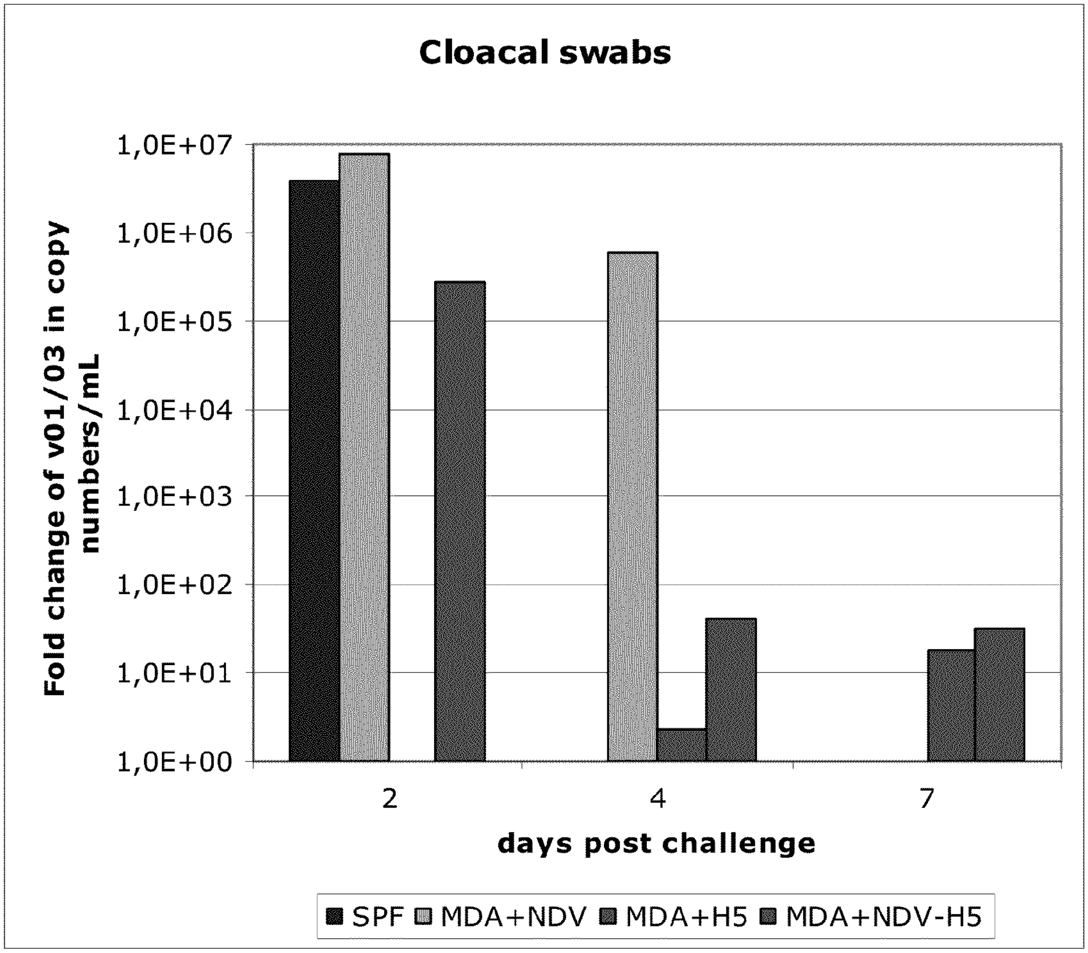

The rapid mortality (mean death time of 3.6-3.8 days) of chickens without AI MDA vaccinated with vAVW01 (Groups 1 and 5) validated the challenge (see Table 5 and FIG. 15). HPAI H5N1 protection level after 1 mucosal administration of vAVW03 in one-day-old SPF chickens protected 90% of the chickens. Surprisingly, all vAVW03-immunized chickens hatched from breeders (G4 in Table 4) vaccinated with NDV only (group 6) were protected from the HPAI challenge indicating that there was no anti-vector NDV MDA interference on the AI protection. The effect of AIV MDA is more difficult to assess since only 7 and 1/10 chickens died after challenge in the control groups (groups 3 and 7); however 7/9 birds vaccinated with vAVW03 (group 4) were protected indicating that protection can be induced in the presence of both NDV and AI MDAs. Vaccinated chickens that died after challenge died at a later time compared to unvaccinated birds (see Table 5 the mean death time and FIG. 15 for the kinetic of mortality). Table 6 shows the number of chickens positive for oral or cloacal shedding and FIG. 16 shows the kinetic of oral (16A) and cloacal (16B) shedding after challenge. The ratio between levels of shedding in vAVW01/vAVW03 is also shown in FIG. 16 for oral (16C) and cloacal (16D) swabs. The vAVW03-vaccinated chickens shed much lower virus and the number of positive swabs was lower after challenge compared with the vAVW01-vaccinated chickens.

TABLE 6

H5N1 shedding in the 8 tested groups was evaluated by real time reverse transcriptase PCR (RRT-PCR) targeting the matrix gene in oral and cloacal swabs at 2, 4, and 7 days post H5N1 HPAI challenge (dpc).

| | | 2dpc | | 4dpc | | 7dpc | |
|---|---|---|---|---|---|---|---|
| Group | Bird-vaccine* | Oral | Cloacal | Oral | Cloacal | Oral | Cloacal |
| 1 | SPF-v01 | 6/6 | 6/6 | NS | NS | NS | NS |
| 2 | SPF-v03 | 7/10 | 0/10 | 10/10 | 4/10 | 3/10 | 1/10 |
| 3 | $MDA^{+}$NDV-v01 | 9/9 | 1/9 | 2/2 | 1/2 | 0/1 | 0/1 |
| 4 | $MDA^{+}$NDV-v03 | 4/10 | 0/10 | 6/10 | 0/10 | 2/10 | 1/10 |
| 5 | $MDA^{+}$NDV-H5-v01 | 8/10 | 1/10 | 9/9 | 4/9 | 5/5 | 1/5 |
| 6 | $MDA^{+}$NDV-H5-v03 | 4/10 | 0/10 | 7/10 | 5/10 | 0/6 | 1/6 |
| 7 | $MDA^{+}$H5-v01 | 8/10 | 3/10 | 8/10 | 4/10 | 5/10 | 1/10 |
| 8 | MDA H5-v03 | 7/10 | 0/10 | 6/10 | 2/10 | 6/10 | 1/10 |

*v01 = vAVW01 and v03 = vAVW03

Figure 17:
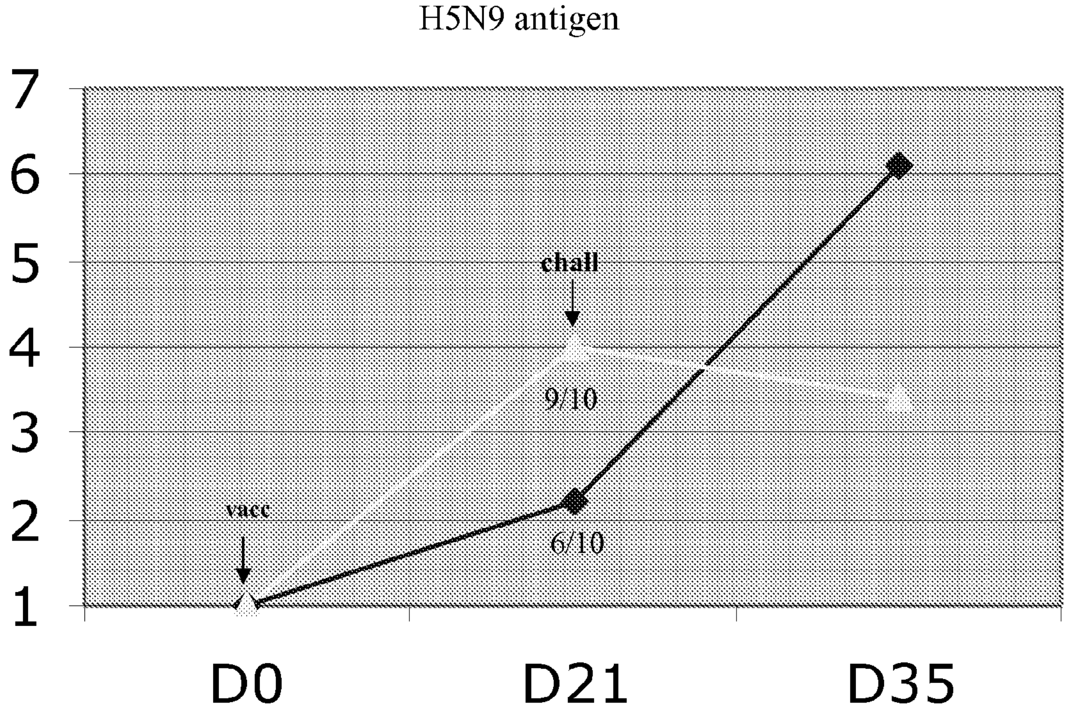
FIG. 17 depicts an NDV MDA effect (SPF: no MDA; NDV: anti-NDV MDAs) on vAVW03-induced AIV HI titers (using H5N9 (A) or H5N1 clade 2.2 (B) antigens) after vaccination (D21) and after challenge (D35). Numbers written on the figure correspond to number of positive serums/total tested. In presence of NDV MDA, AIV HI titers were higher after vaccination and did not increase after challenge compared to results in SPF chicks without NDV MDA.
Figure 17:
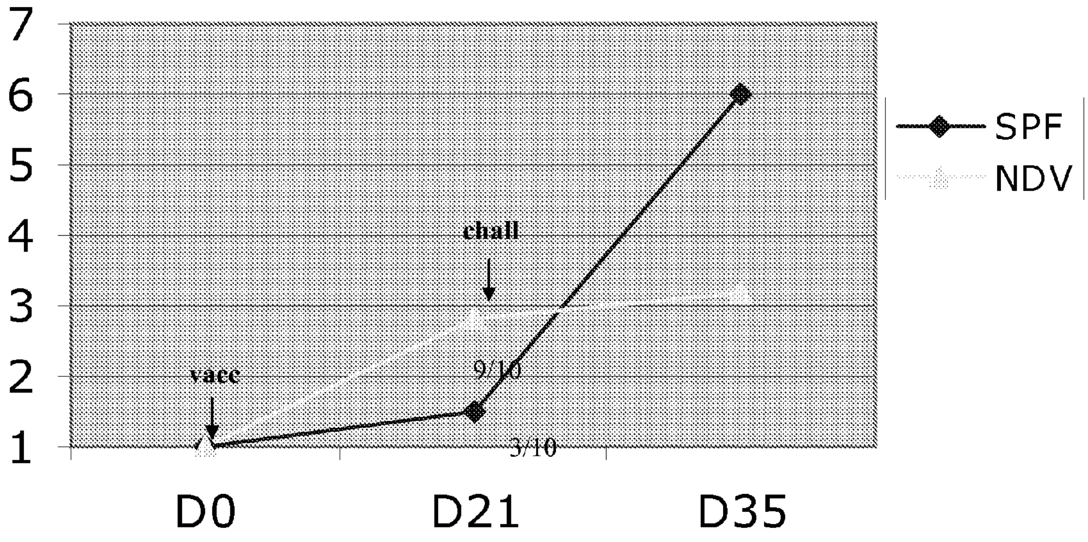

FIG. 17 depicts the NDV MDA effect on vAVW03-induced MV HI titers (using the H5N1 clade 2.2 (A/duck/Hungary/11804/2006) and H5N9 (A/chicken/Italy/A22/1998) antigens) after vaccination (D21) and after challenge (D35). In the presence of NDV MDAs (NDV), on day 21 (after vaccination and before challenge), there were higher mean AIV HI titers after vaccination and a higher number of chickens with detectable HI titers against both antigens. On day 35 (after challenge), there was no AIV HI titer boost after AIV challenge in the progeny of breeders vaccinated with NDV only and 10/10 chickens were protected (versus 9/10 in SPF group). In SPF chickens with no MDA, the clear increase of AIV HI titers after challenge suggested that the challenge virus replicates somewhat in these chickens. The results suggest an unexpected better AIV antibody induction and protection in chickens with NDV MDAs.

Figure 18:
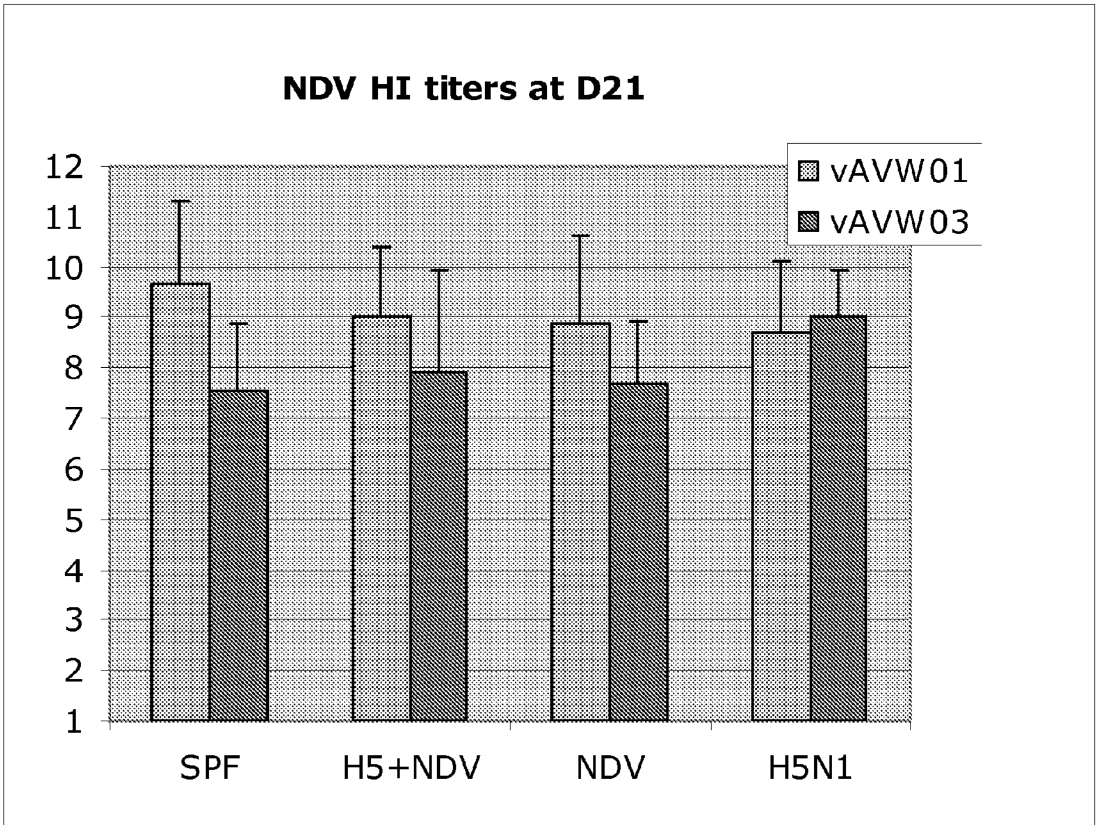
FIG. 18 depicts D21 NDV HI titers post-vaccination (at D0) with vAVW01 or vAVW03 in chickens with no MDA (SPF), AI H5N9 and NDV MDAs (H5N9+NDV), NDV MDAs (NDV) or AI H5N1 (H5N1) MDAs; NDV MDA did not have a negative effect on the level of NDV HI titers induced by vAVW01 or vAVW03.

FIG. 18 depicts NDV HI titers post-vaccination (D21). On Day 21, vAVW01-induced NDV titers were usually higher than those induced by vAVW03. On Day 21, there was no difference in chickens with (from G1 (H5+NDV) or G4 (NDV) breeders) or without (from SPF or G5 (H5N1) breeders) NDV MDA with respect to NDV HI titers, indicating that NDV MDAs did not interfere on vAVW01 or vAVW03-induced NDV HI titers.

Altogether the results of this study indicate clearly that one mucosal administration to one-day-old chickens of a relatively low dose (5 log 10 EID50) of the AVINEW engineered mutant vAVW03 induced an excellent level of protection against an HPAI H5N1 challenge. The presence anti-vector (NDV) MDA had no negative impact on AI protection. In contrast and surprisingly, the protection and AI antibody data suggest a better AI protection when NDV MDAs were present in the one-day-old chickens at the time of vAVW03 vaccination. These results also show that AI protection may be induced by vAVW03 in birds with both NDV and AI maternal antibodies.

Example 4

Protection Against H5N1 HPAI Induced by Engineered AVINEW Mutants in Ducklings

Ducks can be naturally infected with NDV and represents the reservoir for avian influenza A viruses. They may not necessarily show clinical signs after AI infection even with highly pathogenic strains but may transmit the virus to the chickens that are highly susceptible. That is why ducks are called the Trojan horses of AI. The goal of this study was to investigate the possibility to use an engineered NDV as a vector vaccine for influenza in ducks.

Example 4.1

Duck Study 1 in 14 Day-Old Muscovy Ducklings

The objective of the study was to compare (1) the immunogenicity and (2) the H5N1 efficacy induced by two AVINEW engineered mutants expressing the synthetic HA gene from 2 different H5N1 clades (vAVW02 is expressing the HA gene of clade 2.1 A/chicken/Indonesia/7/2003 and vAVW03 the HA from clade 2.2 A/turkey/Turkey/1/2005) with that of the parental Avinew strain in conventional Muscovy ducklings Example 4.1.1

Duck Study 1: Immunogenicity of Engineered Avinew Mutants in Ducklings

One-day-old Muscovy ducklings were tested for NDV and AIV serology and 7/10 ducklings were surprisingly found seropositive for NDV with a mean HI titre of 3.9 log 2. All sera were negative for the AI HI test. Another blood sampling taken at 13 day of age in 10 ducks gave negative ND HI titres and the study was started when ducks were 14 day of age. Three groups were set up, with ten vaccinated and seven contact control ducklings in each. Contacts were separated the days of vaccinations (D0& D21) and were set back into the Group the following day. A fourth group of 5 unvaccinated controls was included (see Table 7).

TABLE 7

Duck study 1: Group setting for the evaluation of immunogenicity of AVINEW mutants expressing HA.

| Group | Nb ducks | Vaccine (D0 & D21) | HA insert | Dose (50 μl eye drop on D0 & D21) |
|---|---|---|---|---|
| 1 | 10 vacc. + 7 contacts | AVINEW | — | 10 chicken doses |
| 2 | 10 vacc. + 7 contacts | vAVW02 | A/ck/Indonesia/7/2003 | 6.5 log10 EID50 |
| 3 | 10 vacc. + 7 contacts | vAVW03 | A/tk/Turkey/1/2005 | 6.5 log10 EID50 |
| 4 | 5 | — | — | — |

Blood sampling were taken at D0, D21 & D42 for NDV and AI HI test and AI SN test using the MDCK cell-adapted M6 11804H5N1 HPAI Hungarian strains. Throat and cloacal swabs in vaccinated animals on D4, D7 & D12 and in contact animals on D7 & D12 were taken for NDV-specific real time PCR (primers M4100 & M4220 and probe M4169) (Wise et al. (2004) *J. Clin Microbiol* 42, 329-348).

Figure 19:
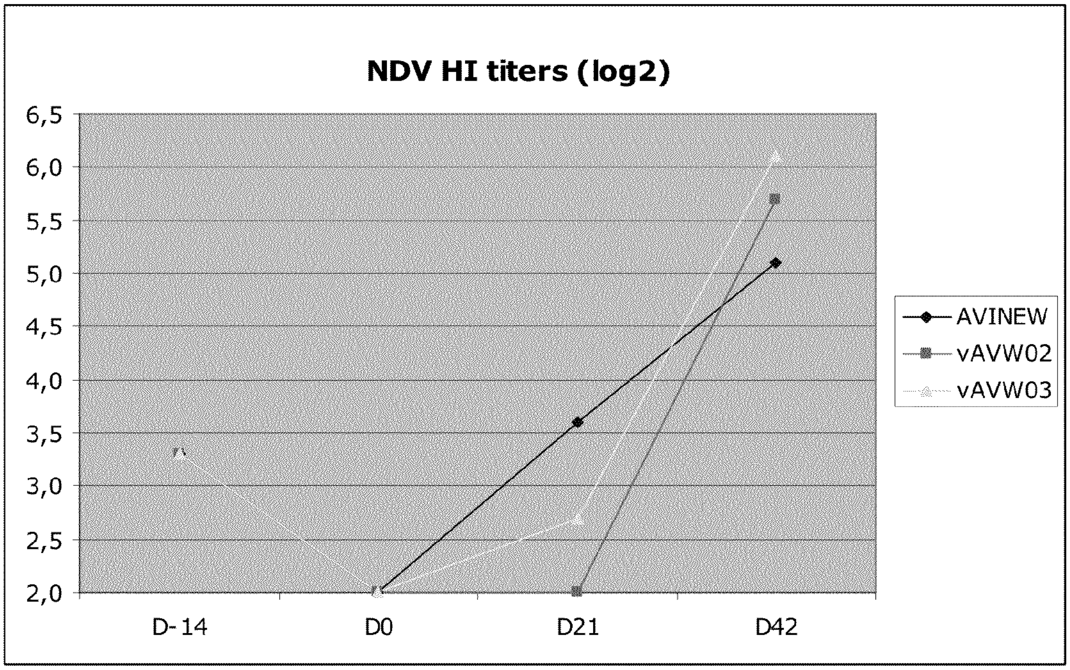
FIG. 19 depicts NDV HI titers after two vaccinations with AVINEW(G1), vAVW02(G2) and vAVW03(G3) at D0 and D21.

The results showed that no adverse reaction was observed, indicating that the 3 vaccines were safe in these experimental conditions. All samples from group 4 (unvaccinated controls) were negative for PCR & serology. All samples from the unvaccinated contact birds in groups 1 to 3 were negative for PCR & serology indicating that the vaccine did not spread from the vaccinated birds to the contacts. NDV HI titres are shown in FIG. 19. At D21, HI titres of G1 (3.6 log 2; 100%≥3 log 2) were significantly higher (ANOVA; p=0.004) than those of G2 (100%≤3 log 2) and G3 (3/10≥3 log 2). However, 3 weeks after the second administration, mean NDV HI titres were similar (ANOVA; p=0.682) in the 3 vaccinated groups (5.1, 5.7 and 6.1 log 2 in group 1, 2 and 3, respectively).

Figure 20:
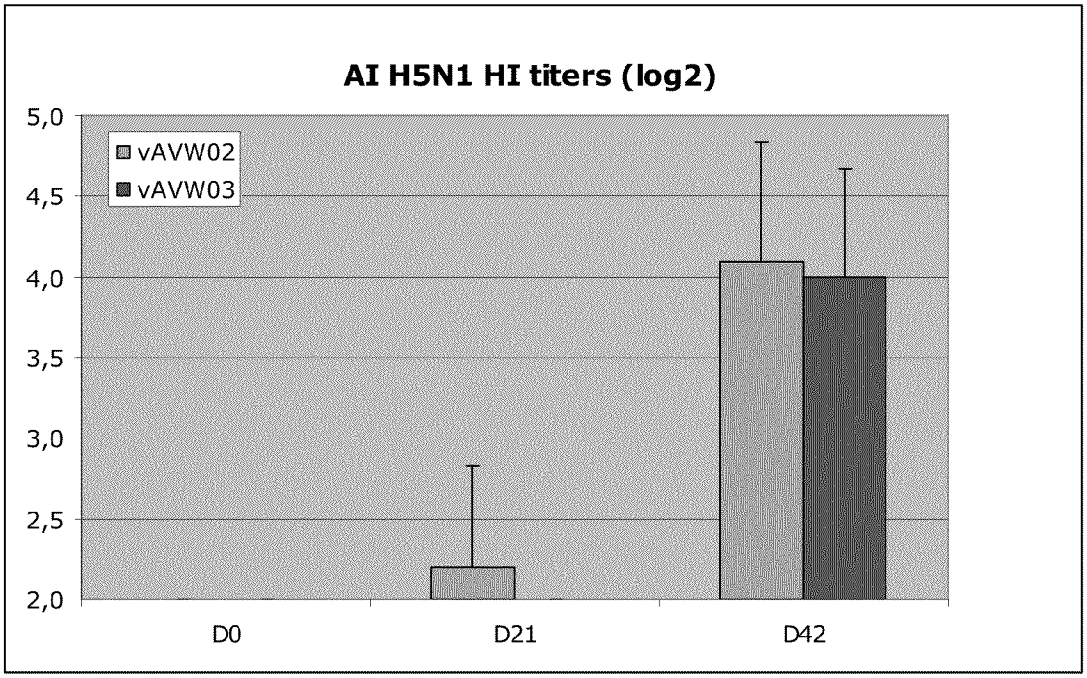
FIG. 20 depicts AI H5N1 HI titers after two vaccinations with vAVW02(G2) or vAVW03(G3) at D0 and D21.

AI H5N1 HI titres are shown in FIG. 20. No detectable HI titres (<3 log 2) was observed at D21 after the first vaccination in ducks from G2 and G3 except 1 duck in G2 that had a 4 log 2 HI titre. After the second administration, HI titres of all ducks were ≥3 log 2 with a mean titre of approx. 4 log 2. There was no significant difference in the AI HI titre induced by the two AVINEW mutants vAVW02 & 03 at both times.

Figure 21:
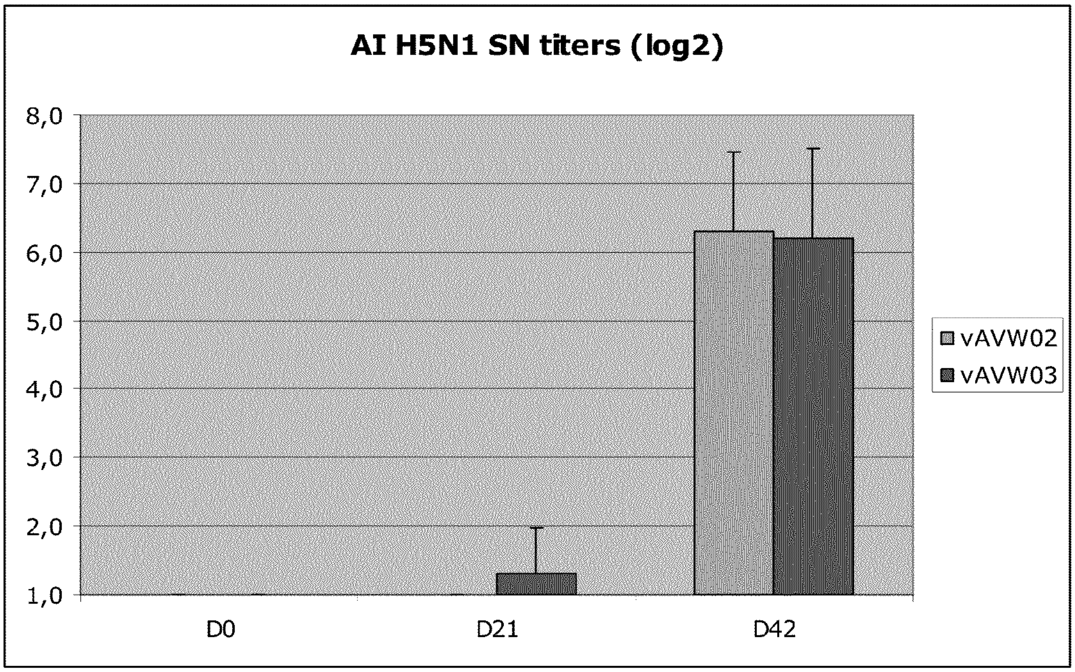
FIG. 21 depicts AI H5N1 SN titers after two vaccinations with vAVW02(G2) or vAVW03(G3) at D0 and D21.
Figure 22A:
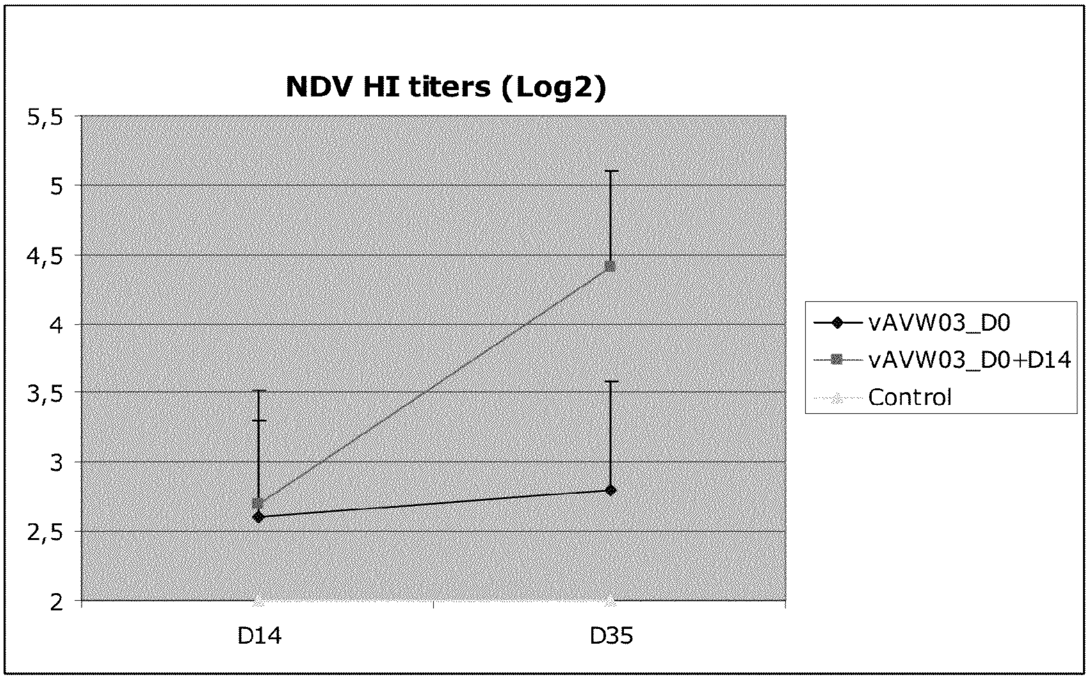
FIGS. 22A and 22 B depict NDV HI titers and AIV SN titer, respectively, induced by 1 (at D0) or 2 (at D0 and D14) eye drop administrations of vAVW03.
Figure 22B:
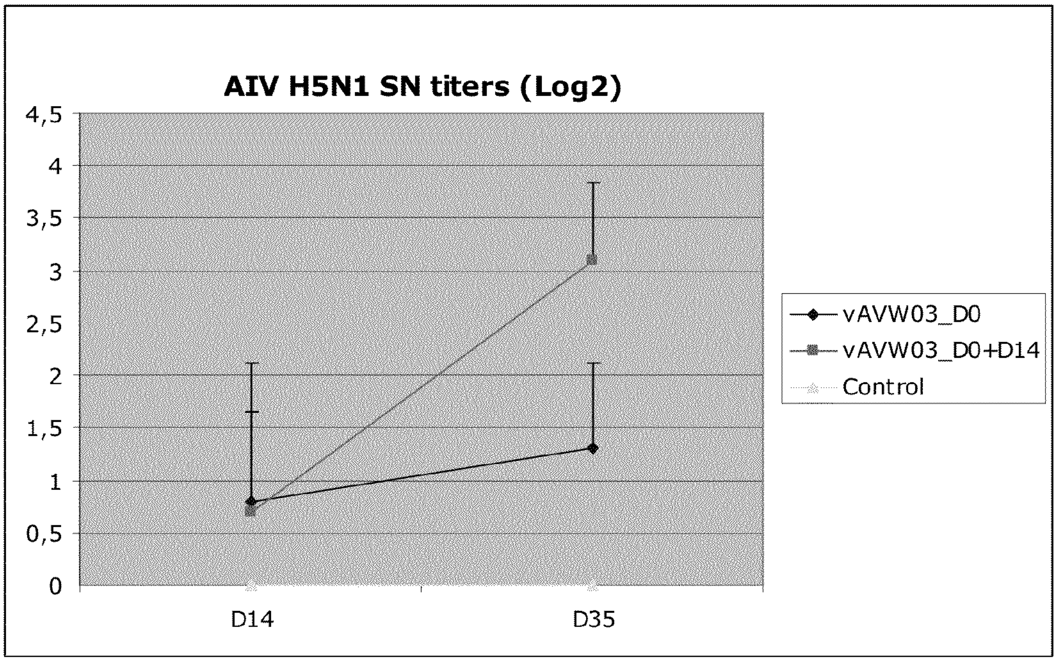
Figure 23:
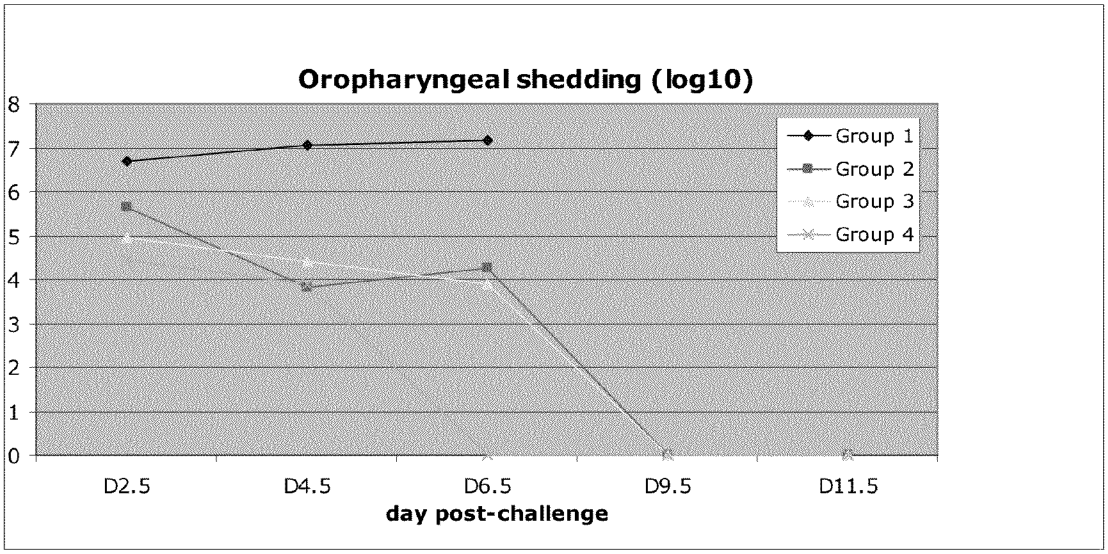
FIGS. 23A-23D depict kinetic of virus load (A and B) and of percentage of positive samples (C and D) in oropharyngeal (A and C) and cloacal (B and D) swabs from unvaccinated (Group 1) or vaccinated (Group 2: 1 administration of vAVW03 at D0; Group 3: 2 administrations of vAVW03 at D0 and D14; Group 4: prime-boost with vFP89 at D0 and vAVW03 at D14) Muscovy ducklings challenged with a HPAI H5N1 isolate at Day 28.
Figure 23:
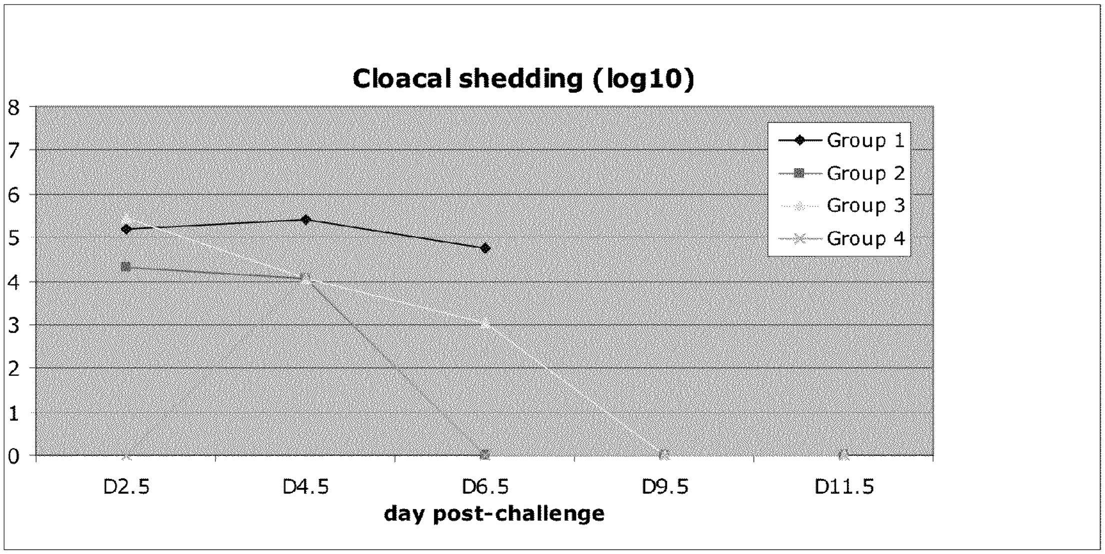
Figure 23:
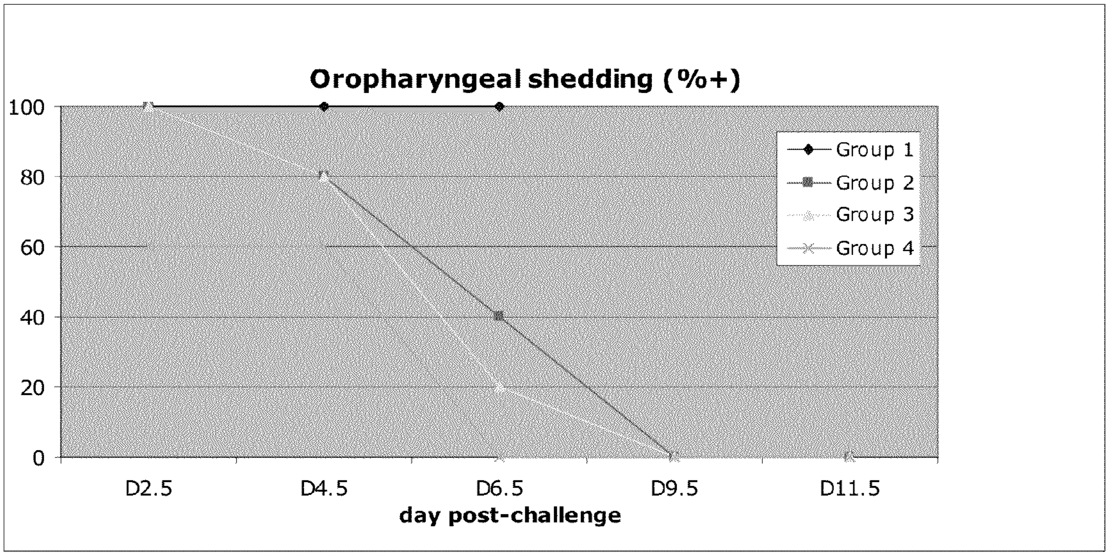
Figure 23:
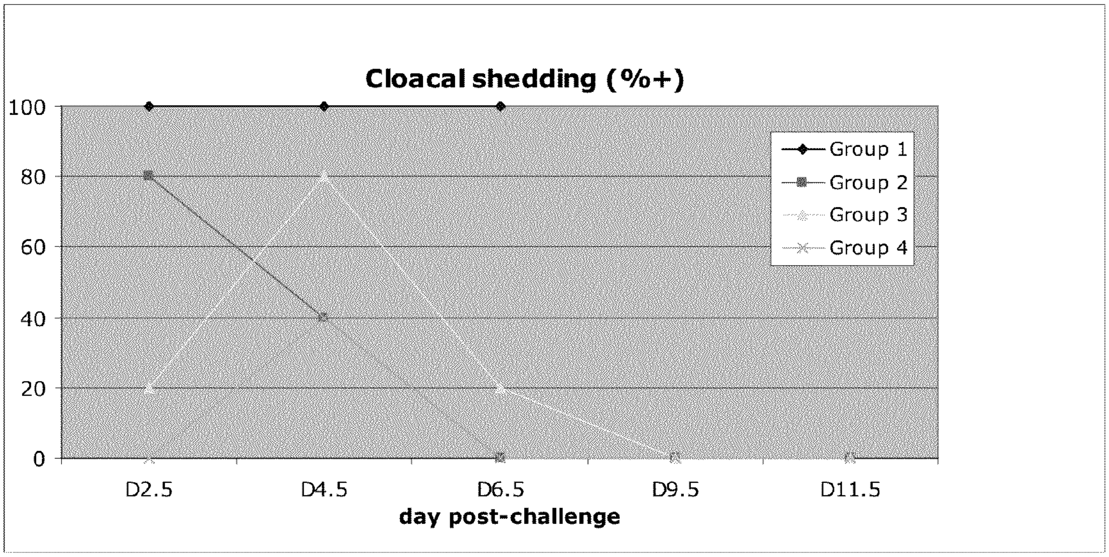
Figure 24A:
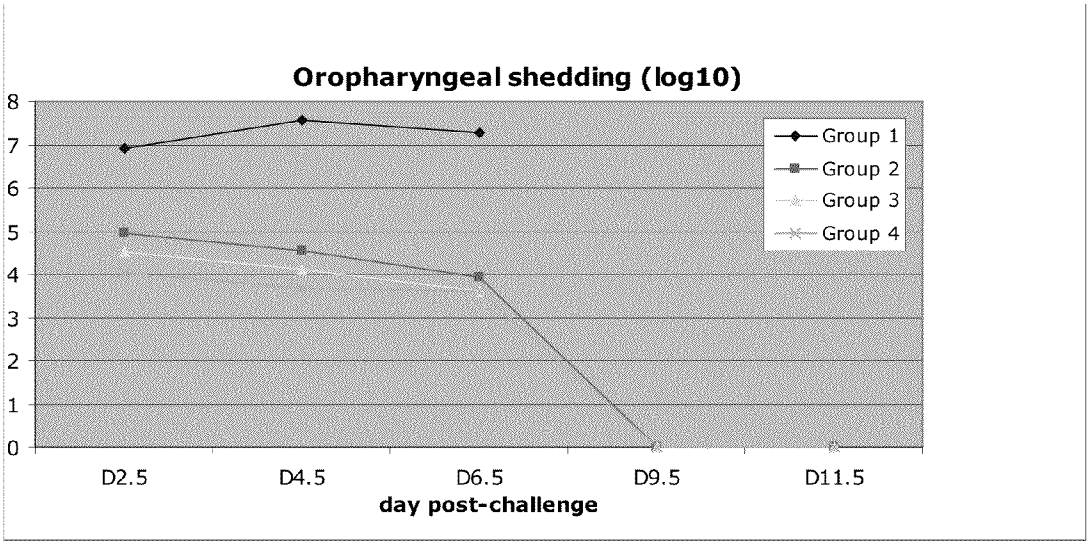
FIGS. 24A-24D depict kinetic of virus load (A and B) and of percentage of positive samples (C and D) in oropharyngeal (A and C) and cloacal (B and D) swabs from unvaccinated (Group 1) or vaccinated (Group 2: 1 administration of vAVW03 at D0; Group 3: 2 administrations of vAVW03 at D0 and D14; Group 4: prime-boost with vFP89 at D0 and vAVW03 at D14) Muscovy ducklings challenged with a HPAI H5N1 isolate at Day 42.
Figure 24B:
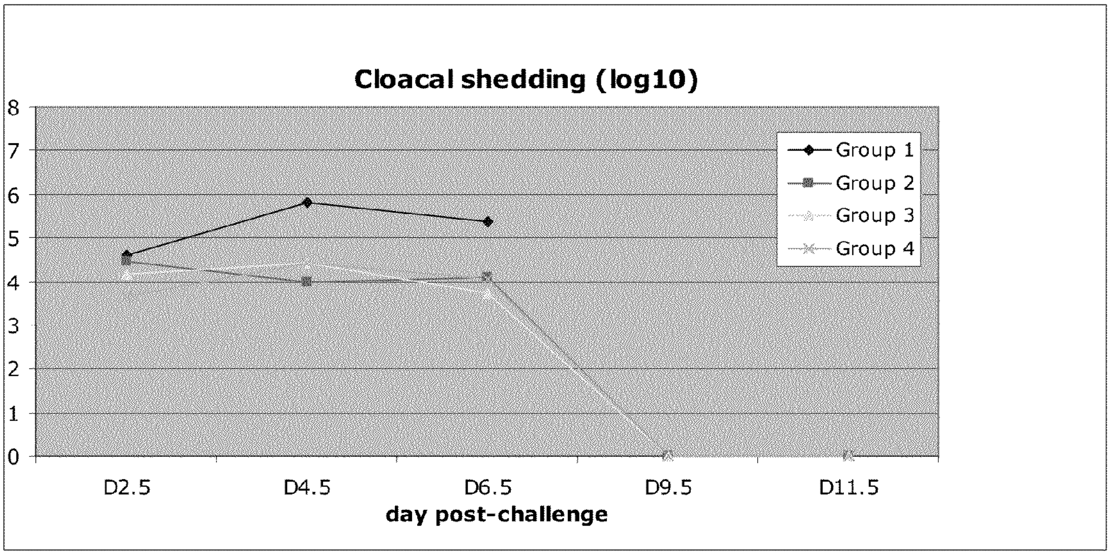
Figure 24C:
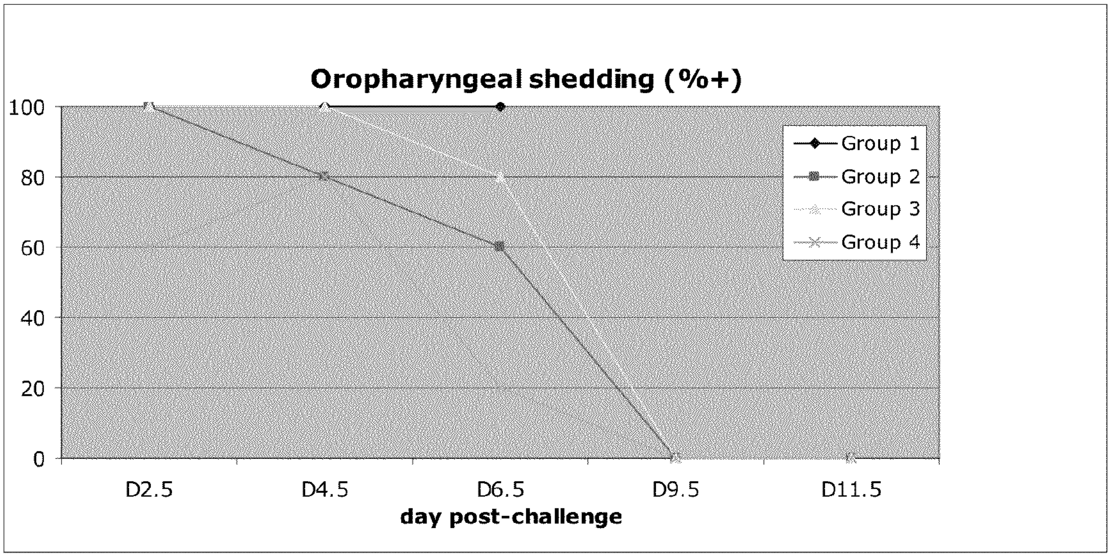
Figure 24D:
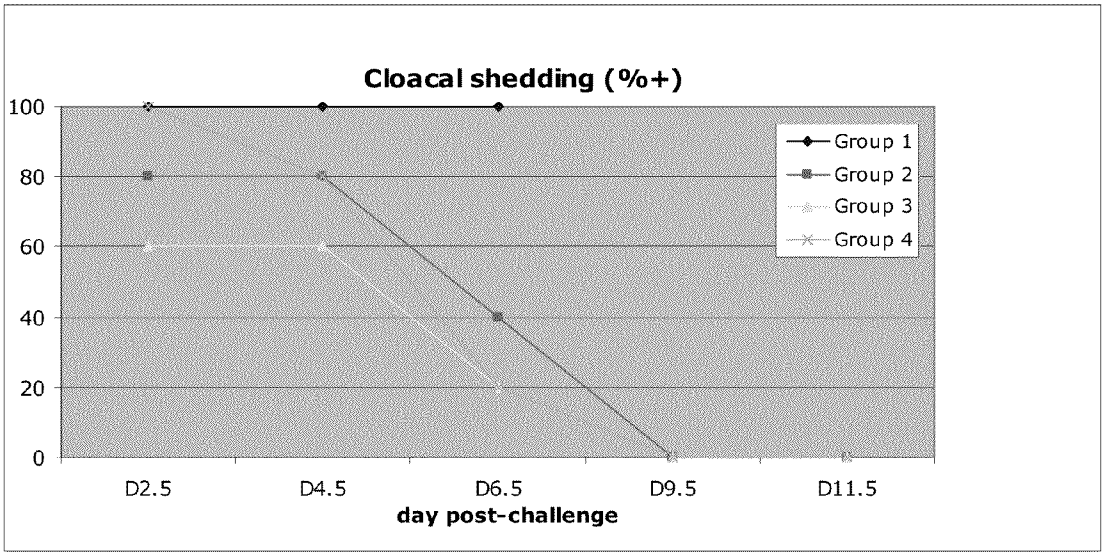

AI H5N1 seroneutralizing (SN) titres are shown in FIG. 21. No detectable SN titres (<2 log 2) was observed at D21 after the first vaccination in ducks from G2 and G3 except 2 ducks in G3 that had a 2 or 3 log 2 SN titre. After the second administration, HI titres of all ducks were ≥4 log 2 with a mean titre of approx. 6.2 log 2. There was no significant difference in the AI HI titre induced by the two AVINEW mutants vAVW02 & 03 at both times.

NDV PCR: Results of NDV PCR are shown in Table 8. Only a few ducks were found positive after the first and second vaccination in groups 1 and 3. All positive samples were from throat swabs except one swab in group 3 at D28. The 2 ducks positive at D25 after the 2$^{nd}$ administration of AVINEW were the only birds positive after the first administration at both D3 and D7. All samples were negative in group 2, despite induction of anti-ND and anti-AI antibodies.

TABLE 8

Duck study 1: Results of NDV real-time PCR testing in throat and cloacal swabs (numbers of positive ducks/total)

| Group | Vaccine (D0&D21) | After V1 D4 | After V1 D7 | After V2 D25 | After V2 D28 |
|---|---|---|---|---|---|
| 1 | AVINEW | 3/10 | 2/10 | 2/10 | 2/10 |
| 2 | vAVW02b | 0/10 | 0/10 | 0/10 | 0/10 |
| 3 | vAVW03 | 7/10 | 2/10 | 2/10 | 3/10* |

*All positive samples were from throat swabs except 1 of the 3 positive birds in G3 at D28 whose cloacal swab was positive.

In summary, the study confirmed the safety of AVINEW and showed that insertion of the HA gene into the AVINEW-AI mutants did not induce adverse reactions in ducklings. AVINEW induced significantly higher NDV HI titres after the first administration than the 2 tested AVINEW-AI mutants, suggesting that insertion of the HA gene impairs slightly the NDV replication. Two eye drop administrations of 10 chicken doses of the AVW-AI mutants were needed to induce positive NDV and AI HI titres as well as AI SN titres in all ducks. There was no difference in the immunogenicity against a clade 2.2H5N1 antigen of the two tested AVINEW-AI mutants despite the presence of HA gene from 2 different clades (clade 2.1 in vAVW02 and clade 2.2 in vAVW03). Only a few birds vaccinated with AVINEW and vAVW03 shed the virus mainly into throat swabs. However, this shedding was insufficient to transmit the vaccine virus to contact ducklings that remained negative during the whole study. Some ducks of this study were subsequently challenged with an H5N1 Hungarian isolate; the results of the challenge are presented in Example 4.1.2.

Example 4.1.2

Duck Study 1: H5N1 Protection Induced by Engineered Avinew Mutants in Muscovy Ducklings A H5N1 challenge study was performed in a few ducks vaccinated with vAVW02 or vAVW03 (see Example 4.1.1). Four of the ducks vaccinated twice by eye drop with vAVW02 or 03 were challenged at 9 weeks of age. Two ducks of groups 1 (AVINEW) were used as negative controls. Mean H5 HI titres were 5.5 log 2 (4 ducks at 5 and 4 at 6 log 2) and mean SN titres were 4.0 log 2 (1 at 3, 6 at 4 and 1 at 5 log 2 SN titre) in the vAVW02 & 03 vaccinated groups. The 8 vaccinated and 2 control ducks were challenged by an IM administration of 4.7 log 10 EID50 of the HPAI H5N1 A/duck/Hungary/11804/2006 (M6 11804) strain. Cloacal and throat swabs were taken at days 2, 7 and 10 after challenge and heart, pancreas, brain and spleen were sampled at necropsy and tested by PCR and histopathology.

The results are summarized in Table 9. The 2 controls died within 48 hours post-infection. Oronasal and cloacal swabs as well as brain, pancreas, heart and spleen were positive for H5N1 by PCR. Histopathology of the different organs showed signs of a peracute H5N1 infection. No clinical signs were observed in the 8 vaccinated ducks during the 10 day observation period. Shedding was only detected in the throat swab of 3 of the 8 vaccinated ducks (2 in G2 and 1 in G3) at day 3 post-challenge. One of these positive ducks (the one in G3) was also positive for AI PCR in the cloacal swab. All other swabs and organs were negative. No lesion was found in the organs of vaccinated ducks.

TABLE 9

Duck study 1: Summary of the results of protection induced by AVINEW vector vaccines in 14 day-old Muscovy ducklings.

| Vaccine | Dose in log10 EID50 | Vaccin. Day | Clinical Signs & mortality | Shedding (PCR) | Organs (PCR) | Organs (lesions) |
|---|---|---|---|---|---|---|
| AVINEW | 6.5 | D0 + D21 | 2/2 (2 dpi) | 2/2 | 2/2 | 2/2 |
| vAVW02 | 6.5 | D0 + D21 | 0/4 | 2/4 (throat) | 0/4 | 0/4 |
| vAVW03 | 6.5 | D0 + D21 | 0/4 | 1/4 (throat + cloacal) | 0/4 | 0/4 |

The result showed that the IM challenge was very severe in the 2 control birds. Full clinical and partial shedding protection was observed in the 8 ducks vaccinated twice by eye drop with an AVINEW vector vaccine expressing a synthetic H5 gene from H5N1 isolate.

Example 4.2

Duck Study 2 in One-Day-Old Muscovy Ducklings

The objective of the duck study in this example was to compare the immunogenicity (example 4.2.1) and the efficacy (example 4.2.2) induced by one or two administrations of the vAVW03 AVINEW mutant expressing the synthetic HA gene from clade 2.2 A/turkey/Turkey/1/2005 in day-old Muscovy ducklings.

Example 4.2.1

Duck Study 2: Immunogenicity of Engineered Avinew Mutants in One-Day-Old Ducklings The animals used in this study were one-day-old Muscovy ducklings that were all found negative for NDV (HI) and AIV (HI & SN) serology. Three groups were set up, with ten vaccinated and five contact control ducklings in each. Contacts were separated the days of vaccinations (D0& D21) and were set back into the Group the following day. A third group of 5 unvaccinated controls was included (see Table 10). Ten vaccinated ducklings from group 1 and 2 were vaccinated by eye drop of 50 μl containing 6.5 log 10 EID50 vAVW03 at D0 (group 1 and 2) and at D14 (group 2, only).

TABLE 10

Duck study 2: Group setting for the evaluation of immunogenicity of 1 or 2 administrations of the AVINEW mutant vAVW03 expressing HA.

| Group | Nb ducks | Vaccine | Vacc. Time |
|---|---|---|---|
| 1 | 10 vacc. + 5 contacts | vAVW03 | D0 |
| 2 | 10 vacc. + 7 contacts | vAVW03 | D0 + D14 |
| 3 | 5 | — | — |

Blood sampling were taken at D0, D14 & D35 and tested for NDV (La Sota antigen) and AI (M6 11804 HPAI H5N1 Hungarian/2006 antigen) antibodies with the HI test and for AI by SN test using the MDCK cell-adapted M6 11804H5N1 HPAI Hungarian strains.

No adverse reaction was observed, confirming the safety of vAVW03 for day-old Muscovy ducklings. NDV HI titres and AI SN titres are presented in FIGS. 22 A and B, respectively. At d14, 2 weeks after the first administration of vAVW03, only 10/20 vaccinated ducks had detectable NDV HI titres (≥3 log 2) and only 8/20 had detectable H5N1 SN titres (≥1 log 2). At d35, HI and SN titres remained similarly low in group 1 (6/10 positive with NDV HI test (mean of 2.9 log 2) and 8/10 positive with SN H5N1 test (mean of 1.3 log 2) and increased in group 2 after the 2$^{nd}$ administration of vAVW03. All samples from the control group (group 3) were negative for both NDV HI test and H5N1 SN test. All serums from unvaccinated contact ducks in groups 1 and 2 were also negative for NDV H1 and H5N1 SN except one duck in group 2 that seroconvert to NDV (3 log 2) and to SN H5N1 (1 log 2). This suggests that the vAVW03 vaccine spread in group 2 from vaccinated to 1 out of the 5 unvaccinated contacts. Some ducks of this study were subsequently challenged with an H5N1 Hungarian isolate; the results of the challenge are presented in Example 4.2.2.

The results showed that the safety of vAVW03 was confirmed in one-day-old ducklings. One eye-drop administration of 6.5 log 10 EID50 of vAVW03 in one-day-old Muscovy ducklings induced detectable low NDV HI titers and H5N1 SN titers in 40-50% birds only. A clear boost effect in NDV and SN H5N1 titers was observed after a second eye drop administration of vAVW03. The detection of low anti-NDV and anti-H5N1 antibody in one unvaccinated duck placed in contact with ducks of group 2 vaccinated twice at D0 and D14 suggests that, in contrast to the previous study, horizontal transmission could happen at a low frequency in the tested conditions.

Example 4.2.2

Duck Study 2: AI H5N1 Efficacy of Engineered AVINEW-AI Mutants in One-Day-Old Ducklings A H5N1 challenge study was performed in a few ducks vaccinated once or twice with the vAVW03 AVINEW-AI mutant expressing the HA gene of a clade 2.2 (see Example 4.2.1).

Five ducks from groups 1 (1 administration at D0) and 2 (2 administrations at D0 and D14) as well as two unvaccinated ducks in contact with birds of groups 1 and 2 and two unvaccinated ducks from group 3 were challenged at 5 weeks of age. The 10 vaccinated, the 4 contact and the 2 control ducks were challenged by an oronasal administration of 4.7 log 10 EID50 of the HPAI H5N1 A/duck/Hungary/11804/2006 (M6 11804) strain. Cloacal and throat swabs were taken at day 4 and day 7 and at day of death. Ten days after the challenge or at time of death, heart, pancreas, brain, liver and spleen were sampled at necropsy and tested by PCR and histopathology.

Individual results are shown in table 11. The 2 controls from group 2 died within 48 hours post-infection. Oronasal and cloacal swabs as well as brain, pancreas, heart and spleen were positive for H5N1 by PCR. Histopathology of the different organs showed signs of a peracute H5N1 infection. No clinical signs were observed in the 10 vaccinated ducks of groups 1 and 2 during the 10 day observation period. One duck in group 1 (#402) did not have detectable NDV and H5N1 antibodies and another duck (#403) had a low NDV HI titre only. This result indicated that these antibody tests may not be fully predictive in terms of clinical protection. Shedding was detected in three of the five ducks of group 1 (2 in both swabs and 1 in throat swab only) and only one duck of group 2 (throat swab only) at D4. At D7, only one duck of group 1 and group 2 were positive for shedding in the throat swab. All other swabs and organs were negative. No lesion was found in the organs of vaccinated ducks. All unvaccinated ducks that were kept in contact with vaccinated birds of group 1 and group 2 died within 2 or 3 days, and were positive by PCR analysis in their swabs and organs as the control ducks from group 3, except one contact duck (#429) from group 2 that was fully protected. Interestingly, it was the only contact duck that showed low levels of NDV and H5N1 antibodies at the time of challenge suggesting that the vaccine has been transmitted from the vaccinated ducks to this contact ducks. This duck did not show any clinical signs and was negative by PCR in its swabs and organs. Study of histopathologic lesions in different organs of the ducks that died after challenge was performed, which included: brain (incipient lymphocytic encephalitis), liver (acute, serous hepatitis with multiplex focal necrosisof the parenchyma), heart (interstitial oedema, petechae in the myocardium), pancreas (hypeaemia, interstitial oedem), small intestine (hyperaemia, oedema in the mucus membrane), spleen (hyperaemia, lymphocyte depletion in the Malpighi bodies), lung (hyperaemia, interstitial oedema, incipient focal interstitial pneumponia), Trachea (oedema in the mucus membrane). The result showed mild histopathologic changes including encephalitis, oedema, hyperaemia and necrosis of hepatocytes in different organs.

TABLE 11

Duck study 2: Individual results of protection in the duck study 2 performed with vAVW03 given once (D0) or twice (D0 and D14) in day-old Muscovy ducklings.

| Group | Bird | NDV HI titre (log2) | AI SN titre (log2) | Clinical signs & mortality | Shedding (PCR)* D2/3 | D4 | D7 | Organs (PCR) | Organs (lesions) |
|---|---|---|---|---|---|---|---|---|---|
| 1 | 401 | 4 | 2 | – | nd | – | – | – | – |
| vAVW03 at | 402 | <3 | <1 | – | nd | T | T | – | – |
| D0 | 403 | 3 | <1 | – | nd | T, C | – | – | – |
| | 405 | 4 | 1 | – | nd | – | – | – | – |
| | 408 | 3 | 2 | – | nd | T, C | – | – | – |
| 2 | 412 | 5 | 3 | – | nd | – | – | – | – |
| vAVW03 at | 413 | 5 | 3 | – | nd | T | T | – | – |
| D0 + D14 | 417 | 5 | 2 | – | nd | – | – | – | – |
| | 419 | 5 | 4 | – | nd | – | – | – | – |
| | 420 | 3 | 2 | – | nd | – | – | – | – |
| 1 | 421 | <3 | <1 | + (D2) | T, C | | | + | + |
| Unvacc. Contacts | 424 | <3 | <1 | + (D3) | T, C | | | + | + |
| 2 | 426 | <3 | <1 | + (D2) | T, C | | | + | + |
| Unvacc. Contacts | 429 | 3 | 1 | – | nd | – | – | – | – |
| 3 | | <3 | <1 | + (D2) | T, C | | | + | + |
| Unvacc. | | <3 | <1 | + (D2) | T, C | | | + | + |

*T = positive throat swab; C = positive cloacal swab

The result showed that the oronasal challenge was very severe despite the relatively low dose used (4.7 log 10 EID50), suggesting that this Hungarian H5N1 isolate (isolated from ducks) has a high level of virulence for Muscovy ducks. Full clinical protection was observed in all vaccinated ducks, even those that received only 1 administration of vAVW03 at day-old, 5 weeks before the challenge and that did have a low or undetectable NDV H1 or H5N1 SN titre. Shedding was observed in a lower number of ducks in group 2 (1/5) that received 2 vaccine administrations compared to group 1 (3/5) that received only one administration. Interestingly, the only contact duck that had detectable NDV and H5N1 antibody titers before challenge likely due to the horizontal transmission of the vAVW03 vaccine from the vaccinated ducks was fully protected.

Example 4.3

Duck Study 3 in One-Day-Old Muscovy Ducklings

The objective of the duck study in this example was to confirm H5N1 protection induced by vAVW03 alone or associated with other vaccines against another H5N1 HPAI isolate in one-day-old SPF Muscovy ducklings.

The study design is shown in Table 12. The immunogenicity of a single vAVW03 administration was compared with that of 2 administrations of vAVW03 and a heterologous prime-boost scheme consisting of priming at D0 with the TROVAC-AIV H5 vector vaccine (fowlpox recombinant vFP89 expressing the native HA gene of the HPAI H5N8 A/turkey/Ireland/1378/1983 isolate; licensed in USA) using 10 chicken doses (about 4.5 log 10 TCID50/dose) by the subcutaneous route followed by vAVW03 at D14 administered by the mucosal route (see details in Table 12). At D28 and D42, 5 ducks of each group were challenged with the French HPAI H5N1 clade 2.2 A/swan/France/06299/06 isolate ($10^6$ EID50/duck).

TABLE 12

Duck study 3 design and results of protection

| Group | Number | Vaccine* (dose)** administered at D0 | D14 | Protected/total (MTD) after H5N1 challenge*** at D28 | D42 |
|---|---|---|---|---|---|
| 1 | 5 + 5 | — | — | 0/5 (3.4) | 0/5 (3.4) |
| 2 | 5 + 5 | vAVW03 (5.5) | — | 5/5 | 5/5 |
| 3 | 5 + 5 | vAVW03 (5.5) | vAVW03 (5.5) | 5/5 | 5/5 |
| 4 | 5 + 5 | TROVAC-AIV H5 (4.5) | vAVW03 (5.5) | 5/5 | 5/5 |

*vAVW03 was administered by the oculo-nasal route with 50 μl vaccine suspension (mineral water used as diluent); TROVAC-AIV H5 was administered by the subcutaneous route with 0.2 ml vaccine suspension (Marek's vaccine diluent used as diluent).
**dose of vAVW03 is expressed in log10 EID50 and of TROVAC-AIV H5 as log10 TCID50; the dose of TROVAC-AIV H5 corresponds to 10 chicken doses of a commercial batch of this vaccine
*The challenge strain was the HPAI H5N1 clade 2.2 A/swan/France/06299/06 isolate; 6 log10 EID50 administered by oculonasal route; MTD: mean time to death in days All non-vaccinated ducks showed clinical signs and died within 4 days after challenge. None of the vaccinated ducks showed clinical signs or died (see Table 12). Oropharyngeal and cloacal swabs were sampled at different times after challenge (2.5, 4.5, 6.5, 9.5, and 11.5 day post-challenge). Viral load was measured by the M-based real-time RTPCR based on Spackman et al (2002) J Clin Microbiol 40:3256-3260. Results of challenge at D28 and D42 are presented at FIGS. 23***a-d* and 24*a-d*, respectively.

The shedding data clearly indicated that the vaccinated ducks shed fewer viruses than the non-vaccinated controls and the percentage of positive birds was also reduced after both challenges at D28 (FIGS. 23*a-d*) and D42 (FIGS. 24*a-d*). There was no difference between samples from group 2 and 3, indicating that one vAVW03 administration at one day of age provided the same protection as two vAVW03 immunizations at D0 and D14 in these conditions. Percentages of positive as well as virus loads were lower in ducks from group 4 that received the heterologous prime-boost regimen compared to those of groups 2 and 3, especially for the challenge at D28. These results indicate that a priming with a fowlpox recombinant expressing another HA gene from the same subtype administered before vAVW03 improves the level of protection compared to 1 or 2 administrations of vAVW03.

The AI HI titers were measured in serums sampled before (D28 and D40) and after (D42 and D57) challenge at D28 and D42, respectively, using an HPAI H5N1 (French isolate 06167i H5N1 clade 2.2.1 close to the challenge strain) as the antigen (See Table 13). Only a few ducks of group 4 had detectable HI titers at D28. It is interesting to note that despite the absence of detectable seroconversion against AI at the time of challenge, all vaccinated ducks were protected against the severe HPAI challenge. This result confirms previous one indicating that HI test cannot be used to predict the efficacy of such engineered NDV AI vaccine.

Fourteen day after challenge at D28, HPAI H5N1 HI titers increased from 0 at D28 to 7.2 log 2 at D42 in groups 2 and 3 whereas in group 4, they increased from 2.3 (D28) to 6.0 (D42). The lower increase of HI titers after challenge in group 4 compared to groups 2 and 3 suggested that the challenge virus replicated less in this group. Such decrease of challenge virus replication in ducks of group 4 was observed in the shedding data after challenge at D28 (see above and FIGS. 23*a-d*).

TABLE 13

Duck study 3. Mean AI HI titers (log2) before and after challenge

| Group | Challenge at D28 D28 (prech.) | D42 (postch.) | Challenge at D42 D40 (prech.) | D57 (postch.) |
|---|---|---|---|---|
| 1 | 0 (0/7) | — | 0 (0/7) | — |
| 2 | 0 (0/7) | 7.2 (5/5) | 0.4 (0/7) | 8.6 (5/5) |
| 3 | 0 (0/5) | 7.2 (5/5) | 0 (0/7) | 8.4 (5/5) |
| 4 | 2.3 (2/6) | 6.0 (4/4) | 0.9 (0/7) | 8.2 (5/5) |

In summary, one (D0) or two (D0 and D14) mucosal deliveries of vAVW03 administered to one-day-old Muscovy ducklings protected them against HPAI H5N1 challenges performed at D28 and D42. A heterologous priming with a fowlpox recombinant expressing an HA from an H5N8 isolate before vAVW03 administration improved the protection against an early challenge at D28.

Example 4.4

Duck Study 4—Duration of Immunity in One-Day-Old Muscovy Ducklings

The objective of the Duck Study in this example was to evaluate the duration of immunity induced by one administration of vAVW03 or that induced by the heterologous TROVAC-AIV H5/vAVW03 prime-boost scheme tested in Duck study 3.

TABLE 14

Duck study 4 design and results of clinical protection

| Group | Number[1] | Vaccine[2] (dose)[3] administered at D2 | D15 | Protected[4]/total (MTD) after H5N1 challenge[5] at D65 | D86 |
|---|---|---|---|---|---|
| 1 | 5 + 5 | — | — | 0-0/5 (4.1) | 0-1/5 (5.4) |
| 2 | 8 + 9 | vAVW03 (5.5) | — | 7-8/8 | 8-8/9 (9.5) |
| 3 | 8 + 8 | TROVAC-AIV H5 (4.5) | vAVW03 (5.5) | 7-8/8 | 8-8/8 |
| 4 | 8 + 8 | — | Inactivated | Not done | 8-8/8 |

[1]Number of ducks for the challenge at D65 + at D86 (Mean Time to Death in days)

[2]vAVW03 was administered by the oculo-nasal route with 50 μl vaccine suspension (mineral water used as diluent); TROVAC-AIV H5 was administered by the subcutaneous route with 0.2 ml vaccine suspension; inactivated vaccine is a commercial oil-adjuvanted inactivated vaccine vaccine that contains Re5 reverse genetics H5N1 isolate including the HA (modified at the cleavage site) and NA genes from the clade 2.3 A/duck/Anhui/1/2006 isolate.

[3]Dose of vAVW03 is expressed in log10 EID50 and of TROVAC-AIV H5 as log10 TCID50; the dose of TROVAC-AIV H5 corresponds to 10 chicken doses of a commercial batch of this vaccine.

[4]Number of birds protected against morbidity – number of birds protected against mortality/total (MTD: mean time to death in days).

[5]The challenge strain was the HPAI H5N1 clade 2.2 A/swan/France/06299/06 isolate; 6 log10 EID50 administered by oculonasal route.

None of the birds developed detectable AI HI antibodies against the HP H5N1 06167i clade 2.2.1 antigen (close to the challenge strain) before challenge.

These late challenges were effective since they induced 100% morbidity and killed most of the unvaccinated control ducks (only one sick bird survived the late challenge at D86; see Table 14). Most birds vaccinated with vAVW03 were protected; only 1/8 showed mild clinical signs and survived at the D65 challenge and 1/9 showed clinical signs and died at the D86 challenge. All birds from the prime-boost (TROVAC AIV-H5 at D2 and vAVW03 at D15) group survived both challenges; only one bird showed clinical signs at the earlier (D65) challenge. None of the birds from group 4 vaccinated with the inactivated Re5 vaccine showed clinical signs or died.

The oropharyngeal and cloacal shedding was also investigated after challenge. All control birds shed viruses at high levels (6.8 and 4.9 equivalent EID50/mL by the oropharyngeal and cloacal routes, respectively) and for at least 9.5 days (for the survivor). In group 2 and 3, the level of shedding was lower (about 1 and 2 log 10 lower, respectively) and it decreased faster than the control group. Shedding profiles in group 4 were close to those observed in group 3.

In conclusion, one administration of vAVW03 to Muscovy ducklings (2 days of age) provided a good level of protective immunity up to 84 days of age. The prime-boost regimen with a fowlpox vector followed by a NDV vector provides a better protective immune response than one administration of the NDV vector and a similar protective response as the inactivated Re5 vaccine.

Example 4.5

Duck Study 5—vAVW003 Efficacy in Pekin Ducklings

The objective of this study was to evaluate the efficacy of vAVW03 in Pekin ducks against an HPAI H5N1 challenge. Seven-day-old Pekin ducklings were vaccinated as shown in Table 15. The challenge strain was the HPAI H5N1 clade 2.2 A/turkey/Turkey/1/2005 isolate; 6 and 7 log 10 EID50 administered by oculonasal route were used at D28 and D42, respectively. Clinical signs (morbidity) and deaths (mortality) were recorded after challenge. Shedding was measured after challenge using a real time RT-PCR in buccal and cloacal swabs taken 2, 5, and 8 days post-challenge (dpc). The study design and results of protection are shown in Table 15.

TABLE 15

Duck study 5 design and results of protection

| Gp | Number | Vaccine[1] (dose)[2] administered at D0 | D14 | Results of challenge at D28 Morbidity | Mortality | Detection[5] | Results of challenge at D42 Morbidity | Mortality | Detection |
|---|---|---|---|---|---|---|---|---|---|
| 1 | 10 | — | — | 6/10 | 5/10 | 10/10 | 3/10 | 6/10 | 9/10 |
| 2 | 10 | — | Re5[4] | 0/9 | 0/9 | 5/9 | 0/10 | 0/10 | 1/10 |
| 3 | 10 | vAVW03 (5.5) | — | 0/10 | 0/10 | 0/10 | 0/10 | 0/10 | 5/10 |
| 4 | 10 | vAVW03 (4.5) | vAVW03 (5.5) | 0/10 | 0/10 | 0/10 | 0/10 | 0/10 | 2/10 |

TABLE 15-continued

Duck study 5 design and results of protection

| Gp | Number | Vaccine[1] (dose)[2] administered at D0 | D14 | Results of challenge at D28 Morbidity | Mortality | Detection[5] | Results of challenge at D42 Morbidity | Mortality | Detection |
|---|---|---|---|---|---|---|---|---|---|
| 5 | 10 | vFP89[3] (4.5) | vAVW03 (5.5) | 0/10 | 0/10 | 0/10 | 0/9 | 0/9 | 4/9 |

[1]vAVW03 was administered by the oculo-nasal route with 50 μl vaccine suspension (mineral water used as diluent); TROVAC-AIV H5 was administered by the subcutaneous route with 0.2 ml vaccine suspension (Marek's vaccine diluent used as diluent).
[2]dose of vAVW03 is expressed in log10 EID50 and of TROVAC-AIV H5 as log10 TCID50; the dose of TROVAC-AIV H5 corresponds to 10 chicken doses of a commercial batch of this vaccine
[3]vFP89: fowlpox vector AIV H5 (see, US 2008/0107681 and US 2008/0107687).
[4]Re5: Oil-adjuvanted inactivated vaccine based on a reverse genetics strain containing the modified HA gene and NA gene from the HPAI H5N1 A/duck/Anhui/1/2006 (clade 2.3).
[5]Number of chickens positive for buccal or cloacal swabs at 2, 5 or 8 dpc.

The results indicated that Pekin ducks are relatively resistant to the H5N1 challenge since only about half of the non-vaccinated birds showed clinical signs or died after challenge. Nevertheless, most of them shed detectable amount of virus indicating active replication of the challenge strain. All vaccinated ducks were clinically protected at both challenge dates and the number of birds shedding virus was reduced compared to the unvaccinated controls. These results indicate that significant protection can be induced by vAVW03 in Pekin ducklings.

Example 4.6

Duck Study 6—vAVW003 Efficacy in One-Day-Old Pekin Ducklings with NDV MDAs

The objective of the Duck Study 6 was to evaluate the HPAI H5N1 efficacy induced by one administration of vAVW03 in Pekin ducks born from breeders vaccinated with an inactivated combo vaccine containing NDV antigen in order to evaluate the effect of NDV MDAs on the vAVW03-induced efficacy. Two-day-old Pekin ducklings with NDV MDAs were used in this study. SPF Muscovy ducklings were also used to validate the challenge. The study design and protection data is presented in Table 16.

TABLE 16

Duck study 6 design and results of protection against HPAI H5N1 challenge

| Group | Ducks Species | Number | Vaccination at D0 Vaccine | dose | Route* | Protection** against Morbidity (MTC) | Mortality (MTD) | % protection |
|---|---|---|---|---|---|---|---|---|
| 1 | Muscovy | 7 | — | | — | 0/5 | 0/5 (3.5) | 0% |
| 2 | Pekin | 7 | — | | — | 2/5 (4.2) | 4/5 (6.5) | 40% |
| 3 | Pekin | 14 | vAVW03 | 5.5 | ON | 8/9 (11.5) | 9/9 | 89% |
| 4 | Pekin | 11 | vAVW03 | 6.5 | ON | 6/9 (6.8) | 6/9 (7.2) | 67% |
| 5 | Pekin | 11 | vAVW03 | 5.5 | Oral | 7/9 (8.5) | 8/9 (6.5) | 78% |
| 6 | Pekin | 11 | vAVW03 | 6.5 | Oral | 8/9 (6.5) | 8/9 (6.5) | 89% |

*ON = oculo-nasal

**The challenge strain was the HPAI H5N1 clade 2.2 A/swan/France/06299/06 isolate; 6 log10 EID50 administered by oculonasal route at D24; MTC: mean time to clinical signs in days; MTD: mean time to death in days The HPAI H5N1 challenge was validated by the rapid mortality (all died 3.5 days post-challenge) of the non-vaccinated Muscovy ducklings used as controls. However, the non-vaccinated Pekin ducks were much more resistant to the H5N1 challenge since only 3/5 showed clinical signs and only 1/5 died 6.5 days post-challenge. Partial protection (from 67 to 89%) against morbidity was induced by vAVW03 and there was no clear dose- or administration route-effect in Pekin ducklings.

All control Pekin ducks shed virus by the oropharyngeal route. The shedding was decreased in load, time and number of positive birds in the vaccinated groups.

This study shows that AI protection can be induced with one administration of vAVW03 in Pekin ducks with NDV MDAs.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What is claimed is:

1. An engineered NDV vector comprising a polynucleotide, wherein the polynucleotide has at least 97% sequence identity to SEQ ID NO:1 or is complementary to a polynucleotide having at least 97% sequence identity to SEQ ID NO:1, and wherein the NDV vector further comprises a heterologous polynucleotide encoding an avian influenza hemagglutinin (HA) antigen, and wherein the HA antigen has the sequence as set forth in SEQ ID NO:15, 17, 19, 21 or 23.

2. The NDV vector of claim 1, wherein the polynucleotide has at least 98% sequence identity to SEQ ID NO:1, or is complementary to a polynucleotide having at least 98% sequence identity to SEQ ID NO:1.

3. The NDV vector of claim 1, wherein the polynucleotide has at least 99% sequence identity to SEQ ID NO:1, or is complementary to a polynucleotide having at least 99% sequence identity to SEQ ID NO:1.

4. The NDV vector of claim 1, wherein the polynucleotide has the sequence as set forth in SEQ ID NO:1, or is complementary to a polynucleotide having the sequence as set forth in SEQ ID NO:1.

5. The NDV vector of claim 1, wherein the heterologous polynucleotide has the sequence as set forth in SEQ ID NO:14, 16, 18, 20, or 22.

6. The NDV vector of claim 1, wherein the HA antigen has the sequence as set forth in SEQ ID NO:15.

7. The NDV vector of claim 1, wherein the HA antigen has the sequence as set forth in SEQ ID NO:17.

8. The NDV vector of claim 1, wherein the HA antigen has the sequence as set forth in SEQ ID NO:19.

9. The NDV vector of claim 1, wherein the HA antigen has the sequence as set forth in SEQ ID NO:21.

10. The NDV vector of claim 1, wherein the HA antigen has the sequence as set forth in SEQ ID NO:23.

11. A composition comprising an engineered Newcastle Disease Virus (NDV) vector, wherein the engineered NDV vector comprises a polynucleotide having at least 97% sequence identity to a polynucleotide having the sequence as set forth in SEQ ID NO:1 or a polynucleotide complementary to a polynucleotide having at least 97% sequence identity to the polynucleotide having the sequence as set forth in SEQ ID NO:1, and wherein the engineered NDV vector further comprises a heterologous polynucleotide encoding an avian influenza hemagglutinin (HA) antigen, and wherein the HA antigen has the sequence as set forth in SEQ ID NO:15, 17, 19, 21 or 23.

12. The composition of claim 11, wherein the heterologous polynucleotide has the sequence as set forth in SEQ ID NO:14, 16, 18, 20, or 22.

13. The composition of claim 11, wherein the polynucleotide has at least 98% sequence identity to SEQ ID NO:1, or is complementary to a polynucleotide having at least 98% sequence identity to SEQ ID NO:1.

14. The composition of claim 11, wherein the polynucleotide has at least 99% sequence identity to SEQ ID NO:1, or is complementary to a polynucleotide having at least 99% sequence identity to SEQ ID NO:1.

15. The composition of claim 11, wherein the polynucleotide has the sequence as set forth in SEQ ID NO:1, or is complementary to a polynucleotide having the sequence as set forth in SEQ ID NO:1.

16. The composition of claim 11, wherein the HA antigen has the sequence as set forth in SEQ ID NO:15.

17. The composition of claim 11, wherein the HA antigen has the sequence as set forth in SEQ ID NO:17.

18. The composition of claim 11, wherein the HA antigen has the sequence as set forth in SEQ ID NO:19.

19. The composition of claim 11, wherein the HA antigen has the sequence as set forth in SEQ ID NO:21.

20. The composition of claim 11, wherein the HA antigen has the sequence as set forth in SEQ ID NO:23.

* * * * *